US008901087B2

(12) United States Patent
Chang et al.

(10) Patent No.: US 8,901,087 B2
(45) Date of Patent: Dec. 2, 2014

(54) SELECTIVE GLYCOSIDASE INHIBITORS AND USES THEREOF

(75) Inventors: Jiang Chang, Beijing (CN); Kun Liu, Edison, NJ (US); Ernest J. McEachern, Vancouver (CA); Changwei Mu, Beijing (CN); Harold G. Selnick, Ambler, PA (US); Feng Shi, Beijing (CN); David J. Vocadlo, Burnaby (CA); Yaode Wang, Beijing (CN); Zhongyong Wei, Beijing (CN); Yuanxi Zhou, Richmond (CA); Yongbao Zhu, Langley (CA)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/883,811

(22) PCT Filed: Nov. 8, 2011

(86) PCT No.: PCT/US2011/059668
§ 371 (c)(1),
(2), (4) Date: Jul. 22, 2013

(87) PCT Pub. No.: WO2012/064680
PCT Pub. Date: May 18, 2012

(65) Prior Publication Data
US 2013/0296301 A1 Nov. 7, 2013

Related U.S. Application Data

(60) Provisional application No. 61/418,596, filed on Dec. 1, 2010.

(30) Foreign Application Priority Data

Nov. 8, 2010 (WO) ................ PCT/CN2010/078528
Oct. 12, 2011 (WO) ................ PCT/CN2011/008069

(51) Int. Cl.
*C08B 37/00* (2006.01)
*C07D 487/02* (2006.01)
*A61K 31/70* (2006.01)
*A61K 31/425* (2006.01)
*C07D 513/04* (2006.01)

(52) U.S. Cl.
CPC .................................. *C07D 513/04* (2013.01)
USPC ................ 514/23; 514/367; 536/54; 548/453

(58) Field of Classification Search
None
See application file for complete search history.

(56) References Cited

U.S. PATENT DOCUMENTS

2010/0016386 A1   1/2010   Vocadlo et al.

FOREIGN PATENT DOCUMENTS

| CN | 101595111 | | 12/2009 |
|---|---|---|---|
| WO | 2006092049 A1 | | 9/2006 |
| WO | 2008025170 A1 | | 3/2008 |
| WO | WO2006/092049 | * | 9/2008 |
| WO | 2010012106 A1 | | 2/2010 |
| WO | 2010012107 A1 | | 2/2010 |
| WO | 2010037207 A1 | | 4/2010 |

OTHER PUBLICATIONS

Arias, et al., "Prolonged Incubation in PUGNAc Results in Increased Protein O-Linked Glycosylation and Insulin Resistance . . . ," Diabetes, 2004, vol. 53, pp. 921-930.
Konrad, et al., "The potential mechanism of the diabetogenic action of streptozotocin: inhibition of pancreatic . . . ," Biochem. J., 2001, vol. 356, pp. 31-41.
Liu, et al., "Accumulation of protein O-GlcNAc modification inhibits proteasomes in the brain and coincides with neuronal . . . ," Journal of Neurochemistry, 2004, vol. 89, pp. 1044-1055.
Parker, et al., "Hyperglycemia and Inhibition of Glycogen Synthase in Streptozotocin-treated Mice," Journal of Biol. Chem., 2004, vol. 279, pp. 20636-20642.
Rao, et al., "Structural insights into the mechanism and inhibition of eukaryotic O-GlcNAc hydrolysis," The EMBO Journal, 2006, vol. 25, pp. 1569-1578.
Rempel, et al., "Covalent inhibitors of glycosidases and their applications in biochemistry and biology," Glycobiology, 2008, vol. 18, No. 8, pp. 570-586.
Vosseller, et al., "Elevated nucleocytoplasmic glycosylation by O-GlcNAc results in insulin resistance associated with defects in Akt activation . . . ," PNAS USA, 2002, vol. 99, 5313-5318.
Yuzwa, et al., "A potent mechanism-inspired O-GlcNAcase inhibitor that blocks phosphorylation of tau in vivo," Nat Chem Bio, 2008, vol. 4, pp. 483-490.
WO12061972 Search Report.
WO12062157 Search Report.
WO12064680 Search Report.

* cited by examiner

*Primary Examiner* — Traviss C McIntosh, III
(74) *Attorney, Agent, or Firm* — J. Eric Thies; John C. Todaro

(57) ABSTRACT

The invention is directed to compounds for selectively inhibiting glycosidases, uses of the compounds and pharmaceutical compositions including the compounds, and methods of treating diseases and disorders related to deficiency or overexpression of O-GlcNAcase, and/or accumulation or deficiency of O-GlcNAc.

43 Claims, No Drawings

SELECTIVE GLYCOSIDASE INHIBITORS AND USES THEREOF

CROSS REFERENCE TO RELATED APPLICATIONS

This application is the national stage application under 35 U.S.C. 371 of International Patent Application No.: PCT/US2011/059668 filed Nov. 8, 2011, which claims the benefit of PCT/CN2011/080691 filed Oct. 12, 2011, which claims the benefit of U.S. application No. 61/418,596 filed Dec. 1, 2010, which claims the benefit of PCT/CN2010/078528 filed Nov. 8, 2010. The aforementioned PCT and provisional applications are incorporated by reference in its entirety as if fully set forth herein.

FIELD OF THE INVENTION

This application relates to compounds which selectively inhibit glycosidases and uses thereof.

BACKGROUND OF THE INVENTION

A wide range of cellular proteins, both nuclear and cytoplasmic, are post-translationally modified by the addition of the monosaccharide 2-acetamido-2-deoxy-β-D-glucopyranoside (β-N-acetylglucosamine) which is attached via an β-glycosidic linkage.[1] This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGT).[2-5] A second enzyme, known as O-GlcNAcase[6,7] removes this post-translational modification to liberate proteins making the O-GlcNAc-modification a dynamic cycle occurring several times during the lifetime of a protein.[8]

O-GlcNAc-modified proteins regulate a wide range of vital cellular functions including, for example, transcription,[9-12] proteasomal degradation,[13] and cellular signaling.[14] O-GlcNAc is also found on many structural proteins.[15-17] For example, it has been found on a number of cytoskeletal proteins, including neurofilament proteins,[18,19] synapsins,[6,20] synapsin-specific clathrin assembly protein AP-3,[7] and ankyrinG.[14] O-GlcNAc modification has been found to be abundant in the brain.[21,22] it has also been found on proteins clearly implicated in the etiology of several diseases including Alzheimer's disease (AD) and cancer.

For example, it is well established that AD and a number of related tauopathies including Downs' syndrome, Pick's disease, Niemann-Pick Type C disease, and amyotrophic lateral sclerosis (ALS) are characterized, in part, by the development of neurofibrillary tangles (NFTs). These NFTs are aggregates of paired helical filaments (PHFs) and are composed of an abnormal form of the cytoskeletal protein "tau". Normally tau stabilizes a key cellular network of microtubules that is essential for distributing proteins and nutrients within neurons. In AD patients, however, tau becomes hyperphosphorylated, disrupting its normal functions, forming PHFs and ultimately aggregating to form NFTs. Six isoforms of tau are found in the human brain. In AD patients, all six isoforms of tau are found in NFTs, and all are markedly hyperphosphorylated.[23,24] Tau in healthy brain tissue bears only 2 or 3 phosphate groups, whereas those found in the brains of AD patients bear, on average, 8 phosphate groups.[25,26] A clear parallel between NFT levels in the brains of AD patients and the severity of dementia strongly supports a key role for tau dysfunction in AD.[27,28] The precise causes of this hyperphosphorylation of tau remain elusive. Accordingly, considerable effort has been dedicated toward: a) elucidating the molecular physiological basis of tau hyperphosphorylation;[29] and b) identifying strategies that could limit tau hyperphosphorylation in the hope that these might halt, or even reverse, the progression of Alzheimer's disease[30-33] Thus far, several lines of evidence suggest that up-regulation of a number of kinases may be involved in hyperphosphorylation of tau,[21,34,35] although very recently, an alternative basis for this hyperphosphorylation has been advanced.[21]

In particular, it has recently emerged that phosphate levels of tau are regulated by the levels of O-GlcNAc on tau. The presence of O-GlcNAc on tau has stimulated studies that correlate O-GlcNAc levels with tau phosphorylation levels. The recent interest in this field stems from the observation that O-GlcNAc modification has been found to occur on many proteins at amino acid residues that are also known to be phosphorylated.[36-38] Consistent with this observation, it has been found that increases in phosphorylation levels result in decreased O-GlcNAc levels and conversely, increased O-GlcNAc levels correlate with decreased phosphorylation levels.[39] This reciprocal relationship between O-GlcNAc and phosphorylation has been termed the "Yin-Yang hypothesis"[40] and has gained strong biochemical support by the recent discovery that the enzyme OGT[4] forms a functional complex with phosphatases that act to remove phosphate groups from proteins.[41] Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD.[7,42] Hyperphosphorylated tau in human AD brains has markedly lower levels of O-GlcNAc than are found in healthy human brains.[21] Very recently, it has been shown that O-GlcNAc levels of soluble tau protein from human brains affected with AD are markedly lower than those from healthy brain.[21] Furthermore, PHF from diseased brain was suggested to lack completely any O-GlcNAc modification whatsoever.[21] The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosamindase inhibitor was used to increase tau O-GlcNAc levels, whereupon it was observed that phosphorylation levels decreased.[21] The implication of these collective results is that by maintaining healthy O-GlcNAc levels in AD patients, such as by inhibiting the action of O-GlcNAcase, one should be able to block hyperphosphorylation of tau and all of the associated effects of tau hyperphosphorylation, including the formation of NFTs and downstream effects. However, because the proper functioning of the β-hexosaminidases is critical, any potential therapeutic intervention for the treatment of AD that blocks the action of O-GlcNAcase would have to avoid the concomitant inhibition of both hexosaminidases A and B.

Neurons do not store glucose and therefore the brain relies on glucose supplied by blood to maintain its essential metabolic functions. Notably, it has been shown that within brain, glucose uptake and metabolism decreases with aging.[43] Within the brains of AD patients marked decreases in glucose utilization occur and are thought to be a potential cause of neurodegeneration.[44] The basis for this decreased glucose supply in AD brain[45-47] is thought to stem from any of decreased glucose transport,[48,49] impaired insulin signaling,[50,51] and decreased blood flow.[52]

In light of this impaired glucose metabolism, it is worth noting that of all glucose entering into cells, 2-5% is shunted into the hexosamine biosynthetic pathway, thereby regulating cellular concentrations of the end product of this pathway, uridine diphosphate-N-acetylglucosamine (UDP-GlcNAc).[53] UDP-GlcNAc is a substrate of the nucleocytoplasmic enzyme O-GlcNAc transferase (OGT),[2-5] which acts to post-translationally add GlcNAc to specific serine and threonine residues of numerous nucleocytoplasmic proteins. OGT recognizes many of its substrates[54,55] and binding partners[41,56] through its tetratricopeptide repeat (TPR) domains.[57,58] As described above, O-GlcNAcase[6,7] removes this post-translational modification to liberate proteins making the O-GlcNAc-modification a dynamic cycle occurring several times during the lifetime of a protein.[8] O-GlcNAc has been found in several proteins on known phosphorylation sites,[10,37,38,59] including tau and neurofilaments.[60] Additionally, OGT shows unusual kinetic behaviour making it exquisitely sensitive to intracellular UDP-GlcNAc substrate concentrations and therefore glucose supply.[41]

Consistent with the known properties of the hexosamine biosynthetic pathway, the enzymatic properties of OGT, and the reciprocal relationship between O-GlcNAc and phosphorylation, it has been shown that decreased glucose availability in brain leads to tau hyperphosphorylation.[44] Therefore the gradual impairment of glucose transport and metabolism, whatever its causes, leads to decreased O-GlcNAc and hyperphosphorylation of tau (and other proteins). Accordingly, the inhibition of O-GlcNAcase should compensate for the age related impairment of glucose metabolism within the brains of health individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention[61] comes from recent studies showing that when transgenic mice harbouring human tau are treated with kinase inhibitors, they do not develop typical motor defects[33] and, in another case,[32] show decreased levels of insoluble tau. These studies provide a clear link between lowering tau phosphorylation levels and alleviating AD-like behavioural symptoms in a murine model of this disease. Indeed, pharmacological modulation of tau hyperphosphorylation is widely recognized as a valid therapeutic strategy for treating AD and other neurodegenerative disorders.[62]

Recent studies[63] support the therapeutic potential of small-molecule O-GlcNAcase inhibitors to limit tau hyperphosphorylation for treatment of AD and related tauopathies. Specifically, the O-GlcNAcase inhibitor thiamet-G has been implicated in the reduction of tau phosphorylation in cultured PC-12 cells at pathologically relevant sites.[63] Moreover, oral administration of thiamet-G to healthy Sprague-Dawley rats has been implicated in reduced phosphorylation of tau at Thy231, Ser396 and Ser422 in both rat cortex and hippocampus.[63].

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animals models of ischemia/reperfusion,[64-70] trauma hemorrhage,[71-73] hypervolemic shock,[74] and calcium paradox.[64,75] Moreover, strong evidence indicates that these cardioprotective effects are mediated by elevated levels of protein O-GlcNAc modification.[64,65,67,70,72,75-78] There is also evidence that the O-GlcNAc modification plays a role in a variety of neurodegenerative diseases, including Parkinson's disease and Huntington's disease.[79]

Humans have three genes encoding enzymes that cleave terminal βN-acetylglucosamine residues from glycoconjugates. The first of these encodes the enzyme O-glycoprotein 2-acetamido-2-deoxy-β-D-glucopyranosidase (O-GlcNAcase). O-GlcNAcase is a member of family 84 of glycoside hydrolases that includes enzymes from organisms as diverse as prokaryotic pathogens to humans (for the family classification of glycoside hydrolases see Coutinho, P. M. & Henrissat, B. (1999) Carbohydrate-Active Enzymes server at URL: http://afmb.cnrs-mrs.fr/CAZY/.[27,28] O-GlcNAcase acts to hydrolyse O-GlcNAc off of serine and threonine residues of post-translationally modified proteins.[1,6,7,80,81] Consistent with the presence of O-GlcNAc on many intracellular proteins, the enzyme O-GlcNAcase appears to have a role in the etiology of several diseases including type II diabetes,[14,82] AD,[16,21,83] and cancer.[22,84] Although O-GlcNAcase was likely isolated earlier on,[18,19] about 20 years elapsed before its biochemical role in acting to cleave O-GlcNAc from serine and threonine residues of proteins was understood.[6] More recently O-GlcNAcase has been cloned,[7] partially characterized,[20] and suggested to have additional activity as a histone acetyltransferase.[20] However, little was known about the catalytic mechanism of this enzyme.

The other two genes, HEXA and HEXB, encode enzymes catalyzing the hydrolytic cleavage of terminal β-N-acetylglucosamine residues from glycoconjugates. The gene products of HEXA and HEXB predominantly yield two dimeric isozymes, hexosaminidase A and hexosaminidase B, respectively. Hexosaminidase A (αβ), a heterodimeric isozyme, is composed of an α- and a β-subunit. Hexosaminidase B (ββ), a homodimeric isozyme, is composed of two β-subunits. The two subunits, α- and β-, bear a high level of sequence identity. Both of these enzymes are classified as members of family 20 of glycoside hydrolases and are normally localized within lysosomes. The proper functioning of these lysosomal β-hexosaminidases is critical for human development, a fact that is underscored by the tragic genetic illnesses, Tay-Sach's and Sandhoff diseases which stem from a dysfunction in, respectively, hexosaminidase A and hexosaminidase B.[85] These enzymatic deficiencies cause an accumulation of glycolipids and glycoconjugates in the lysosomes resulting in neurological impairment and deformation. The deleterious effects of accumulation of gangliosides at the organismal level are still being uncovered.[86] As a result of the biological importance of these β-N-acetyl-glucosaminidases, small molecule inhibitors of glycosidases[87-90] have received a great deal of attention,[91] both as tools for elucidating the role of these enzymes in biological processes and in developing potential therapeutic applications. The control of glycosidase function using small molecules offers several advantages over genetic knockout studies including the ability to rapidly vary doses or to entirely withdraw treatment.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, existing compounds that act to block O-GlcNAcase function are non-specific and act potently to inhibit the lysosomal β-hexosaminidases.

A few of the better characterized inhibitors of β-N-acetyl-glucosaminidases which have been used in studies of O-GlcNAc post-translational modification within both cells and tissues are streptozotocin (STZ), 2"-methyl-α-D-glueopyrano-[2,1-d]-Δ2'-thiazoline (NAG-thiazoline) and O-(2-acetamido-2-deoxy-D-glucopyranosylidene)amino N-phenylcarbamate (PUGNAc).[14,92-95]

STZ has long been used as a diabetogenic compound because it has a particularly detrimental effect on β-islet cells.[96] STZ exerts its cytotoxic effects through both the alkylation of cellular DNA[96,97] as well as the generation of radical species including nitric oxide.[98] The resulting DNA strand breakage promotes the activation of poly(ADP-ribose) polymerase (PARP)[99] with the net effect of depleting cellular NAD+ levels and, ultimately, leading to cell death.[100,101] Other investigators have proposed instead that STZ toxicity is a consequence of the irreversible inhibition of O-GlcNAcase, which is highly expressed within β-islet cells.[92,102] This hypothesis has, however, been brought into question by two independent research groups.[103,104] Because cellular O-GlcNAc levels on proteins increase in response to many forms of cellular stress[105] it seems possible that STZ results in increased O-GlcNAc-modification levels on proteins by inducing cellular stress rather than through any specific and direct action on O-GlcNAcase. Indeed, Hanover and coworkers have shown that STZ functions as a poor and somewhat selective inhibitor of O-GlcNAcase[106] and although it has been proposed by others that STZ acts to irreversibly inhibit O-GlcNAcase,[107] there has been no clear demonstration of this mode of action. Recently, it has been shown that STZ does not irreversibly inhibit O-GlcNAcase.[108]

NAG-thiazoline has been found to be a potent inhibitor of family 20 hexosaminidases,[90,109] and more recently, the family 84 O-GlcNAcases.[108] Despite its potency, a downside to using NAG-thiazoline in a complex biological context is that it lacks selectivity and therefore perturbs multiple cellular processes.

PUGNAc is another compound that suffers from the same problem of lack of selectivity, yet has enjoyed use as an inhibitor of both human O-GlcNAcase[6,110] and the family 20 human β-hexosaminidases.[111] This molecule, developed by Vasella and coworkers, was found to be a potent competitive inhibitor of the β-N-acetyl-glucosaminidases from *Canavalia ensiformis*, *Mucor rouxii*, and the β-hexosaminidase from bovine kidney.[88] It has been demonstrated that administration of PUGNAc in a rat model of trauma hemorrhage decreases circulating levels of the pro-inflammatory cytokines TNF-α and IL-6.[112] It has also been shown that administration of PUGNAc in a cell-based model of lymphocyte activation decreases production of the cytokine IL-2.[113] Recent studies have indicated that PUGNAc can be used in an animal model to reduce myocardial infarct size after left coronary artery occlusions.[114] Of particular significance is the fact that elevation of O-GlcNAc levels by administration of PUGNAc, an inhibitor of O-GlcNAcase, in a rat model of trauma hemorrhage improves cardiac function.[112,115] In addition, elevation of O-GlcNAc levels by treatment with PUGNAc in a cellular model of ischemia/reperfusion injury using neonatal rat ventricular myocytes improved cell viability and reduced necrosis and apoptosis compared to untreated cells.[116]

More recently, it has been suggested that the selective O-GlcNAcase inhibitor NButGT exhibits protective activity in cell-based models of ischemia/reperfusion and cellular stresses, including oxidative stress.[117] This study suggests the use of O-GlcNAcase inhibitors to elevate protein O-GlcNAc levels and thereby prevent the pathogenic effects of stress in cardiac tissue.

International patent applications PCT/CA2006/000300, filed 1 Mar. 2006, published under No. WO 2006/092049 on 8 Sep. 2006; PCT/CA2007/001554, filed 31 Aug. 2007, published under No. WO 2008/025170 on 6 Mar. 2008; PCT/CA2009/001087, filed 31 Jul. 2009, published under No. WO 2010/012106 on 4 Feb. 2010; PCT/CA2009/001088, filed 31 Jul. 2009, published under WO 2010/012107 on 4 Feb. 2010; and PCT/CA2009/001302, filed 16 Sep. 2009, published under WO 2010/037207 on 8 Apr. 2010, describe selective inhibitors of O-GlcNAcase.

SUMMARY OF THE INVENTION

The invention is directed to compounds for selectively inhibiting glycosidases, uses of the compounds and pharmaceutical compositions including the compounds, and methods of treating diseases and disorders related to deficiency or overexpression of O-GlcNAcase, and/or accumulation or deficiency of O-GlcNAc.

DETAILED DESCRIPTION

The invention encompasses compounds of Formula (I) or a pharmaceutically acceptable salt thereof:

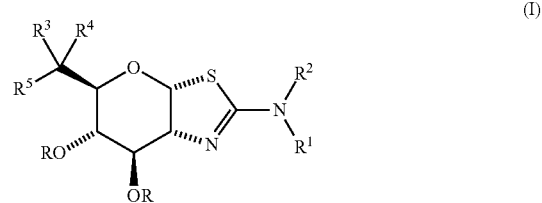

wherein: each R is independently H or C(O)CH$_3$; R$^1$ and R$^2$ are independently selected from the group consisting of: H, C$_{1-6}$alkyl, C$_{2-6}$alkenyl, C$_{1-6}$alkoxy, —(CH$_2$)$_n$-cyclopropyl and —(CH$_2$)$_n$-cyclobutyl wherein n is 0, 1, 2, 3 or 4; or R$^1$ and R$^2$ may be joined together with the nitrogen atom to which they are attached to form azetidine, pyrrolidine, piperidine or isoxazolidine, said C$_{1-6}$alkyl, C$_{2-6}$alkenyl, C$_{1-6}$alkoxy, —(CH$_2$)$_n$-cyclopropyl, —(CH$_2$)$_n$-cyclobutyl, azetidine, pyrrolidine, piperidine and isoxazolidine optionally substituted from one up to the maximum number of substituents with fluoro, hydroxy and methyl; R$^3$ is selected from the group consisting of: C$_{1-8}$alkyl, C$_{2-8}$alkenyl, C$_{2-8}$alkynyl, C$_{3-6}$cycloalkyl, aryl and heteroaryl, each optionally substituted from one up to the maximum number of substituents with fluoro and OH; R$^4$ is selected from the group consisting of H, F, C$_{1-8}$alkyl, C$_{2-8}$alkenyl and C$_{2-8}$alkynyl, each excluding hydrogen optionally substituted from one up to the maximum number of substituents with fluoro and OH; or R$^3$ and R$^4$ and the carbon atom to which they are attached may join together to form vinyl or a 3 to 7-membered carbocyclic or heterocyclic ring, said 3 to 7-membered carbocyclic or heterocyclic ring optionally containing a double bond and optionally substituted from one up to the maximum number of substituents with fluoro and OH; and R$^5$ is selected from H, F, OH and OC(O)CH$_3$; with the proviso that when R$^4$ is F then R$^5$ is other than OH and OC(O)CH$_3$.

The invention also encompasses compounds of Formula (I) or a pharmaceutically acceptable salt thereof:

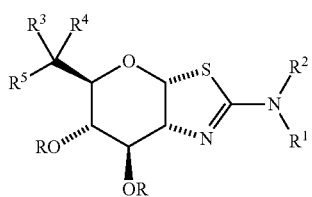

(I)

wherein: each R is independently H or C(O)CH$_3$; R$^1$ and R$^2$ are independently selected from the group consisting of: H, C$_{1-6}$alkyl, —(CH$_2$)$_n$-cyclopropyl and (CH$_2$)$_n$-cyclobutyl wherein n is 0, 1, 2, 3 or 4; or R$^1$ and R$^2$ may be joined together with the nitrogen atom to which they are attached to form azetidine, pyrrolidine or piperidine, said C$_{1-6}$alkyl, C$_{1-6}$alkoxy, —(CH$_2$)$_n$-cyclopropyl, —(CH$_2$)$_n$-cyclobutyl, azetidine, pyrrolidine and piperidine optionally substituted from one up to the maximum number of substituents with fluoro and methyl; R$^3$ is selected from the group consisting of: C$_{1-8}$alkyl, C$_{2-8}$alkenyl, C$_{2-8}$alkynyl, C$_{3-6}$cycloalkyl, aryl and heteroaryl, each optionally substituted from one up to the maximum number of substituents with fluoro and OH; R$^4$ is selected from the group consisting of: H, F, C$_{1-8}$alkyl, C$_{2-8}$alkenyl and C$_{2-8}$alkynyl, each excluding hydrogen optionally substituted from one up to the maximum number of substituents with fluoro and OH; or R$^3$ and R$^4$ and the carbon atom to which they are attached may join together to form vinyl or a 3 to 7-membered carbocyclic or heterocyclic ring, said 3 to 7-membered carbocyclic or heterocyclic ring optionally containing a double bond and optionally substituted from one up to the maximum number of substituents with fluoro and OH; and R$^5$ is selected from H, F and OH; with the proviso that when R$^4$ is F then R$^5$ is other than OH.

The invention also encompasses a genus of compounds of Formula (Ia) or a pharmaceutically acceptable salt thereof:

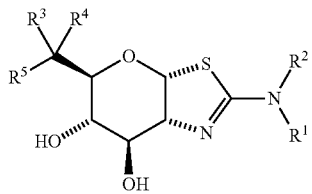

(Ia)

wherein R$^1$ and R$^2$ are independently selected from the group consisting of: H, C$_{1-6}$alkyl, C$_{1-6}$alkoxy, —(CH$_2$)$_n$-cyclopropyl and —(CH$_2$)$_n$-cyclobutyl wherein n is 0, 1, 2, 3 or 4; or R$^1$ and R$^2$ may be joined together with the nitrogen atom to which they are attached to form azetidine, pyrrolidine or piperidine, said C$_{1-6}$alkyl, C$_{1-6}$alkoxy, —(CH$_2$)$_n$-cyclopropyl, —(CH$_2$)$_n$-cyclobutyl, azetidine, pyrrolidine or piperidine optionally substituted from one up to the maximum number of substituents with fluoro or methyl; R$^3$ is selected from the group consisting of: C$_{1-8}$alkyl, C$_{2-8}$alkenyl, C$_{2-8}$alkynyl, C$_{3-6}$cycloalkyl, aryl and heteroaryl, each optionally substituted from one up to the maximum number of substituents with fluoro and OH; R$^4$ is selected from the group consisting of H, F, C$_{1-8}$alkyl, C$_{2-8}$alkenyl and C$_{2-8}$alkynyl, each excluding hydrogen optionally substituted from one up to the maximum number of substituents with fluoro and OH; or R$^3$ and R$^4$ and the carbon atom to which they are attached may join together to form vinyl or a 3 to 7-membered carbocyclic or heterocyclic ring, said 3 to 7-membered carbocy-clic or heterocyclic ring optionally containing a double bond and optionally substituted from one up to the maximum number of substituents with fluoro and OH; and R$^5$ is selected from H, F and OH; with the proviso that when R$^4$ is F then R$^5$ is other than OH.

Within the genus, the invention encompasses a first sub-genus of compounds of Formula (Ia) wherein: R$^1$ and R$^2$ are independently C$_{1-4}$alkyl; R$^3$ is C$_{1-6}$alkyl; R$^4$ is selected from the group consisting of: H and C$_{1-6}$alkyl; and R$^5$ is OH. Within the first sub-genus, the invention further encompasses compounds of Formula (Ia) wherein: R$^1$ and R$^2$ are independently methyl or ethyl; R$^3$ is methyl or ethyl; and R$^4$ is selected from the group consisting of: H, methyl and ethyl.

Also within the genus, the invention encompasses a second sub-genus of compounds of Formula (Ia) wherein: R$^3$ and R$^4$ and the carbon atom to which they are attached may join together to form a 3 to 7-membered carbocyclic or heterocyclic ring, said 3 to 7-membered carbocyclic or heterocyclic ring optionally containing a double bond and optionally substituted from one up to the maximum number of substituents with fluoro and OH.

Also within the genus, the invention encompasses a third sub-genus of compounds of Formula (Ia) wherein: R$^1$ and R$^2$ are independently selected from the group consisting of: H, C$_{1-6}$alkyl and cyclopropylmethyl; or R$^1$ and R$^2$ may be joined together with the nitrogen atom to which they are attached to form azetidine or pyrrolidine, said C$_{1-6}$alkyl, cyclopropylmethyl, azetidine or pyrrolidine optionally substituted with 1 to 3 substituents selected from fluoro and methyl; R$^3$ is selected from the group consisting of: C$_{1-8}$alkyl, C$_{2-8}$alkenyl, C$_{2-8}$alkynyl and C$_{3-6}$cycloalkyl, each optionally substituted with 1 to 3 substituents selected from fluoro and OH; and R$^4$ is selected from the group consisting of: H, F, C$_{1-8}$alkyl, C$_{2-8}$alkenyl and C$_{2-8}$alkynyl, each excluding hydrogen optionally substituted with 1 to 3 substituents selected from fluoro and OH; or R$^3$ and R$^4$ and the carbon atom to which they are attached may join together to form a 3- to 6-membered carbocyclic ring optionally containing a double bond and optionally substituted with 1 to 3 substituents selected from fluoro and OH.

Also within the genus, the invention encompasses a fourth sub-genus of compounds of Formula (Ia) wherein R$^3$ is CF$_3$ and R$^5$ is OH.

The invention also encompasses the compounds that follow or pharmaceutically acceptable salts thereof.

An embodiment of the invention encompasses compounds of Formula (I) wherein: each R is H, R$^5$ is OH, R$^3$ is C$_{1-6}$alkyl, optionally substituted from one up to the maximum number of substituents with fluoro and hydroxy, and R$^4$ is H.

An embodiment of the invention encompasses compounds of Formula (I) wherein: each R is H, R$^5$ is H, R$^3$ is C$_{1-6}$alkyl, optionally substituted from one up to the maximum number of substituents with fluoro and hydroxy, and R$^4$ is H or C$_{1-6}$alkyl.

An embodiment of the invention encompasses compounds of Formula (I) wherein R$^1$ is C$_{1-6}$alkyl, optionally substituted from one up to the maximum number of substituents with hydroxy, and R$^2$ is H.

An embodiment of the invention encompasses compounds of Formula (I) wherein R$^1$ is C$_{2-6}$alkenyl and R$^2$ is H.

An embodiment of the invention encompasses compounds of Formula (I) wherein each R is H and R$^5$ is F.

The invention also encompasses a pharmaceutical composition comprising the compound of Formula (I) or (Ia) in combination with a pharmaceutically acceptable carrier.

The invention also encompasses a method of selectively inhibiting O-GlcNAcase in a subject in need thereof, the method comprising administering to the subject an effective amount of a compound of Formula (I) or (Ia), or a pharmaceutically acceptable salt thereof.

The invention also encompasses a method of elevating the level of O-GlcNAc in a subject in need thereof, the method comprising administering to the subject an effective amount of a compound of Formula (I) or (Ia), or a pharmaceutically acceptable salt thereof.

The invention also encompasses a method of treating a condition that is modulated by O-GlcNAcase, in a subject in need thereof, the method comprising administering to the subject an effective amount of a compound of Formula (I) or (Ia), or a pharmaceutically acceptable salt thereof. An aspect of the invention encompasses this method wherein the condition is selected from one or more of the group consisting of an inflammatory disease, an allergy, asthma, allergic rhinitis, hypersensitivity lung diseases, hypersensitivity pneumonitis, eosinophilic pneumonias, delayed-type hypersensitivity, atherosclerosis, interstitial lung disease (ILD), idiopathic pulmonary fibrosis, ILD associated with rheumatoid arthritis, systemic lupus erythematosus, ankylosing spondylitis, systemic sclerosis, Sjogren's syndrome, polymyositis or dermatomyositis, systemic anaphylaxis or hypersensitivity response, drug allergy, insect sting allergy, autoimmune disease, rheumatoid arthritis, psoriatic arthritis, multiple sclerosis, Guillain-Barré syndrome, systemic lupus erythematosus, myastenia gravis, glomerulonephritis, autoimmune thyroiditis, graft rejection, allograft rejection, graft-versus-host disease, inflammatory bowel disease, Crohn's disease, ulcerative colitis, spondyloarthropathy, scleroderma, psoriasis, T-cell mediated psoriasis, inflammatory dermatosis, dermatitis, eczema, atopic dermatitis, allergic contact dermatitis, urticaria, vasculitis, necrotizing, cutaneous, and hypersensitivity vasculitis, eosinphilic myotis, eosiniphilic fasciitis, solid organ transplant rejection, heart transplant rejection, lung transplant rejection, liver transplant rejection, kidney transplant rejection, pancreas transplant rejection, kidney allograft, lung allograft, epilepsy, pain, fibromyalgia, stroke, neuroprotection.

The invention also encompasses a method of treating a condition selected from the group consisting of a neurodegenerative disease, a tauopathy, cancer and stress, in a subject in need thereof, the method comprising administering to the subject an effective amount of a compound of Formula (I) or (Ia), or a pharmaceutically acceptable salt thereof. An aspect of the invention encompasses this method wherein the condition is selected from one or more of the group consisting of Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (ND), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, Huntington's disease, Parkinson's disease, Schizophrenia, Mild Cognitive Impairment (MCI), Neuropathy (including peripheral neuropathy, autonomic neuropathy, neuritis, and diabetic neuropathy), or Glaucoma. Another aspect of the invention encompasses this method wherein the stress is a cardiac disorder. In another aspect, the cardiac disorder is selected from one or more of the group consisting of ischemia; hemorrhage; hypovolemic shock; myocardial infarction; an interventional cardiology procedure; cardiac bypass surgery; fibrinolytic therapy; angioplasty; and stent placement.

The compounds of the invention are capable of inhibiting an O-glycoprotein 2-acetamido-2-deoxy-β-D-glucopyranosidase (O-GlcNAcase). In some embodiments, the O-GlcNAcase is a mammalian O-GlcNAcase, such as a rat, mouse or human O-GlcNAcase. In some embodiments, the β-hexosaminidase is a mammalian β-hexosaminidase, such as a rat, mouse or human β-hexosaminidase.

Compounds of the invention selectively inhibit the activity of a mammalian O-GlcNAcase over a mammalian β-hexosaminidase. A compound that "selectively" inhibits an O-GlcNAcase is a compound that inhibits the activity or biological function of an O-GlcNAcase, but does not substantially inhibit the activity or biological function of a β-hexosaminidase. For example, in some embodiments, a selective inhibitor of an O-GlcNAcase selectively inhibits the cleavage of 2-acetamido-2-deoxy-β-D-glucopyranoside (O-GlcNAc) from polypeptides. In some embodiments, a selective inhibitor of an O-GlcNAcase selectively binds to an O-GlcNAcase. In some embodiments, a selective inhibitor of an O-GlcNAcase inhibits hyperphosphorylation of a tau protein and/or inhibits formations of NFTs. By "inhibits," "inhibition" or "inhibiting" means a decrease by any value between 10% and 90%, or of any integer value between 30% and 60%, or over 100%, or a decrease by 1-fold, 2-fold, 5-fold, 10-fold or more. It is to be understood that the inhibiting does not require full inhibition. In some embodiments, a selective inhibitor of an O-GlcNAcase elevates or enhances O-GlcNAc levels e.g., O-GlcNAc-modified polypeptide or protein levels, in cells, tissues, or organs (e.g., in brain, muscle, or heart (cardiac) tissue) and in animals. By "elevating" or "enhancing" is meant an increase by any value between 10% and 90%, or of any integer value between 30% and 60%, or over 100%, or an increase by 1-fold, 2-fold, 5-fold, 10-fold, 15-fold, 25-fold, 50-fold, 100-fold or more. In some embodiments, a selective inhibitor of an O-GlcNAcase exhibits a selectivity ratio, as described herein, in the range 10 to 100000, or in the range 100 to 100000, or in the range 1000 to 100000, or at least 10, 20, 50, 100, 200, 500, 1000, 1500, 2000, 2500, 3000, 3500, 4000, 4500, 5000, 6000, 7000, 10,000, 25,000, 50,000, 75,000, or any value within or about the described range.

The compounds of the present invention elevate O-GlcNAc levels on O-GlcNAc-modified polypeptides or proteins in vivo specifically via interaction with an O-GlcNAcase enzyme, and are effective in treating conditions which require or respond to inhibition of O-GlcNAcase activity.

In some embodiments, the compounds of the present invention are useful as agents that produce a decrease in tau phosphorylation and NFT formation. In some embodiments, the compounds are therefore useful to treat Alzheimer's disease and related tauopathies. In some embodiments, the compounds are thus capable of treating Alzheimer's disease and related tauopathies by lowering tau phosphorylation and reducing NFT formation as a result of increasing tau O-GlcNAc levels. In some embodiments, the compounds produce an increase in levels of O-GlcNAc modification on O-GlcNAc-modified polypeptides or proteins, and are therefore useful for treatment of disorders responsive to such increases in O-GlcNAc modification; these disorders include without limitation neurodegenerative, inflammatory, cardiovascular, and immunoregulatory diseases. In some embodiments, the compounds are also useful as a result of other biological activities related to their ability to inhibit the activity of glycosidase enzymes. In alternative embodiments, the compounds of the invention are valuable tools in studying the physiological role of O-GlcNAc at the cellular and organismal level.

In alternative embodiments, the invention provides methods of enhancing or elevating levels of protein O-GlcNAc modification in animal subjects, such as, veterinary and human subjects. In alternative embodiments, the invention provides methods of selectively inhibiting an O-GlcNAcase enzyme in animal subjects, such as, veterinary and human subjects. In alternative embodiments, the invention provides methods of inhibiting phosphorylation of tau polypeptides, or inhibiting formation of NFTs, in animal subjects, such as, veterinary and human subjects.

The invention also encompasses the use of the compounds of the invention for treating one or more of the diseases or conditions described herein. The invention also encompasses the use of the compounds of the invention for the manufacture of a medicament for treating one or more diseases or conditions described herein.

As will be appreciated by a person skilled in the art, Formula (I) above may also be represented alternatively as follows:

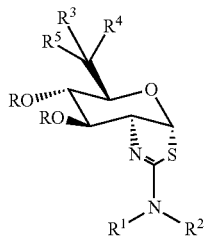

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Throughout this application, it is contemplated that the term "compound" or "compounds" refers to the compounds discussed herein and includes precursors and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

In some embodiments, all of the compounds of the invention contain at least one chiral center. In some embodiments, the formulations, preparation, and compositions including compounds according to the invention include mixtures of stereoisomers, individual stereoisomers, and enantiomeric mixtures, and mixtures of multiple stereoisomers. In general, the compound may be supplied in any desired degree of chiral purity.

"Alkyl" refers to a straight or branched hydrocarbon chain group consisting solely of carbon and hydrogen atoms, containing no unsaturation and including, for example, from one to ten carbon atoms, such as 1, 2, 3, 4, 5, 6, 7, 8, 9, or 10 carbon atoms, and which is attached to the rest of the molecule by a single bond. Unless stated otherwise specifically in the specification, the alkyl group may be optionally substituted by one or more substituents as described herein. Unless stated otherwise specifically herein, it is understood that the substitution can occur on any carbon of the alkyl group.

"Alkenyl" refers to a straight or branched hydrocarbon chain group consisting solely of carbon and hydrogen atoms, containing at least one double bond and including, for example, from two to ten carbon atoms, such as 2, 3, 4, 5, 6, 7, 8, 9, or 10 carbon atoms, and which is attached to the rest of the molecule by a single bond or a double bond. Unless stated otherwise specifically in the specification, the alkenyl group may be optionally substituted by one or more substituents as described herein. Unless stated otherwise specifically herein, it is understood that the substitution can occur on any carbon of the alkenyl group.

"Alkynyl" refers to a straight or branched hydrocarbon chain group consisting solely of carbon and hydrogen atoms, containing at least one triple bond and including, for example, from two to ten carbon atoms. Unless stated otherwise specifically in the specification, the alkenyl group may be optionally substituted by one or more substituents as described herein.

"Aryl" means mono- or bicyclic aromatic rings containing only carbon atoms, including for example, 6-14 members. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like. Unless stated otherwise specifically herein, the term "aryl" is meant to include aryl groups optionally substituted by one or more substituents as described herein.

"Heteroaryl" refers to a single or fused aromatic ring group containing one or more heteroatoms in the ring, for example N, O, S, including for example, 5-14 members, such as 5; 6, 7, 8, 9, 10, 11, 12, 13 or 14 members. Examples of heteroaryl groups include furan, thiophene, pyrrole, oxazole, thiazole, imidazole, pyrazole, isoxazole, isothiazole, 1,2,3-oxadiazole, 1,2,3-triazole, 1,2,4-triazole, 1,3,4-thiadiazole, tetrazole, pyridine, pyridazine, pyrimidine, pyrazine, 1,3,5-triazine, imidazole, benzimidazole, benzoxazole, benzothiazole, indolizine, indole, isoindole, benzofuran, benzothiophene, 1H-indazole, purine, 4H-quinolizine, quinoline, isoquinoline, cinnoline, phthalazine, quinazoline, quinoxaline, 1,8-naphthyridine, pteridine. Unless stated otherwise specifically herein, the term "heteroaryl" is meant to include heteroaryl groups optionally substituted by one or more substituents as described herein.

"Cycloalkyl" refers to a stable monovalent monocyclic, bicyclic or tricyclic hydrocarbon group consisting solely of carbon and hydrogen atoms, having for example from 3 to 15 carbon atoms, and which is saturated and attached to the rest of the molecule by a single bond. Unless otherwise stated specifically herein, the term "cycloalkyl" is meant to include cycloalkyl groups which are optionally substituted as described herein.

The term "3 to 7-membered carbocyclic or heterocyclic ring" means a monocylic carbon ring of 3 to 7 atoms or a monocyclic ring of 3 to 7 atoms containing one or more heterotaoms selected from O, N and S.

"Optional" or "optionally" means that the subsequently described event of circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution. Examples of optionally substituted alkyl groups include, without limitation, methyl, ethyl, propyl, etc. and including cycloalkyls such as cyclopropyl, cyclobutyl, cyclopentyl, cyclohexyl, cycloheptyl, etc.; examples of optionally substituted alkenyl groups include allyl, crotyl, 2-pentenyl, 3-hexenyl, 2-cyclopentenyl, 2-cyclohexenyl, 2-cyclopentenylmethyl, 2-cyclohexenylmethyl, etc. In some embodiments, optionally substituted alkyl and alkenyl groups include $C_{1-6}$ alkyls or alkenyls.

"Halo" refers to bromo, chloro, fluoro, iodo, etc. In some embodiments, suitable halogens include fluorine or chlorine.

Examples of optionally substituted carbonyl groups, or sulfonyl groups include optionally substituted forms of such groups formed from various hydrocarbyls such as alkyl, alkenyl and 5- to 6-membered monocyclic aromatic group (e.g., phenyl, pyridyl, etc.), as described herein.

Therapeutic Indications

The invention provides methods of treating conditions that are modulated, directly or indirectly, by an O-GlcNAcase enzyme or by O-GlcNAc-modified protein levels, for example, a condition that is benefited by inhibition of an O-GlcNAcase enzyme or by an elevation of O-GlcNAc-modified protein levels. Such conditions include, without limitation, glaucoma, schizophrenia, tauopathies, such as Alzheimer's disease, neurodegenerative diseases, cardiovascular diseases, diseases associated with inflammation, diseases associated with immunosuppression and cancers. The compounds of the invention are also useful in the treatment of diseases or disorders related to deficiency or over-expression of O-GlcNAcase or accumulation or depletion of O-GlcNAc, or any disease or disorder responsive to glycosidase inhibition therapy. Such diseases and disorders include, but are not limited to, glaucoma, schizophrenia, neurodegenerative disorders, such as Alzheimer's disease (AD), or cancer. Such diseases and disorders may also include diseases or disorders related to the accumulation or deficiency in the enzyme OGT. Also included is a method of protecting or treating target cells expressing proteins that are modified by O-GlcNAc residues, the dysregulation of which modification results in disease or pathology. The term "treating" as used herein includes treatment, prevention, and amelioration.

In alternative embodiments, the invention provides methods of enhancing or elevating levels of protein O-GlcNAc modification in animal subjects, such as, veterinary and human subjects. This elevation of O-GlcNAc levels can be useful for the prevention or treatment of Alzheimer's disease; prevention or treatment of other neurodegenerative diseases (e.g. Parkinson's disease, Huntington's disease); providing neuroprotective effects; preventing damage to cardiac tissue; and treating diseases associated with inflammation or immunosuppression.

In alternative embodiments, the invention provides methods of selectively inhibiting an O-GlcNAcase enzyme in animal subjects, such as veterinary and human subjects.

In alternative embodiments, the invention provides methods of inhibiting phosphorylation of tau polypeptides, or inhibiting formation of NFTs, in animal subjects, such as, veterinary and human subjects. Accordingly, the compounds of the invention may be used to study and treat AD and other tauopathies.

In general, the methods of the invention are effected by administering a compound according to the invention to a subject in need thereof, or by contacting a cell or a sample with a compound according to the invention, for example, a pharmaceutical composition comprising a therapeutically effective amount of the compound according to Formula (I) or (Ia). More particularly, they are useful in the treatment of a disorder in which the regulation of O-GlcNAc protein modification is implicated, or any condition as described herein. Disease states of interest include Alzheimer's disease (AD) and related neurodegenerative tauopathies, in which abnormal hyperphosphorylation of the microtubule-associated protein tau is involved in disease pathogenesis. In some embodiments, the compounds may be used to block hyperphosphorylation of tau by maintaining elevated levels of O-GlcNAc on tau, thereby providing therapeutic benefit.

The effectiveness of the compounds in treating pathology associated with the accumulation of toxic tau species (for example, Alzheimer's disease and other tauopathies) may be confirmed by testing the ability of the compounds to block the formation of toxic tau species in established cellular[118-120] and/or transgenic animal models of disease.[32,33] Tauopathies that may be treated with the compounds of the invention include: Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, and Glaucoma.

The compounds of this invention are also useful in the treatment of conditions associate with tissue damage or stress, stimulating cells, or promoting differentiation of cells. Accordingly, in some embodiments, the compounds of this invention may be used to provide therapeutic benefit in a variety of conditions or medical procedures involving stress in cardiac tissue, including but not limited to: ischemia; hemorrhage; hypovolemic shock; myocardial infarction; an interventional cardiology procedure; cardiac bypass surgery; fibrinolytic therapy; angioplasty; and stent placement. The effectiveness of the compounds in treating pathology associated with cellular stress (including ischemia, hemorrhage, hypovolemic shock, myocardial infarction, and other cardiovascular disorders) may be confirmed by testing the ability of the compounds to prevent cellular damage in established cellular stress assays,[105,116,117] and to prevent tissue damage and promote functional recovery in animal models of ischemia-reperfusion,[70,114] and trauma-hemorrhage.[72,112,115]

Compounds that selectively inhibit O-GlcNAcase activity may be used for the treatment of diseases that are associated with inflammation, including but not limited to, inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, Guillain-Barré syndrome, systemic lupus erythematosus, myastenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition, compounds that affects levels of protein O-GlcNAc modification may be used for the treatment of diseases associated with immunosuppression, such as in individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; or immunosuppression due to congenital deficiency in receptor function or other causes.

The compounds of the invention may be useful for treatment of neurodegenerative diseases, including Parkinson's disease and Huntington's disease. Other conditions that may be treated are those triggered, affected, or in any other way correlated with levels of O-GlcNAc post-translational protein modification. It is expected that the compounds of this invention may be useful for the treatment of such conditions and in particular, but not limited to, the following for which a association with O-GlcNAc levels on proteins has been established: graft rejection, in particular but not limited to solid organ transplants, such as heart, lung, liver, kidney, and pancreas transplants (e.g. kidney and lung allografts); cancer, in particular but not limited to cancer of the breast, lung, prostate, pancreas, colon, rectum, bladder, kidney, ovary; as well as non-Hodgkin's lymphoma and melanoma; epilepsy, pain, fibromyalgia, or stroke, e.g., for neuroprotection following a stroke.

Pharmaceutical & Veterinary Compositions, Dosages, and Administration

Pharmaceutical compositions including compounds according to the invention, or for use according to the invention, are contemplated as being within the scope of the invention. In some embodiments, pharmaceutical compositions including an effective amount of a compound of Formula (I) or (Ia) are provided.

The compounds of Formula (I) or (Ia) and their pharmaceutically acceptable salts, stereoisomers, solvates, and derivatives are useful because they have pharmacological activity in animals, including humans. In some embodiments, the compounds according to the invention are stable in plasma, when administered to a subject.

In some embodiments, compounds according to the invention, or for use according to the invention, may be provided in combination with any other active agents or pharmaceutical compositions where such combined therapy is useful to modulate O-GlcNAcase activity, for example, to treat neurodegenerative, inflammatory, cardiovascular, or immunoregulatory diseases, or any condition described herein. In some embodiments, compounds according to the invention, or for use according to the invention, may be provided in combination with one or more agents useful in the prevention or treatment of Alzheimer's disease. Examples of such agents include, without limitation, acetylcholine esterase inhibitors (AChEIs) such as Aricept® (Donepezil), Exelon® (Rivastigmine), Razadyne® (Razadyne ER®, Reminyl®, Nivalin®, Galantamine), Cognex® (Tacrine), Dimebon, Huperzine A, Phenserine, Debio-9902 SR (ZT-1 SR), Zanapezil (TAK0147), ganstigmine, NP7557, etc.;

NMDA receptor antagonists such as Namenda® (Axura®, Akatinol®, Ebixa®, Memantine), Dimebon, SGS-742, Neramexane, Debio-9902 SR (ZT-1 SR), etc.; gamma-secretase inhibitors and/or modulators such as Flurizan™ (Tarenflurbil, MPC-7869, R-flurbiprofen), LY450139, MK 0752, E2101, BMS-289948, BMS-299897, BMS-433796, LY-411575, GSI-136, etc.;

beta-secretase inhibitors such as ATG-Z1, CTS-21166, etc.;

alpha-secretase activators, such as NGX267, etc;

amyloid-β aggregation and/or fibrillization inhibitors such as Alzhemed™ (3APS, Tramiprosate, 3-amino-1-propanesulfonic acid), AL-108, AL-208, AZD-103, PBT2, Cereact, ONO-2506PO, PPI-558, etc.;

tau aggregation inhibitors such as methylene blue, etc.;

microtubule stabilizers such as AL-108, AL-208, paclitaxel, etc.;

RAGE inhibitors, such as TTP488, etc.;

5-HT1a receptor antagonists, such as Xaliproden, Lecozotan, etc.;

5-HT4 receptor antagonists, such as PRX-03410, etc.;

kinase inhibitors such as SRN-003-556, amfitrindamide, LiCl, AZD1080, NP031112, SAR-502250, etc.

humanized monoclonal anti-Aβ antibodies such as Bapineuzumab (AAB-001), LY2062430, RN1219, ACU-5A5, etc.;

amyloid vaccines such as AN-1792, ACC-001 neuroprotective agents such as Cerebrolysin, AL-108, AL-208, Huperzine A, etc.;

L-type calcium channel antagonists such as MEM-1003, etc.;

nicotinic receptor antagonists, such as AZD3480, GTS-21, etc.;

nicotinic receptor agonists, such as MEM 3454, Nefiracetam, etc.;

peroxisome proliferator-activated receptor (PPAR) gamma agonists such as Avandia® (Rosglitazone), etc.;

phosphodiesterase IV (PDE4) inhibitors, such as MK-0952, etc.;

hormone replacement therapy such as estrogen (Premarin), etc.;

monoamine oxidase (MAO) inhibitors such as NS2330, Rasagiline (Azilect®), TVP-1012, etc.;

AMPA receptor modulators such as Ampalex (CX 516), etc.; nerve growth factors or NGF potentiators, such as CERE-110 (AAV-NGF), T-588, T-817MA, etc.;

agents that prevent the release of luteinizing hormone (LH) by the pituitary gland, such as leuoprolide (VP-4896), etc.;

GABA receptor modulators such as AC-3933, NGD 97-1, CP-457920, etc.; benzodiazepine receptor inverse agonists such as SB-737552 (S-8510), AC-3933, etc.;

noradrenaline-releasing agents such as T-588, T-817MA, etc.

It is to be understood that combination of compounds according to the invention, or for use according to the invention, with Alzheimer's agents is not limited to the examples described herein, but includes combination with any agent useful for the treatment of Alzheimer's disease. Combination of compounds according to the invention, or for use according to the invention, and other Alzheimer's agents may be administered separately or in conjunction. The administration of one agent may be prior to, concurrent to, or subsequent to the administration of other agent(s).

In alternative embodiments, the compounds may be supplied as "prodrugs" or protected forms, which release the compound after administration to a subject. For example, the compound may carry a protective group which is split off by hydrolysis in body fluids, e.g., in the bloodstream, thus releasing the active compound or is oxidized or reduced in body fluids to release the compound. Accordingly, a "prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood.

The prodrug compound often offers advantages of solubility, tissue compatibility or delayed release in a subject.

The term "prodrug" is also meant to include any covalently bonded carriers which release the active compound of the invention in vivo when such prodrug is administered to a subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and acetamide, formamide, and benzamide derivatives of amine functional groups in the compounds of the invention and the like.

A discussion of prodrugs may be found in "Smith and Williams' Introduction to the Principles of Drug Design," H. J. Smith, Wright, Second Edition, London (1988); Bundgard, H., *Design of Prodrugs* (1985), pp. 7-9, 21-24 (Elsevier, Amsterdam); The Practice of Medicinal Chemistry, Camille G. Wermuth et al., Ch 31, (Academic Press, 1996); A Textbook of Drug Design and Development, P. Krogsgaard-Larson and H. Bundgaard, eds. Ch 5, pgs 113 191 (Harwood Academic Publishers, 1991); Higuchi, T., et al., "Pro-drugs as Novel Delivery Systems," A.C.S. Symposium Series, Vol. 14; or in Bioreversible Carriers in Drug Design, ed. Edward B. Roche, American Pharmaceutical Association and Pergamon Press, 1987, all of which are incorporated in full by reference herein.

Compounds according to the invention, or for use according to the invention, can be provided alone or in combination with other compounds in the presence of a liposome, an adjuvant, or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. Compounds according to the invention may be provided chronically or intermittently. "Chronic" administration refers to administration of the compound(s) in a continuous mode as opposed to an acute mode, so as to maintain the initial therapeutic effect (activity) for an extended period of time. "Intermittent" administration is treatment that is not consecutively done without interruption, but rather is cyclic in nature. The terms "administration," "administrable," or "administering" as used herein should be understood to mean providing a compound of the invention to the subject in need of treatment.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved, for example, by the United States Food and Drug Administration or other governmental agency as being acceptable for use in humans or domestic animals.

The compounds of the present invention may be administered in the form of pharmaceutically acceptable salts. In such cases, pharmaceutical compositions in accordance with this invention may comprise a salt of such a compound, preferably a physiologically acceptable salt, which are known in the art. In some embodiments, the term "pharmaceutically acceptable salt" as used herein means an active ingredient comprising compounds of Formula (I) or (Ia) used in the form of a salt thereof, particularly where the salt form confers on the active ingredient improved pharmacokinetic properties as compared to the free form of the active ingredient or other previously disclosed salt form.

A "pharmaceutically acceptable salt" includes both acid and base addition salts. A "pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

A "pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

Thus, the term "pharmaceutically acceptable salt" encompasses all acceptable salts including but not limited to acetate, lactobionate, benzenesulfonate, laurate, benzoate, malate, bicarbonate, maleate, bisulfate, mandelate, bitartarate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of the compounds of the present invention can be used as a dosage for modifying solubility or hydrolysis characteristics, or can be used in sustained release or prodrug formulations. Also, pharmaceutically acceptable salts of the compounds of this invention may include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

Pharmaceutical formulations will typically include one or more carriers acceptable for the mode of administration of the preparation, be it by injection, inhalation, topical administration, lavage, or other modes suitable for the selected treatment. Suitable carriers are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in *Remington: the Science & Practice of Pharmacy* by Alfonso German), 20$^{th}$ ed., Williams & Wilkins, (2000). Formulations for parenteral administration may, for example, contain excipients, polyalkylene glycols such as polyethylene glycol, oils of vegetable origin, or hydrogenated naphthalenes, Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The compounds or pharmaceutical compositions according to the present invention may be administered by oral or non-oral, e.g., intramuscular, intraperitoneal, intravenous, intracisternal injection or infusion, subcutaneous injection, transdermal or transmucosal routes. In some embodiments, compounds or pharmaceutical compositions in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the compound over a period of time. The compounds may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaryies. In some embodiments, compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The compounds of the invention may be used to treat animals, including mice, rats, horses, cattle, sheep, dogs, cats, and monkeys. However, compounds of the invention can also be used in other organisms, such as avian species (e.g., chickens). The compounds of the invention may also be effective for use in humans. The term "subject" or alternatively referred to herein as "patient" is intended to be referred to an animal, preferably a mammal, most preferably a human, who has been the object of treatment, observation or experiment. However, the compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition requiring modulation of O-GlcNAcase activity.

An "effective amount" of a compound according to the invention includes a therapeutically effective amount or a prophylactically effective amount. A "therapeutically effective amount" refers to an amount effective, at dosages and for periods of time necessary, to achieve the desired therapeutic result, such as inhibition of an O-GlcNAcase, elevation of O-GlcNAc levels, inhibition of tau phosphorylation, or any condition described herein. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as inhibition of an O-GlcNAcase, elevation of O-GlcNAc levels, inhibition of tau phosphorylation, or any condition described herein. Typically, a prophylactic dose is used in subjects prior to or at an earlier stage of disease, so that a prophylactically effective amount may be less than a therapeutically effective amount. A suitable range for therapeutically or prophylactically effective amounts of a compound may be any integer from 0.1 nM-0.1M, 0.1 nM-0.05M, 0.05 nM-15 µM or 0.01 nM-10 µM.

In alternative embodiments, in the treatment or prevention of conditions which require modulation of O-GlcNAcase activity, an appropriate dosage level will generally be about 0.01 to 500 mg per kg subject body weight per day, and can be administered in singe or multiple doses. In some embodiments, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. In general, compounds of the invention should be used without causing substantial toxicity, and as described herein, the compounds exhibit a suitable safety profile for therapeutic use. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions In the compounds of generic Formula (I) or (Ia), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I) or (Ia). For example, different isotopic forms of hydrogen (H) include protium ($^1H$), deuterium ($^2H$) and tritium ($^3H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) or (Ia) can be prepared without undue experimentation by conventional techniques well known to those skilled in the art or by processes analogous to those described in the Schemes and Examples herein using appropriate isotopically-enriched reagents and/or intermediates.

Other Uses and Assays

A compound of Formula (I) or (Ia) may be used in screening assays for compounds which modulate the activity of glycosidase enzymes, preferably the O-GlcNAcase enzyme. The ability of a test compound to inhibit O-GlcNAcase-dependent cleavage of O-GlcNAc from a model substrate may be measured using any assays, as described herein or known to one of ordinary skill in the art. For example, a fluorescence or UV-based assay known in the art may be used. A "test compound" is any naturally-occurring or artificially-derived chemical compound. Test compounds may include, without limitation, peptides, polypeptides, synthesised organic molecules, naturally occurring organic molecules, and nucleic acid molecules. A test compound can "compete" with a known compound such as a compound of Formula (I) or (Ia) by, for example, interfering with inhibition of O-GlcNAcase-dependent cleavage of O-GlcNAc or by interfering with any biological response induced by a compound of Formula (I) or (Ia).

Generally, a test compound can exhibit any value between 10% and 200%, or over 500%, modulation when compared to a compound of Formula (I) or (Ia) or other reference compound. For example, a test compound may exhibit at least any positive or negative integer from 10% to 200% modulation, or at least any positive or negative integer from 30% to 150% modulation, or at least any positive or negative integer from 60% to 100% modulation, or any positive or negative integer over 100% modulation. A compound that is a negative modulator will in general decrease modulation relative to a known compound, while a compound that is a positive modulator will in general increase modulation relative to a known compound.

In general, test compounds are identified from large libraries of both natural products or synthetic (or semi-synthetic) extracts or chemical libraries according to methods known in the art. Those skilled in the field of drug discovery and development will understand that the precise source of test extracts or compounds is not critical to the method(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available. Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla., USA), and PharmaMar, MA, USA. In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

When a crude extract is found to modulate inhibition of O-GlcNAcase-dependent cleavage of O-GlcNAc, or any biological response induced by a compound of Formula (I) or (Ia), further fractionation of the positive lead extract is necessary to isolate chemical constituents responsible for the observed effect. Thus, the goal of the extraction, fractionation, and purification process is the careful characterization and identification of a chemical entity within the crude extract having O-GlcNAcase-inhibitory activities. The same assays described herein for the detection of activities in mixtures of compounds can be used to purify the active component and to test derivatives thereof. Methods of fractionation and purification of such heterogeneous extracts are known in the art. If desired, compounds shown to be useful agents for treatment are chemically modified according to methods known in the art. Compounds identified as being of therapeutic, prophylactic, diagnostic, or other value may be subsequently analyzed using a suitable animal model, as described herein on known in the art.

In some embodiments, the compounds are useful in the development of animal models for studying diseases or disorders related to deficiencies in O-GlcNAcase, over-expression of O-GlcNAcase, accumulation of O-GlcNAc, depletion of O-GlcNAc, and for studying treatment of diseases and disorders related to deficiency or over-expression of O-GlcNAcase, or accumulation or depletion of O-GlcNAc. Such diseases and disorders include neurodegenerative diseases, including Alzheimer's disease, and cancer.

Various alternative embodiments and examples of the invention are described herein. These embodiments and examples are illustrative and should not be construed as limiting the scope of the invention.

EXAMPLES

The following examples are intended to illustrate embodiments of the invention and are not intended to be construed in a limiting manner.

Abbreviations

AIBN=2,2'-Azobisisobutyronitrile
RAST=(Diethylamino)sulfur trifluoride
DCM=dichloromethane
DIBAL-H=Diisobutylaluminum hydride
DMAP=4-dimethylaminopyridine
DMF=N,N-dimethylformamide
DMP=Dess-Martin periodinane
DMSO=dimethyl sulfoxide
EDC=1-(3-Dimethylaminopropyl)-3-ethylcarbodiimide hydrochloride
NBS=N-bromosuccinimide
PMBBr=para-methoxy benzyl bromide
TBAB=tetra-n-butylammonium bromide
TBAF=tetra-n-butylammonium fluoride
TEA=triethylamine
TEAF=tetraethylammonium fluoride
TEMPO=2,2,6,6-tetramethyl-piperidin-1-oxy free radical
TFA=2,2,2-trifluoroacetic acid
THF=tetrahydrofuran Synthesis of Intermediate (5)

1,3,4,6-tetra-O-acetyl-2-deoxy-2-isothiocyanate-β-D-glucopyranose (5)

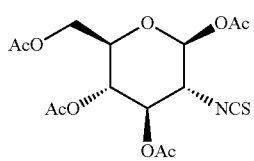

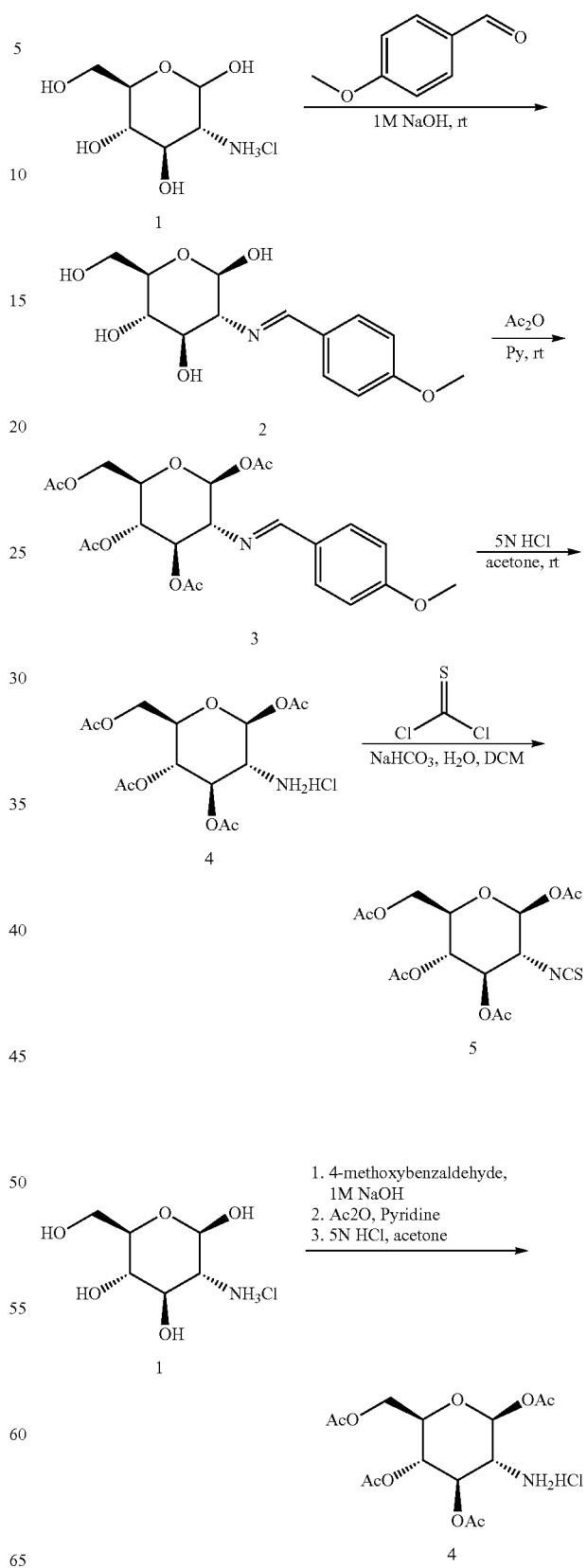

25

(2S,3R,4R,5S,6R)-6-(acetoxymethyl)-3-amino-tetrahydro-2,1-pyran-2,4,5-triyl triacetate hydrochloride (4)

was prepared from compound 1 according to publication: D. J. Silva etc. *J. Org. Chem.*, 1999, 64(16), 5926-5929.

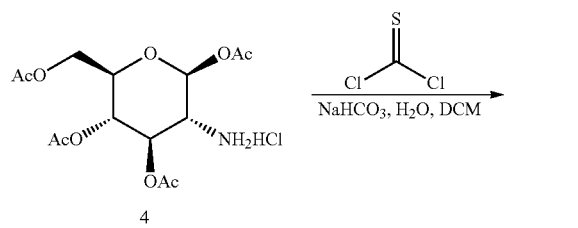

(2S,3R,4R,5S,6R)-6-(acetoxymethyl)-3-isothiocyanato-tetrahydro-2H-pyran-2,4,5-triyl triacetate (5)

was prepared from compound 4 according to publication: M. V. Gonzalez etc. *Carbohydrate Research*, 1986, 154, 49-62.

Example 1

(3aR,5R,6S,7R,7aR)-2-(Dimethylamino)-5-((S)-1-hydroxyethyl)-5,6,7,7a-tetrahydro-3aH-pyrano[3,2-d]thiazole-6,7-diol

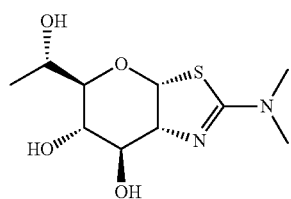 [SMILES: C[C@H](O)[C@H]1O[C@@H]2SC(N(C)C)=N[C@@H]2[C@@H](O)[C@@H]1O]

Scheme II

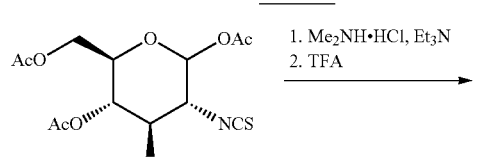

26

-continued

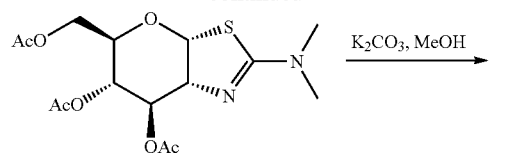

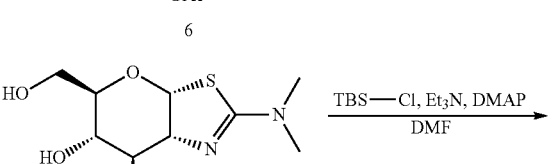

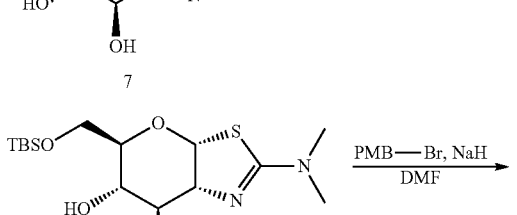

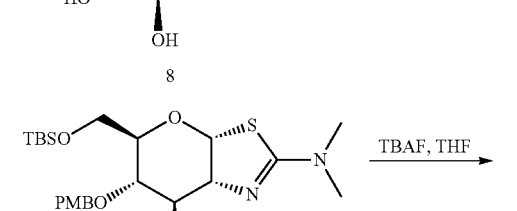

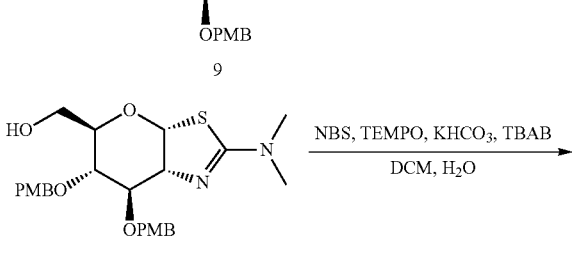

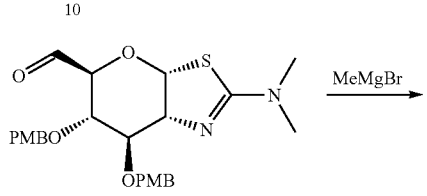

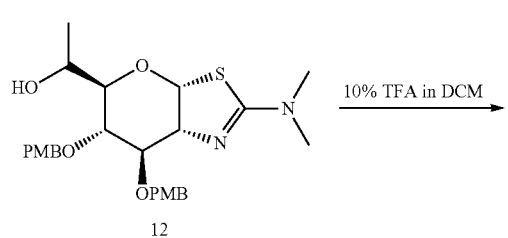

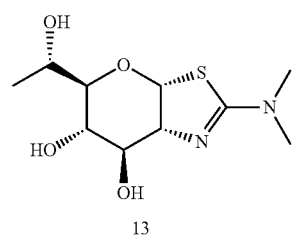

Step 1

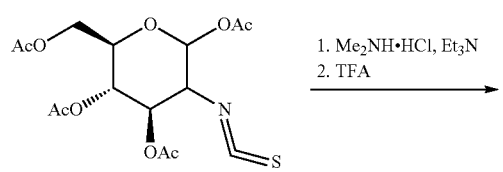

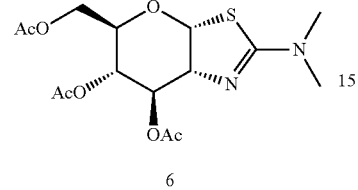

(3aR,5R,6S,7R,7aR)-5-(Acetoxymethyl)-2-(dimethylamino)-5,6,7,7a-tetrahydro-3aH-pyrano[3,2-d]thiazole-6,7-diyl diacetate (6)

To a solution of (3R,4R,5S,6R)-6-(acetoxymethyl)-3-isothiocyanato-tetrahydro-2H-pyran-2,4,5-triyltriacetate (2 g, 5.14 mmol) in dichloromethane (20 mL) was added dimethylamine hydrochloride (460 mg, 5.64 mmol) and triethylamine (675 mg, 6.68 mmol) at 5-10° C. After stirred for 3 h, the reaction mixture was treated with TFA (1.6 g, 14 mmol) overnight at room temperature. The reaction mixture was washed with saturated sodium bicarbonate (50 mL), dried over anhydrous magnesium sulfate, and concentrated under vacuum to provide a residue, which was purified by silica gel column, eluted with 1% MeOH in dichloromethane to give compound 6 as yellow oil (1.65 g, 85%). (ES, m/z): [M+H]$^+$ 374.9; $^1$H NMR (300 MHz, CDCl$_3$) δ 6.24-6.26 (d, J=6.6 Hz, 1H), 5.31-5.43 (m, 1H), 4.94-4.99 (m, 1H), 4.34-4.38 (t, J=10.8 Hz, 1H), 4.16-4.22 (m, 2H), 4.38-4.39 (m, 1H), 3.02 (s, 6H), 2.06-2.12 (m, 9H).

Step 2

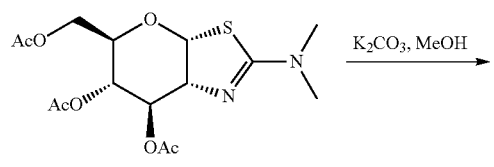

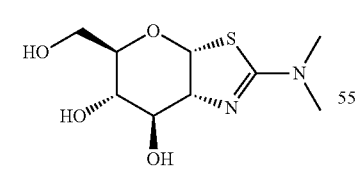

(3aR,5R,6S,7R,7aR)-2-(Dimethylamino)-5-(hydroxymethyl)-5,6,7,7a-tetrahydro-3aH-pyrano[3,2-d]thiazole-6,7-diol (7)

To a solution of (3aR,5R,6S,7R,7aR)-5-(acetoxymethyl)-2-(dimethylamino)-5,6,7,7a-tetrahydro-3aH-pyrano[3,2-d]thiazole-6,7-diyl diacetate (1.65 g, 4.41 mmol) in methanol (20 mL) was added potassium carbonate (25 mg, 0.18 mmol). The resulting mixture was stirred overnight at room temperature to yield a solid. This was collected by filtration, washed with cold methanol and dried. The product 7 was obtained as a light yellow solid (1.05 g, 94%). (ES, m/z): [M+H]$^+$ 248.9; $^1$H NMR (300 MHz, CDCl$_3$) δ 6.33-6.35 (d, J=6.3 Hz, 1H), 4.29-4.33 (t, J=6.0 Hz, 1H), 4.16 (s, 1H), 3.76-3.89 (m, 2H), 3.70 (s, 2H), 3.03 (s, 6H).

Step 3

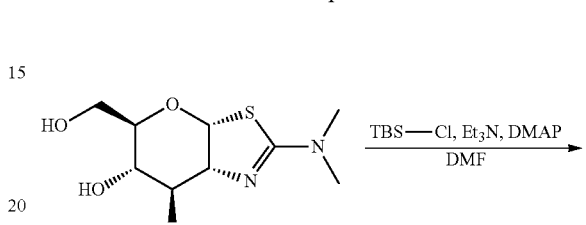

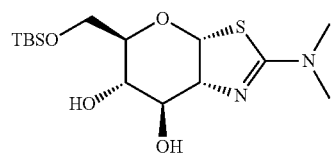

(3aR,5R,6S,7R,7aR)-5-((tert-Butyldimethylsilyloxy)methyl)-2-(dimethylamino)-5,6,7,7a-tetrahydro-3aH-pyrano[3,2-d]thiazole-6,7-diol (8)

To a solution of (3aR,5R,6S,7R,7aR)-2-(dimethylamino)-5-(hydroxymethyl)-5,6,7,7a-tetrahydro-3aH-pyrano[3,2-d]thiazole-6,7-diol (1 g, 4.03 mmol), DMAP (49.2 mg, 0.40 mmol) and triethylamine (611 mg, 6.05 mmol) in DMF (50 mL) was added tert-butylchlorodimethylsilane (665 mg, 4.43 mmol). After stirred overnight at 50° C., the resulting mixture was concentrated under vacuum to provide a residue, which was purified by silica gel column, eluted with 2-5% MeOH in dichloromethane to give compound 8 as a yellow solid (1.0 g, 65%). (ES, m/z): [M+H]$^+$ 263.0; $^1$H NMR (300 MHz, CDCl$_3$) δ 6.33-6.35 (d, J=6.3 Hz, 1H), 4.35-4.39 (t, J=5.7 Hz, 1H), 4.18-4.21 (t, J=4.5 Hz, 1H), 3.81-3.84 (m, 3H), 3.62-3.67 (m, 1H), 3.05 (s, 6H), 0.93 (s, 9H), 0.11 (s, 6H).

Step 4

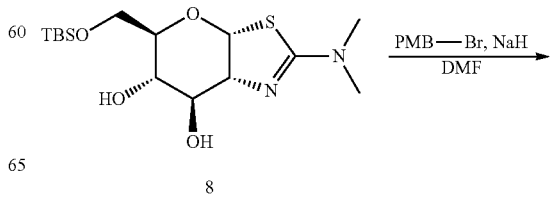

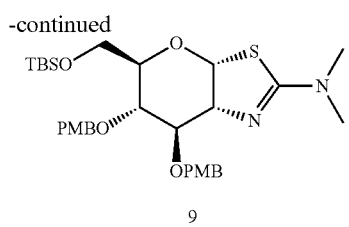

9

(3aR,5R,6S,7R,7aR)-5-((tert-Butyldimethylsilyloxy)methyl)-6,7-bis(4-methoxybenzyloxy)-N,N-dimethyl-5,6,7,7a-tetrahydro-3aH-pyrano[3,2-d]thiazol-2-amine (9)

To a solution of (3aR,5R,6S,7R,7aR)-5-((tert-butyldimethylsilyloxy)methyl)-2-(dimethylamino)-5,6,7,7a-tetrahydro-3aH-pyrano[3,2-d]thiazole-6,7-diol (1 g, 2.76 mmol) in DMF (20 mL) was added sodium hydride (568 mg, 16.6 mmol, 70%) at 15° C., and followed by addition of 1-(bromomethyl)-4-methoxybenzene (2.22 g, 11.0 mmol). The resulting solution was stirred for 3 h at room temperature, quenched by addition of cold water (50 mL), and extracted with dichloromethane (3×50 mL). The combined organic layers were dried over anhydrous magnesium sulfate and concentrated to give a residue, which was purified by silica gel column, eluted with 10-25% ethyl acetate in petroleum ether to give compound 9 as a yellow oil (1.2 g, 64%). (ES, m/z): [M+H]$^+$ 603.1; $^1$H NMR (300 MHz, CDCl$_3$) δ 7.22-7.35 (m, 4H), 6.84-6.92 (m, 4H), 6.27-6.29 (d, J=6.6 Hz, 1H), 4.60-4.76 (m, 4H), 4.36-4.43 (m, 2H), 4.10-4.17 (m, 2H), 3.81 (s, 6H), 3.72 (m, 1H), 3.61 (m, 1H), 2.99 (s, 6H), 0.83 (s, 9H), 0.07 (s, 6H).

Step 5

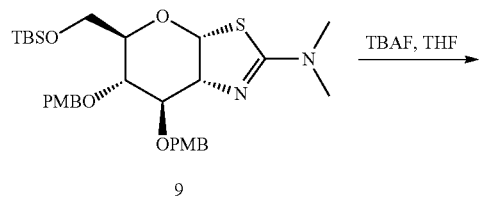

((3aR,5R,6S,7R,7aR)-2-(Dimethylamino)-6,7-bis(4-methoxybenzyloxy)-5,6,7,7a-tetrahydro-3aH-pyrano[3,2-d]thiazol-5-yl)methanol (10)

(3aR,5R,6S,7R,7aR)-6,7-bis(4-methoxybenzyloxy)-5-((tert-butyldimethylsilyloxy)methyl)-N,N-dimethyl-5,6,7,7a-tetrahydro-3aH-pyrano[3,2-d]thiazol-2-amine (9.5 g, 15.8 mmol) in THF (100 mL) was treated with TBAF (8.27 g, 31.6 mmol) overnight at room temperature. The resulting solution was diluted with brine (200 mL), extracted with ethyl acetate (2×200 mL), and dried over anhydrous magnesium sulfate. After removal of solvents, the residue was purified by silica gel column, eluted with 1-2.5% MeOH in dichloromethane to give compound 10 as a yellow oil (7.0 g, 86%). (ES, m/z): [M+H]$^+$ 489.0; $^1$H NMR (300 MHz, CDCl$_3$) δ 7.32-7.62 (m, 2H), 7.22-7.28 (m, 2H), 6.85-6.91 (m, 4H), 6.26-6.28 (d, J=6.6 Hz, 1H), 4.52-4.73 (m, 4H), 4.31-4.34 (d, J=11.4 Hz, 1H), 4.23 (s, 1H), 181 (s, 6H), 3.53-3.76 (m, 4H), 3.01 (m, 6H), 1.78-1.82 (m, 1H).

Step 6

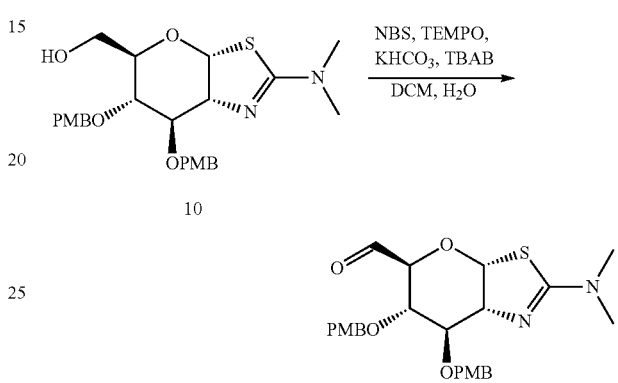

(3aR,5S,6S,7R,7aR)-2-(Dimethylamino)-6,7-bis(4-methoxybenzyloxy)-5,6,7,7a-tetrahydro-3aH-pyrano[3,2-d]thiazole-5-carbaldehyde (11)

To a mixture of ((3aR,5R,6S,7R,7aR)-6,7-bis(4-methoxybenzyloxy)-2-(dimethylamino)-5,6,7,7a-tetrahydro-3aH-pyrano[3,2-d]thiazol-5-yl)methanol (500 mg, 1.0 mmol), TBAB (16.5 mg, 0.05 mmol), KHCO$_3$ (461 mg, 4.6 mmol) and TEMPO (8 mg, 0.05 mmol) in dichloromethane (25 mL) and H$_2$O (5 mL) was added NBS (201 mg, 1.13 mmol) at 15° C. After stirred for 30 min, the reaction mixture was quenched by saturated Na$_2$SO$_3$ (5 mL). The organic layer was dried over anhydrous magnesium sulfate and condensed to provide a residue, which was purified by silica gel column, eluted with 20-30% ethyl acetate in dichloromethane to give compound 11 as a yellow syrup (320 mg, 75% pure). (ES, m/z): [M+H]$^+$ 487.0. $^1$H NMR (300 MHz, CDCl$_3$) δ 9.61 (s, 1H), 7.22-7.34 (m, 4H), 6.83-6.92 (m, 4H), 6.11-6.13 (d, J=6.0 Hz, 1H), 4.17-4.67 (m, 8H), 3.83 (s, 6H), 3.00-3.04 (s, 6H).

Step 7

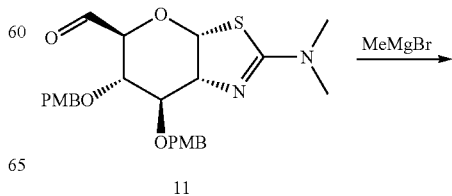

-continued

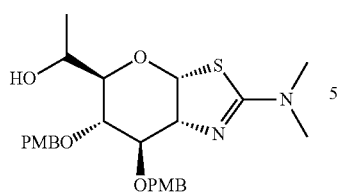

12

-continued

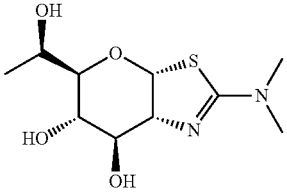

13a

Faster eluting isomer

1-(3aR,5R,6S,7R,7aR)-6,7-Bis(4-methoxybenzyloxy)-2-(dimethylamino)-5,6,7,7a-tetrahydro-3aH-pyrano[3,2-d]thiazol-5-yl)ethanol (12)

To a solution of (3aR,5S,6S,7R,7aR)-6,7-bis(4-methoxybenzyloxy)-2-(dimethylamino)-5,6,7,7a-tetrahydro-3aH-pyrano[3,2-d]thiazole-5-carbaldehyde (260 mg, 0.53 mmol) in THF (10 mL) was added methylmagnesium bromide (0.3 mL, 3M in THF). After stirred for 2 h at room temperature, the reaction mixture was quenched with sat.NH$_4$Cl (aq, 20 mL), extracted with ethyl acetate (3×20 mL). The combined organic layers were dried over anhydrous magnesium sulfate, concentrated under vacuum to give a residue, which was purified by silica gel column, eluted with 1-2% MeOH in dichloromethane to give compound 12 as a yellow syrup (250 mg, 74%, two diastereomers, faster moving one:slower moving one=1:5). (ES, m/z): [M+H]$^+$ 503.0; $^1$H NMR (300 MHz, CDCl$_3$) 7.26-7.35 (m, 2H), 7.22-7.28 (m, 2H), 6.85-6.91 (m, 4H), 6.29-6.31 (d, J=6.9 Hz, 1H), 4.52-4.73 (m, 4H), 4.31-4.34 (d, J=11.4 Hz, 1H), 4.23 (s, 1H), 3.81 (s, 6H), 3.53-3.76 (m, 4H), 3.01 (m, 6H), 1.19-1.21 (d, J=6.6 Hz, 3H).

Step 8

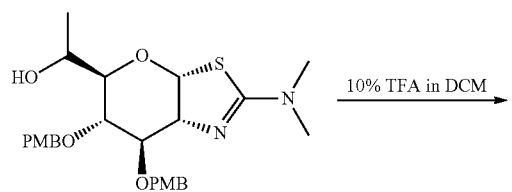

(3aR,5R,6S,7R,7aR)-2-(Dimethylamino)-5-((R)-1-hydroxyethyl)-5,6,7,7a-tetrahydro-3aH-pyrano[3,2-d]thiazole-6,7-diol (13a,) and (3aR,5R,6S,7R,7aR)-2-(dimethylamino)-5-((S)-1-hydroxyethyl)-5,6,7,7a-tetrahydro-3aH-pyrano[3,2-d]thiazole-6,7-diol (13, Example 1)

A solution of 1-((3aR,5R,6S,7R,7aR)-6,7-bis(4-methoxybenzyloxy)-2-(dimethylamino)-5,6,7,7a-tetrahydro-3aH-pyrano[3,2-d]thiazol-5-yl)ethanol (315 mg, 0.63 mmol, a 1:5 mixture of two diastereomers) in dichloromethane (20 mL) was treated with TFA (2 mL) for 1 h at room temperature. The reaction mixture was concentrated under vacuum to give a residue, which was purified by Prep-HPLC under the following conditions [(3#-Agilent 1200 prep HPLC): Column, SunFire Prep C18,19*50 mm 5 um; mobile phase, WATER with 0.03% NH$_4$OH and CH$_3$CN (10% CH$_3$CN up to 45% in 10 min); Detector, UV 220 nm] to afford the faster eluting isomer as a white solid (13a, 6.9 mg, 4.2%): (ES, m/z): [M+H]$^+$ 262.9; $^1$H NMR (300 MHz, CDCl$_3$) δ 6.21-6.23 (d, J=6.6 Hz, 1H), 4.12-4.16 (m, 1H), 3.92-3.99 (m, 2H), 3.48-3.59 (m, 2H), 2.9 (s, 6H), 1.07-1.10 (d, J=6.6 Hz, 3H);

and the slower eluting isomer as white solid (13, Example 1, 52.8 mg, 32%): (ES, m/z): [M+H]$^+$ 262.9; $^1$H NMR (slower eluting isomer, 300 MHz, CDCl$_3$) δ 6.18-6.21 (d, J=6.6 Hz, 1H), 4.13-4.16 (m, 1H), 3.95-3.98 (m, 1H), 3.84-3.88 (m, 1H), 3.58-3.63 (m, 1H), 3.21-3.26 (m, 1H), 2.89 (s, 6H), 1.11-1.13 (d, J=6.6 Hz, 3H).

Example 2

(3aR,5R,6S,7R,7aR)-5-((S)-1-hydroxyethyl)-2-(propylamino)-5,6,7,7a-tetrahydro-3aH-pyrano[3,2-d]thiazole-6,7-diol

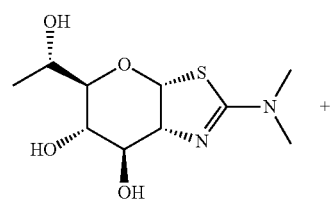

13

Slower eluting isomer

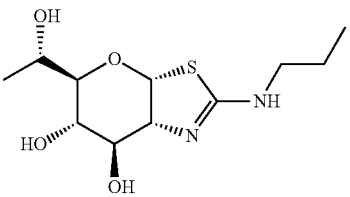 [SMILES: CCCNC1=N[C@@H]2[C@@H](O)[C@H](O)[C@@H]([C@H](C)O)O[C@@H]2S1]

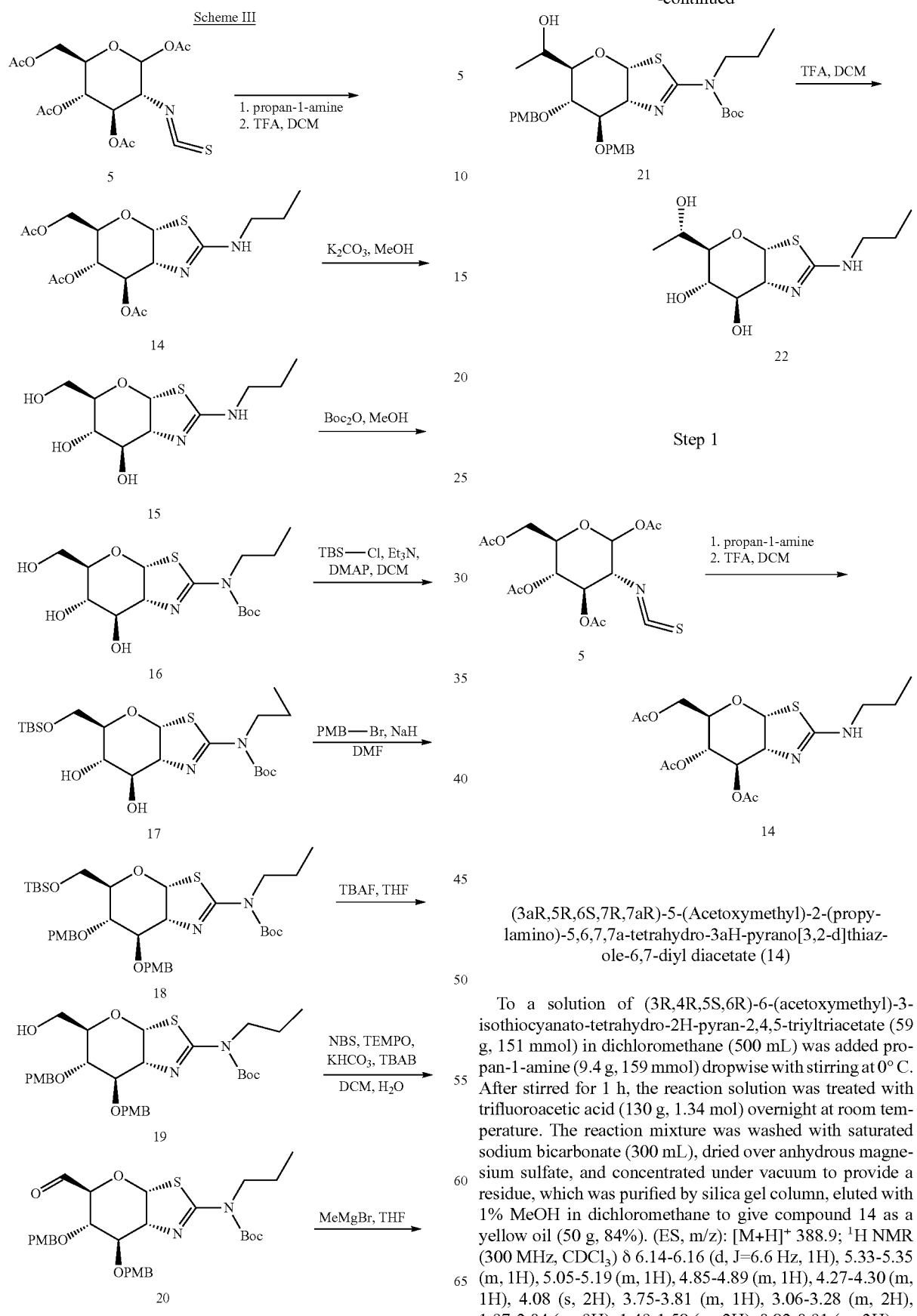

(3aR,5R,6S,7R,7aR)-5-(Acetoxymethyl)-2-(propylamino)-5,6,7,7a-tetrahydro-3aH-pyrano[3,2-d]thiazole-6,7-diyl diacetate (14)

To a solution of (3R,4R,5S,6R)-6-(acetoxymethyl)-3-isothiocyanato-tetrahydro-2H-pyran-2,4,5-triyltriacetate (59 g, 151 mmol) in dichloromethane (500 mL) was added propan-1-amine (9.4 g, 159 mmol) dropwise with stirring at 0° C. After stirred for 1 h, the reaction solution was treated with trifluoroacetic acid (130 g, 1.34 mol) overnight at room temperature. The reaction mixture was washed with saturated sodium bicarbonate (300 mL), dried over anhydrous magnesium sulfate, and concentrated under vacuum to provide a residue, which was purified by silica gel column, eluted with 1% MeOH in dichloromethane to give compound 14 as a yellow oil (50 g, 84%). (ES, m/z): [M+H]$^+$ 388.9; $^1$H NMR (300 MHz, CDCl$_3$) δ 6.14-6.16 (d, J=6.6 Hz, 1H), 5.33-5.35 (m, 1H), 5.05-5.19 (m, 1H), 4.85-4.89 (m, 1H), 4.27-4.30 (m, 1H), 4.08 (s, 2H), 3.75-3.81 (m, 1H), 3.06-3.28 (m, 2H), 1.97-2.04 (m, 9H), 1.49-1.58 (m, 2H), 0.82-0.91 (m, 3H).

Step 2

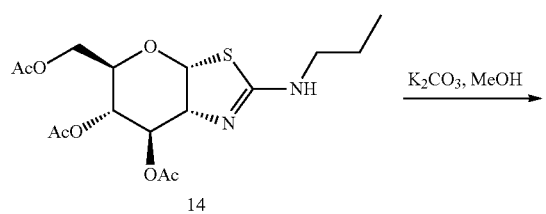

(3aR,5R,6S,7R,7aR)-5-(Hydroxymethyl)-2-(propylamino)-5,6,7,7a-tetrahydro-3aH-pyrano[3,2-d]thiazole-6,7-diol (15)

To a solution of (3aR,5R,6S,7R,7aR)-5-(acetoxymethyl)-2-(propylamino)-5,6,7,7a-tetrahydro-3aH-pyrano[3,2-d]thiazole-6,7-diyl diacetate (100 g, 257 mmol) in methanol (800 mL) was added potassium carbonate (18 g, 130 mmol). The resulting solution was stirred overnight at 40° C. and then cooled down to 0° C. to yield a solid This was collected by filtration, washed with cold methanol and dried. The product 15 was obtained as a white solid (50 g, 74%). (ES, m/z): [M+H]+ 262.9; $^1$H NMR (300 MHz, D2O) δ 6.17-6.19 (d, J=6.3 Hz, 1H), 4.07-4.10 (m, 1H), 3.93-3.96 (m, 1H), 3.71-3.76 (m, 1H), 3.45-3.69 (m, 3H), 3.04-3.13 (m, 2H), 1.39-1.51 (m, 2H), 0.82-0.91 (m, 3H).

Step 3

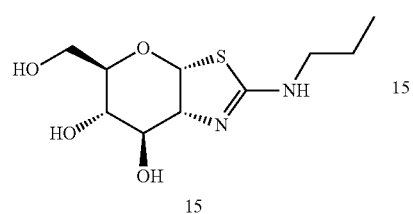

tert-Butyl (3aR,5R,6S,7R,7aR)-6,7-dihydroxy-5-(hydroxymethyl)-5,6,7,7a-tetrahydro-3aH-pyrano[3,2-d]thiazol-2-yl(propyl)carbamate (16)

To a solution of (3aR,5R,6S,7R,7aR)-5-(hydroxymethyl)-2-(propylamino)-5,6,7,7a-tetrahydro-3aH-pyrano[3,2-d]thiazole-6,7-diol (67.6 g, 258 mmol) in methanol (800 mL) was added (Boc)$_2$O (83 g, 384 mmol). After stirred for 3 h at room temperature, the resulting mixture was concentrated under vacuum to provide a residue, which was purified by silica gel column, eluted with 1% MeOH in dichloromethane to give compound 16 as yellow oil (53 g, 46%). (ES, m/z): [M+H]+ 363.0. $^1$H NMR (300 MHz, CDCl$_3$) δ 6.11-6.14 (d, J=6.6 Hz, 1H), 4.16-4.26 (m, 2H), 3.75-3.96 (m, 6H), 3.58-3.63 (m, 1H), 1.50-1.57 (m, 12H), 0.89-0.94 (m, 3H).

Step 4

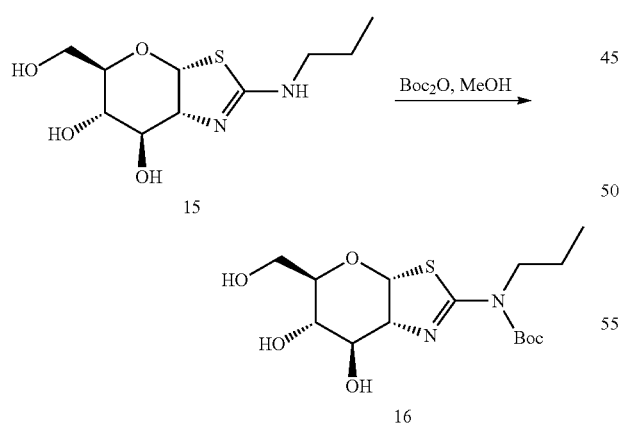

tert-Butyl (3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl(propyl)carbamate (17)

To a stirred solution of tert-butyl (3aR,5R,6S,7R,7aR)-6,7-dihydroxy-5-(hydroxymethyl)-5,6,7,7a-tetrahydro-3aH-pyrano[3,2-d]thiazol-2-yl(propyl)carbamate (45 g, 124 mmol), DMAP (760 mg, 6 mmol) and triethylamine (25.1 g, 248 mmol) in dichloromethane (300 mL) was added tert-butylchlorodimethylsilane (22.4 g, 149 mmol). After stirred for 6 h at room temperature, the mixture was condensed to provide a residue, which was purified by silica gel column, eluted with 10-30% ethyl acetate in petroleum ether to give compound 17 as a yellow oil (43 g. 65%). (ES, m/z): [M+H]+ 477.1; $^1$H NMR (300 MHz, CDCl$_3$) δ 6.12-6.14 (d, J=6.3 Hz, 1H), 4.40-4.45 (m, 1H), 3.84-3.96 (m, 4H), 3.64-3.71 (m, 1H), 3.13-3.30 (m, 3H), 1.67-1.74 (m, 2H), 1.53 (s, 9H), 0.93-0.98 (m, 3H), 0.92 (s, 9H), 0.12 (s, 6H).

Step 5

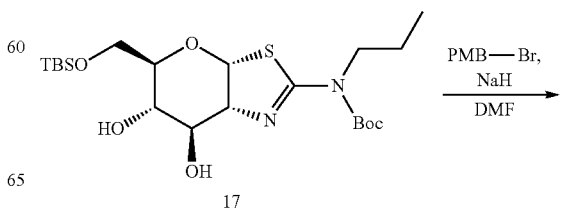

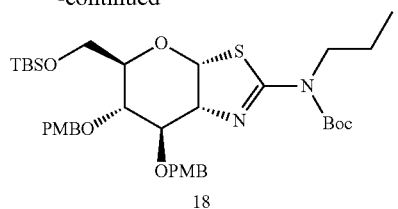

18 tert-Butyl (3aR,5R,6S,7R,7aR)-5-((tert-butyldimethylsilyloxy)methyl)-6,7-bis(4-methoxybenzyloxy)-5,6,7,7a-tetrahydro-3aH-pyrano[3,2-d]thiazol-2-yl(propyl)carbamate (18)

To a solution of tert-butyl (3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl(propyl)carbamate (20 g, 42 mmol) in DMF (300 mL) was added sodium hydride (10 g, 417 mmol) at 15° C. in portions, followed by addition of 1-(bromomethyl)-4-methoxybenzene (33.8 g, 168 mmol). The resulting solution was stirred for 1.5 h at room temperature, quenched by addition of cold water (100 mL), and extracted with dichloromethane (5×100 mL). The combined organic layers were dried over anhydrous magnesium sulfate and concentrated under vacuum to provide a residue, which was purified by silica gel column, eluted with 10-25% ethyl acetate in petroleum ether to give compound 18 as a yellow oil (20 g, 64.8%). (ES, m/z): 717.1; $^1$H NMR (300 MHz, CDCl$_3$) δ 7.32-7.35 (d, J=8.7 Hz, 2H), 7.19-7.22 (d, J=8.7 Hz, 2H), 6.83-6.92 (m. 4H), 6.05-6.07 (d, J=6.9 Hz, 1H), 4.57-4.74 (m, 3H), 4.30-4.39 (m, 2H), 4.14-4.17 (t, J=4.2 Hz, 1H), 3.68-3.84 (m, 11H), 3.41-3.45 (m, 1H), 1.67-1.74 (m, 2H), 1.53 (s, 9H), 0.89 (s, 9H), 0.84 (m, 3H), 0.08 (s, 6H).

Step 6

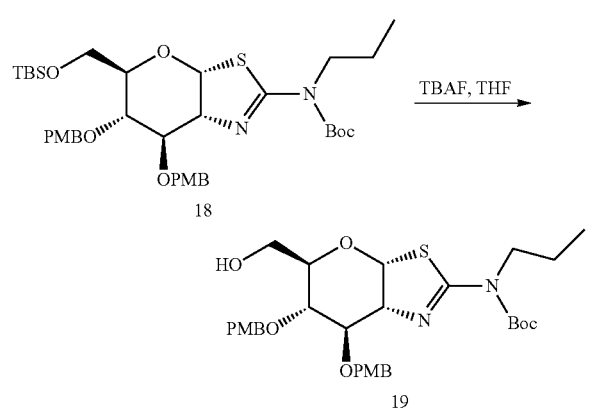

tert-Butyl (3aR,5R,6S,7R,7aR)-5-(hydroxymethyl)-6,7-bis(4-methoxybenzyloxy)-5,6,7,7a-tetrahydro-3aH-pyrano[3,2-d]thiazol-2-yl(propyl)carbamate (19)

To a solution of tert-butyl (5R,6S,7R)-6,7-bis(4-methoxybenzyloxy)-5-((tert-butyldimethylsilyloxy)methyl)-5,6,7,7a-tetrahydro-3aH-pyrano[3,2-d]thiazol-2-yl(propyl)carbamate (19 g, 26.50 mmol) in tetrahydrofuran (100 mL) was treated with TBAF (13.8 g, 53 mmol) overnight at room temperature. The resulting solution was diluted with brine (200 mL), extracted with ethyl acetate (2×200 mL), and dried over anhydrous magnesium sulfate. After removal of solvents, the residue was purified by silica gel column, eluted with 10-30% ethyl acetate in petroleum ether to give compound 19 as a yellow oil (14.5 g, 91%). (ES, m/z): [M+H]$^+$ 603.0; $^1$H NMR (300 MHz, CDCl$_3$) 7.32-7.35 (d, J=8.7 Hz, 2H), 7.17-7.20 (d, J=8.7 Hz, 2H), 6.83-6.92 (m. 4H), 6.04-6.06 (d, J=6.9 Hz, 1H), 4.64-4.66 (m, 2H), 4.40-4.48 (m, 1H), 4.17-4.38 (m, 3H), 3.72-3.83 (m, 9H), 3.45-3.60 (m, 2H), 3.43-3.45 (m, 1H), 1.58-1.63 (m, 2H), 1.53 (s, 9H), 0.78-0.83 (t, J=7.2 Hz, 3H).

Step 7

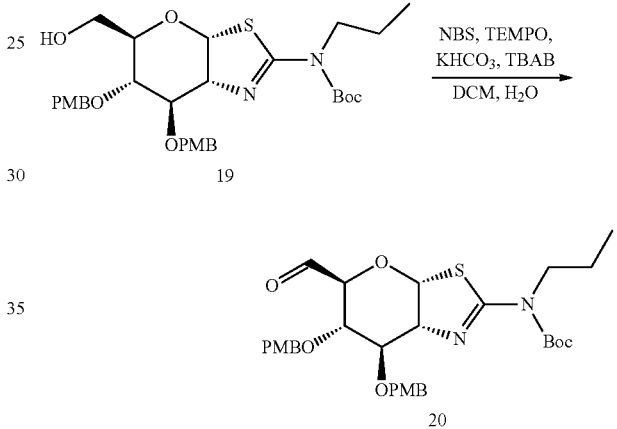

tert-Butyl (3aR,5S,6S,7R,7aR)-5-formyl-6,7-bis(4-methoxybenzyloxy)-5,6,7,7a-tetrahydro-3aH-pyrano[3,2-d]thiazol-2-yl(propyl)carbamate (20)

To a mixture of tert-butyl (5R,6S,7R)-6,7-bis(4-methoxybenzyloxy)-5-(hydroxymethyl)-5,6,7,7a-tetrahydro-3aH-pyrano[3,2-d]thiazol-2-yl(propyl)carbamate (2 g, 3.32 mmol), KHCO$_3$ (1.49 bg, 15 mmol), TBAB (53 mg, 0.16 mmol) and TEMPO (26 mg, 0.17 mmol) in dichloromethane (60 mL) and H$_2$O (12 mL) was added NBS (592 mg, 3.33 mmol) at 15° C. After stirred for 30 min, the reaction mixture was quenched by saturated Na$_2$SO$_3$ (10 mL). The organic layer was dried over anhydrous magnesium sulfate and condensed to provide a residue, which was purified by silica gel column, eluted with 20-30% AcOEt in dichloromethane to give compound 20 as a yellow syrup (1.2 g, purity 60%). (ES, m/z): [M+H]$^+$ 601.1. $^1$H NMR (300 MHz, CDCl$_3$) δ 9.61 (s, 1H), 7.23-7.28 (m, 4H), 6.82-6.86 (m, 4H), 6.19-6.21 (d, J=6.9 Hz, 1H), 4.60-4.67 (m, 2H), 4.41-4.55 (m, 3H), 4.02-4.03 (m, 1H), 3.88-3.93 (m, 1H), 3.68-3.81 (m, 9H), 1.46-1.53 (m, 11H), 0.83-0.86 (t, J=7.5 Hz, 3H).

Step 8

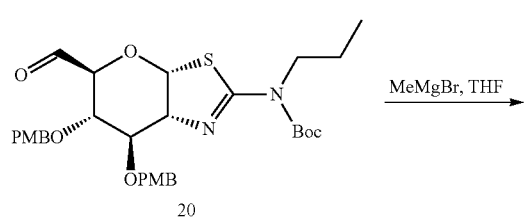

tert-Butyl (3aR,5R,6S,7R,7aR)-1-hydroxyethyl)-6,7-bis(4-methoxybenzyloxy)-5,6,7,7a tetrahydro-3aH-pyrano[3,2-d]thiazol-2-yl(propyl)carbamate (21)

To a solution of tert-butyl (3aR,5S,6S,7R,7aR)-6,7-bis(4-methoxybenzyloxy)-5-formyl-5,6,7,7a-tetrahydro-3aH-pyrano[3,2-d]thiazol-2-yl(propyl)carbamate (600 mg, 1.00 mmol, 60% purity) in tetrahydrofuran (20 mL) was added methylmagnesium bromide (1 mL, 3M in THF, 3 mmol). After stirred for 10 min at r.t, the reaction was quenched with sat.NH₄Cl (aq, 20 mL), extracted with dichloromethane (4×10 mL). The combined organic layers were dried over anhydrous magnesium sulfate, and concentrated under vacuum to provide a residue, which was purified by silica gel column, eluted with 30% AcOEt in dichloromethane to give compound 21 as a yellow syrup (300 mg, 81%, two diastereomers, faster moving one: slower moving one=1:3). (ES, m/z): [M+H]⁺ 617.0; ¹H NMR (300 MHz, CDCl₃) δ 7.16-7.72 (m, 5H), 6.83-6.93 (m, 4H), 6.05-6.08 (m, 1H), 4.67 (s, 2H), 4.30-4.44 (m, 2H), 4.27-4.35 (m, 2H), 3.67-3.95 (m, 10H), 3.20-3.31 (m, 1H), 1.71-1.76 (m, 1H), 1.53-1.55 (m, 14H), 0.78-0.83 (m, 3H).

Step 9

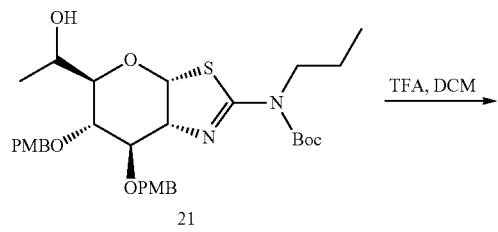

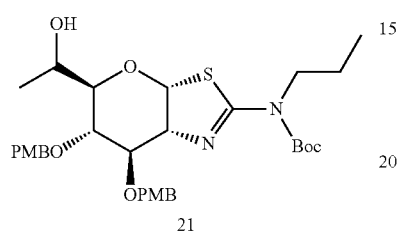

(3aR,5R,6S,7R,7aR)-5-((S)-1-Hydroxyethyl)-2-(propylamino)-5,6,7,7a-tetrahydro-3aH-pyrano[3,2-d]thiazole-6,7-diol (22)

A solution of tert-butyl (3aR,5R,6S,7R,7aR)-6,7-bis(4-methoxybenzyloxy)-1-hydroxyethyl)-5,6,7,7a-tetrahydro-3aH-pyrano[3,2-d]thiazol-2-yl(propyl)carbamate (300 mg, 0.49 mmol, a mixture of two diastereomers, faster moving one:slower moving one=1:3) in 20 mL dichloromethane was treated with 2 mL TFA. After stirred overnight at room temperature, the resulting mixture was concentrated under vacuum to give a crude product, which was purified by Prep-HPLC with the following conditions [(Agilent 1200 detecl), Column, 19*150 mm; mobile phase, WATER WITH 0.03% NH₄OH and CH₃CN (10% CH₃CN up to 45% in 10 min); Detector, 254 nm 220 nm] to afford compound 22 (Example 2) as white solid (TFA salt, 143.1 mg, 75%). (ES, m/z): [M+H]+277.0; ¹H NMR (300 MHz, D₂O): δ: 6.49-6.45 (m, 1H), 4.14-4.69 (m, 1H), 3.86-3.99 (m, 2H), 3.59-3.66 (m, 1H), 3.32-3.36 (m, 1H), 3.24-3.30 (m, 2H), 1.47-1.59 (m, 3H), 1.10-1.13 (m, 3H).

Example 3

(3aR,5S,6S,7R,7aR)-5-(2-Hydroxypropan-2-yl)-2-(methylamino)-5,6,7,7a-tetrahydro-3aH-pyrano[3,2-d]thiazole-6,7-diol

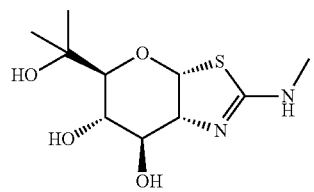 [SMILES: CNC1=N[C@@H]2[C@@H](O)[C@H](O)[C@@H](C(C)(C)O)O[C@@H]2S1]

Scheme IV

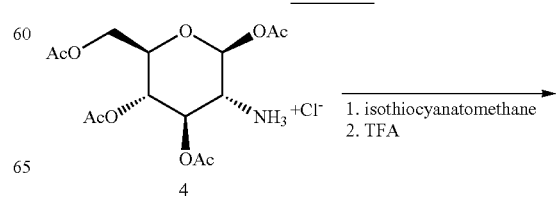

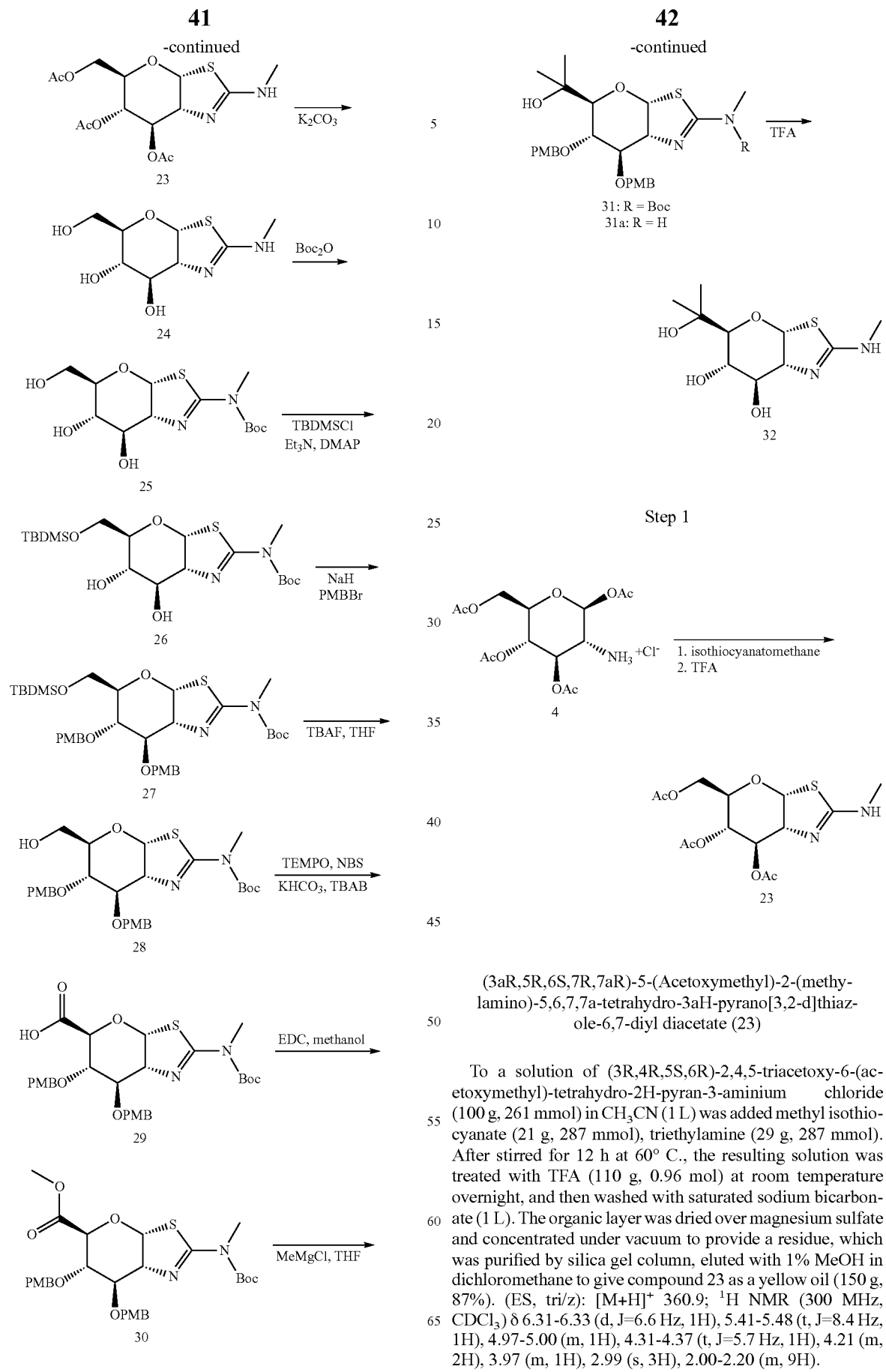

(3aR,5R,6S,7R,7aR)-5-(Acetoxymethyl)-2-(methylamino)-5,6,7,7a-tetrahydro-3aH-pyrano[3,2-d]thiazole-6,7-diyl diacetate (23)

To a solution of (3R,4R,5S,6R)-2,4,5-triacetoxy-6-(acetoxymethyl)-tetrahydro-2H-pyran-3-aminium chloride (100 g, 261 mmol) in CH$_3$CN (1 L) was added methyl isothiocyanate (21 g, 287 mmol), triethylamine (29 g, 287 mmol). After stirred for 12 h at 60° C., the resulting solution was treated with TFA (110 g, 0.96 mol) at room temperature overnight, and then washed with saturated sodium bicarbonate (1 L). The organic layer was dried over magnesium sulfate and concentrated under vacuum to provide a residue, which was purified by silica gel column, eluted with 1% MeOH in dichloromethane to give compound 23 as a yellow oil (150 g, 87%). (ES, tri/z): [M+H]$^+$ 360.9; $^1$H NMR (300 MHz, CDCl$_3$) δ 6.31-6.33 (d, J=6.6 Hz, 1H), 5.41-5.48 (t, J=8.4 Hz, 1H), 4.97-5.00 (m, 1H), 4.31-4.37 (t, J=5.7 Hz, 1H), 4.21 (m, 2H), 3.97 (m, 1H), 2.99 (s, 3H), 2.00-2.20 (m, 9H).

Step 2

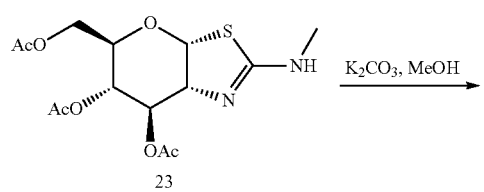

(3aR,5R,6S,7aR)-5-(Hydroxymethyl)-2-(methylamino)-5,6,7,7a-tetrahydro-3aH-pyrano[3,2-d]thiazole-6,7-diol (24)

A solution of (3aR,5R,6S,7R,7aR)-5-(acetoxymethyl)-2-(methylamino)-5,6,7,7a-tetrahydro-3aH-pyrano[3,2-d]thiazole-6,7-diyl diacetate (150 g, 417 mmol) in methanol (1 L) was treated with potassium carbonate (11.5 g, 83 mmol). The resulting mixture was stirred overnight at room temperature to yield a solid. This was collected by filtration, washed with cold methanol and dried. The product 24 was obtained as a yellow solid (85 g, 87%). (ES, m/z): [M+H]⁺ 235.1; ¹H NMR (300 MHz, D₂O) δ 6.14-6.16 (d, J=6.3 Hz, 1H), 4.03-4.07 (m, 1H), 3.89-3.92 (m, 1H), 3.65-3.70 (m, 1H), 3.48-3.56 (m, 2H), 3.41-3.45 (m, 1H), 2.69 (s, 3H).

Step 3

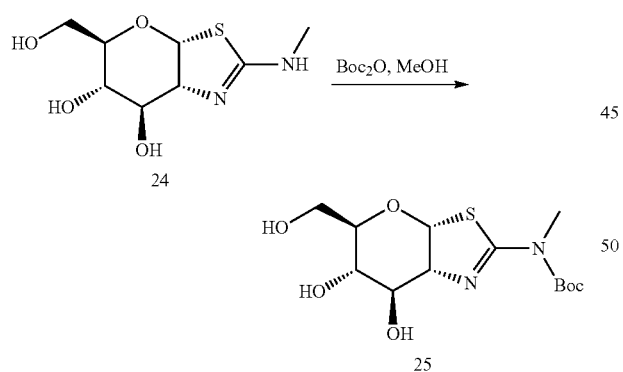

tert-Butyl (3aR,5R,6S,7R,7aR)-6,7-dihydroxy-5-(hydroxymethyl)-5,6,7,7a-tetrahydro-3aH-pyrano[3,2-d]thiazol-2-yl(methyl)carbamate (25)

A solution of (3aR,5R,6S,7R,7aR)-5-(hydroxymethyl)-2-(methylamino)-5,6,7,7a-tetrahydro-3aH-pyrano[3,2-d]thiazole-6,7-diol (85 g, 363 mmol) in methanol (600 mL) was treated with Boc₂O (117.7 g, 540 mmol) and triethylamine (73.3 g, 726 mmol). The resulting solution was stirred overnight at 45° C., and then concentrated under vacuum to give a residue, which was purified by silica gel column, eluted with 2.5% methanol in dichloromethane to give compound 25 as a yellow solid (90 g, 74%). (ES, m/z): [M+H]⁺ 334.8; ¹H NMR (300 MHz, CDCl₃) δ 6.14-6.17 (d, J=6.9 Hz, 1H), 4.19-4.23 (t, J=6.3 Hz, 1H), 4.10-4.14 (t, J=5.4 Hz, 1H), 3.79-3.84 (m, 3H), 3.60-3.64 (m, 2H), 3.14 (s, 3H), 1.55 (s, 9H).

Step 4

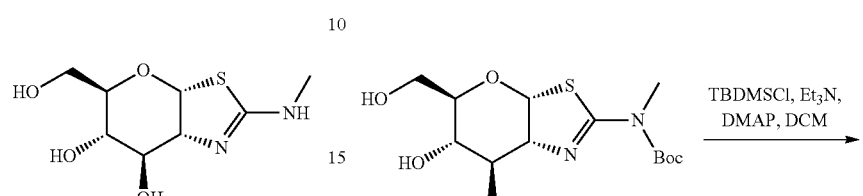

tert-Butyl (3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl(methyl)carbamate (26)

To a mixture of tert-butyl (3aR,5R,6S,7R,7aR)-6,7-dihydroxy-5-(hydroxymethyl)-5,6,7,7a-tetrahydro-3aH-pyrano[3,2-d]thiazol-2-yl(methyl)carbamate (30 g, 90 mmol), DMAP (550 mg, 4.5 mmol) and triethylamine (18.2 g, 180 mmol) in dichloromethane (200 mL) was added tert-butylchlorodimethylsilane (16.3 g, 108 mmol) at 0° C. The resulting solution was stirred for 4 h at room temperature, and then concentrated under vacuum to provide a residue, which was purified by silica gel column, eluted with 1% methanol in dichloromethane to give compound 26 as a white solid (20 g, 50%). (ES, m/z): [M+H]⁺ 449.0; ¹H NMR (300 MHz, CDCl₃) δ 6.10-6.12 (d, J=6.9 Hz, 1H), 4.15-4.24 (m, 2H), 3.83-3.97 (m, 5H), 3.60 (m, 1H), 2.58-2.66 (m, 2H), 1.55 (s, 9H), 1.18 (m, 3H), 0.91 (s, 9H), 0.09 (s,

Step 5

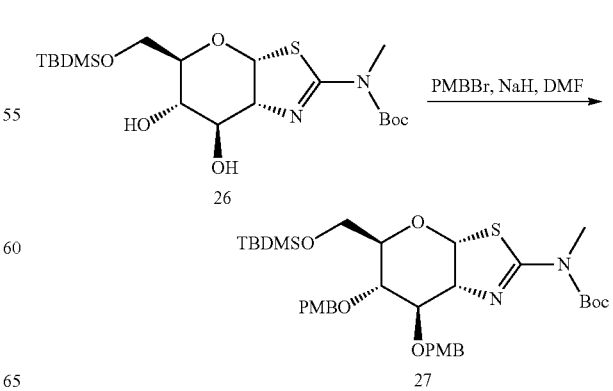

tert-Butyl (3aR,5R,6S,7R,7aR)-5-((tert-butyldimethylsilyloxy)methyl)-6,7-bis(4-methoxybenzyloxy)-5,6,7,7a-tetrahydro-3aH-pyrano[3,2-d]thiazol-2-yl (methyl)carbamate (27)

To a solution of (3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl(methyl)carbamate (20 g, 45 mmol) in DMF (150 mL) was added sodium hydride (10.7 g, 446 mmol) in portion at 0° C., and followed by addition of 1-(bromomethyl)-4-methoxybenzene (36 g, 179 mmol). The resulting solution was stirred for 2 h at room temperature, quenched with cold water (200 mL), and extracted with ethyl acetate (3×500 mL). The combined organic layers were washed with brine (5×200 mL), dried over anhydrous magnesium sulfate, and concentrated under vacuum to afford a residue, which was purified by silica gel column, eluted with 10% ethyl acetate in petroleum ether to give compound 27 as a yellow liquid (21 g, 68%). (ES, m/z): [M+H]$^+$ 689.1. $^1$H NMR (300 MHz, CDCl$_3$) δ 7.31-7.37 (m, 2H), 7.22-7.28 (m, 2H), 6.10-6.12 (d, J=6.9 Hz, 1H), 4.60-4.74 (m, 4H), 4.20-4.47 (m, 4H), 3.82 (s, 6H), 3.69 (s, 3H), 3.33-3.37 (m, 2H), 1.56 (s, 9H), 0.89 (s, 9H), 0.05 (s, 6H).

Step 6

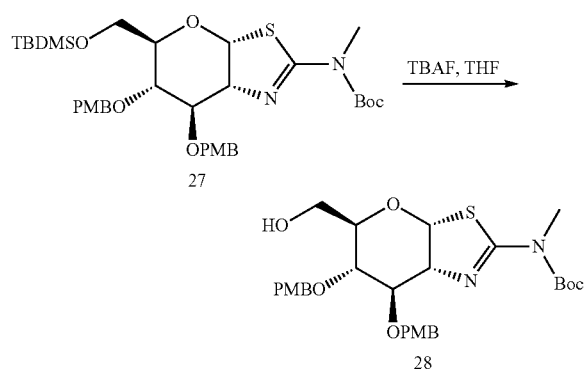

tert-Butyl (3aR,5R,6S,7R,7aR)-5-(hydroxymethyl)-6,7-bis(4-methoxybenzyloxy)-5,6,7,7a-tetrahydro-3aH-pyrano[3,2-d]thiazol-2-yl(methyl)carbamate (28)

A solution of (3aR,5R,6S,7R,7aR)-5-((tert-butyldimethylsilyloxy)methyl)-6,7-bis(4-methoxybenzyloxy)-5,6,7,7a-tetrahydro-3aH-pyrano[3,2-d]thiazol-2-yl(methyl)carbamate (1.54 g, 2.24 mmol) in THF (30 mL) was treated with TBAF (1.17 g, 4.5 mmol) overnight at room temperature. The resulting solution was diluted with brine (20 mL), extracted with ethyl acetate (2×50 mL), and dried over anhydrous magnesium sulfate. After removal of solvents, the residue was purified by silica gel column, eluted with 20% ethyl acetate in petroleum ether to give compound 28 as a yellow solid (0.8 g, 62%). (ES, m/z): [M+H]$^+$ 575.2, $^1$H NMR (300 MHz, CDCl$_3$) δ 7.33-7.36 (d, J=7.8 Hz, 2H), 7.20-7.22 (d, J=8.1 Hz, 2H), 6.08-6.10 (d, J=6.3 Hz, 1H), 4.27-4.71 (m, 6H), 3.82 (s, 6H), 3.48-3.70 (m, 4H), 3.33 (s, 3H), 1.76-1.80 (t, J=7.2 Hz, 1H), 1.54 (s, 9H).

Step 7

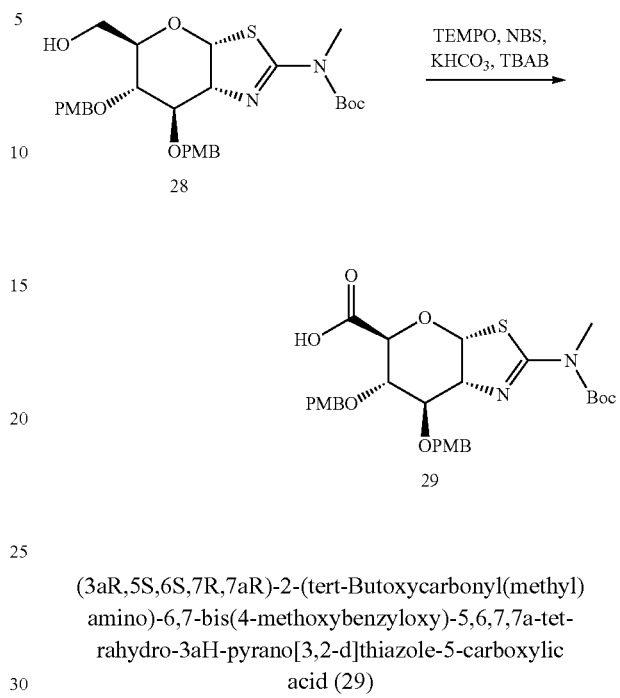

(3aR,5S,6S,7R,7aR)-2-(tert-Butoxycarbonyl(methyl)amino)-6,7-bis(4-methoxybenzyloxy)-5,6,7,7a-tetrahydro-3aH-pyrano[3,2-d]thiazole-5-carboxylic acid (29)

A mixture of tert-butyl (3aR,5R,6S,7R,7aR)-5-(hydroxymethyl)-6,7-bis(4-methoxybenzyloxy)-5,6,7,7a-tetrahydro-3aH-pyrano[3,2-d]thiazol-2-yl(methyl)carbamate (1 g, 1.74 mmol), KHCO$_3$ (780 mg, 7.8 mmol), TBAB (28 mg, 0.09 mmol) and TEMPO (14 mg, 0.09 mmol) in dichloromethane (30 mL) and H$_2$O (6 mL) was treated with NBS (620 mg, 3.5 mmol) overnight at room temperature. The reaction mixture was adjusted to acidic (pH at 3) with hydrochloric acid, and then extracted with dichloromethane (3×20 mL). The combined organic layers were dried over anhydrous sodium sulfate and concentrated under vacuum to provide a residue, which was purified by a silica gel column, eluted with 20~50% ethyl acetate in petroleum ether to give compound 29 as a white solid (600 mg, 58%). (ES, m/z): [M+H]$^+$ 589.0, $^1$H NMR (300 MHz, CDCl$_3$) δ 7.25-7.32 (m, 2H), 6.85-6.90 (m, 2H), 6.08-6.10 (d, J=6.3 Hz, 1H), 4.50-4.62 (m, 5H), 4.22-4.29 (m, 2H), 3.97 (m, 1H), 3.81 (s, 6H), 3.34 (s, 3H), 1.54 (s, 9H).

Step 8

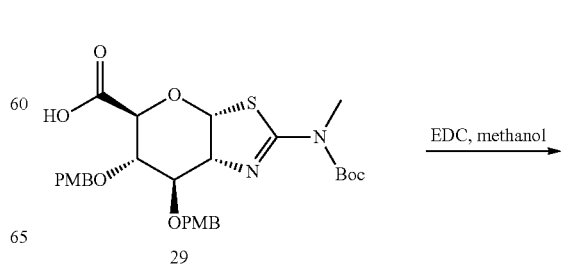

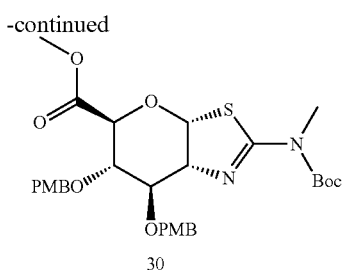

30

(3aR,5S,6S,7R,7aR)-Methyl 6,7-bis(4-methoxybenzyloxy)-2-(tert-butoxycarbonyl)-5,6,7,7a-tetrahydro-3aH-pyrano[3,2-d]thiazole-5-carboxylate (30)

A solution of (3aR,5S,6S,7R,7aR)-2-(tert-butoxycarbonyl(methyl)amino)-6,7-bis(4-methoxybenzyloxy)-5,6,7,7a-tetrahydro-3aH-pyrano[3,2-d]thiazole-5-carboxylic acid (600 mg, 1.02 mmol) in methanol (30 mL) was treated with EDC (392 mg, 2.04 mmol) for 2 h at room temperature. After removal of solvents, the residue was purified by a silica gel column, eluted with 20% ethyl acetate in petroleum ether to give compound 30 (510 mg, 83%). (ES, m/z): [M+H]+ 603.0, $^1$H NMR (300 MHz, CDCl$_3$) δ 7.22-7.29 (m, 4H), 6.83-6.91 (m, 4H), 6.07-6.09 (d, J=5.7 Hz, 1H), 4.48-4.61 (m, 4H), 4.30-4.31 (m, 1H), 4.22-4.29 (m, 2H), 4.17-4.19 (t, J=4.8 Hz, 1H), 3.82 (s, 6H), 3.67 (s, 3H), 3.30 (s, 3H), 1.54 (s, 9H).

Step 9

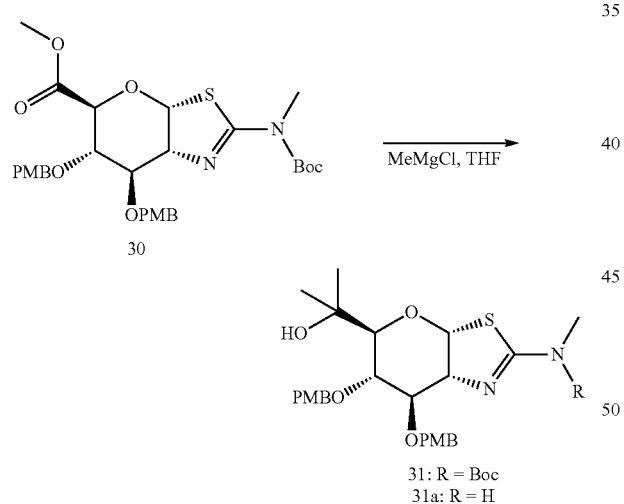

31: R = Boc
31a: R = H tert-Butyl (3aR,5S,6S,7R,7aR)-6,7-bis(4-methoxybenzyloxy)-5-(2-hydroxypropan-2-yl)-5,6,7,7a-tetrahydro-3aH-pyrano[3,2-d]thiazol-2-yl(methyl)carbamate (31) and 2-((3aR,5S,6S,7R,7aR)-6,7-bis(4-methoxybenzyloxy)-2-(methylamino)-5,6,7,7a-tetrahydro-3aH-pyrano[3,2-d]thiazol-5-yl)propan-2-ol (31a)

Compound 30 (510 mg) in THF (20 mL) was treated with methylmagnesium chloride (1 mL, 3M in THF) for 2 h at room temperature. The reaction was quenched with brine (20 mL), and extracted with dichloromethane (3×20 mL). The combined organic layers were dried over anhydrous magnesium sulfate and concentrated under vacuum to provide a residue, which was purified by a silica gel column, eluted with 20% ethyl acetate in petroleum ether to give compound 31 as a yellow oil (308 mg, 57%). (ES, m/z): [M+H]+ 603.3; $^1$H NMR (300 MHz, CDCl$_3$) δ 7.34-7.37 (d, J=8.4 Hz, 2H), 7.19-7.22 (d, J=8.4 Hz, 2H), 6.90-6.93 (dd, J=2.1 Hz, 1.8 Hz, 2H), 6.83-6.86 (dd, J=2.1 Hz, 1.8 Hz, 2H), 6.15-6.18 (d, J=7.2 Hz, 1H), 4.68 (s, 2H), 4.35-4.48 (m, 3H), 4.23-4.26 (d, J=4.5 Hz, 1H), 3.86 (s, 6H), 3.26 (s, 3H), 3.21 (d, J=8.1 Hz, 1H), 1.54 (s, 9H); and then eluted with 1% MeOH in dichloromethane to give 31a as a white solid (152 mg, 31%). (ES, m/z): [M+H]+ 503.3; $^1$H NMR (300 MHz, CDCl$_3$) δ 7.28-7.34 (m, 4H), 6.85-6.92 (m, 4H), 6.34-6.37 (d, J=7.2 Hz, 1H), 4.49-4.68 (m, 5H), 4.25-4.29 (m, 2H), 3.76-3.86 (m, 8H), 3.34-3.37 (m, 1H), 3.90 (s, 3H).

Step 10

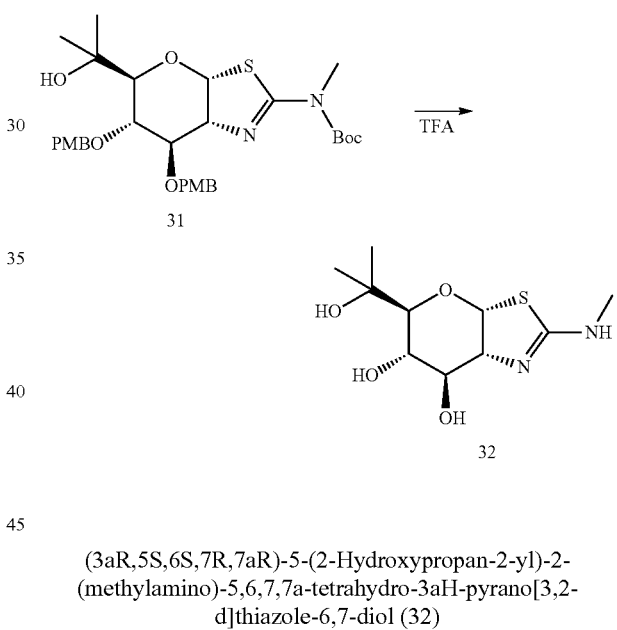

(3aR,5S,6S,7R,7aR)-5-(2-Hydroxypropan-2-yl)-2-(methylamino)-5,6,7,7a-tetrahydro-3aH-pyrano[3,2-d]thiazole-6,7-diol (32)

A solution of tert-butyl (3aR,5S,6S,7R,7aR)-5-(2-hydroxypropan-2-yl)-6,7-bis(4-methoxybenzyloxy)-5,6,7,7a-tetrahydro-3aH-pyrano[3,2-d]thiazol-2-yl(methyl)carbamate (200 mg, 0.33 mmol) in DCM (20 mL) was treated with trifluoroacetic acid (2 mL) overnight at room temperature. The reaction mixture was condensed to give a residue, which was purified by Prep-HPLC with the following conditions [(3#-Agilent 1200 detect prep HPLC): Column, C18, 19*150 mm, 5 um; mobile phase, water with 0.03% ammonia and CH$_3$CN (10% CH$_3$CN up to 45% in 10 min); Detector, UV220 nm] to give compound 32 (Example 3) as a white solid (67.9 mg, 78%). (ES, m/z): [M+H]+ 263.1; $^1$H NMR (300 MHz, D$_2$O) δ 6.20-6.22 (d, J=6.3 Hz, 1H), 4.31 (m, 1H), 4.28-4.30 (m, 1H), 3.68-3.71 (m, 1H), 3.14-3.17 (d, 2H), 2.71 (s, 3H), 1.10 (s, 3H), 1.07 (s, 3H).

Example 4

(3aR,5S,6S,7R,7aR)-2-(dimethylamino)-5-(2-hydroxypropan-2-yl)-5,6,7,7a-tetrahydro-3aH-pyrano[3,2-d]thiazole-6,7-diol

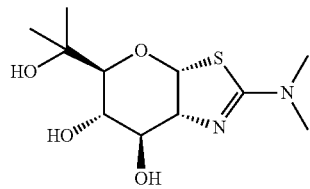 [SMILES: CN(C)C1=N[C@@H]2[C@@H](O)[C@H](O)[C@@H](C(C)(C)O)O[C@@H]2S1]

Scheme V

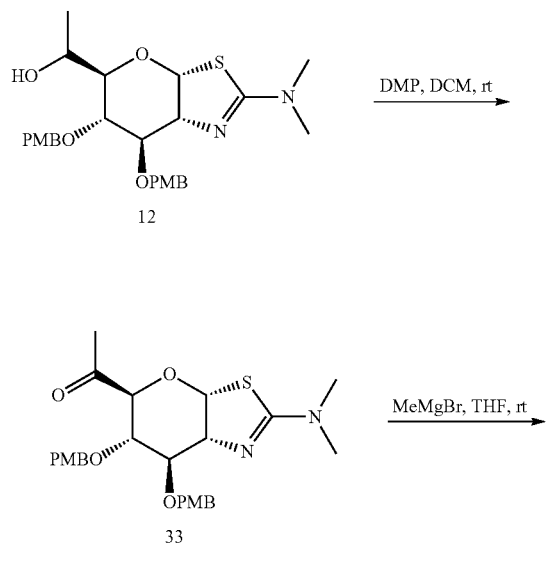

Step 1

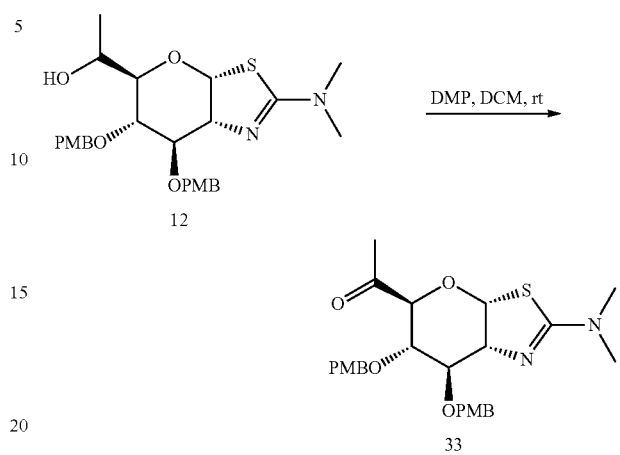

1-(3aR,5S,6S,7R,7aR)-2-(dimethylamino)-6,7-bis(4-methoxybenzyloxy)-5,6,7,7a-tetrahydro-3aH-pyrano[3,2-d]thiazol-5-yl)ethanone (33)

A solution of 1-((3aR,5R,6S,7R,7aR)-6,7-bis(4-methoxybenzyloxy)-2-(dimethylamino)-5,6,7,7a-tetrahydro-3aH-pyrano[3,2-d]thiazol-5-yl)ethanol (700 mg, 139 mmol, a mixture of diastereomers: faster moving one:slower moving one=1:5) in dichloromethane (25 mL) was treated with DMP (1.18 g, 2.78 mmol) for 2 h at room temperature. The reaction mixture was quenched by saturated $Na_2S_2O_4$ (25 mL) and saturated $NaHCO_3$ (25 mL), extracted with dichloromethane (2×50 mL). The combined organic layers were concentrated under vacuum to provide a residue, which was purified by a silica gel column with 10% AcOEt in dichloromethane to give compound 33 as a yellow oil (550 mg, 71%). (ES, m/z): [M+H]$^+$ 500.9; $^1$H NMR (300 MHz, CDCl$_3$) δ 7.24-7.30 (m, 4H), 6.83-6.90 (m, 4H), 6.27-6.29 (d, J=6.3 Hz, 1H), 3.80-4.60 (m, 14H), 3.02 (s, 6H), 2.16 (s, 3H).

Step 2

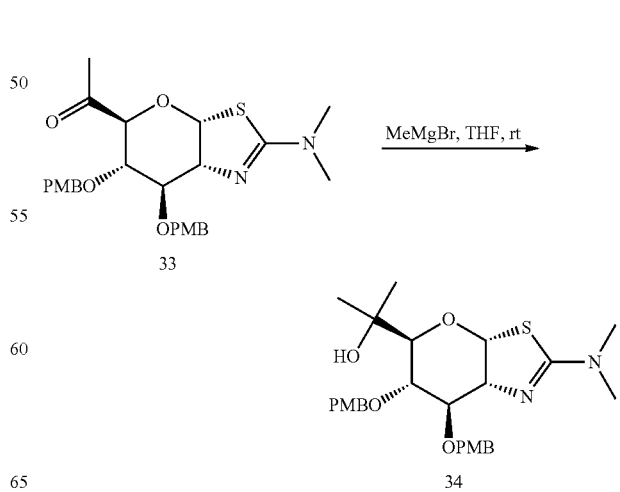

2-03aR,5S,6S,7R,7aR)-2-(Dimethylamino)-6,7-bis (4-methoxybenzyloxy)-5,6,7,7a-tetrahydro-3aH-pyrano[3,2-d]thiazol-5-yl)propan-2-ol (34)

A solution of 1-((3aR,5S,6S,7R,7aR)-6,7-bis(4-methoxybenzyloxy)-2-(dimethylamino)-5,6,7,7a-tetrahydro-3aH-pyrano[3,2-d]thiazol-5-yl)ethanone (500 mg, 1.00 mmol) in THF (20 mL) was treated with methylmagnesium bromide (1 mL, 3M in THF) for 1 h at room temperature, then quenched by brine (50 mL), and extracted with ethyl acetate (3×50 mL). The combined organic layers were dried over anhydrous magnesium sulfate and concentrated under vacuum to provide a residue, which was purified by a silica gel column with 1% methanol in dichloromethane to give compound 34 as a yellow oil (480 mg, 84%). (ES, m/z): [M+H]$^+$ 516.9; 111 NMR (300 MHz, CDCl$_3$) δ 7.33-7.36 (d, J=8.7 Hz, 2H), 6.83-6.94 (m, 4H), 6.32-6.34 (d, J=6.9 Hz, 1H), 4.47-4.71 (m, 5H), 4.28-4.36 (m, 2H), 3.82 (s, 6H), 3.36-3.49 (m, 1H), 3.29 (s, 6H), 1.18 (s, 6H).

Step 3

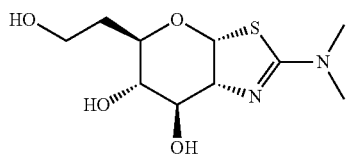 [SMILES: CN(C)C1=N[C@@H]2[C@@H](O)[C@H](O)[C@@H](CCO)O[C@@H]2S1]

(3aR,5S,6S,7R,7aR)-2-(Dimethylamino)-5-(2-hydroxypropan-2-yl)-5,6,7,7a-tetrahydro-3aH-pyrano[3,2-d]thiazole-6,7-diol (35 as its TFA salt)

A solution of 2-((3aR,5S,6S,7R,7aR)-6,7-bis(4-methoxybenzyloxy)-2-(dimethylamino)-5,6,7,7a-tetrahydro-3aH-pyrano[3,2-d]thiazol-5-yl)propan-2-ol (480 mg, 0.93 mmol) in dichloromethane (20 mL) was treated with TFA (2 mL) for 1 h at room temperature. The reaction mixture was condensed to give a residue, which was purified by Prep-HPLC with the following conditions [(3#-Agilent 1200 prep HPLC): Column, SunFire Prep C18,19*50 mm 5 um; mobile phase, WATER with 0.03% NH$_4$OH and CH$_3$CN (10% CH$_3$CN up to 45% in 10 min; Detector, UV 220 nm)] to give compound 35 (Example 4) as a white solid (TFA salt, 238 mg, 92%). (ES, m/z): [M+H]+276.9, $^1$H NMR (300 MHz, CDCl$_3$) δ 6.46-6.48 (d, J=7.5 Hz, 1H), 4.46-4.49 (m, 1H), 4.08-4.10 (m, 1H), 3.81-3.87 (m, 1H), 3.28-3.30 (d, J=8.4 Hz, 1H), 3.18 (s, 3H), 3.12 (s, 3H), 1.07-1.20 (m, 6H).

Example 5

(3aR,5R,6S,7R,7aR)-2-(Dimethylamino)-5-(2-hydroxyethyl)-5,6,7,7a-tetrahydro-3aH-pyrano[3,2-d]thiazole-6,7-diol

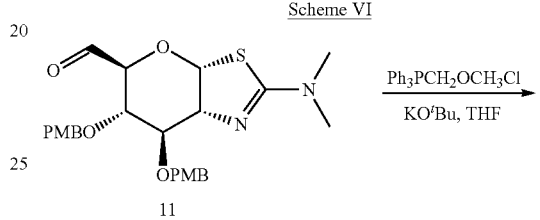

Scheme VI

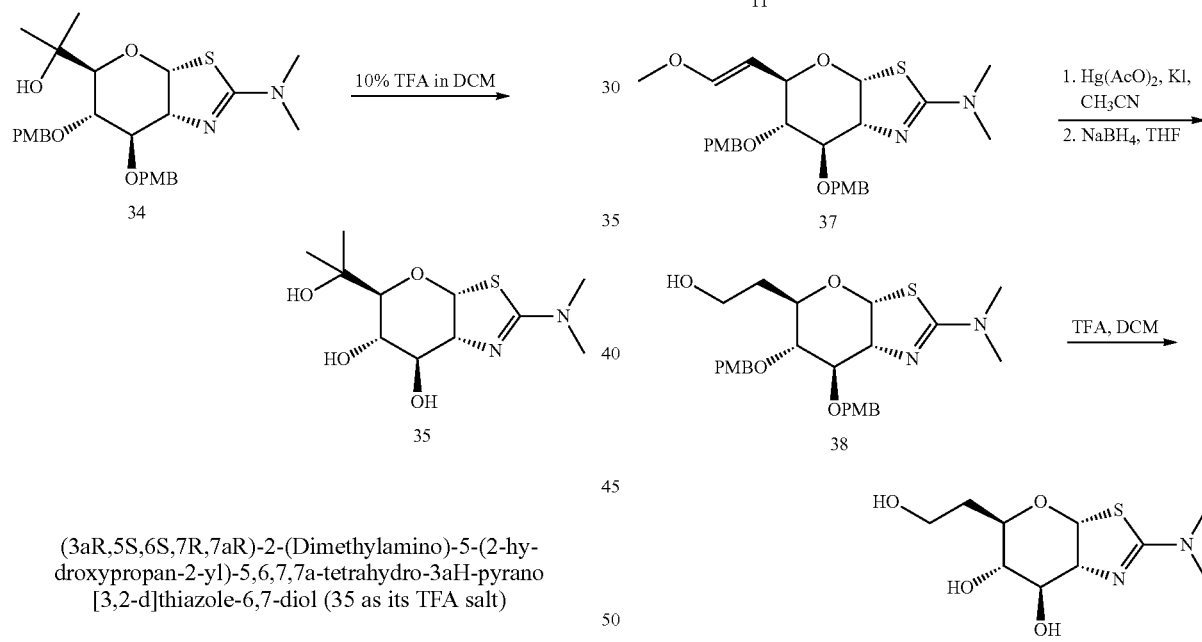

Step 1

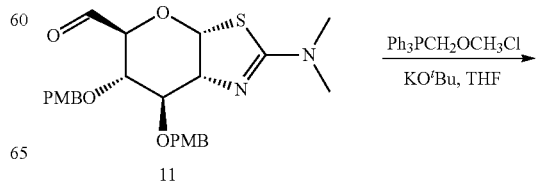

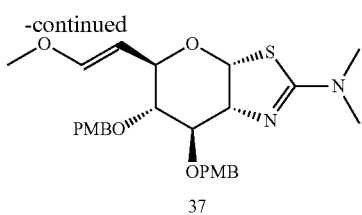

37

(3aR,5R,6R,7R,7aR,E)-6,7-Bis(4-methoxybenzy-
loxy)-5-(2-methoxyvinyl)-N,N-dimethyl-5,6,7,7a-
tetrahydro-3aH-pyrano[3,2-d]thiazol-2-amine (37)

A solution of Ph$_3$PCH$_2$OCH$_3$Br (2.0 g, 5.90 mmol) in THF (30 mL) was treated with t-BuOK (645 mg, 5.76 mmol) at −10° C. for 30 min, and followed by addition of (3aR,5S,6S,7R,7aR)-2-(dimethylamino)-6,7-bis(4-methoxybenzyloxy)-5,6,7,7a-tetrahydro-3aH-pyrano[3,2-d]thiazole-5-carbaldehyde (700 mg, 1.37 mmol). After stirred for 3 h at 0° C., the resulting solution was quenched with ice-water (20 mL), and extracted with ethyl acetate (2×20 mL). The combined organic layers were dried over anhydrous magnesium sulfate and concentrated to give a residue, which was purified by a silica gel column, eluted with 10-50% ethyl acetate in petroleum ether to give the product 37 as a yellow oil (100 mg, 14%). (ES, m/z) [M+H]$^+$ 515.0; $^1$H NMR (300 MHz, CDCl$_3$) δ 7.15-7.35 (m, 4H), 6.84-6.98 (m, 4H), 6.45 (d, J=7.8 Hz, 1H), 6.28 (d, J=6.3 Hz, 1H), 5.21 (m, 1H), 4.45-4.89 (m, 4H), 4.18 (t, J=5.7 Hz, 1H), 3.94 (t, J=4.8 Hz, 1H), 3.87-3.91 (m, 1H), 3.78 (s, 6H), 3.56-3.65 (m, 1H), 3.52 (s, 3H), 2.92 (s, 6H).

Step 2

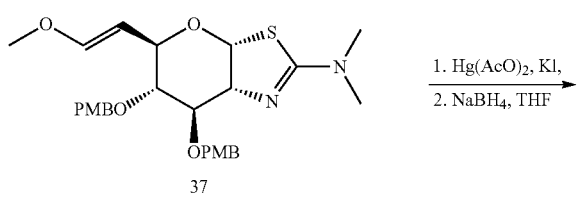

2-03aR,5R,6R,7R,7aR)-2-(Dimethylamino)-6,7-bis
(4-methoxybenzyloxy)-5,6,7,7a-tetrahydro-3aH-
pyrano[3,2-d]thiazol-5-yl)ethanol (38)

To a cold solution of 37 (100 mg, 0.18 mmol) in acetonitrile (20 mL) at −5° C. was added a solution of Hg(OAc)$_2$ (68 mg, 0.21 mmol) in water (10 mL) dropwise. After stirred at 0° C. for 4 h, the reaction mixture was treated with potassium iodide (40 mg, 0.24 mmol) in water (1.6 mL) for 10 min. The reaction solution was quenched with water, extracted with dichloromethane (40 mL), and dried over MgSO$_4$. Removal of solvents gave crude 2-((3aR,5R,6R,7R,7aR)-6,7-bis(4-methoxybenzyloxy)-2-(dimethylamino)-5,6,7,7a-tetrahydro-3aH-pyrano[3,2-d]thiazol-5-yl)acetaldehyde. To a solution of the crude product in dry THF (20 mL) was added NaBH$_4$ (16 mg, 0.42 mmol) at 0° C. in portions. After stirred at 0° C. overnight, the reaction solution was quenched with water (25 mL) and extracted with ethyl acetate (2×20 mL). The combined organic phases were washed with saturated aqueous NH$_4$Cl, dried over MgSO$_4$, and concentrated to give a residue, which was purified by silica gel chromatography, eluted with 20-50% ethyl acetate in petroleum ether to give the product 38 as a light yellow oil (50 mg, 48%). (ES, m/z)[M+H]$^+$ 503.0; $^1$H NMR (300 MHz, CDCl$_3$) δ 7.15-7.35 (m, 4H), 6.84-6.98 (m, 4H), 6.28 (d, J=6.3 Hz, 1H), 4.45-4.89 (m, 4H), 4.18 (t, J=5.7 Hz, 1H), 3.94 (t, J=4.8 Hz, 1H), 3.87-3.91 (m, 1H), 3.78 (s, 6H), 3.56-3.65 (m, 3H), 2.92 (s, 6H), 1.89-1.98 (m, 1H), 1.62-1.73 (m, 1H).

Step 3

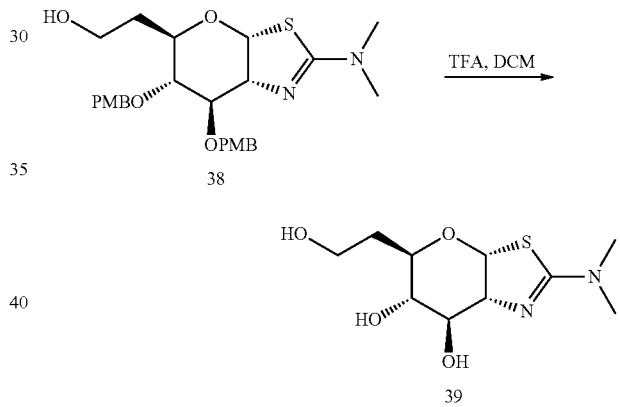

(3aR,5R,6S,7R,7aR)-2-(Dimethylamino)-5-(2-hy-
droxyethyl)-5,6,7,7a-tetrahydro-3aH-pyrano[3,2-d]
thiazole-6,7-diol (39)

A solution of 2-03aR,5R,6R,7R,7aR)-2-(dimethylamino)-6,7-bis(4-methoxybenzyloxy)-5,6,7,7a-tetrahydro-3aH-pyrano[3,2-d]thiazol-5-yl)ethanol (100 mg, 0.18 mmol) in dichloromethane (20 mL) was treated with TFA overnight at room temperature. Removal of solvents provided a residue, which was purified by Prep-HPLC with the following conditions: (Agilent 1200 prep HPLC: Column, Sun fire prep. C18; mobile phase, water with 0.03% trifluoroacetic acid and CH$_3$CN (10% up to 20% in time 10); Detector, 220 nm.) to give the product 39 (Example 5) as a white solid (5.0 mg, 11%). (ES, m/z)[M+H]$^+$ 263.0; $^1$HNMR (300 MHz, D$_2$O) δ 6.29 (d, J=6.3 Hz, 1H), 4.18 (t, J=5.7 Hz, 1H), 3.98 (t, J=4.8 Hz, 1H), 3.56-3.65 (m, 3H), 3.39-3.43 (m, 1H), 2.92 (s, 6H), 1.89-1.98 (m, 1H), 1.62-1.72 (m, 1H).

Example 6 & 7

(3aR,5R,6S,7R,7aR)-2-(Dimethylamino)-5-ethyl-5,6,7,7a-tetrahydro-3aH-pyrano[3,2-d]thiazole-6,7-diol and (3aR,5R,6S,7R,7aR)-2-(dimethylamino)-5-vinyl-5,6,7,7a-tetrahydro-3aH-pyrano[3,2-d]thiazole-6,7-diol

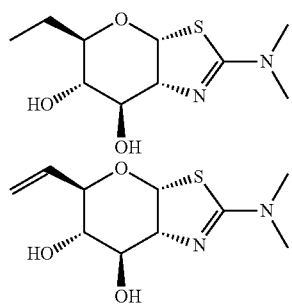

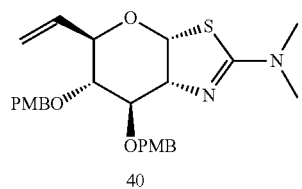

(3aR,5R,6R,7R,7aR)-6,7-Bis(4-methoxybenzyloxy)-N,N-dimethyl-5-vinyl-5,6,7,7a-tetrahydro-3aH-pyrano[3,2-d]thiazol-2-amine (40)

To a suspension of methyltriphenylphosphonium bromide (5.9 g, 16.5 mmol) in THF (70 mL) was treated with n-BuLi (5.9 ml, 2.5 M in THF) for 30 min at 0° C., and followed by addition of (3aR,5S,6S,7R,7aR)-2-(dimethylamino)-6,7-bis(4-methoxybenzyloxy)-5,6,7,7a-tetrahydro-3aH-pyrano[3,2-d]thiazole-5-carbaldehyde (1.6 g, 3.29 mmol) in THF (10 mL). After stirred overnight at room temperature, the reaction mixture was quenched with water (50 mL), extracted with dichloromethane (3×50 mL). The organic phases was combined and dried over MgSO₄, concentrated under vacuum to give a residue, which was purified by a silica gel column, eluted with 30% ethyl acetate in petroleum ether to give compound 40 as a yellow oil (520 mg, purity 57% by LC-MS). This material was used in the next step without further purification. (ES, m/z): [M+H]⁺ 485.0.

Scheme VII

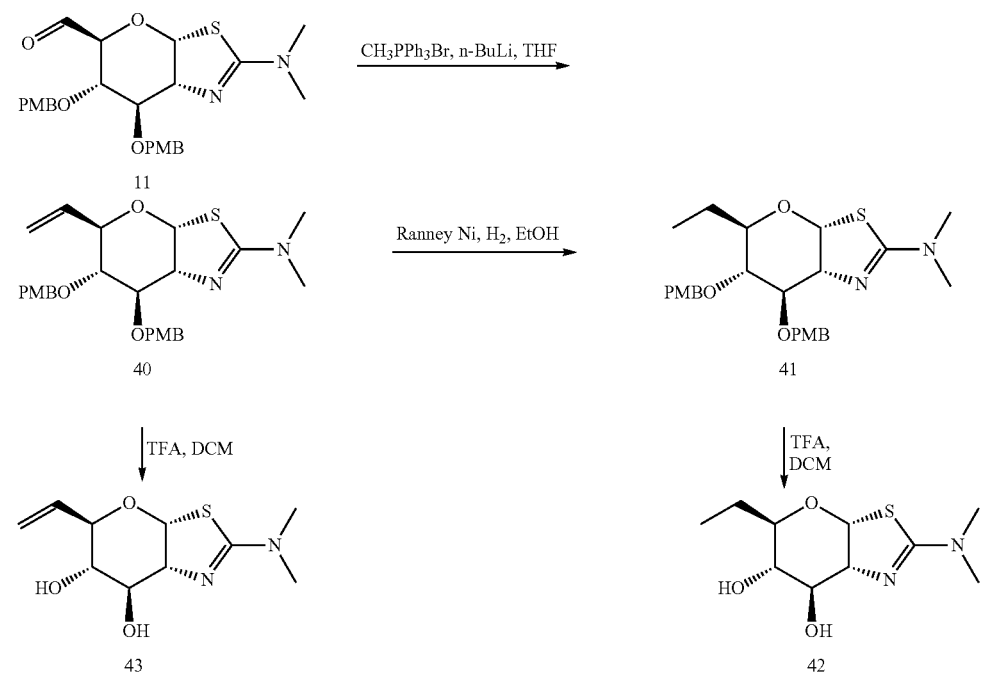

Step 1

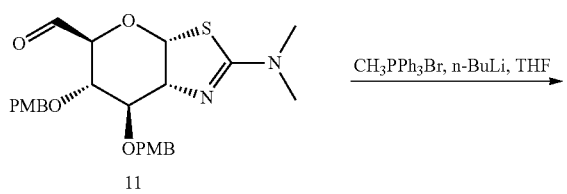

Step 2

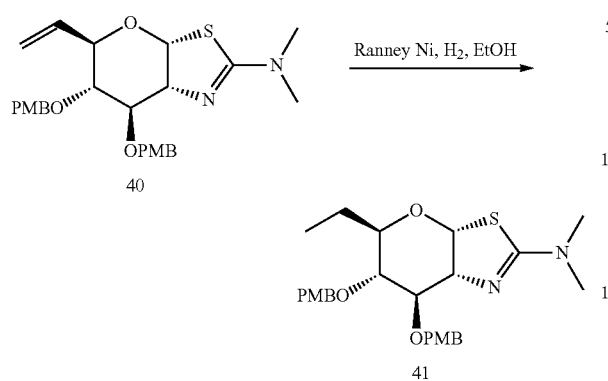

(3aR,5R,6R,7R,7aR)-5-Ethyl-6,7-bis(4-methoxybenzyloxy)-N,N-dimethyl-5,6,7,7a-tetrahydro-3aH-pyrano[3,2-d]thiazol-2-amine (41)

A solution of above crude compound 2 (300 mg, purity 57% by LC-MS) was dissolved into ethanol (20 mL) and treated with Ranney Ni (200 mg) under $H_2$ atmosphere overnight at room temperature. After filtration, the organic solution was concentrated to give crude compound 41 (260 mg, purity 54% by LC-MS), which was used in the next step without further purification. (ES, m/z): [M+H]$^+$ 487.0.

Step 3

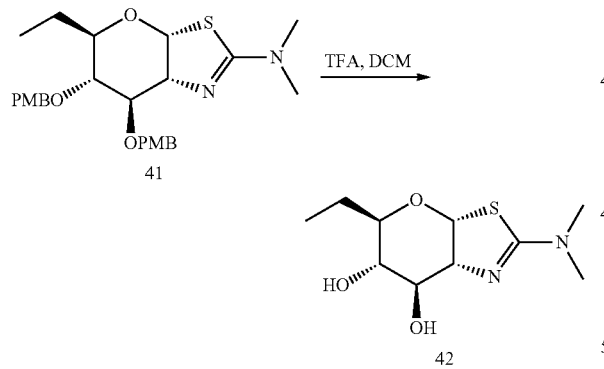

(3aR,5R,6S,7R,7aR)-2-(Dimethylamino)-5-ethyl-5,6,7,7a-tetrahydro-3aH-pyrano[3,2-d]thiazole-6,7-diol (42)

A solution of above crude product 41 (260 mg, purity 54% by LC-MS) in dichloromethane (10 mL) was treated with TFA (1 mL) for 4 hours at room temperature. The solution was adjusted to pH at 8 with $NH_4OH$, and then condensed to give a crude product, which was purified by Prep-HPLC with the following conditions (Agilent 1200 prep HPLC: Column, SunFire Prep C18,19*50 mm 5 um; mobile phase, WATER with 0.03% $NH_4OH$ and $CH_3CN$ (10% $CH_3CN$ up to 45% in 10 min; Detector, UV 220 nm) to provide compound 42 (Example 6) as a white solid (38 mg). (ES, m/z): [M+H]$^+$ 247.0. $^1$H NMR (300 MHz, D$_2$O) δ 6.18-6.21 (d, J=6.6 Hz, 1H), 4.09-4.13 (t, J=6.0 Hz, 1H), 3.91-3.94 (t, J=4.8 Hz, 1H), 3.42-3.44 (m, 2H), 2.92 (s, 6H), 1.69-1.77 (m, 1H), 1.40-1.50 (m, 1H), 0.84-0.89 (t, J=7.5 Hz, 3H).

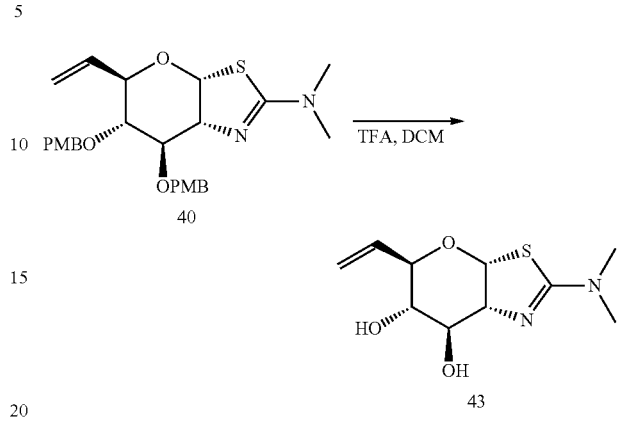

(3aR,5R,6S,7R,7aR)-2-(Dimethylamino)-5-vinyl-5,6,7,7a-tetrahydro-3aH-pyrano[3,2-d]thiazole-6,7-diol (43)

A solution of above crude product 40 (220 mg, purity 57% by LC-MS) in dichloromethane (10 mL) was treated with TFA (1 mL) for 4 hours at room temperature. The solution was adjusted to pH at 8 with $NH_4OH$, and then condensed to give a crude product, which was purified by Prep-HPLC with the following conditions (Agilent 1200 prep HPLC: Column, SunFire Prep C18, 19*50 mm 5 um; mobile phase, WATER with 0.03% $NH_4OH$ and $CH_3CN$ (10% $CH_3CN$ up to 45% in 10 min; Detector, UV 220 nm) to provide compound 43 (Example 7) as a white solid (35.7 mg). (ES, m/z): 245.0. $^1$H NMR (300 MHz, D$_2$O) δ 6.20-6.22 (d, J=6.3 Hz, 1H), 5.79-5.87 (m, 1H), 5.30-5.38 (m, 2H), 3.98-4.08 (m, 2H), 3.87-3.91 (t, J=6.0 Hz, 1H), 3.46-3.52 (m, 1H), 2.93 (s, 6H).

Example 8

(3aR,5R,6S,7R,7aR)-5-Ethyl-2-(methylamino)-5,6,7,7a-tetrahydro-3aH-pyrano[3,2-d]thiazole-6,7-diol

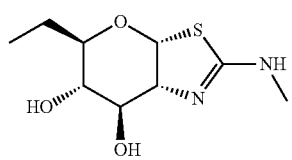

Scheme VIII

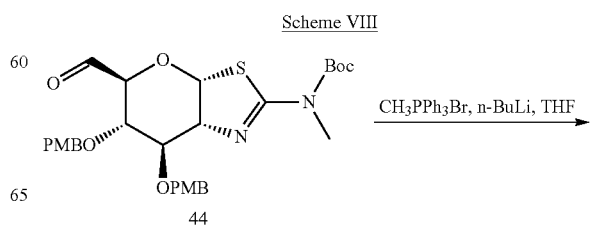

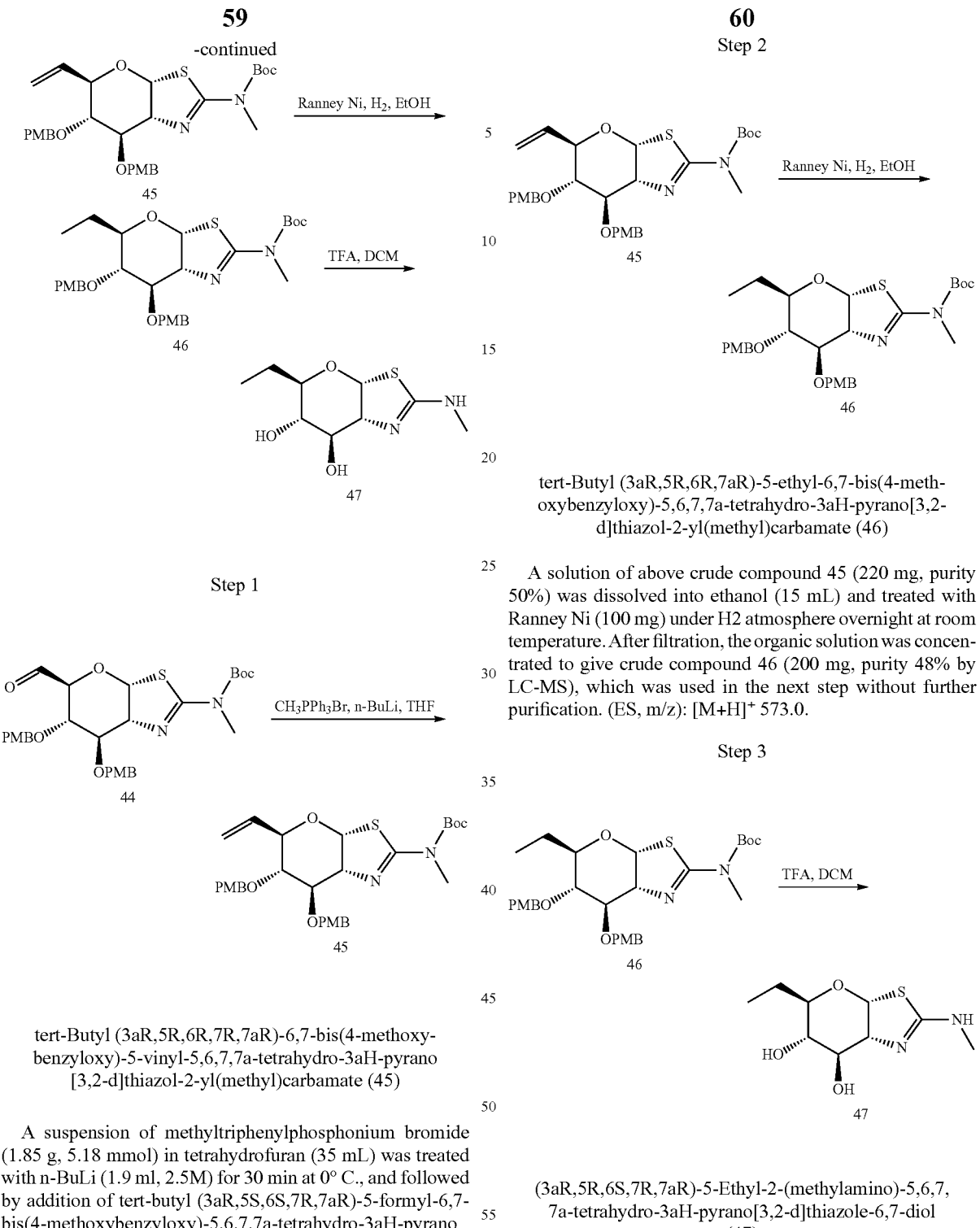

Step 1 tert-Butyl (3aR,5R,6R,7R,7aR)-6,7-bis(4-methoxybenzyloxy)-5-vinyl-5,6,7,7a-tetrahydro-3aH-pyrano[3,2-d]thiazol-2-yl(methyl)carbamate (45)

A suspension of methyltriphenylphosphonium bromide (1.85 g, 5.18 mmol) in tetrahydrofuran (35 mL) was treated with n-BuLi (1.9 ml, 2.5M) for 30 min at 0° C., and followed by addition of tert-butyl (3aR,5S,6S,7R,7aR)-5-formyl-6,7-bis(4-methoxybenzyloxy)-5,6,7,7a-tetrahydro-3aH-pyrano[3,2-d]thiazol-2-yl(methyl)carbamate (44) prepared from compound 28 by a procedure identical to that described for the conversion of 10 to 11) (0.6 g, 1.05 mmol) in THF (5 mL). The resulting solution was stirred overnight at room temperature, quenched by water (25 mL), and extracted with dichloromethane (3×25 ml). The combined organic layers were dried over magnesium sulfate and concentrated under vacuum to give a residue, which was purified by a silica gel column, eluted with 20% ethyl acetate in petroleum ether to give crude compound 45 as a yellow oil (220 mg, purity 50% by LC-MS). (ES, m/z): [M+H]+ 571.0.

Step 2 tert-Butyl (3aR,5R,6R,7R,7aR)-5-ethyl-6,7-bis(4-methoxybenzyloxy)-5,6,7,7a-tetrahydro-3aH-pyrano[3,2-d]thiazol-2-yl(methyl)carbamate (46)

A solution of above crude compound 45 (220 mg, purity 50%) was dissolved into ethanol (15 mL) and treated with Ranney Ni (100 mg) under H2 atmosphere overnight at room temperature. After filtration, the organic solution was concentrated to give crude compound 46 (200 mg, purity 48% by LC-MS), which was used in the next step without further purification. (ES, m/z): [M+H]+ 573.0.

Step 3

(3aR,5R,6S,7R,7aR)-5-Ethyl-2-(methylamino)-5,6,7,7a-tetrahydro-3aH-pyrano[3,2-d]thiazole-6,7-diol (47)

A solution of above crude product 46 (200 mg, purity 48% by LC-MS) in dichloromethane (10 mL) was treated with TFA (1 mL) for 4 hours at room temperature. The solution was adjusted to pH at 8 with NH4OH, and then condensed to give a crude product, which was purified by Prep-HPLC with the following conditions (Agilent 1200 prep HPLC: Column, SunFire Prep C18,19*50 mm 5 um; mobile phase, WATER with 0.03% NH4OH and CH3CN (10% CH3CN up to 45% in 10 min; Detector, UV 220 nm) to provide the title compound 47 (Example 8) as a white solid (7.6 mg). (ES, m/z): [M+H]+

233.0. $^1$H NMR (300 MHz, D$_2$O) δ 6.18-6.20 (d, J=6.3 Hz, 1H), 4.09-4.13 (t, J=6.0 Hz, 1H), 3.92-3.95 (t, J=4.8 Hz, 1H), 3.36-3.45 (m, 2H), 2.75 (s, 3H), 1.65-1.75 (m, 1H), 1.38-1.48 (m, 1H), 0.81-0.86 (t, J=7.5 Hz, 3H).

Example 9

(3aR,5S,6S,7R,7aR)-2-(Dimethylamino)-5-((S)-1-fluoroethyl)-5,6,7,7a-tetrahydro-3aH-pyrano[3,2-d]thiazole-6,7-diol

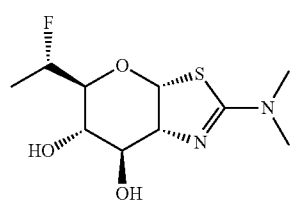 [SMILES: C[C@H](F)[C@H]1O[C@@H]2SC(N(C)C)=N[C@@H]2[C@@H](O)[C@@H]1O]

Scheme IX

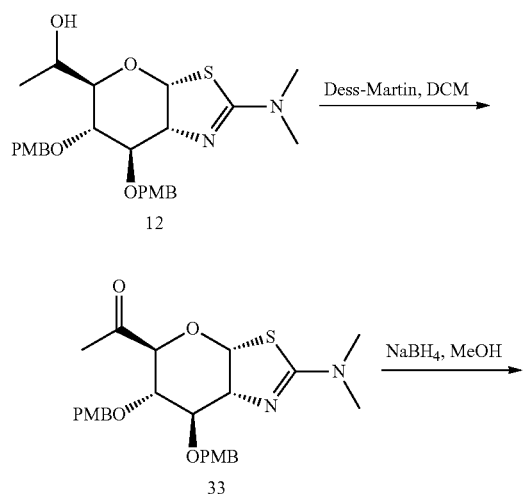

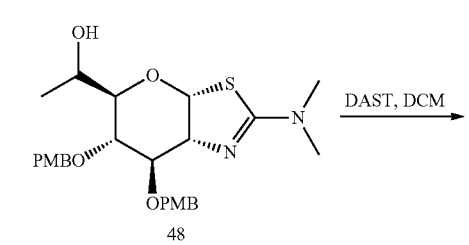

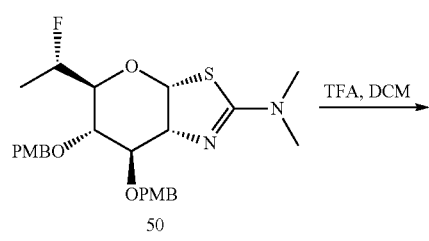

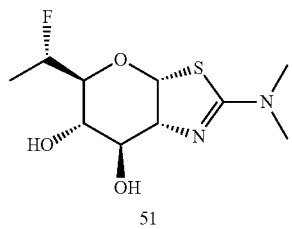

51

Step 1

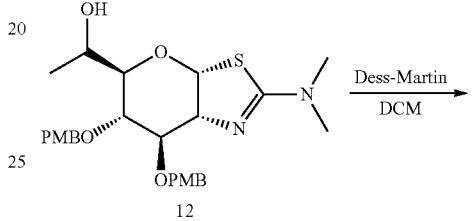

1-((3aR,5S,6S,7R,7aR)-2-(Dimethylamino)-6,7-bis(4-methoxybenzyloxy)-5,6,7,7a-tetrahydro-3aH-pyrano[3,2-d]thiazol-5-yl)ethanone (33)

A solution of 1-((3aR,5R,6S,7R,7aR)-2-(dimethylamino)-6,7-bis(4-methoxybenzyloxy)-5,6,7,7a-tetrahydro-3aH-pyrano[3,2-d]thiazol-5-yl)ethanol (450 mg, 0.90 mmol, mixture of diastereomers, faster eluting isomer: slower eluting isomer 1:5 by HPLC and $^1$HNMR) in dichloromethane (20 mL) was treated with Dess-Martin reagent (760 mg, 1.80 mmol) for 2 hours at room temperature. The reaction mixture was quenched by sat. aqueous Na$_2$S$_2$O$_3$ solution (20 mL) and sat. aqueous NaHCO$_3$ solution (20 mL), and extracted with dichloromethane (2×20 mL). The combined, organic layers were dried over anhydrous sodium sulfate and concentrated under reduced pressure to provide a residue, which was purified by silica gel column, eluted with 2-3% methanol in dichloromethane to give compound 33 as a yellow syrup (400 mg, 88%). (ES, m/z): [M+H]$^+$ 501.0; $^1$H NMR (300 MHz, CDCl$_3$) δ 7.25-7.30 (m, 4H), 6.83-6.90 (m, 4H), 6.29-6.31 (d, J=6.0 Hz, 1H), 4.26-4.64 (m, 6H), 3.81-3.98 (m, 8H), 2.96-3.02 (m, 6H), 2.17 (s, 3H).

Step 2

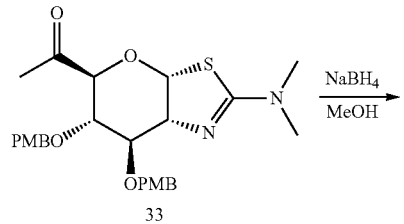
33

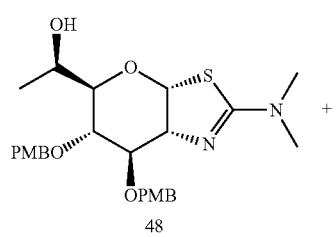
48

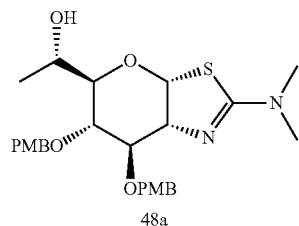
48a (R)-1-((3aR,5R,6S,7R,7aR)-2-(Dimethylamino)-6,7-bis(4-methoxybenzyloxy)-5,6,7,7a-tetrahydro-3aH-pyrano[3,2-d]thiazol-5-yl)ethanol (48) and (S)-1-((3aR,5R,6S,7R,7aR)-2-(dimethylamino)-6,7-bis(4-methoxybenzyloxy)-5,6,7,7a-tetrahydro-3aH-pyrano[3,2-d]thiazol-5-yl)ethanol (48a)

A solution of 1-((3aR,5S,6S,7R,7aR)-2-(dimethylamino)-6,7-bis(4-methoxybenzyloxy)-5,6,7,7a-tetrahydro-3aH-pyrano[3,2-d]thiazol-5-yl)ethanone (400 mg, 0.80 mmol) in methanol (10 mL) was treated with NaBH$_4$ (150 mg, 3.95 mmol) for 1 hour at room temperature. The reaction was quenched by water (10 mL), and extracted with ethyl acetate (3×20 mL). The combined organic layers were dried over anhydrous sodium sulfate and concentrated under reduced pressure to provide a residue, which was purified by Chiral-HPLC, eluted with 20% ethanol in hexane to give compound 48 as a light yellow oil (slower eluting isomer by Chiral-HPLC, 270 mg, 67%). (ES, m/z): [M+H]$^+$ 503.0; $^1$H NMR (300 MHz, CDCl$_3$) δ 7.22-7.36 (m, 4H), 6.84-6.92 (m, 4H), 6.34 (broad, 1H), 4.53-4.71 (m, 4H), 4.25-4.35 (m, 2H), 3.76-3.94 (m, 8H), 3.45-3.49 (dd, J=4.2 Hz, 4.5 Hz, 1H), 3.01 (s, 6H), 1.19-1.21 (d, J=6.0 Hz, 1H), 1.11-1.13 (d, J=6.0 Hz, 3H); and compound 48a as a light yellow oil (faster eluting isomer by Chiral-HPLC, 113 mg, 28%). (ES, m/z): [M+H]$^+$ 503.0; $^1$H NMR (300 MHz, CDCl$_3$) δ 7.32-7.35 (d, J=8.4 Hz, 2H), 7.24-7.27 (d, J=8.7 Hz, 2H), 6.83-6.91 (m, 4H), 6.31-6.33 (d, J=6.6 Hz, 1H), 4.60-4.71 (m, 2H), 4.53-4.57 (m, 2H), 4.25-4.35 (m, 2H), 3.85-3.87 (m, 7H), 3.73-3.75 (d, J=8.7 Hz, 1H), 3.32-3.36 (dd, J=3.6 Hz, 3.3 Hz, 1H), 3.01 (s, 6H), 1.92-1.94 (d, J=7.5 Hz, 1H), 1.19-1.21 (d, J=6.3 Hz, 3H).

Step 3

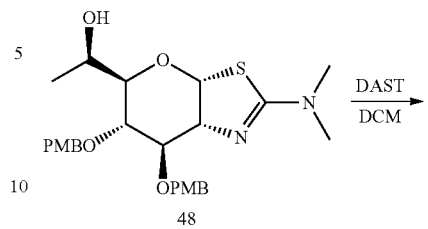
48

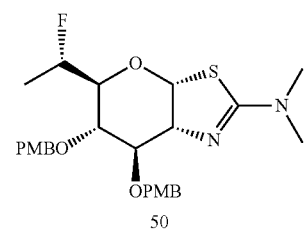
50

(3aR,5S,6S,7R,7aR)-5-((S)-1-Fluoroethyl)-6,7-bis(4-methoxybenzyloxy)-N,N-dimethyl-5,6,7,7a-tetrahydro-3aH-pyrano[3,2-d]thiazol-2-amine (50)

A solution of (R)-1-((3aR,5R,6S,7R,7aR)-2-(dimethylamino)-6,7-bis(4-methoxybenzyloxy)-5,6,7,7a-tetrahydro-3aH-pyrano[3,2-d]thiazol-5-yl)ethanol (280 mg, 0.56 mmol) in dichloromethane (10 mL) was treated with DAST (900 mg, 5.59 mmol) at −78° C. for 10 min and at 0° C. for 1 hr. The reaction was quenched by sat. aqueous Na$_2$CO$_3$ solution (30 mL), and extracted with dichloromethane (2×20 mL). The combined organic layers were dried over anhydrous sodium sulfate and concentrated under reduced pressure to provide a residue, which was purified by silica gel column, eluted with 1-2% methanol in dichloromethane to give compound 50 as a yellow syrup (240 mg, 85%). (ES, m/z): [M+H]$^+$ 505.0; $^1$H NMR (300 MHz, CDCl$_3$) δ 7.22-7.43 (m, 4H), 6.83-6.94 (m, 4H), 6.38-6.50 (m, 1H), 4.58-4.78 (m, 6H), 3.75-3.90 (m, 8H), 3.46-3.50 (m, 1H), 3.05-3.18 (m, 6H), 1.27-1.36 (m, 3H).

Step 4

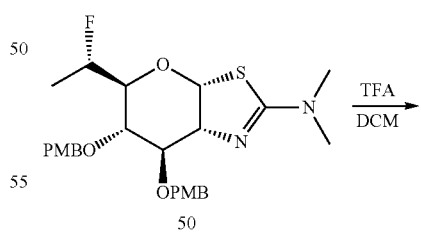
50

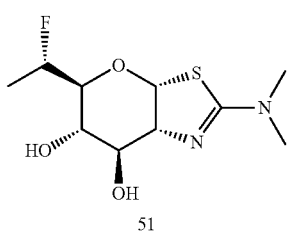
51

(3aR,5S,6S,7R,7aR)-2-(Dimethylamino)-5-((S)-1-fluoroethyl)-5,6,7,7a-tetrahydro-3aH-pyrano[3,2-d]thiazole-6,7-diol (51)

A solution of (3aR,5S,6S,7R,7aR)-5-((S)-1-fluoroethyl)-6,7-bis(4-methoxybenzyloxy)-N,N-dimethyl-5,6,7,7a-tetrahydro-3aH-pyrano[3,2-d]thiazol-2-amine (240 mg, 0.48 mmol) in dichloromethane (20 mL) was treated with TFA (2 mL) for 1 h at room temperature. The reaction mixture was concentrated under reduced pressure to give a residue, which was purified by Prep-HPLC under the following conditions [(Agilent 1200 prep HPLC): Column, SunFire Prep C18, 19*50 mm 5 um; mobile phase, water with 0.03% NH$_4$OH and CH$_3$CN (10% CH$_3$CN up to 45% in 10 min); Detector, UV 220 nm] to afford compound 51 (Example 9) as a white solid (30 mg, 24%). (ES, m/z): [M+H]$^+$ 265.0; $^1$H NMR (300 MHz, D$_2$O) δ 6.23-6.25 (d, J=6.0 Hz, 1H), 4.93-4.99 (m, 0.5H), 4.77-4.84 (m, 0.5H), 4.17 (t, J=6.0 Hz, 1H), 4.00 (t, J=6.0 Hz, 1H), 3.71-3.74 (m, 1H), 3.36-3.49 (m, 1H), 2.94 (s, 1H), 1.25-1.35 (dd, J=6.6 Hz, 6.3 Hz, 3H).

Example 10 and 11

(3aR,5S,6S,7R,7aR)-2-(dimethylamino)-5-((S)-2,2,2-trifluoro-1-hydroxyethyl)-5,6,7,7a-tetrahydro-3aH-pyrano[3,2-d]thiazole-6,7-diol and (3aR,5S,6S,7R,7aR)-2-(dimethylamino)-5-((R)-2,2,2-trifluoro-1-hydroxyethyl)-5,6,7,7a-tetrahydro-3aH-pyrano[3,2-d]thiazole-6,7-diol

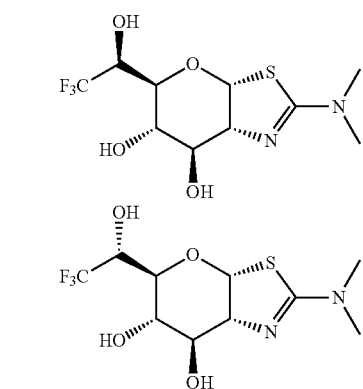

Scheme X

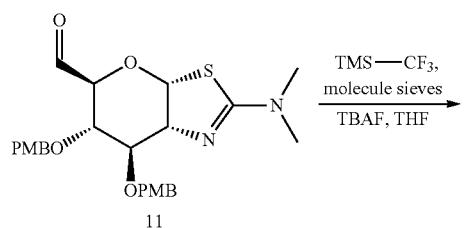

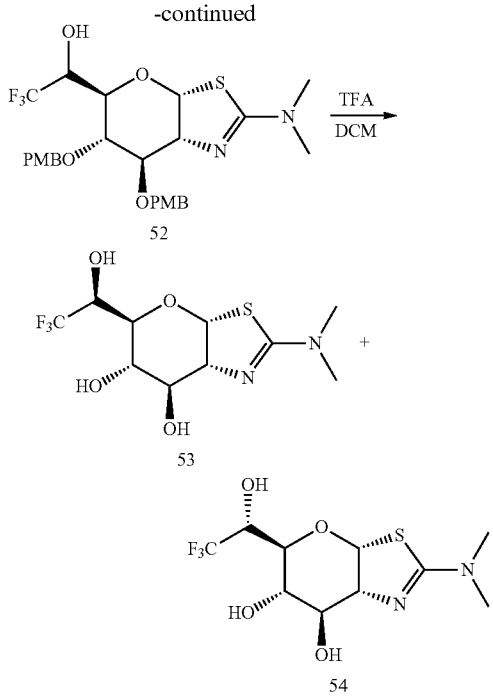

1-((3aR,5R,6S,7R,7aR)-2-(Dimethylamino)-6,7-bis(4-methoxybenzyloxy)-5,6,7,7a-tetrahydro-3aH-pyrano[3,2-d]thiazol-5-yl)-2,2,2-trifluoroethanol (52, mixture of two diastereomers)

To a stirred mixture of TBAF (107 mg, 0.41 mmol) and 4 Å molecule sieves in THF (20 mL) was added a solution of (3aR,5S,6S,7R,7aR)-2-(dimethylamino)-6,7-bis(4-methoxybenzyloxy)-5,6,7,7a-tetrahydro-3aH-pyrano[3,2-d]thiazole-5-carbaldehyde (1) (400 mg, 0.82 mmol) and TMS-CF$_3$ (230 mg, 1.64 mmol) in THF (5 mL) at 0° C. After stirring for 4 hours at 0° C., the reaction was quenched by brine (30 mL), and extracted with ethyl acetate (3×20 mL). The combined organic layers were dried over anhydrous sodium sulfate and

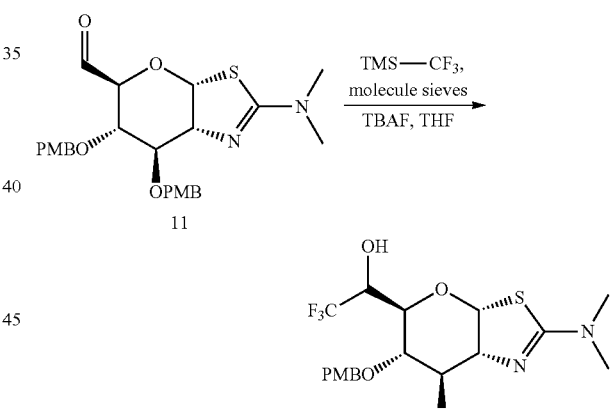

Step 1 concentrated under reduced pressure to provide a residue, which was purified by silica gel column, eluted with 2-3% methanol in dichloromethane to give compound 52 as a yellow syrup (300 mg, 65%, a mixture of diastereomers, faster eluting isomer:slower moving isomer=1:2 by Chiral-HPLC). (ES, m/z): [M+H]$^+$ 557.0; $^1$H NMR (300 MHz, CDCl$_3$) δ 7.20-7.35 (m, 4H), 6.85-6.92 (m, 4H), 6.25-6.27 (d, J=6.6 Hz, 1H), 4.56-4.69 (m, 5H), 4.30-4.36 (m, 2H), 3.82-3.83 (m, 8H), 2.99-3.00 (m, 6H).

Step 2

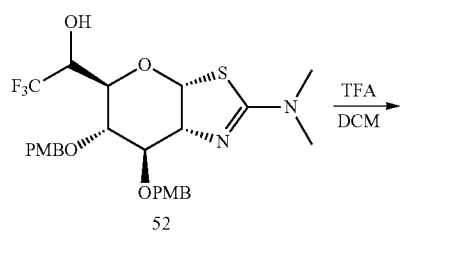

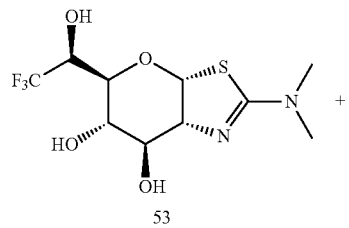

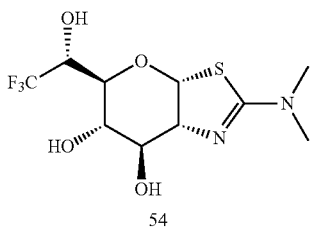

(3aR,5S,6S,7R,7aR)-2-(dimethylamino)-5-((S)-2,2,2-trifluoro-1-hydroxyethyl)-5,6,7,7a-tetrahydro-3aH-pyrano[3,2-d]thiazole-6,7-diol (53) and (3aR,5S,6S,7R,7aR)-2-(dimethylamino)-5-((R)-2,2,2-trifluoro-1-hydroxyethyl)-5,6,7,7a-tetrahydro-3aH-pyrano[3,2-d]thiazole-6,7-diol (54)

A solution of 1-((3aR,5R,6S,7R,7aR)-2-(dimethylamino)-6,7-bis(4-methoxybenzyloxy)-5,6,7,7a-tetrahydro-3aH-pyrano[3,2-d]thiazol-5-yl)-2,2,2-trifluoroethanol (52, a mixture of two diastereomers from previous step) (400 mg, 0.72 mmol) in dichloromethane (20 mL) was treated with TFA (2 mL) for 1 h at room temperature. The reaction mixture was concentrated under reduced pressure to give a residue, which was purified by Prep-HPLC under the following conditions [(Agilent 1200 prep HPLC): Column, SunFire Prep C18, 19*50 mm 5 um; mobile phase, water with 0.03% NH$_4$OH and CH$_3$CN (10% CH$_3$CN up to 45% in 10 min); Detector, UV 220 nm] to afford compound 53 (Example 10) as a white solid (faster eluting isomer, 62 mg, 27%): (ES, m/z): [M+H]$^+$ 316.9; $^1$H NMR (300 MHz, D$_2$O) δ 6.19-6.21 (d, J=6.6 Hz, 1H), 4.22-4.27 (m, 1H), 4.04 (t, J=6.6 Hz, 1H), 3.86-3.90 (m, 1H), 3.71-3.76 (m, 1H), 2.93 (s, 6H); Compound 54 (Example 11) as a white solid (slower eluting isomer, 55 mg, 24%). (ES, m/z): [M+H]$^+$ 316.9; $^1$H NMR (300 MHz, D$_2$O) δ 6.25-6.27 (d, J=6.3 Hz, 1H), 4.26-4.34 (m, 1H), 4.10 (t, J=6.0 Hz, 1H), 3.94 (t, J=5.4 Hz, 1H), 3.72-3.82 (m, 1H), 2.92 (s, 6H).

Example 12

(3aR,5S,6S,7R,7aR)-5-(1,1-Difluoroethyl)-2-(dimethylamino)-5,6,7,7a-tetrahydro-3aH-pyrano[3,2-d]thiazole-6,7-diol

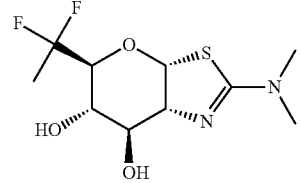 [SMILES: CN(C)C1=N[C@@H]2[C@@H](O)[C@H](O)[C@@H](C(C)(F)F)O[C@@H]2S1]

Scheme XI

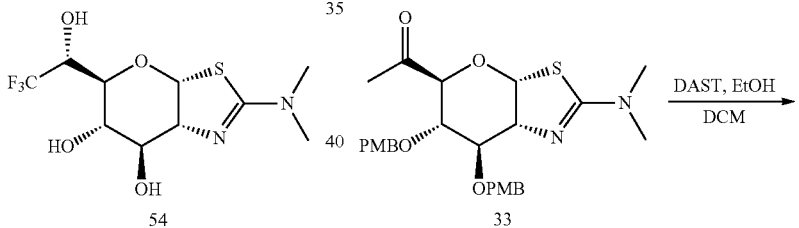

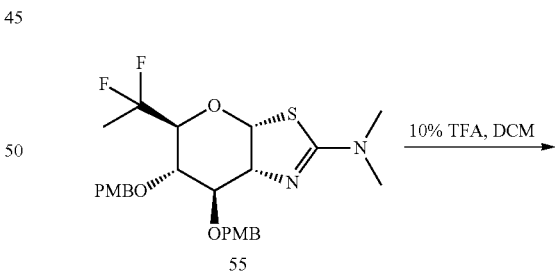

Step 1

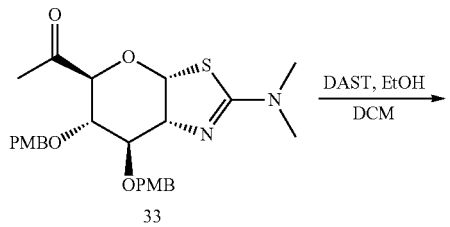

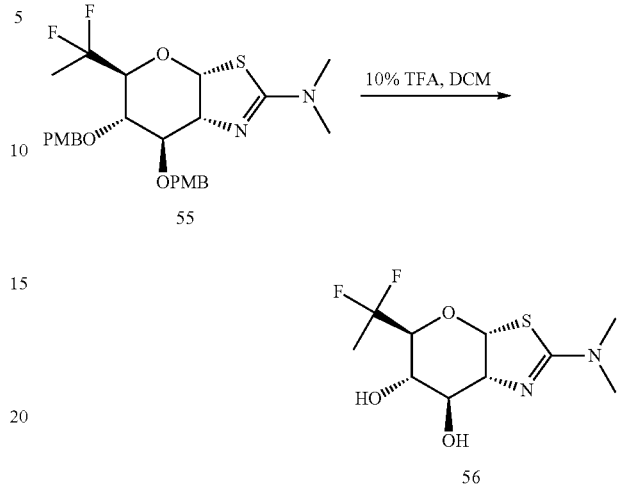

Step 2

(S)-1-((3aR,5R,6S,7R,7aR)-2-(Dimethylamino)-6,7-bis(4-methoxybenzyloxy)-5,6,7,7a-tetrahydro-3aH-pyrano[3,2-d]thiazol-5-yl)ethanol (55)

A solution of 1-((3aR,5S,6S,7R,7aR)-2-(dimethylamino)-6,7-bis(4-methoxybenzyloxy)-5,6,7,7a-tetrahydro-3aH-pyrano[3,2-d]thiazol-5-yl)ethanone (280 mg, 0.56 mmol) in dichloromethane (10 mL) was treated with (diethylamino)sulfur trifluoride (451 g, 2.80 mol) and ethanol (5.2 mg, 0.11 mmol) overnight at room temperature. The reaction was then quenched by addition of sat. aqueous sodium carbonate solution (50 mL), and extracted with dichloromethane (3×20 mL). The combined organic layers were dried over anhydrous magnesium sulfate and condensed under vacuum to give a crude product 55 (140 mg), which was used in the next step without further purification. (ES, m/z) [M+H]$^+$ 523.0; $^1$H NMR (300 MHz, CD$_3$Cl) δ $^1$H NMR (300 MHz, CDCl$_3$) δ 7.24-7.30 (m, 4H), 6.84-6.95 (m, 4H), 6.30-6.32 (m, 1H), 4.57-4.62 (m, 4H), 4.27-4.35 (m, 2H), 3.81-3.91 (m, 8H), 2.99-3.01 (m, 6H), 1.56-1.62 (m, 3H).

1-O3aR,5S,6S,7R,7aR)-2-(Dimethylamino)-6,7-bis(4-methoxybenzyloxy)-5,6,7,7a-tetrahydro-3aH-pyrano[3,2-d]thiazol-5-yl)ethanone (56)

A solution of crude product 2 (140 mg, 0.27 mmol, 1.00 equiv) in dichloromethane (10 mL) was treated with TFA (1 mL) for 2 hrs at room temperature, and then condensed o give a residue, which was purified by Prep-HPLC with the following conditions [(Prep-HPLC): Column, 19*150 mm; mobile phase, Water with 0.03% ammonia and CH3CN (10% CH3CN up to 35% in 10 min); Detector, 220 nm.] to give the title compound 56 (Example 12) as a white solid (76.3 mg, 40%). (ES, m/z) [M+H]$^+$ 282.9; $^1$H NMR (300 MHz, D$_2$O) δ 6.23 (d, J=6.6 Hz, 1H), 4.35 (t, J=5.1 Hz, 1H), 4.14 (t, J=2.7 Hz, 1H), 3.91-3.95 (m, 1H), 3.57-3.67 (m, 1H), 2.94 (s, 6H), 1.59 (t, J=19.8 Hz, 3H).

The following examples were synthesized according to procedures analogous to the schemes and examples outlined above.

TABLE 1

| Example | structure | Name | MH+ |
|---------|-----------|------|-----|
| 13 | 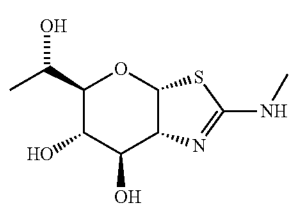 [SMILES: CNC1=N[C@@H]2[C@@H](O)[C@H](O)[C@@H]([C@H](C)O)O[C@@H]2S1] | (3aR,5R,6S,7R,7aR)-5-((S)-1-hydroxyethyl)-2-(methylamino)-5,6,7,7a-tetrahydro-3aH-pyrano[3,2-d]thiazole-6,7-diol(Slower eluting isomer) | 249.1 |
| 14 | 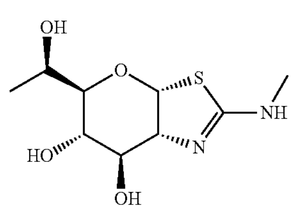 [SMILES: CNC1=N[C@@H]2[C@@H](O)[C@H](O)[C@@H]([C@@H](C)O)O[C@@H]2S1] | (3aR,5R,6S,7R,7aR)-5-((R)-1-hydroxyethyl)-2-(methylamino)-5,6,7,7a-tetrahydro-3aH-pyrano[3,2-d]thiazole-6,7-diol(Faster eluting isomer) | 249.0 |

TABLE 1-continued

| Example | structure | Name | MH+ |
|---|---|---|---|
| 15 | 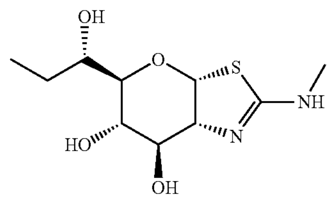 [SMILES: CC[C@H](O)[C@H]1O[C@@H]2SC(NC)=N[C@@H]2[C@@H](O)[C@@H]1O] | (3aR,5R,6S,7R,7aR)-5-((S)-1-hydroxypropyl)-2-(methylamino)-5,6,7,7a-tetrahydro-3aH-pyrano[3,2-d]thiazole-6,7-diol(Slower eluting isomer) | 262.1 |
| 16 | 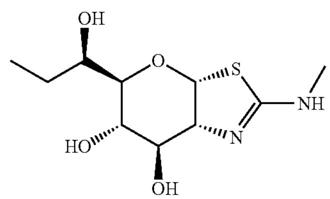 [SMILES: CC[C@@H](O)[C@H]1O[C@@H]2SC(NC)=N[C@@H]2[C@@H](O)[C@@H]1O] | (3aR,5R,6S,7R,7aR)-5-((R)-1-hydroxypropyl)-2-(methylamino)-5,6,7,7a-tetrahydro-3aH-pyrano[3,2-d]thiazole-6,7-diol(Faster eluting isomer) | 262.1 |
| 17 | 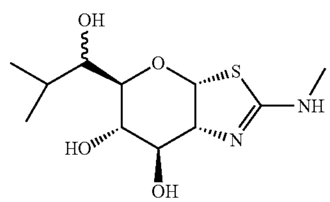 [SMILES: CNC1=N[C@@H]2[C@@H](O)[C@H](O)[C@@H](C(O)C(C)C)O[C@@H]2S1] | (3aR,5R,6S,7R,7aR)-5-(1-hydroxy-2-methylpropyl)-2-(methylamino)-5,6,7,7a-tetrahydro-3aH-pyrano[3,2-d]thiazole-6,7-diol (faster moving isomer: slower moving isomer = 30:1) | 277.1 |
| 18 | 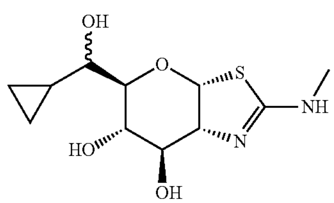 [SMILES: CNC1=N[C@@H]2[C@@H](O)[C@H](O)[C@@H](C(O)C3CC3)O[C@@H]2S1] | (3aR,5R,6S,7R,7aR)-5-(cyclopropyl(hydroxy)methyl)-2-(methylamino)-5,6,7,7a-tetrahydro-3aH-pyrano[3,2-d]thiazole-6,7-diol (faster moving isomer: slower moving isomer = 1:49) | 275.1 |
| 19 | 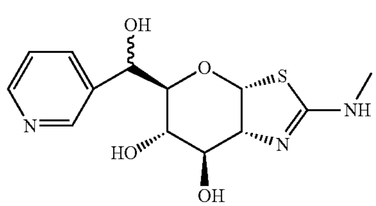 [SMILES: CNC1=N[C@@H]2[C@@H](O)[C@H](O)[C@@H](C(O)c3cccnc3)O[C@@H]2S1] | (3aR,5R,6S,7R,7aR)-5-(hydroxy(pyridin-3-yl)methyl)-2-(methylamino)-5,6,7,7a-tetrahydro-3aH-pyrano[3,2-d]thiazole-6,7-diol (faster moving isomer: slower moving isomer = 1:1) | 312.1 |
| 20 | 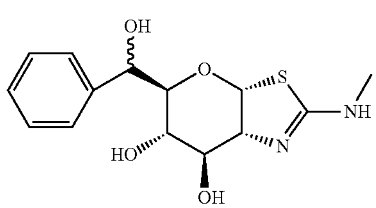 [SMILES: CNC1=N[C@@H]2[C@@H](O)[C@H](O)[C@@H](C(O)c3ccccc3)O[C@@H]2S1] | (3aR,5R,6S,7R,7aR)-5-(hydroxy(phenyl)methyl)-2-(methylamino)-5,6,7,7a-tetrahydro-3aH-pyrano[3,2-d]thiazole-6,7-diol (faster moving isomer: slower moving isomer = 1:18) | 311.1 |
| 21 | 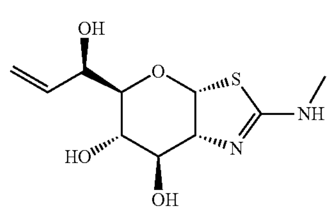 [SMILES: C=C[C@@H](O)[C@H]1O[C@@H]2SC(NC)=N[C@@H]2[C@@H](O)[C@@H]1O] | (3aR,5R,6S,7R,7aR)-5-((R)-1-hydroxyallyl)-2-(methylamino)-5,6,7,7a-tetrahydro-3aH-pyrano[3,2-d]thiazole-6,7-diol (Faster eluting isomer) | 261.1 |

TABLE 1-continued

| Example | structure | Name | MH+ |
|---|---|---|---|
| 22 | 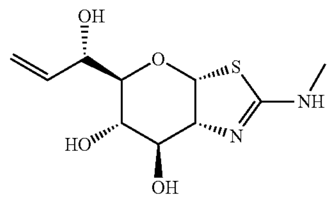 [SMILES: C=C[C@H](O)[C@H]1O[C@@H]2SC(NC)=N[C@@H]2[C@@H](O)[C@@H]1O] | (3aR,5R,6S,7R,7aR)-5-((S)-1-hydroxyallyl)-2-(methylamino)-5,6,7,7a-tetrahydro-3aH-pyrano[3,2-d]thiazole-6,7-diol (Slower eluting isomer) | 261.1 |
| 23 | 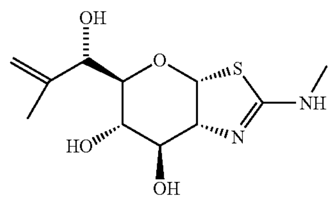 [SMILES: C=C(C)[C@H](O)[C@H]1O[C@@H]2SC(NC)=N[C@@H]2[C@@H](O)[C@@H]1O] | (3aR,5R,6S,7R,7aR)-5-((S)-1-hydroxy-2-methylallyl)-2-(methylamino)-5,6,7,7a-tetrahydro-3aH-pyrano[3,2-d]thiazole-6,7-diol (Slower eluting isomer) | 275.1 |
| 24 | 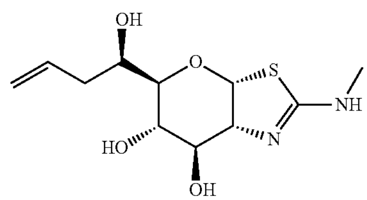 [SMILES: C=CC[C@@H](O)[C@H]1O[C@@H]2SC(NC)=N[C@@H]2[C@@H](O)[C@@H]1O] | (3aR,5R,6S,7R,7aR)-5-((R)-1-hydroxybut-3-enyl)-2-(methylamino)-5,6,7,7a-tetrahydro-3aH-pyrano[3,2-d]thiazole-6,7-diol (Faster eluting isomer) | 275.0 |
| 25 | 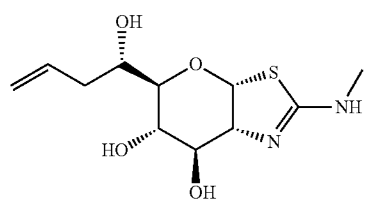 [SMILES: C=CC[C@H](O)[C@H]1O[C@@H]2SC(NC)=N[C@@H]2[C@@H](O)[C@@H]1O] | (3aR,5R,6S,7R,7aR)-5-((S)-1-hydroxybut-3-enyl)-2-(methylamino)-5,6,7,7a-tetrahydro-3aH-pyrano[3,2-d]thiazole-6,7-diol(Slower eluting isomer) | 275.0 |
| 26 | 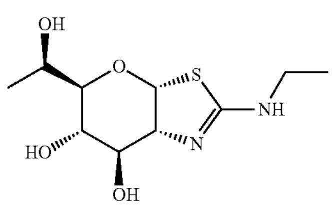 [SMILES: CCNC1=N[C@@H]2[C@@H](O)[C@H](O)[C@@H]([C@@H](C)O)O[C@@H]2S1] | (3aR,5R,6S,7R,7aR)-2-(ethylamino)-5-((R)-1-hydroxyethyl)-5,6,7,7a-tetrahydro-3aH-pyrano[3,2-d]thiazole-6,7-diol(Faster eluting isomer) | 263.1 |
| 27 | 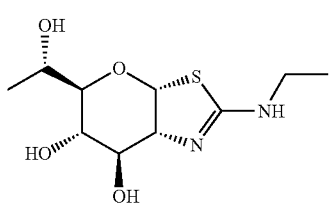 [SMILES: CCNC1=N[C@@H]2[C@@H](O)[C@H](O)[C@@H]([C@H](C)O)O[C@@H]2S1] | (3aR,5R,6S,7R,7aR)-2-(ethylamino)-5-((S)-1-hydroxyethyl)-5,6,7,7a-tetrahydro-3aH-pyrano[3,2-d]thiazole-6,7-diol(Slower eluting isomer) | 263.1 |
| 28 | 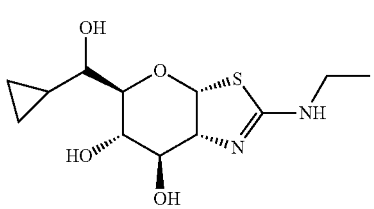 [SMILES: CCNC1=N[C@@H]2[C@@H](O)[C@H](O)[C@@H](C(O)C3CC3)O[C@@H]2S1] | (3aR,5R,6S,7R,7aR)-5-(cyclopropyl(hydroxy)methyl)-2-(ethylamino)-5,6,7,7a-tetrahydro-3aH-pyrano[3,2-d]thiazole-6,7-diol | 289.1 |

TABLE 1-continued

| Example | structure | Name | MH+ |
|---|---|---|---|
| 29 | 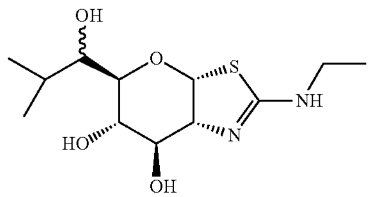 [SMILES: CCNC1=N[C@@H]2[C@@H](O)[C@H](O)[C@@H](C(O)C(C)C)O[C@@H]2S1] | (3aR,5R,6S,7R,7aR)-2-(ethylamino)-5-(1-hydroxy-2-methylpropyl)-5,6,7,7a-tetrahydro-3aH-pyrano[3,2-d]thiazole-6,7-diol (faster moving isomer: slower moving isomer = 31:1) | 291.2 |
| 30 | 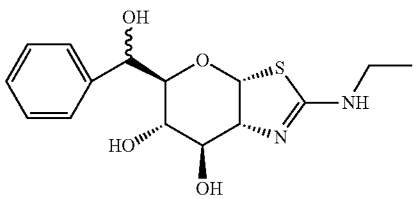 [SMILES: CCNC1=N[C@@H]2[C@@H](O)[C@H](O)[C@@H](C(O)c3ccccc3)O[C@@H]2S1] | (3aR,5R,6S,7R,7aR)-2-(ethylamino)-5-(hydroxy(phenyl)methyl)-5,6,7,7a-tetrahydro-3aH-pyrano[3,2-d]thiazole-6,7-diol (faster moving isomer: slower moving isomer = 1:20) | 325.2 |
| 31 | 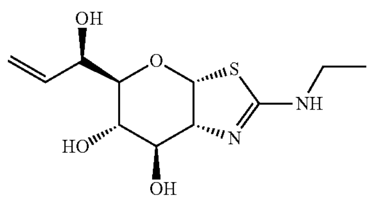 [SMILES: C=C[C@@H](O)[C@H]1O[C@@H]2SC(NCC)=N[C@@H]2[C@@H](O)[C@@H]1O] | (3aR,5R,6S,7R,7aR)-2-(ethylamino)-5-((R)-1-hydroxyallyl)-5,6,7,7a-tetrahydro-3aH-pyrano[3,2-d]thiazole-6,7-diol (Faster eluting isomer) | 275.2 |
| 32 | 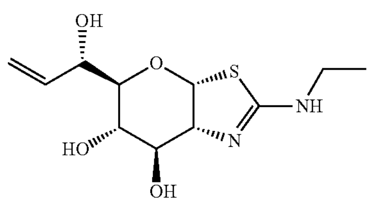 [SMILES: C=C[C@H](O)[C@H]1O[C@@H]2SC(NCC)=N[C@@H]2[C@@H](O)[C@@H]1O] | (3aR,5R,6S,7R,7aR)-2-(ethylamino)-5-((S)-1-hydroxyallyl)-5,6,7,7a-tetrahydro-3aH-pyrano[3,2-d]thiazole-6,7-diol (Slower eluting isomer) | 275.1 |
| 33 | 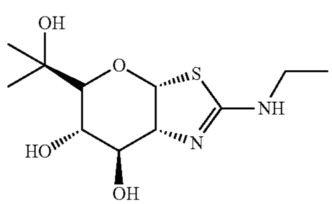 | (3aR,5R,6S,7R,7aR)-2-(ethylamino)-5-(2-hydroxypropan-2-yl)-5,6,7,7a-tetrahydro-3aH-pyrano[3,2-d]thiazole-6,7-diol | 277.1 |
| 34 | 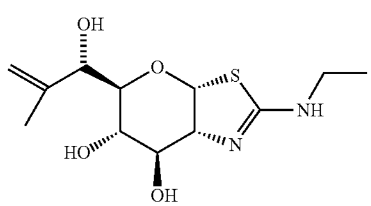 [SMILES: C=C(C)[C@H](O)[C@H]1O[C@@H]2SC(NCC)=N[C@@H]2[C@@H](O)[C@@H]1O] | (3aR,5R,6S,7R,7aR)-2-(ethylamino)-5-(S)(-1-hydroxy-2-methylallyl)-5,6,7,7a-tetrahydro-3aH-pyrano[3,2-d]thiazole-6,7-diol(Slower eluting isomer) | 289.2 |
| 35 | 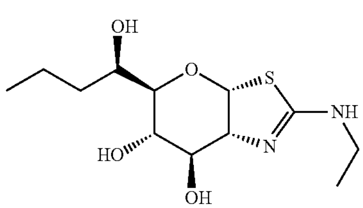 [SMILES: CCC[C@@H](O)[C@H]1O[C@@H]2SC(NCC)=N[C@@H]2[C@@H](O)[C@@H]1O] | (3aR,5R,6S,7R,7aR)-2-(ethylamino)-5-((R)-1-hydroxybutyl)-5,6,7,7a-tetrahydro-3aH-pyrano[3,2-d]thiazole-6,7-diol (Faster eluting isomer) | 291.0 |

TABLE 1-continued

| Example | structure | Name | MH+ |
|---|---|---|---|
| 36 | 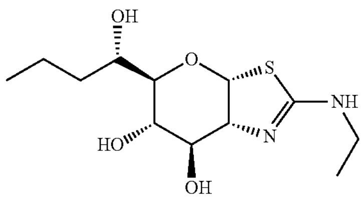 [SMILES: CCC[C@H](O)[C@H]1O[C@@H]2SC(NCC)=N[C@@H]2[C@@H](O)[C@@H]1O] | (3aR,5R,6S,7R,7aR)-2-(ethylamino)-5-((S)-1-hydroxybutyl)-5,6,7,7a-tetrahydro-3aH-pyrano[3,2-d]thiazole-6,7-diol (Slower eluting isomer) | 291.0 |
| 37 | 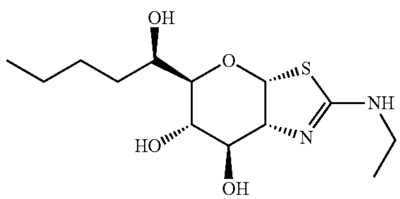 [SMILES: CCCC[C@@H](O)[C@H]1O[C@@H]2SC(NCC)=N[C@@H]2[C@@H](O)[C@@H]1O] | (3aR,5R,6S,7R,7aR)-2-(ethylamino)-5-((R)-1-hydroxypentyl)-5,6,7,7a-tetrahydro-3aH-pyrano[3,2-d]thiazole-6,7-diol (Faster eluting isomer) | 305.0 |
| 38 | 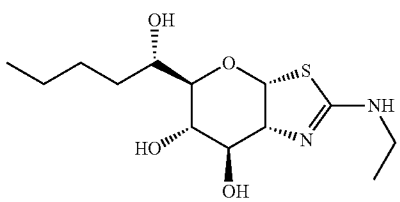 [SMILES: CCCC[C@H](O)[C@H]1O[C@@H]2SC(NCC)=N[C@@H]2[C@@H](O)[C@@H]1O] | (3aR,5R,6S,7R,7aR)-2-(ethylamino)-5-((S)-1-hydroxypentyl)-5,6,7,7a-tetrahydro-3aH-pyrano[3,2-d]thiazole-6,7-diol (Slower eluting isomer) | 305.0 |
| 39 | 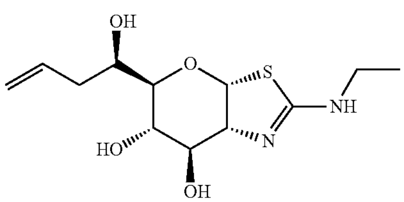 [SMILES: C=CC[C@@H](O)[C@H]1O[C@@H]2SC(NCC)=N[C@@H]2[C@@H](O)[C@@H]1O] | (3aR,5R,6S,7R,7aR)-2-(ethylamino)-5-((R)-1-hydroxybut-3-enyl)-5,6,7,7a-tetrahydro-3aH-pyrano[3,2-d]thiazole-6,7-diol(Faster eluting isomer) | 289.0 |
| 40 | 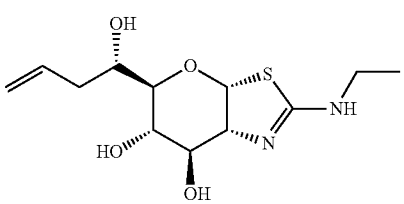 [SMILES: C=CC[C@H](O)[C@H]1O[C@@H]2SC(NCC)=N[C@@H]2[C@@H](O)[C@@H]1O] | (3aR,5R,6S,7R,7aR)-2-(ethylamino)-5-((S)-1-hydroxybut-3-enyl)-5,6,7,7a-tetrahydro-3aH-pyrano[3,2-d]thiazole-6,7-diol(Slower eluting isomer) | 289.0 |
| 41 | 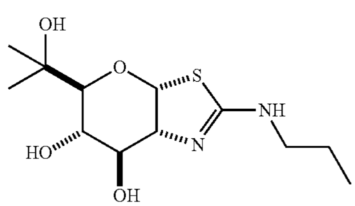 | (3aR,5S,6S,7R,7aR)-5-(2-hydroxypropan-2-yl)-2-(propylamino)-5,6,7,7a-tetrahydro-3aH-pyrano[3,2-d]thiazole-6,7-diol | 291.0 |
| 42 | 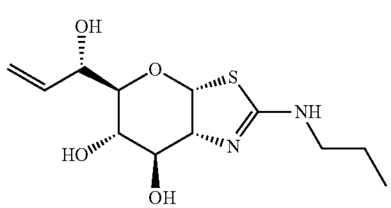 [SMILES: C=C[C@H](O)[C@H]1O[C@@H]2SC(NCCC)=N[C@@H]2[C@@H](O)[C@@H]1O] | (3aR,5R,6S,7R,7aR)-5-((S)-1-hydroxyallyl)-2-(propylamino)-5,6,7,7a-tetrahydro-3aH-pyrano[3,2-d]thiazole-6,7-diol (Slower eluting isomer) | 289.0 |

TABLE 1-continued

| Example | structure | Name | MH+ |
|---|---|---|---|
| 43 | 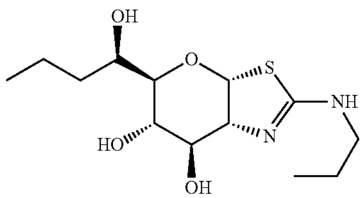 [SMILES: CCCNC1=N[C@@H]2[C@@H](O)[C@H](O)[C@@H]([C@H](O)CCC)O[C@@H]2S1] | (3aR,5R,6S,7R,7aR)-5-((R)-1-hydroxybutyl)-2-(propylamino)-5,6,7,7a-tetrahydro-3aH-pyrano[3,2-d]thiazole-6,7-diol (Faster eluting isomer) | 305.0 |
| 44 | 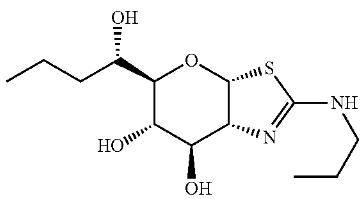 [SMILES: CCCNC1=N[C@@H]2[C@@H](O)[C@H](O)[C@@H]([C@@H](O)CCC)O[C@@H]2S1] | (3aR,5R,6S,7R,7aR)-5-((S)-1-hydroxybutyl)-2-(propylamino)-5,6,7,7a-tetrahydro-3aH-pyrano[3,2-d]thiazole-6,7-diol (Slower eluting isomer) | 305.0 |
| 45 | 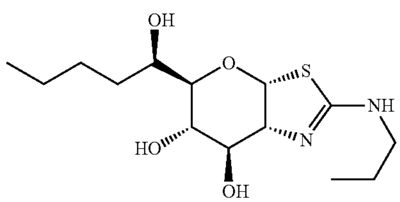 [SMILES: CCCC[C@@H](O)[C@H]1O[C@@H]2SC(NCCC)=N[C@@H]2[C@@H](O)[C@@H]1O] | (3aR,5R,6S,7R,7aR)-5-((R)-1-hydroxypentyl)-2-(propylamino)-5,6,7,7a-tetrahydro-3aH-pyrano[3,2-d]thiazole-6,7-diol (Faster eluting isomer) | 319.0 |
| 46 | 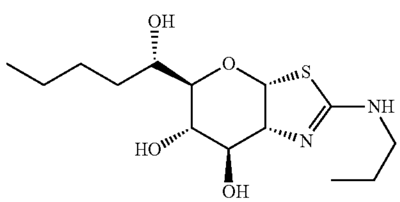 [SMILES: CCCC[C@H](O)[C@H]1O[C@@H]2SC(NCCC)=N[C@@H]2[C@@H](O)[C@@H]1O] | (3aR,5R,6S,7R,7aR)-5-((S)-1-hydroxypentyl)-2-(propylamino)-5,6,7,7a-tetrahydro-3aH-pyrano[3,2-d]thiazole-6,7-diol (Slower eluting isomer) | 319.0 |
| 47 | 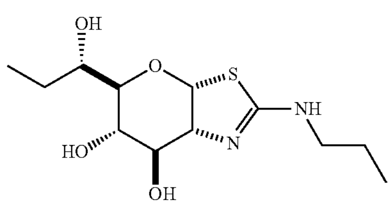 | (3aR,5R,6S,7R,7aR)-5-(1-hydroxypropyl)-2-(propylamino)-5,6,7,7a-tetrahydro-3aH-pyrano[3,2-d]thiazole-6,7-diol (Slower eluting isomer) | 291.0 |
| 48 | 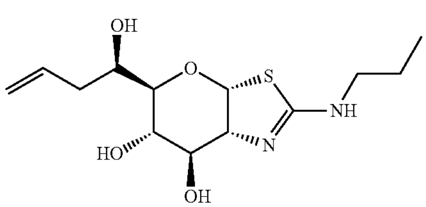 [SMILES: C=CC[C@@H](O)[C@H]1O[C@@H]2SC(NCCC)=N[C@@H]2[C@@H](O)[C@@H]1O] | (3aR,5R,6S,7R,7aR)-5-((R)-1-hydroxybut-3-enyl)-2-(propylamino)-5,6,7,7a-tetrahydro-3aH-pyrano[3,2-d]thiazole-6,7-diol(Faster eluting isomer) | 303.0 |
| 49 | 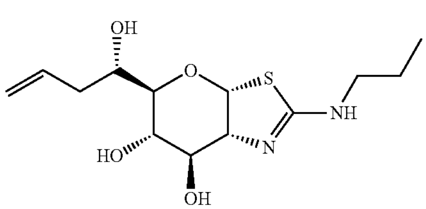 [SMILES: C=CC[C@H](O)[C@H]1O[C@@H]2SC(NCCC)=N[C@@H]2[C@@H](O)[C@@H]1O] | (3aR,5R,6S,7R,7aR)-5-((S)-1-hydroxybut-3-enyl)-2-(propylamino)-5,6,7,7a-tetrahydro-3aH-pyrano[3,2-d]thiazole-6,7-diol(Slower eluting isomer) | 303.0 |

TABLE 1-continued

| Example | structure | Name | MH+ |
|---|---|---|---|
| 50 | 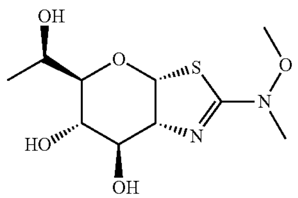 [SMILES: CON(C)C1=N[C@@H]2[C@@H](O)[C@H](O)[C@@H]([C@@H](C)O)O[C@@H]2S1] | (3aR,5R,6S,7R,7aR)-5-((R)-1-hydroxyethyl)-2-(methoxy(methyl)amino)-5,6,7,7a-tetrahydro-3aH-pyrano[3,2-d]thiazole-6,7-diol(Faster eluting isomer) | 279.0 |
| 51 | 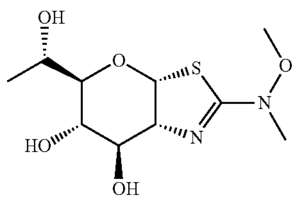 [SMILES: CON(C)C1=N[C@@H]2[C@@H](O)[C@H](O)[C@@H]([C@H](C)O)O[C@@H]2S1] | (3aR,5R,6S,7R,7aR)-5-((S)-1-hydroxyethyl)-2-(methoxy(methyl)amino)-5,6,7,7a-tetrahydro-3aH-pyrano[3,2-d]thiazole-6,7-diol(Slower eluting isomer) | 279.0 |
| 52 | 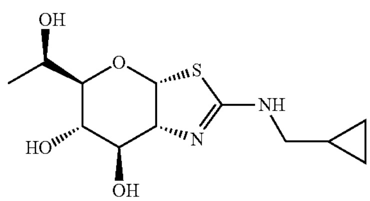 [SMILES: C[C@@H](O)[C@H]1O[C@@H]2SC(NCC3CC3)=N[C@@H]2[C@@H](O)[C@@H]1O] | (3aR,5R,6S,7R,7aR)-2-(cyclopropylmethylamino)-5-((R)-1-hydroxyethyl)-5,6,7,7a-tetrahydro-3aH-pyrano[3,2-d]thiazole-6,7-diol(Faster eluting isomer) | 289.0 |
| 53 | 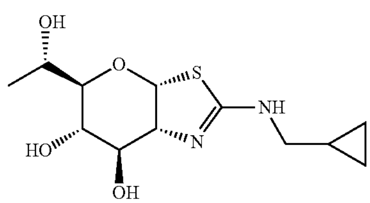 [SMILES: C[C@H](O)[C@H]1O[C@@H]2SC(NCC3CC3)=N[C@@H]2[C@@H](O)[C@@H]1O] | (3aR,5R,6S,7R,7aR)-2-(cyclopropylmethylamino)-5-((S)-1-hydroxyethyl)-5,6,7,7a-tetrahydro-3aH-pyrano[3,2-d]thiazole-6,7-diol(Slower eluting isomer) | 289.0 |
| 54 | 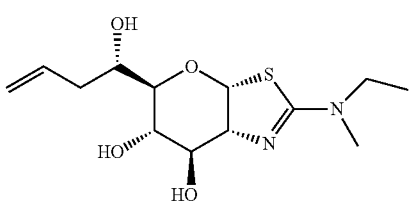 [SMILES: C=CC[C@H](O)[C@H]1O[C@@H]2SC(N(C)CC)=N[C@@H]2[C@@H](O)[C@@H]1O] | (3aR,5R,6S,7R,7aR)-2-(ethyl(methyl)amino)-5-((S)-1-hydroxybut-3-enyl)-5,6,7,7a-tetrahydro-3aH-pyrano[3,2-d]thiazole-6,7-diol (Slower eluting isomer) | 303.0 |
| 55 | 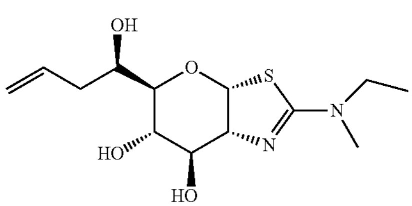 [SMILES: C=CC[C@@H](O)[C@H]1O[C@@H]2SC(N(C)CC)=N[C@@H]2[C@@H](O)[C@@H]1O] | (3aR,5R,6S,7R,7aR)-2-(ethyl(methyl)amino)-5-((R)-1-hydroxybut-3-enyl)-5,6,7,7a-tetrahydro-3aH-pyrano[3,2-d]thiazole-6,7-diol (Faster eluting isomer) | 303.0 |
| 56 | 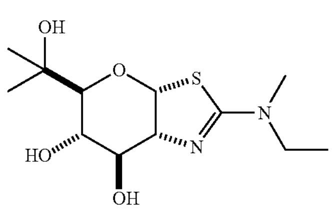 | (3aR,5S,6S,7R,7aR)-2-(ethyl(methyl)amino)-5-(2-hydroxypropan-2-yl)-5,6,7,7a-tetrahydro-3aH-pyrano[3,2-d]thiazole-6,7-diol | 290.9 |

TABLE 1-continued

| Example | structure | Name | MH+ |
|---|---|---|---|
| 57 | 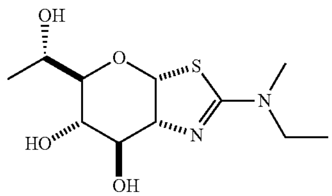 | (3aR,5R,6S,7R,7aR)-2-(ethyl(methyl)amino)-5-(1-hydroxyethyl)-5,6,7,7a-tetrahydro-3aH-pyrano[3,2-d]thiazole-6,7-diol (Slower eluting isomer) | 276.9 |
| 58 | 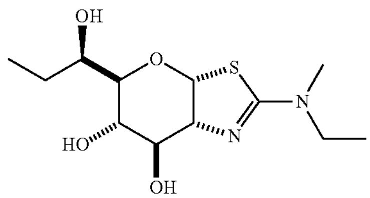 | (3aR,5R,6S,7R,7aR)-2-(ethyl(methyl)amino)-5-((R)-1-hydroxypropyl)-5,6,7,7a-tetrahydro-3aH-pyrano[3,2-d]thiazole-6,7-diol (Faster eluting isomer) | 291.0 |
| 59 | 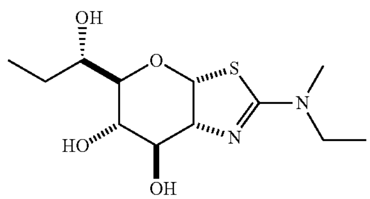 | (3aR,5R,6S,7R,7aR)-2-(ethyl(methyl)amino)-5-(1-hydroxypropyl)-5,6,7,7a-tetrahydro-3aH-pyrano[3,2-d]thiazole-6,7-diol (Slower eluting isomer) | 290.9 |
| 60 | 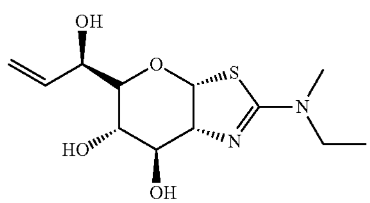 [SMILES: C=C[C@@H](O)C1O[C@@H]2SC(N(C)CC)=N[C@@H]2[C@@H](O)[C@@H]1O] | (3aR,5S,6S,7R,7aR)-2-(ethyl(methyl)amino)-5-((R)-1-hydroxyallyl)-5,6,7,7a-tetrahydro-3aH-pyrano[3,2-d]thiazole-6,7-diol (Faster eluting isomer) | 289.0 |
| 61 | 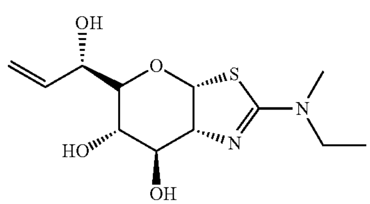 | (3aR,5S,6S,7R,7aR)-2-(ethyl(methyl)amino)-5-(1-hydroxyallyl)-5,6,7,7a-tetrahydro-3aH-pyrano[3,2-d]thiazole-6,7-diol (Slower eluting isomer) | 289.0 |
| 62 | 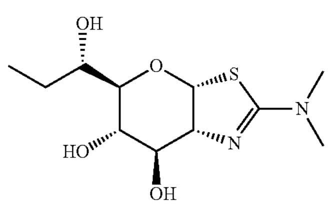 [SMILES: CC[C@H](O)[C@H]1O[C@@H]2SC(N(C)C)=N[C@@H]2[C@@H](O)[C@@H]1O] | (3aR,5R,6S,7R,7aR)-2-(dimethylamino)-5-((S)-1-hydroxypropyl)-5,6,7,7a-tetrahydro-3aH-pyrano[3,2-d]thiazole-6,7-diol (Slower eluting isomer) | 276.9 |
| 63 | 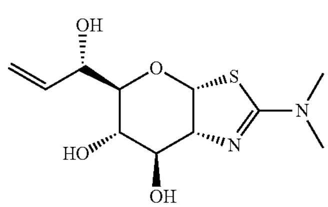 [SMILES: C=C[C@H](O)[C@H]1O[C@@H]2SC(N(C)C)=N[C@@H]2[C@@H](O)[C@@H]1O] | (3aR,5R,6S,7R,7aR)-2-(dimethylamino)-5-((S)-1-hydroxyallyl)-5,6,7,7a-tetrahydro-3aH-pyrano[3,2-d]thiazole-6,7-diol (Slower eluting isomer) | 274.9 |

TABLE 1-continued

| Example | structure | Name | MH+ |
|---|---|---|---|
| 64 | 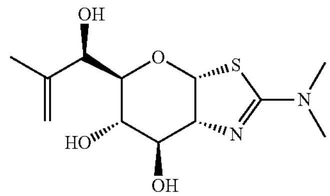 [SMILES: C=C(C)[C@@H](O)[C@H]1O[C@@H]2SC(N(C)C)=N[C@@H]2[C@@H](O)[C@@H]1O] | (3aR,5R,6S,7R,7aR)-2-(dimethylamino)-5-((R)-1-hydroxy-2-methylallyl)-5,6,7,7a-tetrahydro-3aH-pyrano[3,2-d]thiazole-6,7-diol(Faster eluting isomer) | 289.0 |
| 65 | 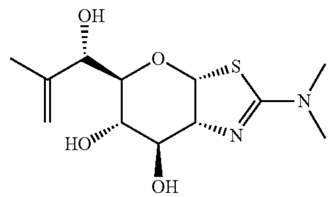 [SMILES: C=C(C)[C@H](O)[C@H]1O[C@@H]2SC(N(C)C)=N[C@@H]2[C@@H](O)[C@@H]1O] | (3aR,5R,6S,7R,7aR)-2-(dimethylamino)-5-((S)-1-hydroxy-2-methylallyl)-5,6,7,7a-tetrahydro-3aH-pyrano[3,2-d]thiazole-6,7-diol(Slower eluting isomer) | 289.0 |
| 66 | 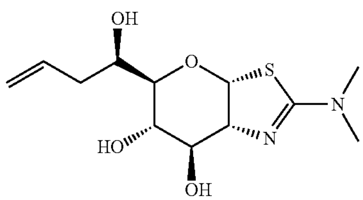 [SMILES: C=CC[C@@H](O)[C@H]1O[C@@H]2SC(N(C)C)=N[C@@H]2[C@@H](O)[C@@H]1O] | (3aR,5R,6S,7R,7aR)-2-(dimethylamino)-5-((R)-1-hydroxybut-3-enyl)-5,6,7,7a-tetrahydro-3aH-pyrano[3,2-d]thiazole-6,7-diol(Faster eluting isomer) | 289.0 |
| 67 | 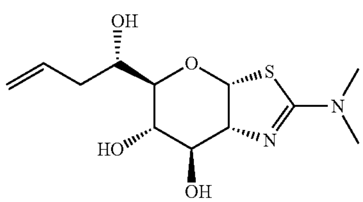 [SMILES: C=CC[C@H](O)[C@H]1O[C@@H]2SC(N(C)C)=N[C@@H]2[C@@H](O)[C@@H]1O] | (3aR,5R,6S,7R,7aR)-2-(dimethylamino)-5-((S)-1-hydroxybut-3-enyl)-5,6,7,7a-tetrahydro-3aH-pyrano[3,2-d]thiazole-6,7-diol(Slower eluting isomer) | 289.0 |
| 68 | 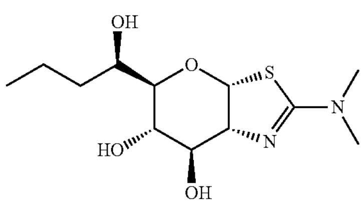 [SMILES: CCC[C@@H](O)[C@H]1O[C@@H]2SC(N(C)C)=N[C@@H]2[C@@H](O)[C@@H]1O] | (3aR,5R,6S,7R,7aR)-2-(dimethylamino)-5-((R)-1-hydroxybutyl)-5,6,7,7a-tetrahydro-3aH-pyrano[3,2-d]thiazole-6,7-diol (Faster eluting isomer) | 291.0 |
| 69 | 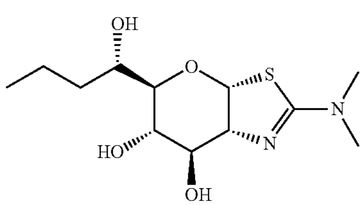 [SMILES: CCC[C@H](O)[C@H]1O[C@@H]2SC(N(C)C)=N[C@@H]2[C@@H](O)[C@@H]1O] | (3aR,5R,6S,7R,7aR)-2-(dimethylamino)-5-((S)-1-hydroxybutyl)-5,6,7,7a-tetrahydro-3aH-pyrano[3,2-d]thiazole-6,7-diol (Slower eluting isomer) | 291.0 |
| 70 | 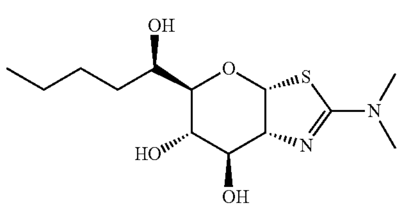 [SMILES: CCCC[C@@H](O)[C@H]1O[C@@H]2SC(N(C)C)=N[C@@H]2[C@@H](O)[C@@H]1O] | (3aR,5R,6S,7R,7aR)-2-(dimethylamino)-5-((R)-1-hydroxypentyl)-5,6,7,7a-tetrahydro-3aH-pyrano[3,2-d]thiazole-6,7-diol (Faster eluting isomer) | 305.0 |

TABLE 1-continued

| Example | structure | Name | MH+ |
|---|---|---|---|
| 71 | 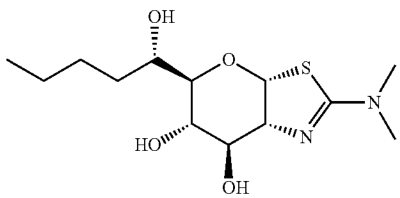 [SMILES: CCCC[C@H](O)[C@H]1O[C@@H]2SC(N(C)C)=N[C@@H]2[C@@H](O)[C@@H]1O] | (3aR,5R,6S,7R,7aR)-2-(dimethylamino)-5-((S)-1-hydroxypentyl)-5,6,7,7a-tetrahydro-3aH-pyrano[3,2-d]thiazole-6,7-diol (Slower eluting isomer) | 305.0 |
| 72 | 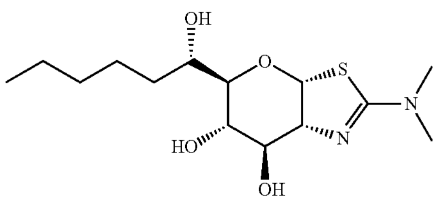 [SMILES: CCCCC[C@H](O)[C@H]1O[C@@H]2SC(N(C)C)=N[C@@H]2[C@@H](O)[C@@H]1O] | (3aR,5R,6S,7R,7aR)-2-(dimethylamino)-5-((S)-1-hydroxyhexyl)-5,6,7,7a-tetrahydro-3aH-pyrano[3,2-d]thiazole-6,7-diol(Slower eluting isomer) | 319.0 |
| 73 | 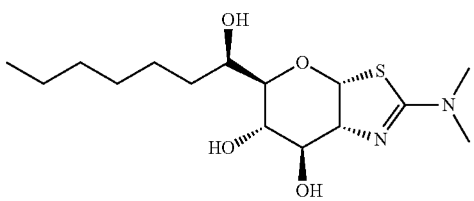 [SMILES: CCCCCC[C@@H](O)[C@H]1O[C@@H]2SC(N(C)C)=N[C@@H]2[C@@H](O)[C@@H]1O] | (3aR,5R,6S,7R,7aR)-2-(dimethylamino)-5-((R)-1-hydroxyheptyl)-5,6,7,7a-tetrahydro-3aH-pyrano[3,2-d]thiazole-6,7-diol (Faster eluting isomer) | 333.0 |
| 74 | 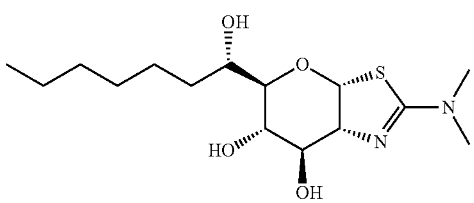 [SMILES: CCCCCC[C@H](O)[C@H]1O[C@@H]2SC(N(C)C)=N[C@@H]2[C@@H](O)[C@@H]1O] | (3aR,5R,6S,7R,7aR)-2-(dimethylamino)-5-((S)-1-hydroxyheptyl)-5,6,7,7a-tetrahydro-3aH-pyrano[3,2-d]thiazole-6,7-diol(Slower eluting isomer) | 333.0 |
| 75 | 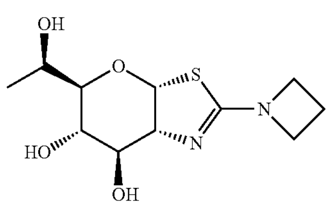 [SMILES: C[C@@H](O)[C@H]1O[C@@H]2SC(N3CCC3)=N[C@@H]2[C@@H](O)[C@@H]1O] | (3aR,5R,6S,7R,7aR)-2-(azetidin-1-yl)-5-((R)-1-hydroxyethyl)-5,6,7,7a-tetrahydro-3aH-pyrano[3,2-d]thiazole-6,7-diol (Faster eluting isomer) | 274.9 |
| 76 | 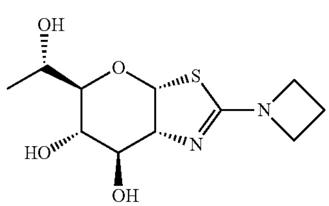 | (3aR,5R,6S,7R,7aR)-2-(azetidin-1-yl)-5-((S)-1-hydroxyethyl)-5,6,7,7a-tetrahydro-3aH-pyrano[3,2-d]thiazole-6,7-diol (Slower eluting isomer) | 274.9 |
| 77 | 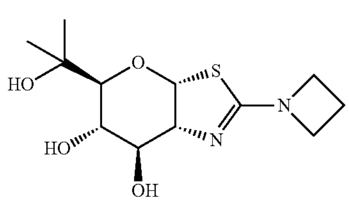 [SMILES: CC(C)(O)[C@H]1O[C@@H]2SC(N3CCC3)=N[C@@H]2[C@@H](O)[C@@H]1O] | (3aR,5S,6S,7R,7aR)-2-(azetidin-1-yl)-5-(2-hydroxypropan-2-yl)-5,6,7,7a-tetrahydro-3aH-pyrano[3,2-d]thiazole-6,7-diol | 288.9 |

TABLE 1-continued

| Example | structure | Name | MH+ |
|---|---|---|---|
| 78 | 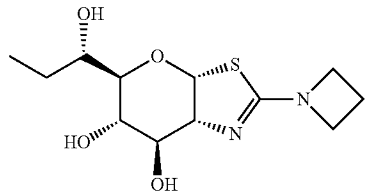 [SMILES: CC[C@H](O)[C@H]1O[C@@H]2SC(N3CCC3)=N[C@@H]2[C@@H](O)[C@@H]1O] | (3aR,5R,6S,7R,7aR)-2-(azetidin-1-yl)-5-((S)-1-hydroxypropyl)-5,6,7,7a-tetrahydro-3aH-pyrano[3,2-d]thiazole-6,7-diol (Slower eluting isomer) | 288.9 |
| 79 | 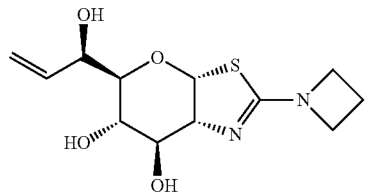 [SMILES: C=C[C@@H](O)[C@H]1O[C@@H]2SC(N3CCC3)=N[C@@H]2[C@@H](O)[C@@H]1O] | (3aR,5R,6S,7R,7aR)-2-(azetidin-1-yl)-5-((R)-1-hydroxyallyl)-5,6,7,7a-tetrahydro-3aH-pyrano[3,2-d]thiazole-6,7-diol(Faster eluting isomer) | 286.9 |
| 80 | 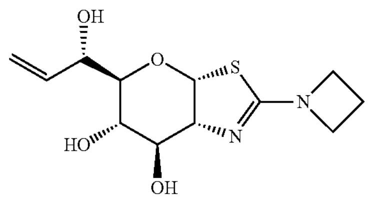 [SMILES: C=C[C@H](O)[C@H]1O[C@@H]2SC(N3CCC3)=N[C@@H]2[C@@H](O)[C@@H]1O] | (3aR,5R,6S,7R,7aR)-2-(azetidin-1-yl)-5-((S)-1-hydroxyallyl)-5,6,7,7a-tetrahydro-3aH-pyrano[3,2-d]thiazole-6,7-diol(Slower eluting isomer) | 286.9 |
| 81 | 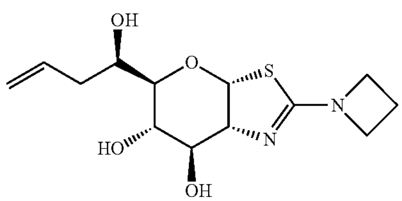 [SMILES: C=CC[C@@H](O)[C@H]1O[C@@H]2SC(N3CCC3)=N[C@@H]2[C@@H](O)[C@@H]1O] | (3aR,5R,6S,7R,7aR)-2-(azetidin-1-yl)-5-((R)-1-hydroxybut-3-enyl)-5,6,7,7a-tetrahydro-3aH-pyrano[3,2-d]thiazole-6,7-diol(Faster eluting isomer) | 301.0 |
| 82 | 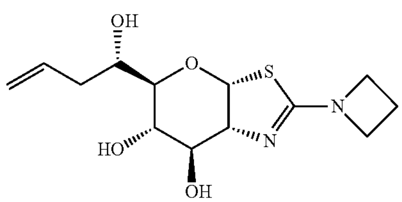 [SMILES: C=CC[C@H](O)[C@H]1O[C@@H]2SC(N3CCC3)=N[C@@H]2[C@@H](O)[C@@H]1O] | (3aR,5R,6S,7R,7aR)-2-(azetidin-1-yl)-5-((S)-1-hydroxybut-3-enyl)-5,6,7,7a-tetrahydro-3aH-pyrano[3,2-d]thiazole-6,7-diol(Slower eluting isomer) | 301.0 |
| 83 | 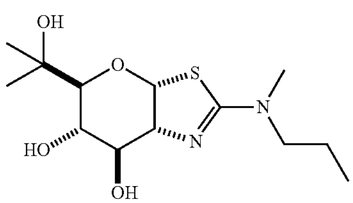 | (3aR,5S,6S,7R,7aR)-5-(2-hydroxypropan-2-yl)-2-(methyl(propyl)amino)-5,6,7,7a-tetrahydro-3aH-pyrano[3,2-d]thiazole-6,7-diol | 305.0 |
| 84 | 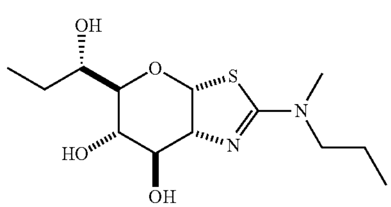 | (3aR,5R,6S,7R,7aR)-5-(1-hydroxypropyl)-2-(methyl(propyl)amino)-5,6,7,7a-tetrahydro-3aH-pyrano[3,2-d]thiazole-6,7-diol (Slower eluting isomer) | 305.0 |

TABLE 1-continued

| Example | structure | Name | MH+ |
|---|---|---|---|
| 85 | 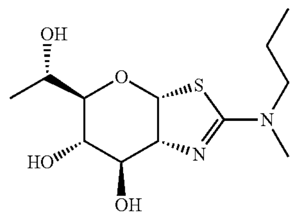 [SMILES: CCCN(C)C1=N[C@@H]2[C@@H](O)[C@H](O)[C@@H]([C@H](C)O)O[C@@H]2S1] | (3aR,5R,6S,7R,7aR)-5-((S)-1-hydroxyethyl)-2-(methyl(propyl)amino)-5,6,7,7a-tetrahydro-3aH-pyrano[3,2-d]thiazole-6,7-diol(Slower eluting isomer) | 291.0 |
| 86 | 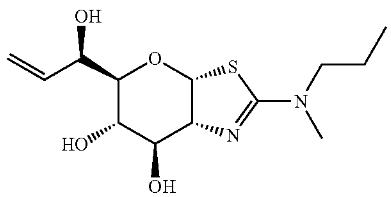 [SMILES: C=C[C@@H](O)[C@H]1O[C@@H]2SC(N(C)CCC)=N[C@@H]2[C@@H](O)[C@@H]1O] | (3aR,5R,6S,7R,7aR)-5-((R)-1-hydroxyallyl)-2-(methyl(propyl)amino)-5,6,7,7a-tetrahydro-3aH-pyrano[3,2-d]thiazole-6,7-diol(Faster eluting isomer) | 303.0 |
| 87 | 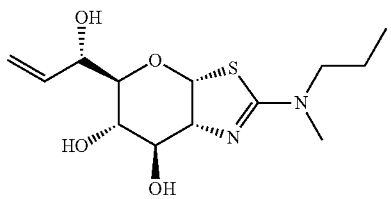 [SMILES: C=C[C@H](O)[C@H]1O[C@@H]2SC(N(C)CCC)=N[C@@H]2[C@@H](O)[C@@H]1O] | (3aR,5R,6S,7R,7aR)-5-((S)-1-hydroxyallyl)-2-(methyl(propyl)amino)-5,6,7,7a-tetrahydro-3aH-pyrano[3,2-d]thiazole-6,7-diol(Slower eluting isomer) | 303.0 |
| 88 | 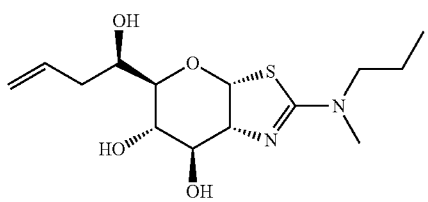 [SMILES: C=CC[C@@H](O)[C@H]1O[C@@H]2SC(N(C)CCC)=N[C@@H]2[C@@H](O)[C@@H]1O] | (3aR,5R,6S,7R,7aR)-5-((R)-1-hydroxybut-3-enyl)-2-(methyl(propyl)amino)-5,6,7,7a-tetrahydro-3aH-pyrano[3,2-d]thiazole-6,7-diol (Faster eluting isomer) | 317.0 |
| 89 | 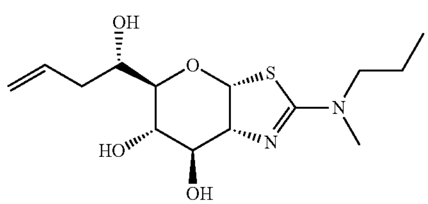 [SMILES: C=CC[C@H](O)[C@H]1O[C@@H]2SC(N(C)CCC)=N[C@@H]2[C@@H](O)[C@@H]1O] | (3aR,5R,6S,7R,7aR)-5-((S)-1-hydroxybut-3-enyl)-2-(methyl(propyl)amino)-5,6,7,7a-tetrahydro-3aH-pyrano[3,2-d]thiazole-6,7-diol(Slower eluting isomer) | 317.0 |
| 90 | 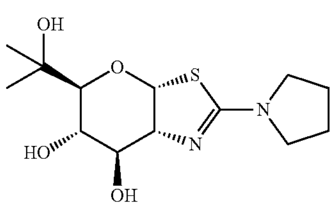 [SMILES: CC(C)(O)[C@H]1O[C@@H]2SC(N3CCCC3)=N[C@@H]2[C@@H](O)[C@@H]1O] | (3aR,5S,6S,7R,7aR)-5-(2-hydroxypropan-2-yl)-2-(pyrrolidin-1-yl)-5,6,7,7a-tetrahydro-3aH-pyrano[3,2-d]thiazole-6,7-diol | 302.9 |
| 91 | 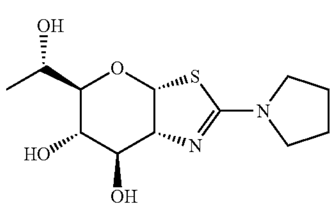 [SMILES: C[C@H](O)[C@H]1O[C@@H]2SC(N3CCCC3)=N[C@@H]2[C@@H](O)[C@@H]1O] | (3aR,5R,6S,7R,7aR)-5-((S)-1-hydroxyethyl)-2-(pyrrolidin-1-yl)-5,6,7,7a-tetrahydro-3aH-pyrano[3,2-d]thiazole-6,7-diol (Slower eluting isomer) | 289.0 |

TABLE 1-continued

| Example | structure | Name | MH+ |
|---|---|---|---|
| 92 | 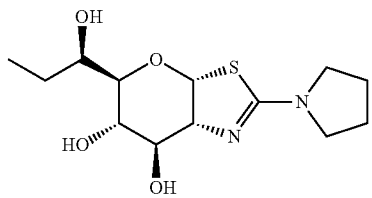 [SMILES: CC[C@@H](O)[C@H]1O[C@@H]2SC(N3CCCC3)=N[C@@H]2[C@@H](O)[C@@H]1O] | (3aR,5R,6S,7R,7aR)-5-((R)-1-hydroxypropyl)-2-(pyrrolidin-1-yl)-5,6,7,7a-tetrahydro-3aH-pyrano[3,2-d]thiazole-6,7-diol (Faster eluting isomer) | 302.9 |
| 93 | 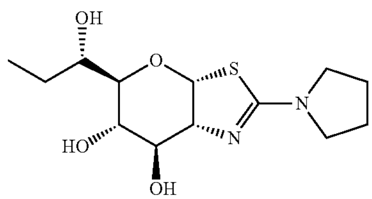 [SMILES: CC[C@H](O)[C@H]1O[C@@H]2SC(N3CCCC3)=N[C@@H]2[C@@H](O)[C@@H]1O] | (3aR,5R,6S,7R,7aR)-5-((S)-1-hydroxypropyl)-2-(pyrrolidin-1-yl)-5,6,7,7a-tetrahydro-3aH-pyrano[3,2-d]thiazole-6,7-diol (Slower eluting isomer) | 302.9 |
| 94 | 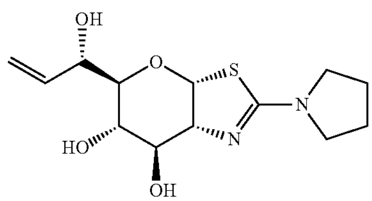 [SMILES: C=C[C@H](O)[C@H]1O[C@@H]2SC(N3CCCC3)=N[C@@H]2[C@@H](O)[C@@H]1O] | (3aR,5R,6S,7R,7aR)-5-((S)-1-hydroxyallyl)-2-(pyrrolidin-1-yl)-5,6,7,7a-tetrahydro-3aH-pyrano[3,2-d]thiazole-6,7-diol(Slower eluting isomer) | 301.0 |
| 95 | 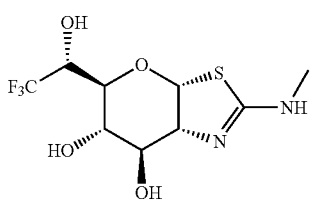 [SMILES: CNC1=N[C@@H]2[C@@H](O)[C@H](O)[C@@H]([C@@H](O)C(F)(F)F)O[C@@H]2S1] | (3aR,5S,6S,7R,7aR)-2-(methylamino)-5-((R)-2,2,2-trifluoro-1-hydroxyethyl)-5,6,7,7a-tetrahydro-3aH-pyrano[3,2-d]thiazole-6,7-diol | 303.0 |
| 97 | 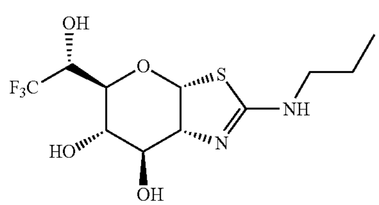 [SMILES: CCCNC1=N[C@@H]2[C@@H](O)[C@H](O)[C@@H]([C@@H](O)C(F)(F)F)O[C@@H]2S1] | (3aR,5S,6S,7R,7aR)-2-(propylamino)-5-((R)-2,2,2-trifluoro-1-hydroxyethyl)-5,6,7,7a-tetrahydro-3aH-pyrano[3,2-d]thiazole-6,7-diol | 331.0 |
| 98 | 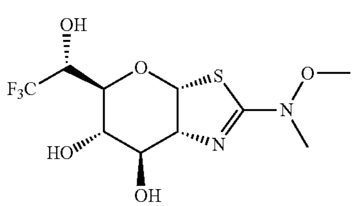 [SMILES: CON(C)C1=N[C@@H]2[C@@H](O)[C@H](O)[C@@H]([C@@H](O)C(F)(F)F)O[C@@H]2S1] | (3aR,5S,6S,7R,7aR)-2-(methoxy(methyl)amino)-5-((R)-2,2,2-trifluoro-1-hydroxyethyl)-5,6,7,7a-tetrahydro-3aH-pyrano[3,2-d]thiazole-6,7-diol | 332.9 |
| 99 | 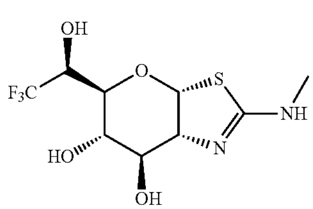 [SMILES: CNC1=N[C@@H]2[C@@H](O)[C@H](O)[C@@H]([C@H](O)C(F)(F)F)O[C@@H]2S1] | (3aR,5S,6S,7R,7aR)-2-(methylamino)-5-((S)-2,2,2-trifluoro-1-hydroxyethyl)-5,6,7,7a-tetrahydro-3aH-pyrano[3,2-d]thiazole-6,7-diol | 303.0 |

TABLE 1-continued

| Example | structure | Name | MH+ |
|---|---|---|---|
| 101 | 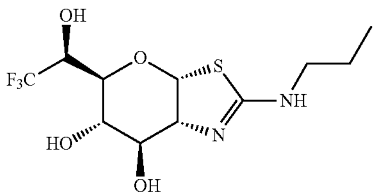 [SMILES: CCCNC1=N[C@@H]2[C@@H](O)[C@H](O)[C@@H]([C@H](O)C(F)(F)F)O[C@@H]2S1] | (3aR,5S,6S,7R,7aR)-2-(propylamino)-5-((S)-2,2,2-trifluoro-1-hydroxyethyl)-5,6,7,7a-tetrahydro-3aH-pyrano[3,2-d]thiazole-6,7-diol | 331.0 |
| 102 | 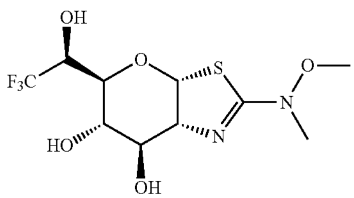 [SMILES: CON(C)C1=N[C@@H]2[C@@H](O)[C@H](O)[C@@H]([C@H](O)C(F)(F)F)O[C@@H]2S1] | (3aR,5S,6S,7R,7aR)-2-(methoxy(methyl)amino)-5-((S)-2,2,2-trifluoro-1-hydroxyethyl)-5,6,7,7a-tetrahydro-3aH-pyrano[3,2-d]thiazole-6,7-diol | 332.9 |
| 103 | 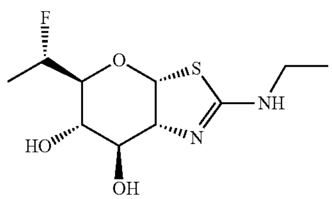 [SMILES: CCNC1=N[C@@H]2[C@@H](O)[C@H](O)[C@@H]([C@H](C)F)O[C@@H]2S1] | (3aR,5S,6S,7R,7aR)-2-(ethylamino)-5-((S)-1-fluoroethyl)-5,6,7,7a-tetrahydro-3aH-pyrano[3,2-d]thiazole-6,7-diol | 265.7 |
| 104 | 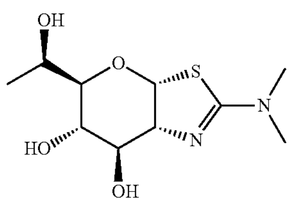 [SMILES: C[C@@H](O)[C@H]1O[C@@H]2SC(N(C)C)=N[C@@H]2[C@@H](O)[C@@H]1O] | (3aR,5R,6S,7R,7aR)-2-(dimethylamino)-5-((R)-1-hydroxyethyl)-5,6,7,7a-tetrahydro-3aH-pyrano[3,2-d]thiazole-6,7-diol | 262.9 |
| 105 | 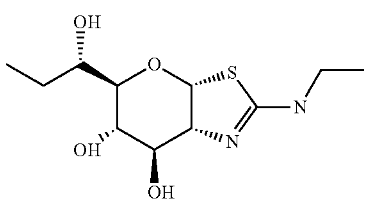 [SMILES: CCNC1=N[C@@H]2[C@@H](O)[C@H](O)[C@@H]([C@@H](O)CC)O[C@@H]2S1] | (3aR,5R,6S,7R,7aR)-2-(ethylamino)-5-((S)-1-hydroxypropyl)-5,6,7,7a-tetrahydro-3aH-pyrano[3,2-d]thiazole-6,7-diol | 277.2 |
| 106 | 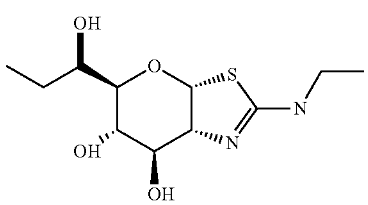 [SMILES: CCNC1=N[C@@H]2[C@@H](O)[C@H](O)[C@@H]([C@H](O)CC)O[C@@H]2S1] | (3aR,5R,6S,7R,7aR)-2-(ethylamino)-5-((R)-1-hydroxypropyl)-5,6,7,7a-tetrahydro-3aH-pyrano[3,2-d]thiazole-6,7-diol | 277.2 |
| 107 | 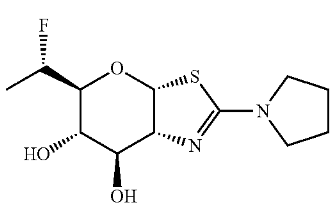 [SMILES: C[C@H](F)[C@H]1O[C@@H]2SC(N3CCCC3)=N[C@@H]2[C@@H](O)[C@@H]1O] | (3aR,5S,6S,7R,7aR)-5-((S)-1-fluoroethyl)-2-(pyrrolidin-1-yl)-5,6,7,7a-tetrahydro-3aH-pyrano[3,2-d]thiazole-6,7-diol(Slower eluting isomer) | 291.0 |

TABLE 1-continued

| Example | structure | Name | MH+ |
|---|---|---|---|
| 108 | 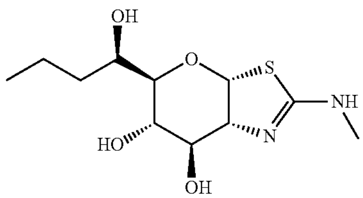 [SMILES: CCC[C@@H](O)[C@H]1O[C@@H]2SC(NC)=N[C@@H]2[C@@H](O)[C@@H]1O] | (3aR,5R,6S,7R,7aR)-5-((R)-1-hydroxybutyl)-2-(methylamino)-5,6,7,7a-tetrahydro-3aH-pyrano[3,2-d]thiazole-6,7-diol(Faster eluting isomer) | 305.0 |
| 109 | 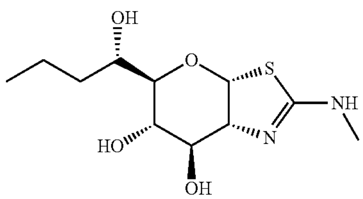 [SMILES: CCC[C@H](O)[C@H]1O[C@@H]2SC(NC)=N[C@@H]2[C@@H](O)[C@@H]1O] | (3aR,5R,6S,7R,7aR)-5-((S)-1-hydroxybutyl)-2-(methylamino)-5,6,7,7a-tetrahydro-3aH-pyrano[3,2-d]thiazole-6,7-diol(Slower eluting isomer) | 305.0 |
| 110 | 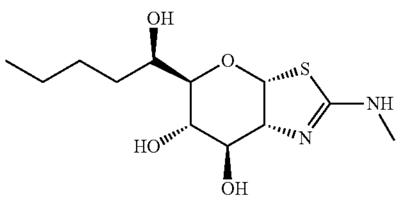 [SMILES: CCCC[C@@H](O)[C@H]1O[C@@H]2SC(NC)=N[C@@H]2[C@@H](O)[C@@H]1O] | (3aR,5R,6S,7R,7aR)-5-((R)-1-hydroxypentyl)-2-(methylamino)-5,6,7,7a-tetrahydro-3aH-pyrano[3,2-d]thiazole-6,7-diol(Faster eluting isomer) | 291.0 |
| 111 | 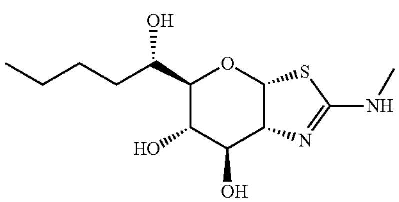 [SMILES: CCCC[C@H](O)[C@H]1O[C@@H]2SC(NC)=N[C@@H]2[C@@H](O)[C@@H]1O] | (3aR,5R,6S,7R,7aR)-5-((S)-1-hydroxypentyl)-2-(methylamino)-5,6,7,7a-tetrahydro-3aH-pyrano[3,2-d]thiazole-6,7-diol(Slower eluting isomer) | 291.0 |
| 112 | 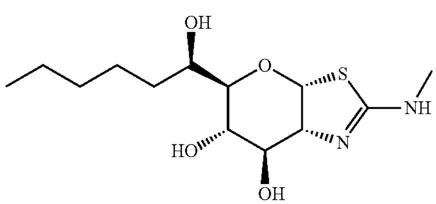 [SMILES: CCCCC[C@@H](O)[C@H]1O[C@@H]2SC(NC)=N[C@@H]2[C@@H](O)[C@@H]1O] | (3aR,5R,6S,7R,7aR)-5-((R)-1-hydroxyhexyl)-2-(methylamino)-5,6,7,7a-tetrahydropyrano[3,2-d]thiazole-6,7-diol(Faster eluting isomer) | 305.0 |
| 113 | 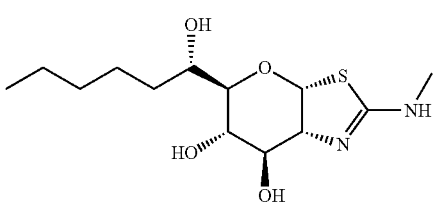 [SMILES: CCCCC[C@H](O)[C@H]1O[C@@H]2SC(NC)=N[C@@H]2[C@@H](O)[C@@H]1O] | (3aR,5R,6S,7R,7aR)-5-((S)-1-hydroxyhexyl)-2-(methylamino)-5,6,7,7a-tetrahydro-3aH-pyrano[3,2-d]thiazole-6,7-diol(Slower eluting isomer) | 305.0 |
| 114 | 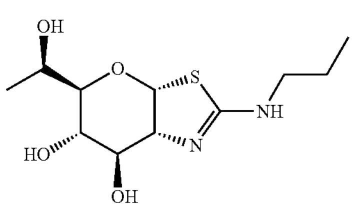 [SMILES: CCCNC1=N[C@@H]2[C@@H](O)[C@H](O)[C@@H]([C@@H](C)O)O[C@@H]2S1] | (3aR,5R,6S,7R,7aR)-5-((R)-1-hydroxyethyl)-2-(propylamino)-5,6,7,7a-tetrahydro-3aH-pyrano[3,2-d]thiazole-6,7-diol(Faster eluting isomer) | 277.0 |

TABLE 1-continued

| Example | structure | Name | MH+ |
|---|---|---|---|
| 115 | 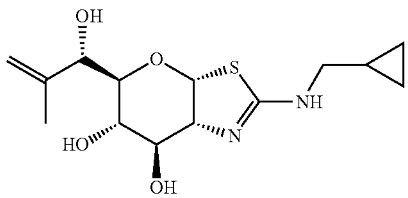 [SMILES: C=C(C)[C@H](O)[C@H]1O[C@@H]2SC(NCC3CC3)=N[C@@H]2[C@@H](O)[C@@H]1O] | (3aR,5R,6S,7R,7aR)-2-(cyclopropylmethylamino)-5-((S)-1-hydroxy-2-methylallyl)5,6,7,7a-tetrahydro-3aH-pyrano[3,2-d]thiazole-6,7-diol(Slower eluting isomer) | 315.0 |
| 116 | 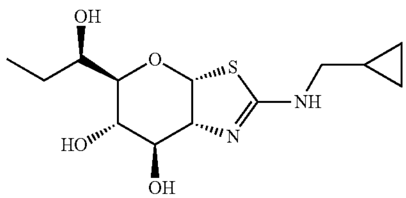 [SMILES: CC[C@@H](O)[C@H]1O[C@@H]2SC(NCC3CC3)=N[C@@H]2[C@@H](O)[C@@H]1O] | (3aR,5R,6S,7R,7aR)-2-(cyclopropylmethylamino)-5-((R)-1-hydroxypropyl)-5,6,7,7a-tetrahydro-3aH-pyrano[3,2-d]thiazole-6,7-diol(Faster eluting isomer) | 303.0 |
| 117 | 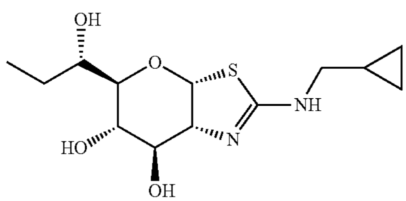 | (3aR,5R,6S,7R,7aR)-2-(cyclopropylmethylamino)-5-((S)-1-hydroxypropyl)-5,6,7,7a-tetrahydro-3aH-pyrano[3,2-d]thiazole-6,7-diol(Slower eluting isomer) | 303.0 |
| 118 | 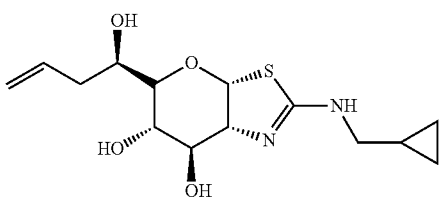 [SMILES: C=CC[C@@H](O)C1O[C@@H]2SC(NCC3CC3)=N[C@@H]2[C@@H](O)[C@@H]1O] | (3aR,5S,6S,7R,7aR)-2-(cyclopropylmethylamino)-5-((R)-1-hydroxybut-3-enyl)-5,6,7,7a-tetrahydro-3aH-pyrano[3,2-d]thiazole-6,7-diol(Faster eluting isomer) | 315.0 |
| 119 | 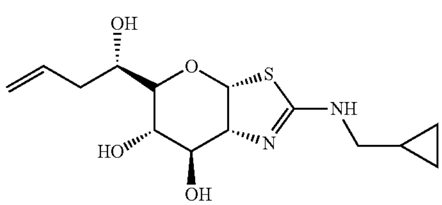 | (3aR,5S,6S,7R,7aR)-2-(cyclopropylmethylamino)-5-((S)1-hydroxybut-3-enyl)-5,6,7,7a-tetrahydro-3aH-pyrano[3,2-d]thiazole-6,7-diol(Slower eluting isomer) | 315.0 |
| 120 | 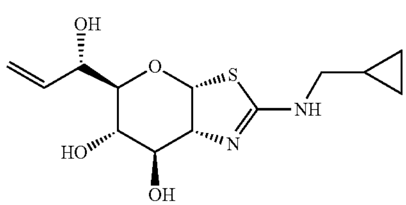 [SMILES: C=C[C@H](O)[C@H]1O[C@@H]2SC(NCC3CC3)=N[C@@H]2[C@@H](O)[C@@H]1O] | (3aR,5R,6S,7R,7aR)-2-(cyclopropylmethylamino)-5-((S)-1-hydroxyallyl)-5,6,7,7a-tetrahydro-3aH-pyrano[3,2-d]thiazole-6,7-diol(Slower eluting isomer) | 301.0 |
| 121 | 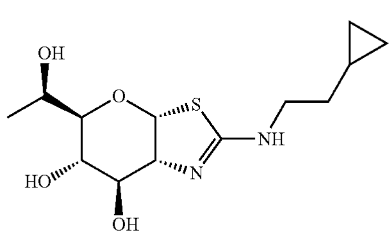 [SMILES: C[C@@H](O)[C@H]1O[C@@H]2SC(NCCC3CC3)=N[C@@H]2[C@@H](O)[C@@H]1O] | (3aR,5R,6S,7R,7aR)-2-(2-cyclopropylethylamino)-5-((R)-1-hydroxyethyl)-5,6,7,7a-tetrahydro-3aH-pyrano[3,2-d]thiazole-6,7-diol(Faster eluting isomer) | 303.0 |

TABLE 1-continued

| Example | structure | Name | MH+ |
|---|---|---|---|
| 122 | 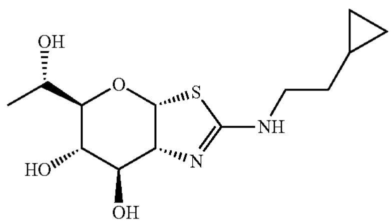 [SMILES: C[C@H](O)[C@H]1O[C@@H]2SC(NCCC3CC3)=N[C@@H]2[C@@H](O)[C@@H]1O] | (3aR,5R,6S,7R,7aR)-2-(2-cyclopropylethylamino)-5-((S)-1-hydroxyethyl)-5,6,7,7a-tetrahydro-3aH-pyrano[3,2-d]thiazole-6,7-diol(Slower eluting isomer) | 303.0 |
| 123 | 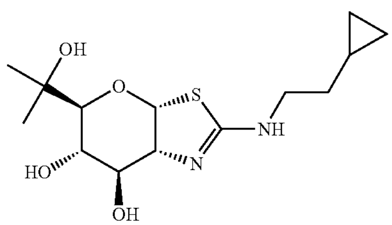 [SMILES: CC(C)(O)[C@H]1O[C@@H]2SC(NCCC3CC3)=N[C@@H]2[C@@H](O)[C@@H]1O] | (3aR,5S,6S,7R,7aR)-2-(2-cyclopropylethylamino)-5-(2-hydroxypropan-2-yl)-5,6,7,7a-tetrahydro-3aH-pyrano[3,2-d]thiazole-6,7-diol | 317.0 |
| 124 | 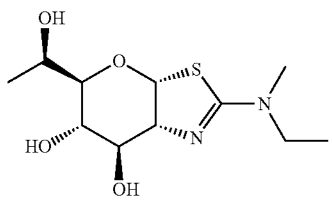 [SMILES: CCN(C)C1=N[C@@H]2[C@@H](O)[C@H](O)[C@@H]([C@@H](C)O)O[C@@H]2S1] | (3aR,5R,6S,7R,7aR)-2-(ethyl(methyl)amino)-5-((R)-1-hydroxyethyl)-5,6,7,7a-tetrahydro-3aH-pyrano[3,2-d]thiazole-6,7-diol(Faster eluting isomer) | 276.9 |
| 125 | 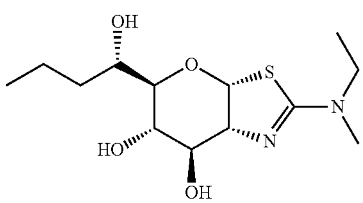 [SMILES: CCC[C@H](O)[C@H]1O[C@@H]2SC(N(C)CC)=N[C@@H]2[C@@H](O)[C@@H]1O] | (3aR,5R,6S,7R,7aR)-2-(ethyl(methyl)amino)-5-((S)-1-hydroxybutyl)-5,6,7,7a-tetrahydro-3aH-pyrano[3,2-d]thiazole-6,7-diol(Slower eluting isomer) | 305.0 |
| 126 | 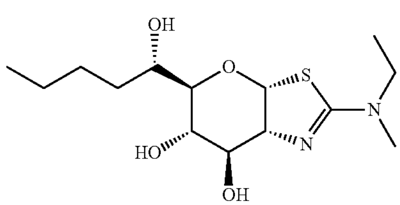 [SMILES: CCCC[C@H](O)[C@H]1O[C@@H]2SC(N(C)CC)=N[C@@H]2[C@@H](O)[C@@H]1O] | (3aR,5R,6S,7R,7aR)-2-(ethyl(methyl)amino)-5-((S)-1-hydroxypentyl)-5,6,7,7a-tetrahydro-3aH-pyrano[3,2-d]thiazole-6,7-diol(Slower eluting isomer) | 319.0 |
| 127 | 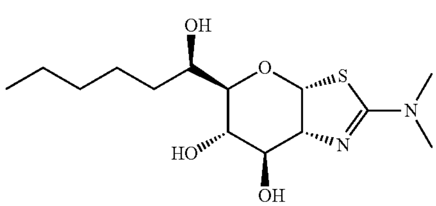 [SMILES: CCCCC[C@@H](O)[C@H]1O[C@@H]2SC(N(C)C)=N[C@@H]2[C@@H](O)[C@@H]1O] | (3aR,5R,6S,7R,7aR)-2-(dimethylamino)-5-((R)-1-hydroxyhexyl)-5,6,7,7a-tetrahydro-3aH-pyrano[3,2-d]thiazole-6,7-diol(Faster eluting isomer) | 319.0 |
| 128 | 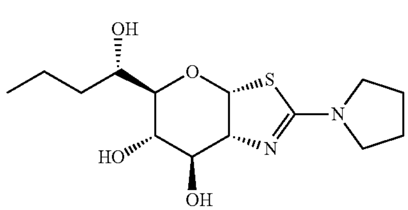 [SMILES: CCC[C@H](O)[C@H]1O[C@@H]2SC(N3CCCC3)=N[C@@H]2[C@@H](O)[C@@H]1O] | (3aR,5R,6S,7R,7aR)-5-((S)-1-hydroxybutyl)-2-(pyrrolidin-1-yl)-5,6,7,7a-tetrahydro-3aH-pyrano[3,2-d]thiazole-6,7-diol(Slower eluting isomer) | 317.0 |

TABLE 1-continued

| Example | structure | Name | MH+ |
|---|---|---|---|
| 129 | 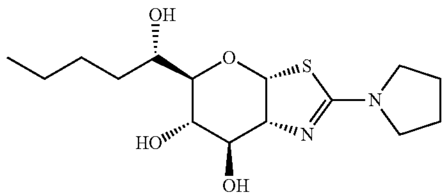 [SMILES: CCCC[C@H](O)[C@H]1O[C@@H]2SC(N3CCCC3)=N[C@@H]2[C@@H](O)[C@@H]1O] | (3aR,5R,6S,7R,7aR)-5-((S)-1-hydroxypentyl)-2-(pyrrolidin-1-yl)-5,6,7,7a-tetrahydro-3aH-pyrano[3,2-d]thiazole-6,7-diol(Slower eluting isomer) | 331.0 |
| 130 | 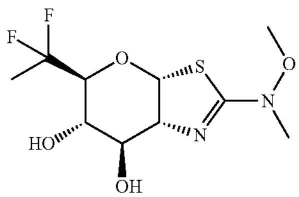 [SMILES: CON(C)C1=N[C@@H]2[C@@H](O)[C@H](O)[C@@H](C(C)(F)F)O[C@@H]2S1] | (3aR,5S,6S,7R,7aR)-5-(1,1-difluoroethyl)-2-(methoxy(methyl)amino)-5,6,7,7a-tetrahydro-3aH-pyrano[3,2-d]thiazole-6,7-diol | 299.0 |
| 131 | 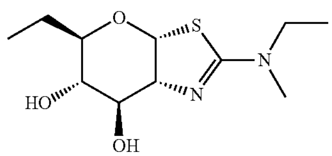 [SMILES: CC[C@H]1O[C@@H]2SC(N(C)CC)=N[C@@H]2[C@@H](O)[C@@H]1O] | (3aR,5R,6S,7R,7aR)-5-ethyl-2-(ethyl(methyl)amino)-5,6,7,7a-tetrahydro-3aH-pyrano[3,2-d]thiazole-6,7-diol | 261.0 |
| 132 | 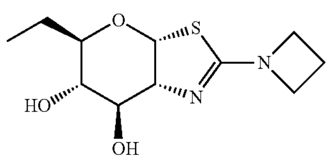 [SMILES: CC[C@H]1O[C@@H]2SC(N3CCC3)=N[C@@H]2[C@@H](O)[C@@H]1O] | (3aR,5R,6S,7R,7aR)-2-(azetidin-1-yl)-5-ethyl-5,6,7,7a-tetrahydro-3aH-pyrano[3,2-d]thiazole-6,7-diol | 259.0 |
| 133 | 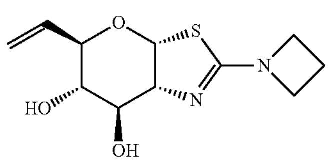 [SMILES: C=C[C@H]1O[C@@H]2SC(N3CCC3)=N[C@@H]2[C@@H](O)[C@@H]1O] | (3aR,5R,6S,7R,7aR)-2-(azetidin-1-yl)-5-vinyl-5,6,7,7a-tetrahydro-3aH-pyrano[3,2-d]thiazole-6,7-diol | 257.0 |
| 134 | 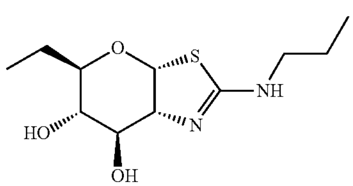 [SMILES: CCCNC1=N[C@@H]2[C@@H](O)[C@H](O)[C@@H](CC)O[C@@H]2S1] | (3aR,5R,6S,7R,7aR)-5-ethyl-2-(propylamino)-5,6,7,7a-tetrahydro-3aH-pyrano[3,2-d]thiazole-6,7-diol | 261.0 |
| 135 | 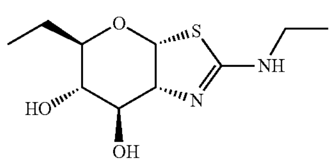 [SMILES: CCNC1=N[C@@H]2[C@@H](O)[C@H](O)[C@@H](CC)O[C@@H]2S1] | (3aR,5R,6S,7R,7aR)-5-ethyl-2-(ethylamino)-5,6,7,7a-tetrahydro-3aH-pyrano[3,2-d]thiazole-6,7-diol | 247.0 |
| 136 | 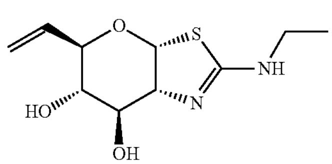 [SMILES: C=C[C@H]1O[C@@H]2SC(NCC)=N[C@@H]2[C@@H](O)[C@@H]1O] | (3aR,5R,6S,7R,7aR)-2-(ethylamino)-5-vinyl-5,6,7,7a-tetrahydro-3aH-pyrano[3,2-d]thiazole-6,7-diol | 245.0 |

Examples 137 and 138

(3aR,5S,6S,7R,7aR)-5-(1-hydroxycyclopentyl)-2-(methylamino)-5,6,7,7a-tetrahydro-3aH-pyrano[3,2-d]thiazole-6,7-diol and (3aR,5S,6S,7R,7aR)-5-(1-hydroxycyclopent-3-enyl)-2-(methylamino)-5,6,7,7a-tetrahydro-3aH-pyrano[3,2-d]thiazole-6,7-diol

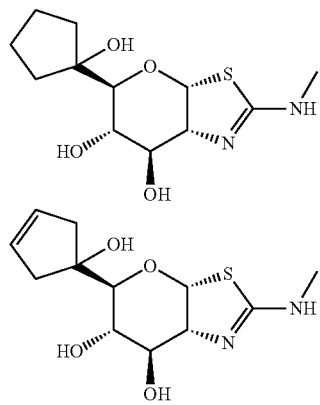

4-((3aR,5S,6S,7R,7aR)-6,7-bis(4-methoxybenzyloxy)-2-(methylamino)-5,6,7,7a-tetrahydro-3aH-pyrano[3,2-d]thiazol-5-yl)hepta-1,6-dien-4-ol

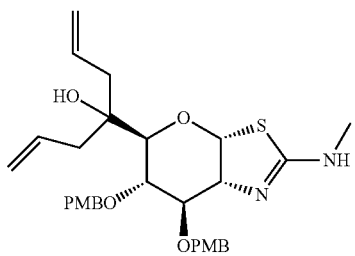
57

A solution of (3aR,5S,6S,7R,7aR)-methyl 2-(tert-butoxycarbonyl(methyl)amino)-6,7-bis(4-methoxybenzyloxy)-5,6,7,7a-tetrahydro-3aH-pyrano[3,2-d]thiazole-5-carboxylate (1.0 g, 1.66 mmol) in THF (15 mL) was treated with allyl- Scheme XII

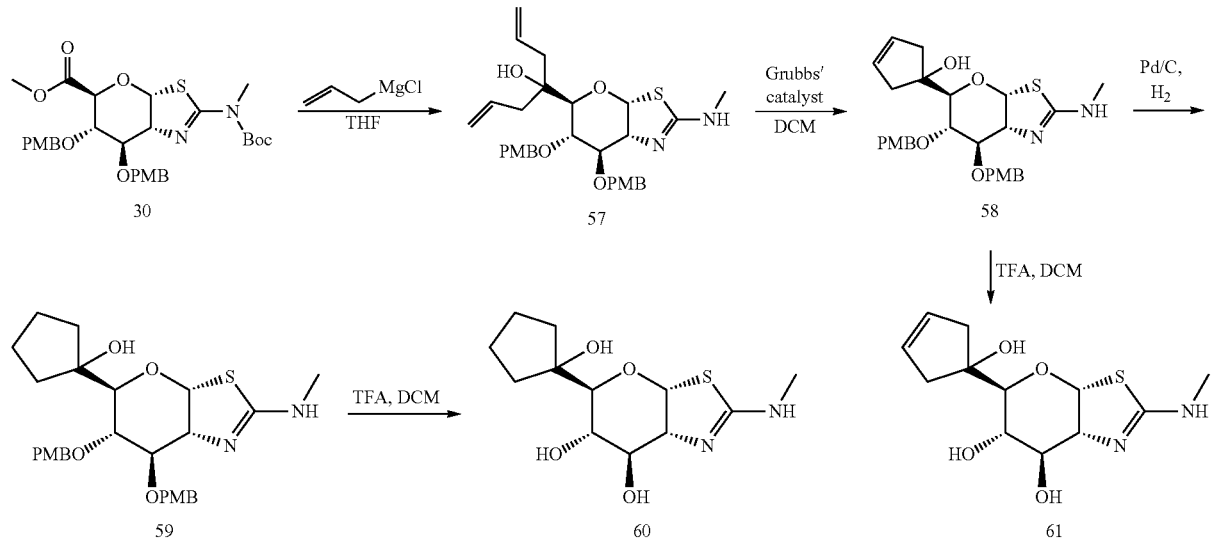

Step 1

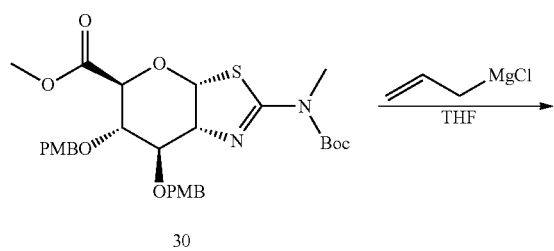

magnesium chloride (8.0 mL, 0.5 M in THF) for 1 hour at room temperature. The reaction was quenched by aqueous NH$_4$Cl (20 mL), and extracted with ethyl acetate (2×30 mL). The combined organic layers were dried over anhydrous sodium sulfate and concentrated under reduced pressure to give a residue, which was purified by a silica gel column with 1% methanol in dichloromethane to afford the title compound as a yellow oil (0.75 g, 81%), (ES, m/z) [M+H]$^+$ 555.0; $^1$H NMR (300 MHz, CDCl$_3$) δ 7.23-7.35 (m, 4H), 6.84-6.93 (m, 4H), 6.34-6.37 (d, J=6.9 Hz, 1H), 5.86-5.92 (m, 2H), 5.06-5.11 (m, 4H), 4.65-4.66 (m, 2H), 4.50-4.54 (m, 2H), 4.26-4.33 (m, 2H), 3.96-3.99 (d, J=8.4 Hz, 1H), 3.81-3.83 (m, 6H), 3.51-3.54 (d, J=8.4 Hz, 1H), 2.92 (s, 3H), 2.22-2.31 (m, 4H).

Step 2

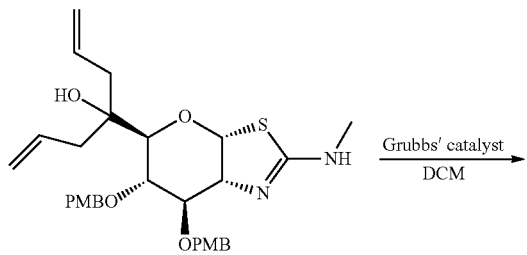

57

1-((3aR,5S,6S,7R,7aR)-6,7-bis(4-methoxybenzy-loxy)-2-(methylamino)-5,6,7,7a-tetrahydro-3aH-pyrano[3,2-d]thiazol-5-yl)cyclopent-3-enol To a solution of compound 57 (0.60 g, 1.08 mmol) in dichloromethane (10 mL) was added Grubbs' catalyst (0.19 g, 0.22 mmol) under nitrogen atmosphere. After stirring for 12 hours at room temperature, the reaction mixture was concentrated under reduced pressure to afford a residue, which was purified by a silica gel column with 30%-40% ethyl acetate in petroleum ether to afford compound 58 as a grey oil (0.35 g, 61%). (ES, m/z) [M+H]$^+$ 527.0; $^1$H NMR (300 MHz, CDCl$_3$) δ 7.24-7.35 (m, 4H), 6.85-6.92 (m, 4H), 6.34-6.36 (d, J=6.9 Hz, 1H), 5.66-5.67 (m, 2H), 4.49-4.65 (m, 4H), 4.28-4.31 (m, 2H), 3.90-3.93 (d, J=8.4 Hz, 1H), 3.81-3.82 (m, 6H), 3.55-3.57 (d, J=8.4 Hz, 1H), 2.92 (s, 3H), 2.58-2.78 (m, 2H), 2.23-2.34 (m, 2H).

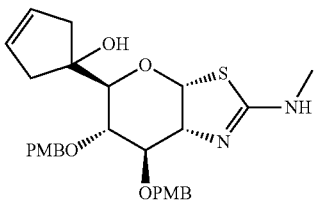

58

Step 3

1-03aR,5S,6S,7R,7aR)-6,7-bis(4-methoxybenzy-loxy)-2-(methylamino)-5,6,7,7a-tetrahydra-3aH-pyrano[3,2-d]thiazol-5-yl)cyclopentanol A mixture of compound 58 (0.35 g, 0.67 mmol) and Pd/C (0.10 g) in methanol (20 mL) was stirred under hydrogen atmosphere for 20 hours at room temperature. The reaction mixture was filtered and the filtrate was concentrated under vacuum to afford a residue, which was purified by a silica gel column with 30%-40% ethyl acetate in petroleum ether to afford crude compound 59 as a yellow oil (300 mg), which was employed in the next step without further purification. [M+H]$^+$ 529.0.

Step 4

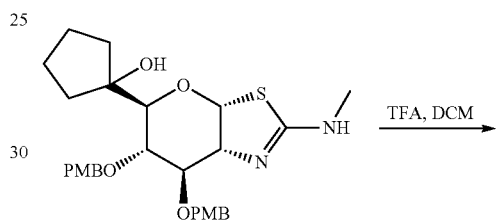

59

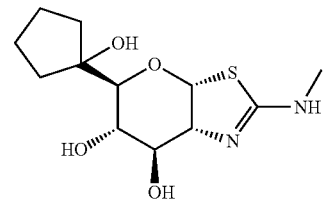

60

(3aR,5S,6S,7R,7aR)-5-(1-hydroxycyclopentyl)-2-(methylamino)-5,6,7,7a-tetrahydro-3aH-pyrano[3,2-d]thiazole-6,7-diol A solution of the above compound 59 (100 mg) in dichloromethane (5 mL) was treated with TFA (0.5 mL) for 4 hours at room temperature. The reaction solution was concentrated under reduced pressure. The residue was purified by Prep-HPLC with the following conditions [(Agilent 1200 prep HPLC): Column, SunFire Prep C18,19*50 mm 5 um; mobile phase, H$_2$O with 0.03% NH$_4$OH and CH$_3$CN (10% CH$_3$CN up to 45% in 10 min); Detector, UV 220 nm] to afford compound 60 (Example 137) as a white solid (5.0 mg). (ES, m/z): [M+H]$^+$ 289.0; $^1$H NMR (300 MHz, D$_2$O) δ 6.22-6.24 (d, J=6.9 Hz, 1H), 4.29-4.32 (m, 1H), 4.12-4.14 (m, 1H), 3.80-3.83 (m, 1H), 3.30-3.33 (d, J=8.4 Hz, 1H), 2.74 (s, 3H), 1.51-1.66 (m, 8H).

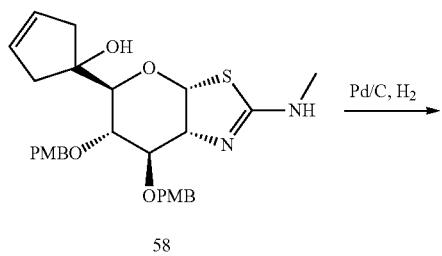

58

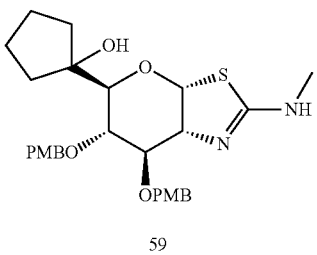

59

Step 5

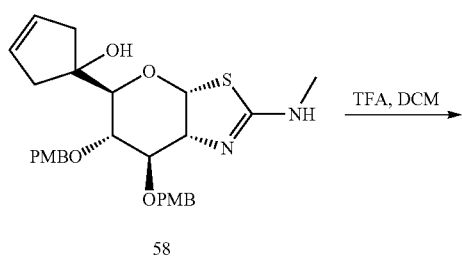

58

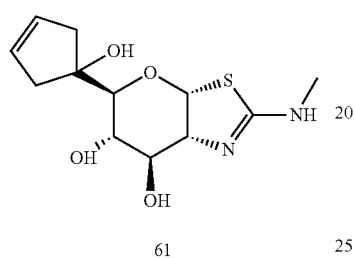

61

(3aR,5S,6S,7R,7aR)-5-(1-hydroxycyclopent-3-enyl)-
2-(methylamino)-5,6,7,7a-tetrahydro-3aH-pyrano[3,
2-d]thiazole-6,7-diol A solution of compound 58 (100 mg, 0.19 mmol)) in dichloromethane (5 mL) was treated with TFA (0.5 mL) for 4 hours at room temperature. The reaction solution was concentrated under reduced pressure. The residue was purified by Prep-HPLC with the following conditions [(Agilent 1200 prep HPLC): Column, SunFire Prep C18, 19*50 mm 5 um; mobile phase, H$_2$O with 0.03% NH$_4$OH and CH$_3$CN (10% CH$_3$CN up to 45% in 10 min); Detector, UV 220 nm] to afford compound 61 (Example 138) as a white solid (15.0 mg, 27%). (ES, m/z): [M+H]$^+$ 287.0; $^1$H NMR (300 MHz, D$_2$O) δ 6.25-6.28 (d, J=6.9 Hz, 1H), 5.62-5.64 (m, 2H), 4.31-4.37 (m, 1H), 4.13-4.15 (m, 1H), 3.76-3.81 (m, 1H), 3.44-3.47 (d, J=8.4 Hz, 1H), 2.76 (s, 3H), 2.58-2.64 (m, 2H), 2.16-2.31 (m, 2H).

Examples 139 and 140

(3aR,5S,6S,7R,7aR)-5-(2-fluoropropan-2-yl)-2-(methylamino)-5,6,7,7a-tetrahydro-3aH-pyrano[3,2-d]thiazole-6,7-diol and (3aR,5R,6S,7R,7aR)-2-(methylamino)-5-(prop-1-en-2-yl)-5,6,7,7a-tetrahydro-3aH-pyrano[3,2-d]thiazole-6,7-diol

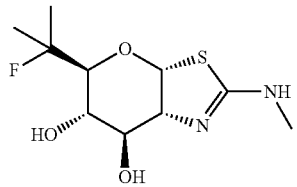

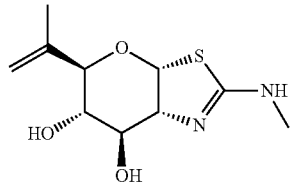

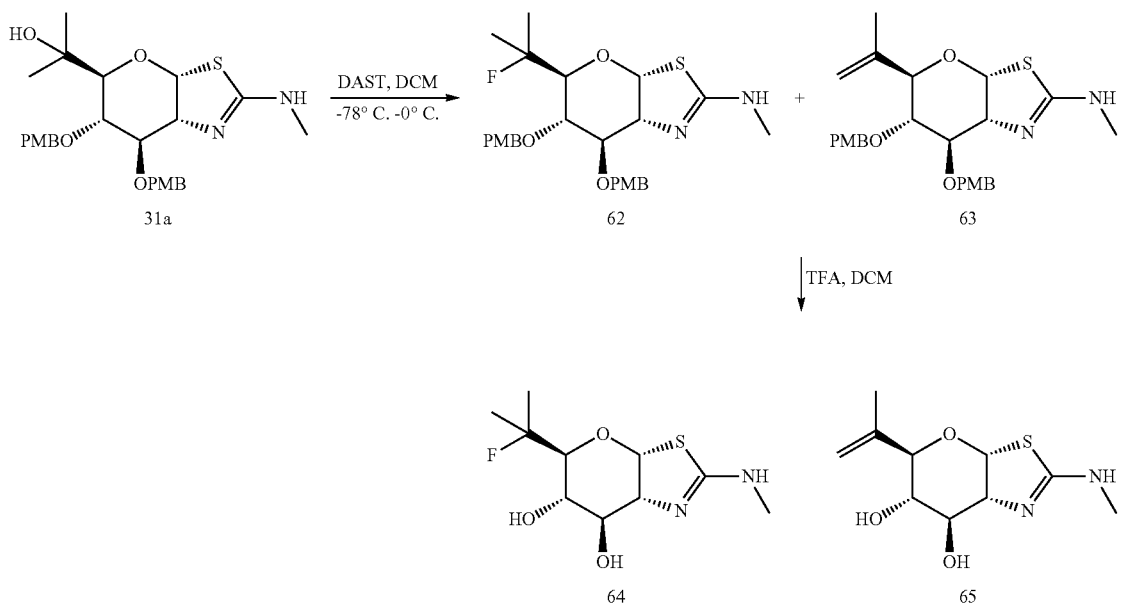

Step 1

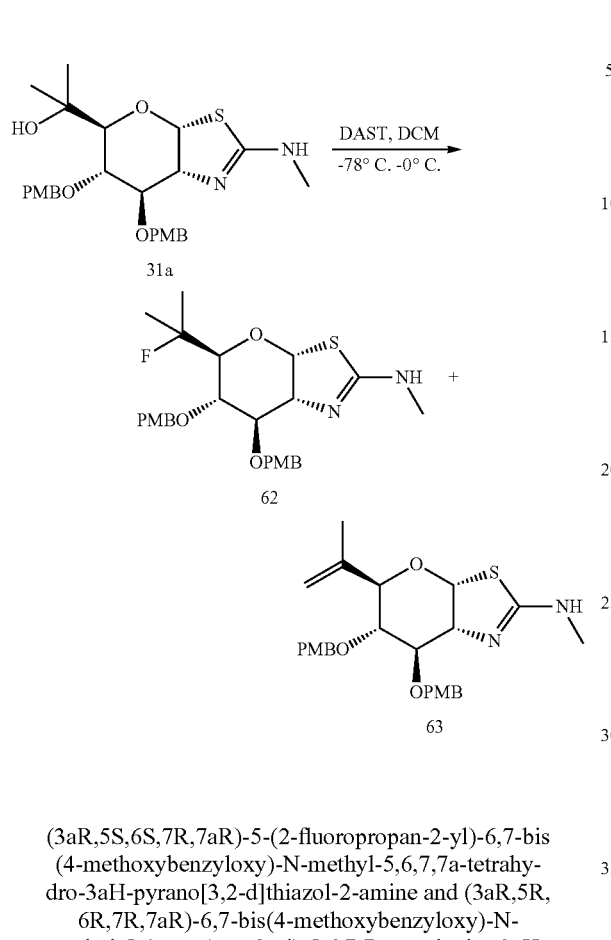

(3aR,5S,6S,7R,7aR)-5-(2-fluoropropan-2-yl)-6,7-bis (4-methoxybenzyloxy)-N-methyl-5,6,7,7a-tetrahydro-3aH-pyrano[3,2-d]thiazol-2-amine and (3aR,5R, 6R,7R,7aR)-6,7-bis(4-methoxybenzyloxy)-N-methyl-5-(prop-1-en-2-yl)-5,6,7,7a-tetrahydro-3aH-pyrano[3,2-d]thiazol-2-amine To a solution of 2-((3aR,5S,6S,7R,7aR)-6,7-bis(4-methoxybenzyloxy)-2-(methylamino)-5,6,7,7a-tetrahydro-3aH-pyrano[3,2-d]thiazol-5-yl)propan-2-ol (450.0 mg, 0.90 mmol) in dichloromethane (20 mL) was added DAST (720.0 mg, 4.47 mmol) at −78° C. After stirred for 1 hour at 0° C., the reaction was quenched by aqueous potassium carbonate, extracted with dichloromethane (2×50 mL), dried over anhydrous sodium sulfate, and concentrated under reduced pressure to afford a mixture of 62 and 63 as a yellow oil (400.0 mg), which was used for next step without further purification: (ES, m/z) [M+H]+ 505.0 and (ES, m/z) [M+H]+ 485.0.

Step 2

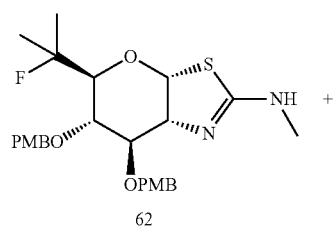

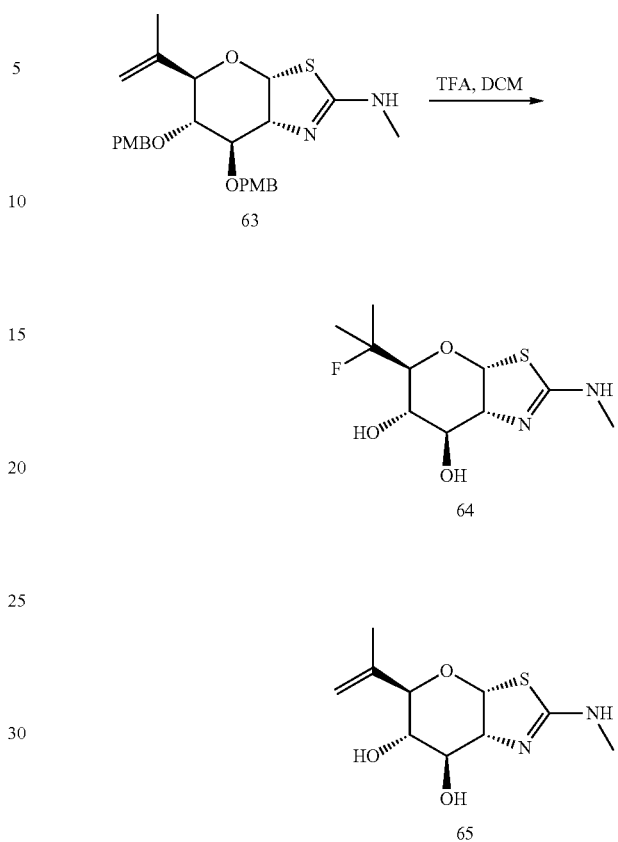

(3aR,5S,6S,7R,7aR)-5-(2-fluoropropan-2-yl)-2-(methylamino)-5,6,7,7a-tetrahydro-3aH-pyrano[3,2-d]thiazole-6,7-diol and (3aR,5R,6S,7R,7aR)-2-(methylamino)-5-(prop-1-en-2-yl)-5,6,7,7a-tetrahydro-3aH-pyrano[3,2-d]thiazole-6,7-diol A solution of the above crude products (400.0 mg) in dichloromethane (20 mL) was treated with trifluoroacetic acid (2 mL) for 2 hours at room temperature. Removal of volatiles gave a residue, which was purified by Prep-HPLC with the following conditions [(Agilent 1200 prep HPLC): Column, SunFire Prep C18,19*50 mm 5 um; mobile phase, H₂O with 0.03% TFA and CH₃CN (10% CH₃CN up to 45% in 10 min); Detector, UV 220 nm] to afford compound 64 (Example 139) as its TFA salt as a white solid (50.0 mg). (ES, m/z): [M+H]+ 265.0; ¹H NMR (300 MHz, CD₃OD) δ 6.56-6.58 (d, J=7.2 Hz, 1H), 4.48-4.49 (m, 1H), 4.12-4.14 (m, 1H), 3.92-3.94 (m, 1H), 3.44-3.51 (m, 1H), 3.07 (s, 3H), 1.45-1.47 (d, J=6.3 Hz, 3H), 1.37-1.39 (d, J=6.6 Hz, 3H); and compound 65 (Example 140) as its TFA salt as a white solid (17.8 mg). (ES, m/z): [M+H]+ 245.0; ¹H NMR (300 MHz, D₂O) δ 6.57-6.61 (m, 1H), 5.10-5.11 (m, 2H), 4.09-4.19 (m, 2H), 3.84-3.94 (m, 1H), 3.58-3.66 (m, 1H), 2.97 (s, 3H), 1.71 (s, 3H).

113
Example 141
(3aR,5R,6S,7R,7aR)-2-(2-Fluoroethylamino)-5-((S)-1-hydroxyethyl)-5,6,7,7a-tetrahydro-3aH-pyrano[3,2-d]thiazole-6,7-diol
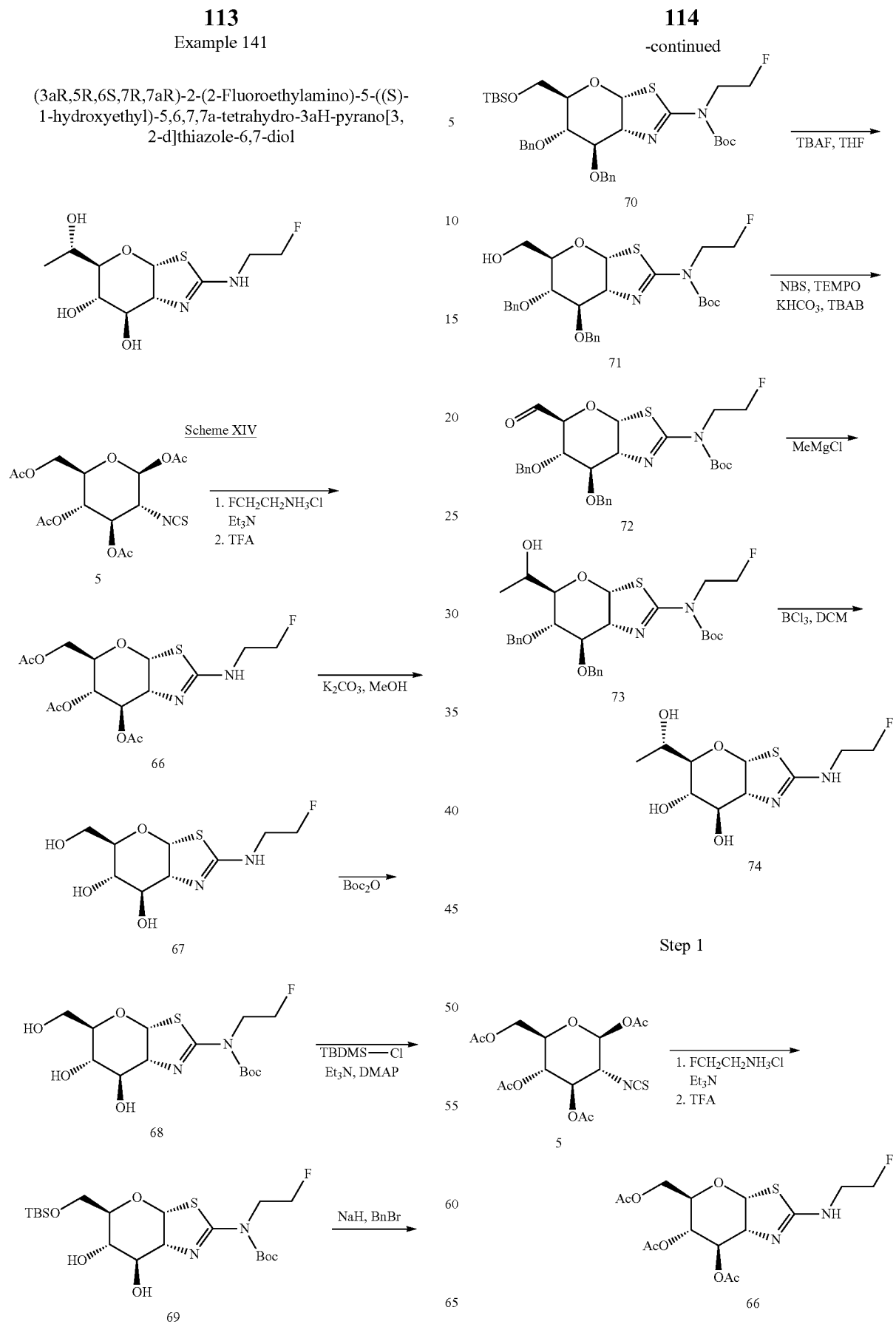

(3aR,5R,6S,7R,7aR)-5-(Acetoxymethyl)-2-(2-fluoroethylamino)-5,6,7,7a-tetrahydro-3aH-pyrano[3,2-d]thiazole-6,7-diyl diacetate (66)

A solution of (2S,3R,4R,5S,6R)-6-(acetoxymethyl)-3-isothiocyanato-tetrahydro-2H-pyran-2,4,5-triyl triacetate (30 g, 77 mmol) in dichloromethane (100 mL) was added 2-fluoroethylamine hydrochloride (8.4 g, 84 mmol) and triethylamine (11.7 mL, 115 mmol). The resulting solution was stirred for 1 hour at room temperature, and then condensed to give a light yellow foam, which was dissolved into dichloromethane (100 mL) and treated with 2,2,2-trifluoroacetic acid (75.6 g, 663 mmol) overnight at room temperature. The reaction mixture was quenched by saturated aqueous sodium carbonate (500 mL), washed with sodium chloride (3×50 mL), dried over anhydrous magnesium sulfate, and concentrated under vacuum to give a residue, which was purified by a silica gel column, eluting with 50% ethyl acetate in petroleum ether to provide compound 66 as a light yellow oil (24 g, 70%). (ES, m/z) [M+H]$^+$ 393.0; $^1$H NMR (300 MHz, CDCl$_3$) δ 6.27-6.29 (d, J=6.60 Hz, 1H), 5.42-5.44 (1, J=2.7 Hz, 1H), 4.95-4.99 (dd, J=1.8 Hz, 9.5 Hz, 1H), 4.70-4.73 (m, 1H), 4.54-4.65 (m, 1H), 4.37-4.39 (t, J=0.9 Hz, 1H), 4.16-4.17 (m, 2H), 3.81-3.87 (m, 1H), 3.56-3.71 (m, 2H), 2.09 (s, 3H), 2.11 (s, 3H), 2.14 (s, 3H),

Step 2

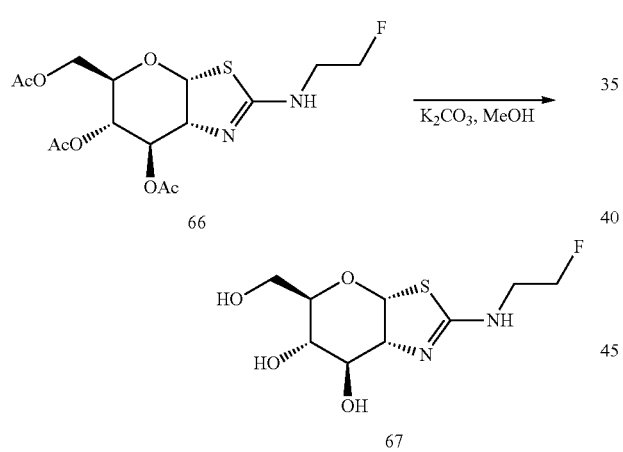

(3aR,5R,6S,7R,7aR)-2-(2-Fluoroethylamino)-5-(hydroxymethyl)-5,6,7,7a-tetrahydro-3aH-pyrano[3,2-d]thiazole-6,7-diol (67)

A solution of (3aR,5R,6S,7R,7aR)-5-(acetoxymethyl)-2-(2-fluoroethylamino)-5,6,7,7a-tetrahydro-3aH-pyrano[3,2-d]thiazole-6,7-diyl diacetate (29 g, 74 mmol) in methanol (200 mL) was treated with potassium carbonate (1 g, 7 mmol) overnight at room temperature. The solids were collected by filtration and washed with dichloromethane (3×50 mL) to afford compound 67 as a white solid (18 g, 92%). (ES, m/z) [M+H]$^+$ 266.9; $^1$H NMR (300 MHz, D$_2$O) δ 6.21-6.23 (d, J=6.3 Hz, 1H), 4.55-4.59 (m, 1H), 4.40-4.44 (m, 1H), 4.10-4.14 (t, J=5.7 Hz, 1H), 3.95-3.98 (t, J=5.4 Hz, 1H), 3.70-3.75 (m, 1H), 3.40-3.62 (m, 5H).

Step 3

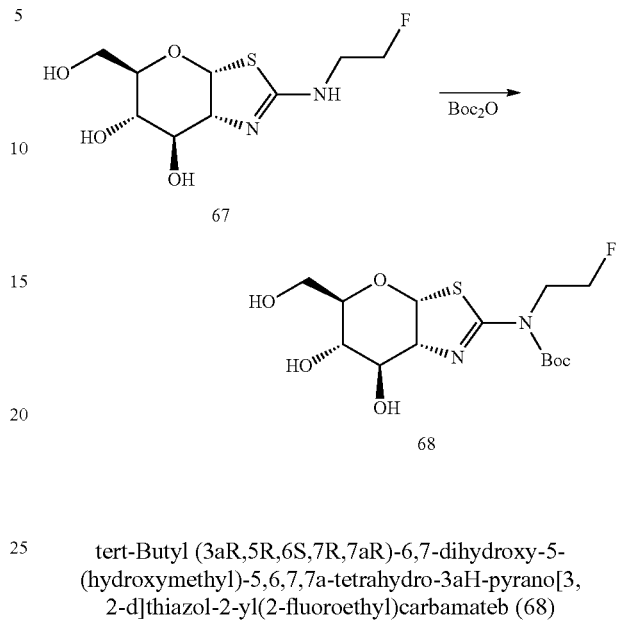

tert-Butyl (3aR,5R,6S,7R,7aR)-6,7-dihydroxy-5-(hydroxymethyl)-5,6,7,7a-tetrahydro-3aH-pyrano[3,2-d]thiazol-2-yl(2-fluoroethyl)carbamateb (68)

To a solution of (3aR,5R,6S,7R,7aR)-2-(2-fluoroethylamino)-5-(hydroxymethyl)-5,6,7,7a-tetrahydro-3aH-pyrano[3,2-d]thiazole-6,7-diol (13.7 g, 51 mmol) in methanol (100 mL) was added di-tert-butyl dicarbonate (22 g, 102 mmol) and triethylamine (8.6 mL). After stirred overnight at room temperature, the resulting mixture was concentrated under vacuum to give a residue, which was purified by a silica gel column, eluting with 20% methanol in dichloromethane to give compound 68 as a white syrup (16 g, 85%). (ES, m/z) [M+H]$^+$ 367.0; $^1$H NMR (300 MHz, CDCl$_3$) δ 6.18-6.20 (d, J=6.3 Hz, 1H), 4.70-4.76 (m, 1H), 4.55-4.60 (m, 1H), 4.43-4.48 (m, 1H), 4.27-4.30 (m, 1H), 3.86-3.98 (m, 3H), 3.71-3.79 (m, 2H), 3.49-3.62 (m, 2H), 1.57 (s, 9H).

Step 4

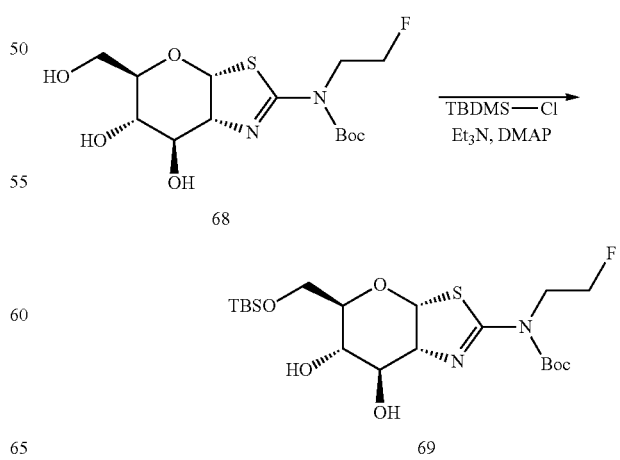

tert-Butyl (3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl(2-fluoroethyl)carbamate (69)

To a solution of tert-butyl (3aR,5R,6S,7R,7aR)-6,7-dihydroxy-5-(hydroxymethyl)-5,6,7,7a-tetrahydro-3aH-pyrano[3,2-d]thiazol-2-yl(2-fluoroethyl)carbamate (16 g, 43.7 mmol) in dichloromethane (100 mL) was added tert-butylchlorodimethylsilane (7.6 g, 50.7 mmol), 4-dimethylaminopyridine (530 mg, 4.34 mmol) and triethylamine (6.6 g, 65 mmol). After stirred for 6 h at room temperature, the resulting mixture was concentrated under vacuum to give a residue, which was purified by a silica gel column, eluting with 20% petroleum in ethyl acetate to give compound 69 as pale yellow oil (10 g, 48%). (ES, m/z) [M+H]$^+$ 481.0; $^1$H NMR (300 MHz, CDCl$_3$) δ 6.17-6.19 (d, J=6.3 Hz, 1H), 4.42-4.74 (m, 3H), 3.52-4.26 (m, 7H), 1.56 (s, 9H), 0.92 (s, 9H), 0.10 (s, 6H).

Step 5

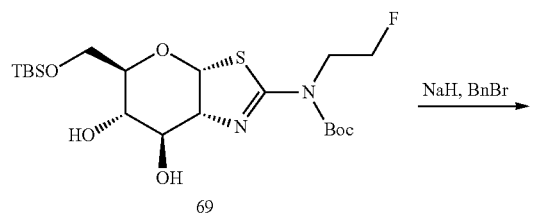

tert-Butyl (3aR,5R,6S,7R,7aR)-6,7-bis(benzyloxy)-5-((tert-butyldimethylsilyloxy)methyl)-5,6,7,7a-tetrahydro-3aH-pyrano[3,2-d]thiazol-2-yl(2-fluoroethyl)carbamate (70)

A solution of tert-butyl (3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl(2-fluoroethyl)carbamate (2.0 g, 4.2 mmol) in N,N-dimethylformamide (30 mL) was treated with sodium hydride (510 mg, 21 mmol) for 10 min at 10° C. in a nitrogen atmosphere, and followed by addition of 1-(bromomethyl)benzene (2.2 g, 13 mmol). After stirred for 15 min, the reaction was quenched with saturated aqueous NH$_4$Cl and extracted with dichloromethane (3×30 mL). The organic layers were dried over anhydrous magnesium sulfate and concentrated under vacuum to give a residue, which was purified by a silica gel column, eluting with 1.5-3% ethyl acetate in petroleum ether to provide compound 70 as a yellow oil (0.7 g, 25%). (ES, m/z) [M+H]$^+$ 660.8; $^1$H NMR (300 MHz, CDCl$_3$) δ 7.28-7.43 (m, 10H), 6.11-6.13 (d, J=6.3 Hz, 1H), 4.60-4.74 (m, 4H), 4.30-4.41 (m, 6H), 3.73-3.75 (m, 3H), 3.37-3.44 (m, 1H), 1.54 (s, 9H), 0.90 (s, 9H), 0.06 (s, 6H).

Step 6

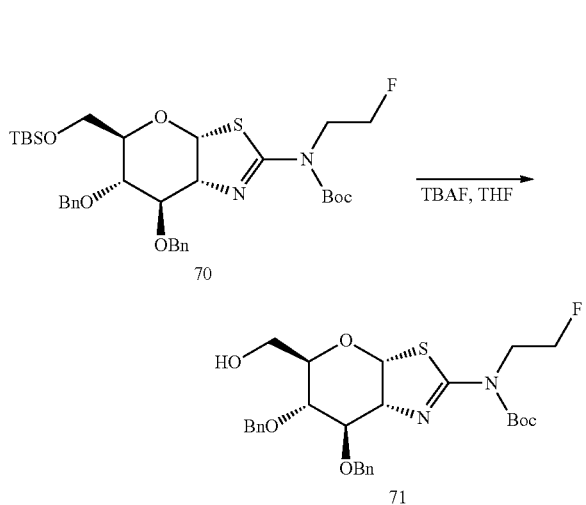 [SMILES: CC(C)(C)OC(=O)N(CCF)C1=N[C@@H]2[C@@H](OCc3ccccc3)[C@H](OCc3ccccc3)[C@@H](CO[Si](C)(C)C(C)(C)C)O[C@@H]2S1 ; CC(C)(C)OC(=O)N(CCF)C1=N[C@@H]2[C@@H](OCc3ccccc3)[C@H](OCc3ccccc3)[C@@H](CO)O[C@@H]2S1]

tert-Butyl (3aR,5R,6S,7R,7aR)-6,7-bis(benzyloxy)-5-(hydroxymethyl)-5,6,7,7a-tetrahydro-3aH-pyrano[3,2-d]thiazol-2-yl(2-fluoroethyl)carbamate (71)

A solution of tert-butyl (3aR,5R,6S,7R,7aR)-6,7-bis(benzyloxy)-5-((tert-butyldimethylsilyloxy)methyl)-5,6,7,7a-tetrahydro-3aH-pyrano[3,2-d]thiazol-2-yl(2-fluoroethyl)carbamate (1.36 g, 2.06 mmol) in THF (30 mL) was treated with tetrabutylammonium fluoride (1.1 g, 4.2 mmol) for 2 hrs at room temperature. The reaction mixture was quenched with H$_2$O (10 mL), extracted with ethyl acetate (3×50 mL), dried over anhydrous magnesium sulfate, and concentrated under vacuum to give a residue, which was purified by a silica gel column, eluting with 10%-20% ethyl acetate in petroleum ether to provide compound 71 as a pale yellow oil (600 mg, 53%). (ES, m/z) [M+H]$^+$ 546.8; $^1$H NMR (300 MHz, CDCl$_3$) δ 7.24-7.43 (m, 10H), 6.09-6.11 (d, J=4.2 Hz, 1H), 4.60-4.66 (m, 2H), 4.50-4.54 (m, 1H), 4.46-4.47 (m, 1H), 4.40-4.45 (m, 2H), 4.27-4.39 (m, 2H), 4.12-4.22 (m, 2H), 3.72-3.79 (m, 1H), 3.67-3.71 (m, 1H), 3.55-3.63 (m, 1H), 3.40-3.45 (m, 1H), 1.54 (s, 9H).

Step 7

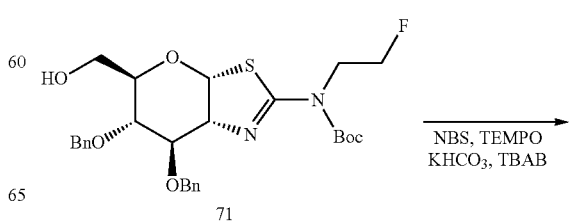

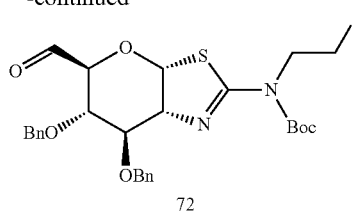

tert-Butyl (3aR,5S,6S,7R,7aR)-6,7-bis(benzyloxy)-5-formyl-5,6,7,7a-tetrahydro-3aH-pyrano[3,2-d]thiazol-2-yl(2-fluoroethyl)carbamate (72)

A mixture of tert-butyl (3aR,5R,6S,7R,7aR)-6,7-bis(benzyloxy)-5-(hydroxymethyl)-5,6,7,7a-tetrahydro-3aH-pyrano[3,2-d]thiazol-2-yl(2-fluoroethyl)carbamate (600 mg, 1.10 mmol), KHCO$_3$ (495 mg, 4.95 mmol), TBAB (18 mg, 0.06 mmol) and TEMPO (9 mg, 0.06 mmol) in dichloromethane (17 mL) and water (2 mL) was treated with NBS (215 mg, 1.21 mmol) for 15 min at 10-15° C. The reaction mixture was quenched by saturated aqueous Na$_2$SO$_3$ (5 mL), extracted with dichloromethane (3×15 mL), dried over magnesium sulfate, and concentrated under vacuum to give a residue, which was purified by a silica gel column, eluting with 20% ethyl acetate in petroleum ether to provide compound 72 as a yellow syrup (0.4 g, 67%). (ES, m/z) [M+H]$^+$ 545.0; $^1$H NMR (300 MHz, CDCl$_3$) δ 9.64 (s, 1H), 7.23-7.39 (m, 10H), 6.09-6.11 (d, J=6.3 Hz, 1H), 4.55-4.75 (m, 5H), 4.34-4.45 (m, 2H), 4.13-4.28 (m, 3H), 3.90-4.12 (m, 2H), 1.54 (s, 9H).

Step 8

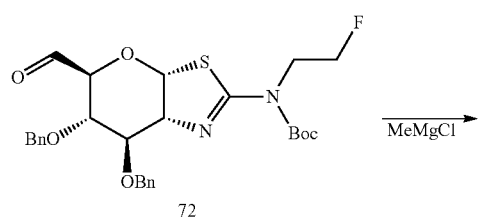

tert-Butyl (3aR,5R,6S,7R,7aR)-6,7-bis(benzyloxy)-5-(1-hydroxyethyl)-5,6,7,7a-tetrahydro-3aH-pyrano[3,2-d]thiazol-2-yl(2-fluoroethyl)carbamate (73)

To a solution of tert-butyl (3aR,5S,6S,7R,7aR)-6,7-bis(benzyloxy)-5-formyl-5,6,7,7a-tetrahydro-3aH-pyrano[3,2-d]thiazol-2-yl(2-fluoroethyl)carbamate (400 mg, 0.73 mmol) in THF (20 mL) was added methylmagnesium chloride (1 mL, 3M in THF). After stirred for 3 hours at 0-5° C., the resulting solution was quenched with saturated aqueous NH$_4$Cl (10 mL) and extracted with ethyl acetate (3×30 mL). The organic layers were dried over anhydrous magnesium sulfate and concentrated under vacuum to give a residue, which was purified by a silica gel column, eluting with 20% ethyl acetate in petroleum ether to give compound 73 as a yellow oil (0.37 g, 90%, diasteromers' ratio is 1:4). (ES, m/z) [M+H]$^+$ 561.0; $^1$H NMR (300 MHz, CDCl$_3$) δ 7.25-7.44 (m, 10H), 6.13-6.15 (d, J=6.9 Hz, 1H), 4.73-4.78 (m, 2H), 4.54-4.68 (m, 2H), 4.28-4.49 (m, 4H), 4.07-4.25 (m, 2H), 3.75-3.97 (m, 2H), 3.12-3.17 (m, 1H), 1.54 (s, 9H), 1.22-1.24 (d, J=6.3 Hz, 3H).

Step 9

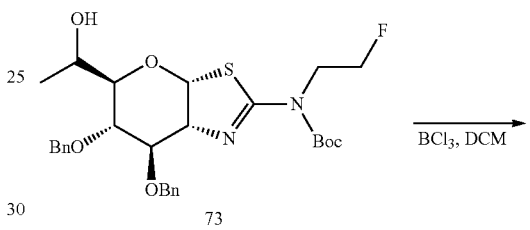

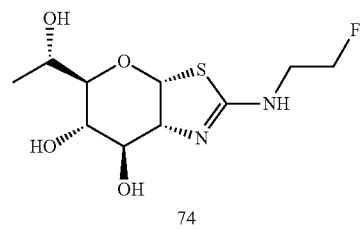

(3aR,5R,6S,7R,7aR)-2-(2-Fluoroethylamino)-5-((S)-1-hydroxyethyl)-5,6,7,7a-tetrahydro-3H-pyrano[3,2-d]thiazole-6,7-diol 2,2,2-trifluoroacetate (74)

A solution of tert-butyl (3aR,5R,6S,7R,7aR)-6,7-bis(benzyloxy)-5-(1-hydroxyethyl)-5,6,7,7a-tetrahydro-3aH-pyrano[3,2-d]thiazol-2-yl(2-fluoroethyl)carbamate (250 mg, 0.45 mmol) in dichloromethane (7 mL) was treated with BCl$_3$ (7 mL, 1M in dichloromethane) at −20-10° C. for 2 hrs. The reaction was quenched with methanol and concentrated under vacuum to give a crude product (0.25 g), which was purified by Prep-HPLC (Agilent 1200 prep HPLC; Column, X-Bridge 19*150 mm 5 um; mobile phase, water with 0.05% trifluoroacetic acid and CH$_3$CN (10% up to 20% in time 10); Detector, 220 nm.) to provide compound 74 (Example 141) as a white solid (55.7 mg, 45%). (ES, m/z) [M+H]$^+$ 281.0; $^1$H NMR (300 MHz, D$_2$O) δ 6.53-6.55 (d, J=6.9 Hz, 1H), 4.61-4.78 (m, 1H), 4.47-4.52 (m, 1H), 4.22-4.30 (m, 1H), 3.93-4.04 (m, 2H), 3.58-3.73 (m, 3H), 3.38-3.42 (m, 1H), 1.15-1.17 (d, J=6.6 Hz, 3H).

Example 142

(3aR,5R,6S,7R,7aR)-2-(3-Fluoropropylamino)-5-((S)-1-hydroxyethyl)-5,6,7,7a-tetrahydro-3aH-pyrano[3,2-d]thiazole-6,7-diol

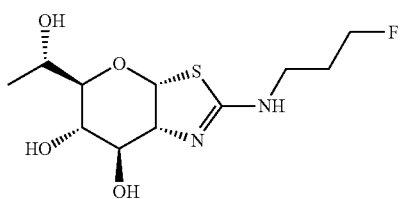 [SMILES: C[C@H](O)[C@H]1O[C@@H]2SC(NCCCF)=N[C@@H]2[C@@H](O)[C@@H]1O]

The title compound was synthesized following procedures analogous to Example 141. (ES, m/z) [M+]+ 295.0; 1H NMR (300 MHz, D₂O) δ 6.51-6.57 (m, 1H), 4.60-4.67 (m, 1H), 4.41-4.45 (m, 1H), 4.22-4.30 (m, 1H), 3.96-4.00 (m, 2H), 3.58-3.65 (m, 4H), 1.89-2.07 (m, 2H), 1.15-1.19 (m, 3H).

Example 143

(3aR,5R,6S,7R,7aR)-5-(3-Hydroxypropyl)-2-(methylamino)-5,6,7,7a-tetrahydro-3aH-pyrano[3,2-d]thiazole-6,7-diol

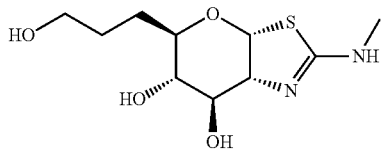 [SMILES: CNC1=N[C@@H]2[C@@H](O)[C@H](O)[C@@H](CCCO)O[C@@H]2S1]

Scheme XV

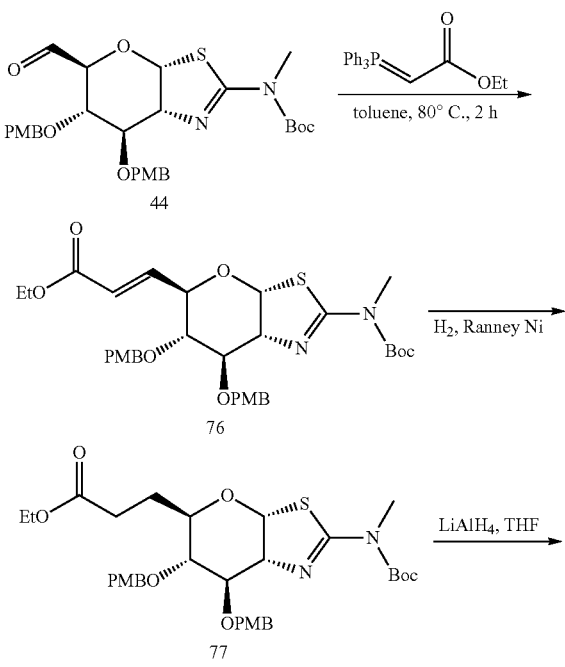

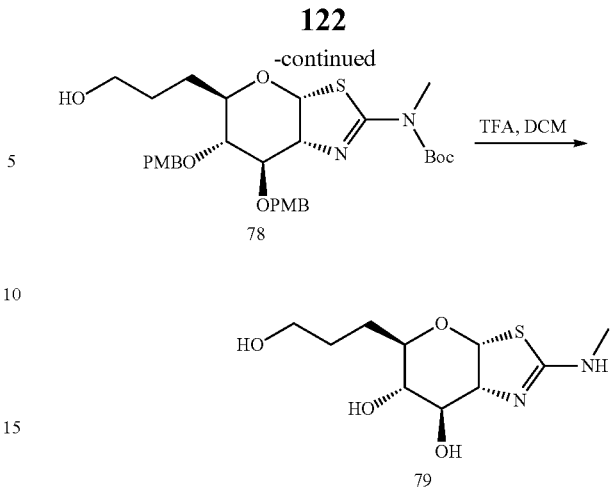

Step 1

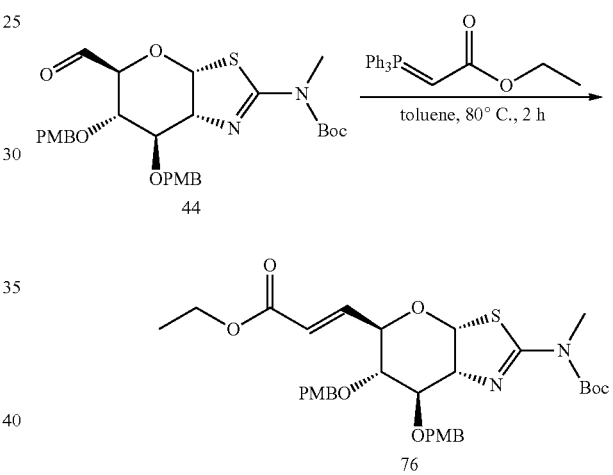

(E)-Ethyl 3-03aR,5R,6R,7R,7aR)-2-(tert-butoxycarbonyl(methyl)amino)-6,7-bis(4-methoxybenzyloxy)-5,6,7,7a-tetrahydro-3aH-pyrano[3,2-d]thiazol-5-yl)acrylate (76)

A solution of 44 (420 mg, 0.51 mmol) in toluene (20 mL) was treated with (carbethoxymethylene)triphenylphosphorane (280 mg, 0.81 mmol) overnight at 80° C. The reaction mixture was concentrated under vacuum to give a residue, which was purified by a silica gel column, eluting with 10% ethyl acetate in petroleum ether to provide compound 76 as a light yellow solid (231 mg, 70%). (ES, m/z) [M+H]+ 643.3; ¹H NMR (300 MHz, CDCl₃) δ 7.31-7.34 (d, J=8.4 Hz, 2H), 7.20-7.22 (d, J=8.7 Hz, 2H), 6.85-6.96 (m, 5H), 6.02-6.08 (m, 2H), 4.63-4.71 (m, 2H), 4.53-4.59 (m, 1H), 4.35-4.41 (m, 1H), 4.16-4.35 (m, 4H), 3.98-3.99 (m, 1H), 3.82 (s, 6H), 3.48-3.52 (m, 1H), 3.20 (s, 3H), 1.54 (s, 9H), 1.26-1.31 (t, J=6.9 Hz, 3H).

Step 2

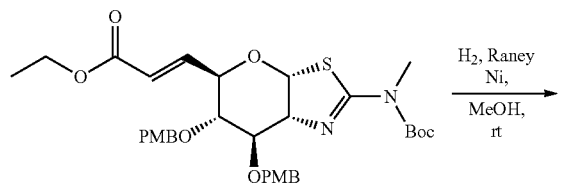

Ethyl 3-((3aR,5R,6R,7R,7aR)-2-(tert-butoxycarbonyl(methyl)amino)-6,7-bis(4-methoxybenzyloxy)-5,6,7,7a-tetrahydro-3aH-pyrano[3,2-d]thiazol-5-yl)propanoate (77)

A mixture of compound 76 (100 mg, 0.16 mmol) and Raney Ni (20 mg) in methanol (10 mL) was stirred under hydrogen atmosphere overnight at room temperature. After removal of solids, the solution was concentrated under vacuum to give 77 as a yellow oil (80 mg, 76%). (ES, m/z) [M+H]+ 645.3; 1H NMR (300 MHz, CDCl3) δ 7.34-7.35 (d, J=6.6 Hz, 2H), 7.19-7.20 (d, J=6.6 Hz, 2H), 6.84-6.93 (m, 4H), 6.02-6.04 (d, J=6.9 Hz, 1H), 4.60-4.71 (m, 2H), 4.49-4.52 (d, J=8.1 Hz, 1H), 4.37-4.40 (m, 1H), 4.27-4.30 (d, J=8.1 Hz, 1H), 4.22-4.24 (m, 1H), 4.07-4.14 (m, 2H), 3.82 (s, 6H), 3.80-3.81 (m, 1H), 3.40-3.43 (m, 1H), 3.10 (s, 3H), 2.25-2.45 (m, 2H), 2.01-2.09 (m, 1H), 1.66-1.74 (m, 1H), 1.54 (s, 9H), 1.22-1.29 (t, J=6.9 Hz, 3H).

Step 3

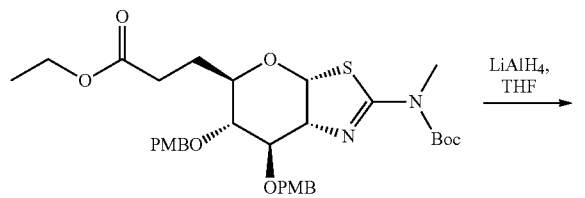

-continued

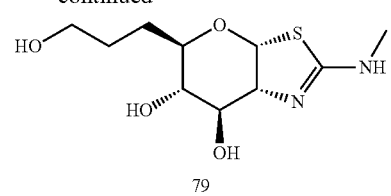

(3aR,5R,6S,7R,7aR)-5-(3-Hydroxypropyl)-2-(methylamino)-5,6,7,7a-tetrahydro-3aH-pyrano[3,2-d]thiazole-6,7-diol (79)

A solution of compound 77 (150 mg, 0.23 mmol) in THF (10 mL) was treated with LiAlH4 (26.6 mg, 0.70 mmol) for 3 h at room temperature. The reaction mixture was then quenched by addition of saturated aqueous NH4Cl (20 mL), extracted with dichloromethane (3×30 mL), and dried over anhydrous magnesium sulfate. The filtrate was concentrated under vacuum to give crude compound 78 as a yellow oil (90 mg), which was dissolved into dichloromethane (10 mL) and treated with TFA (1 mL) overnight at room temperature. Removal of volatiles gave a residue, which was purified by Prep-HPLC with the following conditions: [(Agilent 1200 prep HPLC: Column, Sun fire prep. C18; mobile phase, water with 0.03% trifluoroacetic acid and CH3CN (10% up to 20% in time 10); Detector, 220 nm.)] to give the title compound 79 (Example 143) as a white solid (10.8 mg, 23%). (ES, m/z) [M+H]+ 263.1; 1H NMR (300 MHz, D2O) δ 6.18-6.20 (d, J=6.3 Hz, 1H), 4.08-4.12 (m, 1H), 3.89-3.93 (m, 1H), 3.36-3.51 (m, 4H), 2.74-2.76 (m, 3H), 1.68-1.76 (m, 1H), 1.33-1.62 (m, 3H).

Example 144

(3aR,5R,6S,7R,7aR)-2-(Ethylamino)-5-(2-hydroxyethyl)-5,6,7,7a-tetrahydro-3aH-pyrano[3,2-d]thiazole-6,7-diol

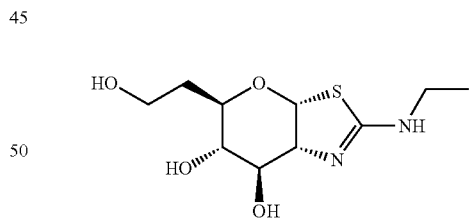

Scheme XVI

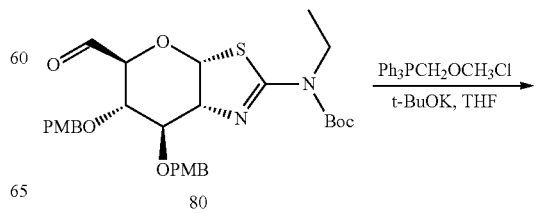

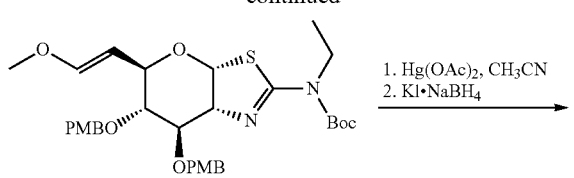

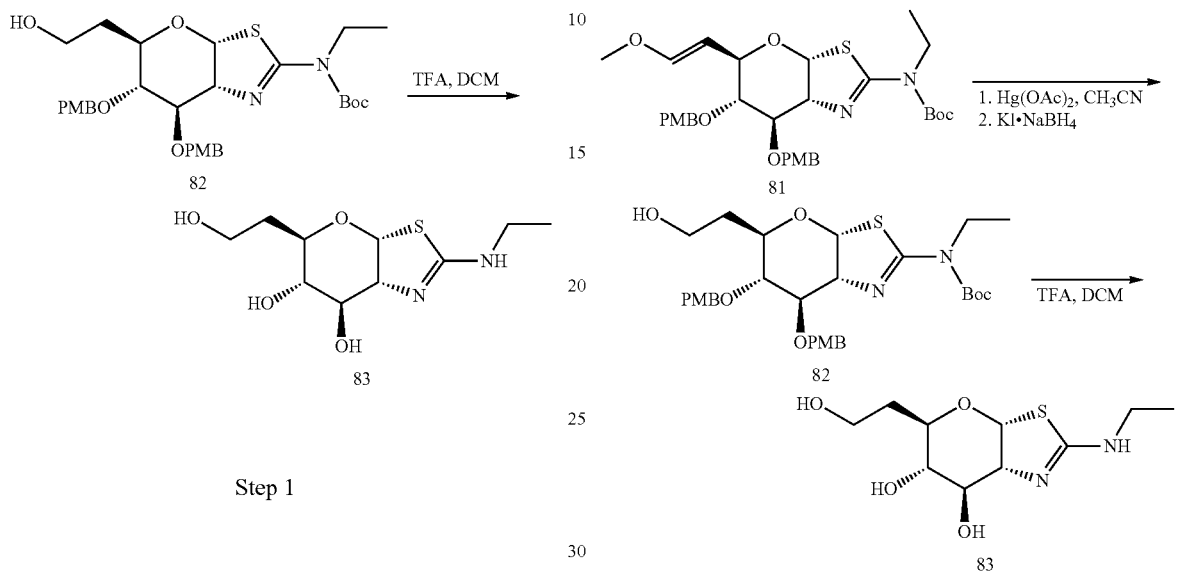

Step 1

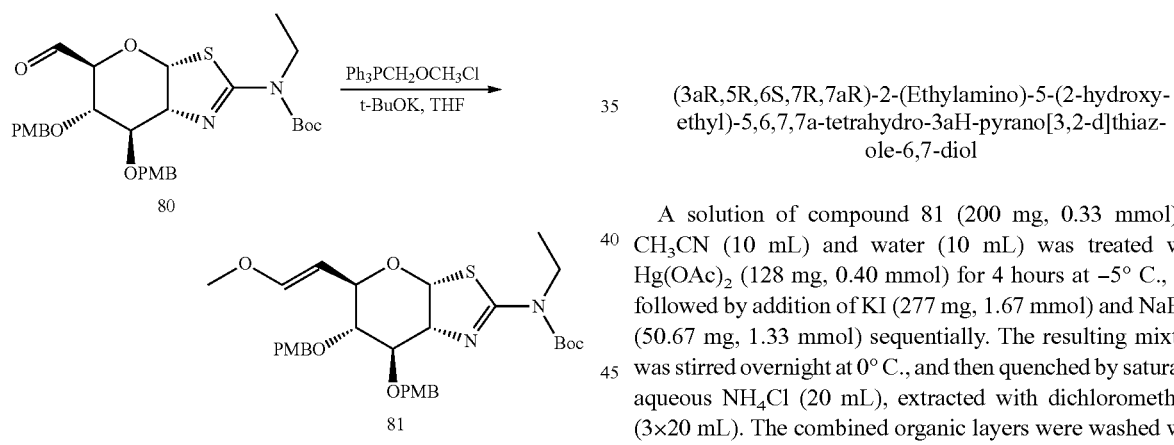

tert-Butyl (3aR,5R,6R,7R,7aR)-6,7-bis(4-methoxybenzyloxy)-5-((E)-2-methoxyvinyl)-6,7,7a-tetrahydro-3aH-pyrano[3,2-d]thiazol-2-yl(ethyl)carbamate (81)

A solution of Ph$_3$PCH$_2$OCH$_3$Cl (613 mg, 1.79 mmol) in THF (20 mL) was treated with potassium t-butoxide (191 mg, 1.71 mmol) at 0° C. in a nitrogen atmosphere for 30 min, and followed by addition of 80 (500 mg, 0.85 mmol) in THF (5 mL). The resulting solution was stirred for 3 hours at 25° C., and then quenched by saturated aqueous NH$_4$Cl (20 mL), extracted with dichloromethane (3×20 mL). The combined organic layers were washed with brine (2×20 mL), dried over anhydrous magnesium sulfate, and concentrated under vacuum to give a residue, which was purified by a silica gel column, eluting with 30% ethyl acetate in petroleum ether to give compound 81 as a light yellow solid (200 mg, 38%). (ES, m/z) [M+H]$^+$ 615.3.

Step 2

(3aR,5R,6S,7R,7aR)-2-(Ethylamino)-5-(2-hydroxyethyl)-5,6,7,7a-tetrahydro-3aH-pyrano[3,2-d]thiazole-6,7-diol A solution of compound 81 (200 mg, 0.33 mmol) in CH$_3$CN (10 mL) and water (10 mL) was treated with Hg(OAc)$_2$ (128 mg, 0.40 mmol) for 4 hours at −5° C., and followed by addition of KI (277 mg, 1.67 mmol) and NaBH$_4$ (50.67 mg, 1.33 mmol) sequentially. The resulting mixture was stirred overnight at 0° C., and then quenched by saturated aqueous NH$_4$Cl (20 mL), extracted with dichloromethane (3×20 mL). The combined organic layers were washed with brine (2×20 mL), dried over anhydrous magnesium sulfate, and condensed to give crude compound 82 as a yellow foam, which was dissolved into dichloromethane (10 mL) and treated with TFA (1 mL) overnight at room temperature. Removal of volatiles provided a residue, which was purified by Prep-HPLC with the following conditions [(Prep-HPLC): Column, 19*150 mm; mobile phase, WATER with 0.03% NH$_3$H$_2$O and CH$_3$CN (10% CH$_3$CN up to 45% in 10 min); Detector, 220 nm.] to give the title compound 83 (Example 144) as a yellow solid (8.1 mg, 28%). (ES, m/z) [M+H]$^+$ 263.1; $^1$H NMR (300 MHz, D$_2$O) δ 6.18-6.20 (d, J=6.3 Hz, 1H), 4.06-4.10 (t, J=5.4 Hz, 1H), 3.87-3.91 (t, J=3.9 Hz, 1H), 3.50-3.64 (m, 3H), 3.38-3.42 (m, 1H), 3.10-3.22 (m, 2H), 1.88-1.99 (s, 1H), 1.65-1.69 (m, 1H), 0.96-1.05 (t, J=6.9 Hz, 3H).

The following Example 145 was prepared in a similar fashion to Example 144.

Example 145

| Example | structure | Name | MH+ |
|---|---|---|---|
| 145 | 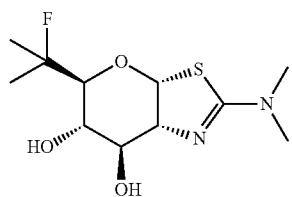 [SMILES: CN(C)C1=N[C@@H]2[C@@H](O)[C@H](O)[C@@H](C(C)(C)F)O[C@@H]2S1] | (3aR,5R,6S,7R,7aR)-5-(2-hydroxyethyl)-2-(methylamino)-5,6,7,7a-tetrahydro-3aH-pyrano[3,2-d]thiazole-6,7-diol | 249.1 |

Example 146

(3aR,5S,6S,7R,7aR)-2-(Dimethylamino)-5-(2-fluoropropan-2-yl)-5,6,7,7a-tetrahydro-3aH-pyrano[3,2-d]thiazole-6,7-diol

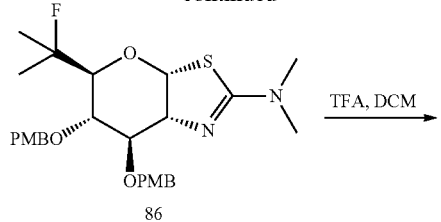

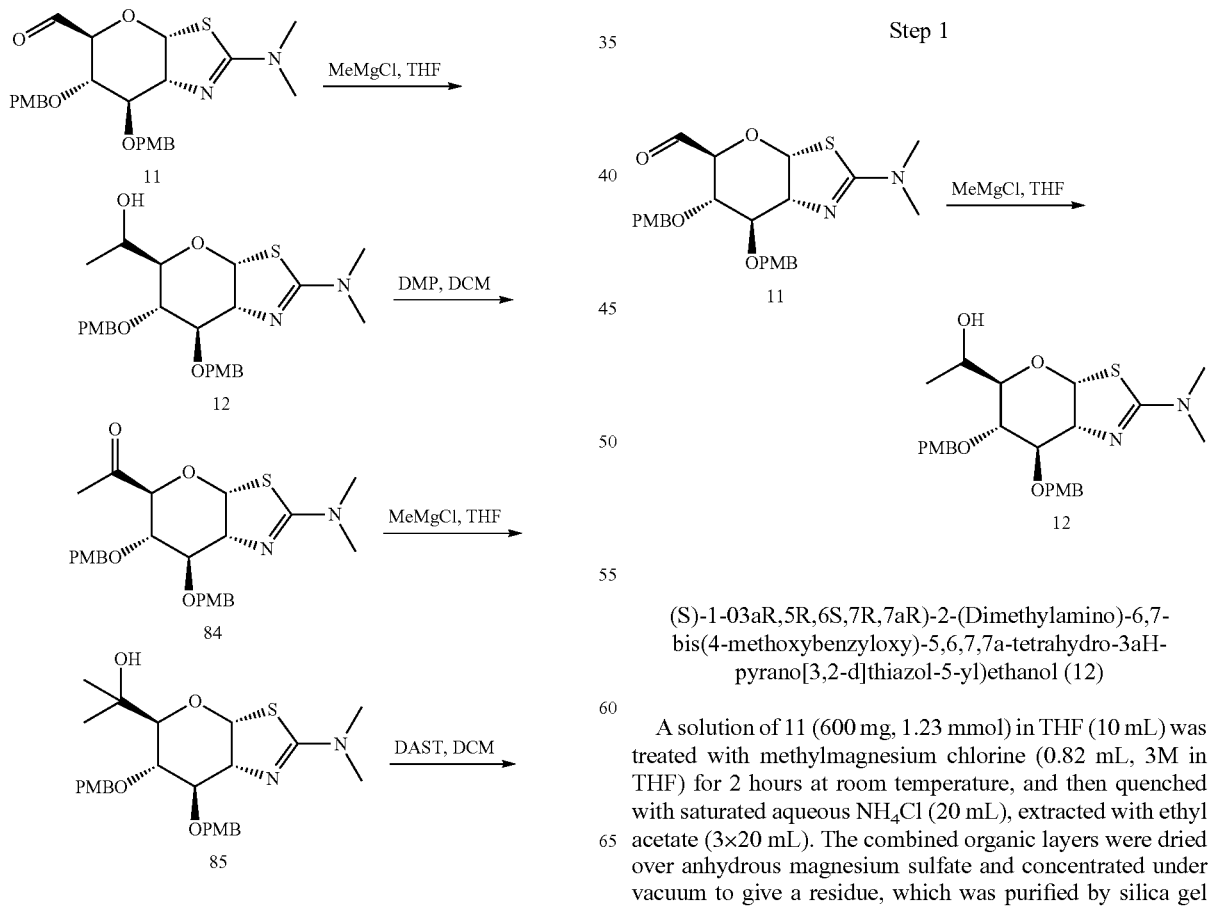

Step 1

(S)-1-03aR,5R,6S,7R,7aR)-2-(Dimethylamino)-6,7-bis(4-methoxybenzyloxy)-5,6,7,7a-tetrahydro-3aH-pyrano[3,2-d]thiazol-5-yl)ethanol (12)

A solution of 11 (600 mg, 1.23 mmol) in THF (10 mL) was treated with methylmagnesium chlorine (0.82 mL, 3M in THF) for 2 hours at room temperature, and then quenched with saturated aqueous $NH_4Cl$ (20 mL), extracted with ethyl acetate (3×20 mL). The combined organic layers were dried over anhydrous magnesium sulfate and concentrated under vacuum to give a residue, which was purified by silica gel column, eluting with 1-2% methanol in dichloromethane to give compound (12) as a yellow syrup (500 mg, 81%, diastereomers' ratio is ~1:4). (ES, m/z): [M+H]+ 503.0. $^1$H NMR (300 MHz, CDCl$_3$) δ 7.23-7.35 (m, 4H), 6.85-6.92 (m, 4H), 6.30-6.32 (d, J=6.6 Hz, 1H), 4.52-4.67 (m, 4H), 4.33-4.37 (m, 2H), 3.81-3.84 (m, 8H), 3.35-3.50 (m, 1H), 2.99-3.02 (m, 6H), 1.11-1.21 (m, 3H).

Step 2

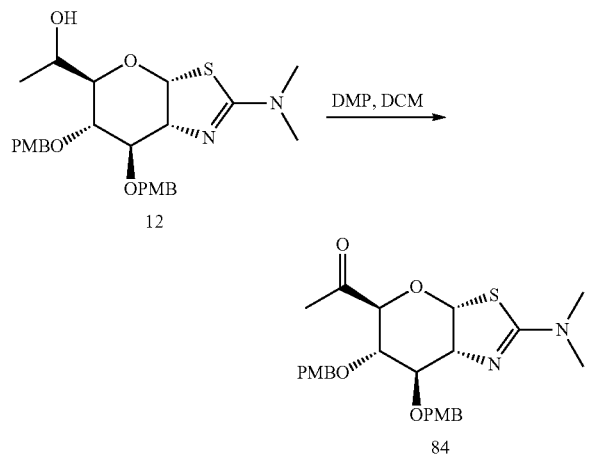

1-03aR,5S,6S,7R,7aR)-2-(Dimethylamino)-6,7-bis (4-methoxybenzyloxy)-5,6,7,7a-tetrahydro-3aH-pyrano[3,2-d]thiazol-5-yl)ethanone (84)

A solution of 12 (450 mg, 0.90 mmol) in dichloromethane (20 mL) was treated with Dess-Martin reagent (760 mg, 1.80 mmol) for 2 hours at room temperature, and then quenched by saturated aqueous Na$_2$S$_2$O$_3$ (20 mL) and saturated aqueous NaHCO$_3$ (20 mL), extracted with dichloromethane (2×20 mL). The combined organic layers were dried over anhydrous sodium sulfate and concentrated under reduced pressure to provide a residue, which was purified by silica gel column, eluting with 2-3% methanol in dichloromethane to give compound (84) as a yellow syrup (400 mg, 88%). (ES, m/z): [M+H]+ 501.0. NMR (300 MHz, CDCl$_3$) δ 7.25-7.30 (m, 4H), 6.83-6.90 (m, 4H), 6.29-6.31 (d, J=6.0 Hz, 1H), 4.26-4.64 (m, 6H), 3.81-3.98 (m, 8H), 2.96-3.02 (m, 6H), 2.17 (s, 3H).

Step 3

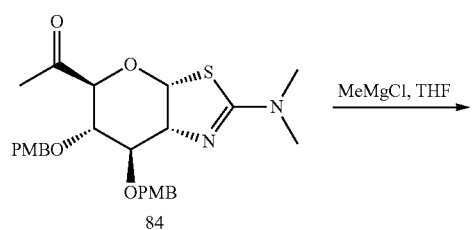

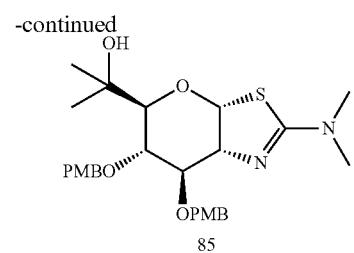

2-03aR,5S,6S,7R,7aR)-2-(Dimethylamino)-6,7-bis (4-methoxybenzyloxy)-5,6,7,7a-tetrahydro-3aH-pyrano[3,2-d]thiazol-5-yl)propan-2-ol (85)

A solution of compound 84 (100 mg, 0.2 mmol) in THF (10 mL) was treated with methylmagnesium chlorine (0.5 mL, 3M in THF) for 2 hours at room temperature, then quenched with saturated aqueous NH$_4$Cl (20 mL), extracted with ethyl acetate (3×20 mL). The combined organic layers were dried over anhydrous magnesium sulfate, concentrated under vacuum to give a residue, which was purified by silica gel column, eluting with 1-2% methanol in dichloromethane to give compound (85) as a yellow syrup (100 mg, 97%). (ES, m/z): [M+H]+ 517.0. $^1$H NMR (300 MHz, CDCl$_3$) δ 7.22-7.36 (m, 4H), 6.83-6.92 (m, 4H), 6.32-6.34 (d, J=6.9 Hz, 1H), 4.25-4.70 (m, 7H), 3.81 (s, 6H), 3.33-3.36 (d, J=8.7 Hz, 1H), 2.98 (s, 6H), 1.18 (s, 6H).

Step 4

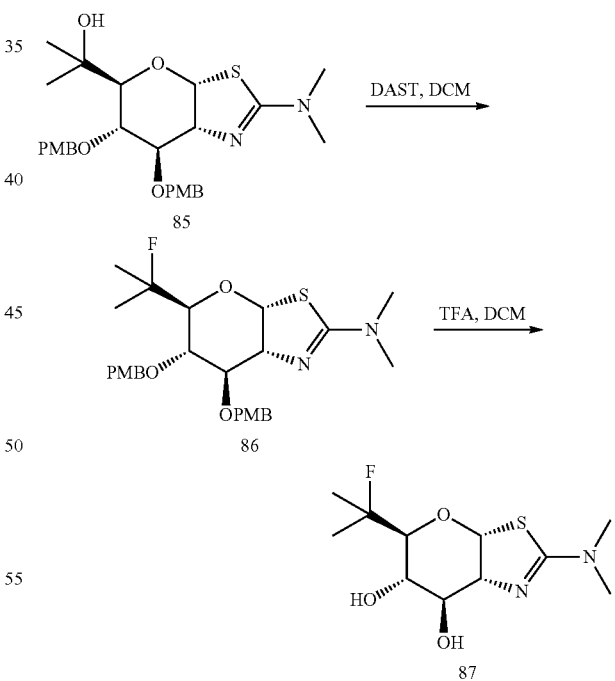

(3aR,5S,6S,7R,7aR)-2-(Dimethylamino)-5-(2-fluoropropan-2-yl)-5,6,7,7a-tetrahydro-3aH-pyrano[3,2-d]thiazole-6,7-diol (87)

A solution of 85 (100 mg, 0.19 mmol) in dichloromethane (10 mL) was treated with DAST (156 mg, 0.97 mmol) at −78°

C. for 30 min. The reaction mixture was allowed to warm up to room temperature gradually. After stirring for another 30 min, the reaction was quenched with saturated aqueous Na₂CO₃ (10 mL) and extracted with dichloromethane (3×10 mL). The combined organic layers were dried over anhydrous MgSO₄ and concentrated under reduced pressure to give crude compound 86 as a yellow oil (100 mg), which was dissolved into dichloromethane (10 mL) and treated with TFA (1 mL) for 1 hour at room temperature. Removal of volatiles gave a residue, which was purified by Prep-HPLC with the following conditions [(Agilent 1200 Detect Prep-HPLC): Column, SunFire Prep C18; mobile phase, water with 0.03% ammonia and CH₃CN; Detector, UV220 nm] to afford the title compound 87 (Example 146) as a white solid (34.8 mg, 65%). (ES, m/z): [M+H]⁺ 279.0; ¹H NMR (300 MHz, D₂O) δ 6.21-6.23 (d, J=6.6 Hz, 1H), 4.33-4.36 (t, J=6.3 Hz, 1H), 4.14-4.16 (t, J=2.7 Hz, 1H), 3.78-3.81 (m, 1H), 3.30-3.39 (m, 1H), 2.91 (s, 6H), 1.34 (s, 3H) 1.27 (s, 3H).

Example 147

(3aR,5S,6S,7R,7aR)-5-(1,1-Difluoroethyl)-2-(propylamino)-5,6,7,7a-tetrahydro-3aH-pyrano[3,2-d]thiazole-6,7-diol

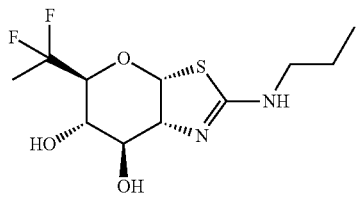 [SMILES: CCCNC1=N[C@@H]2[C@@H](O)[C@H](O)[C@@H](C(C)(F)F)O[C@@H]2S1]

SCHEME XVIII

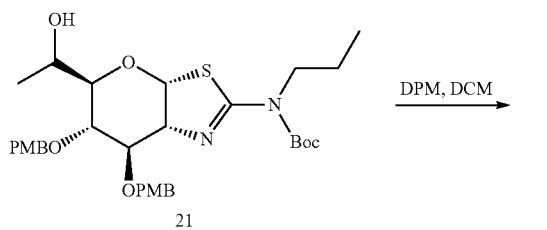

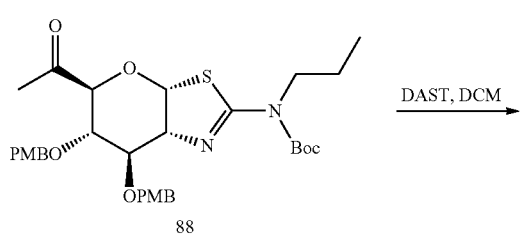

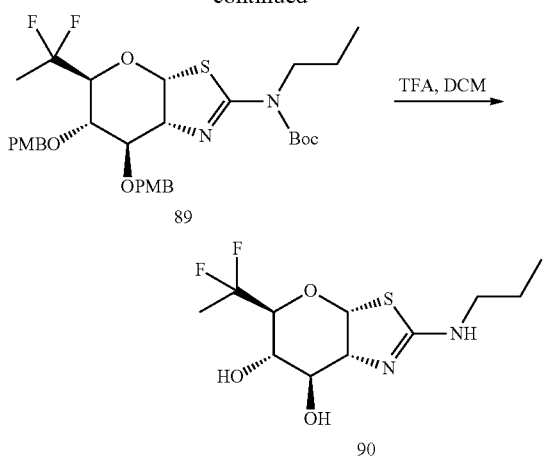

Step 1

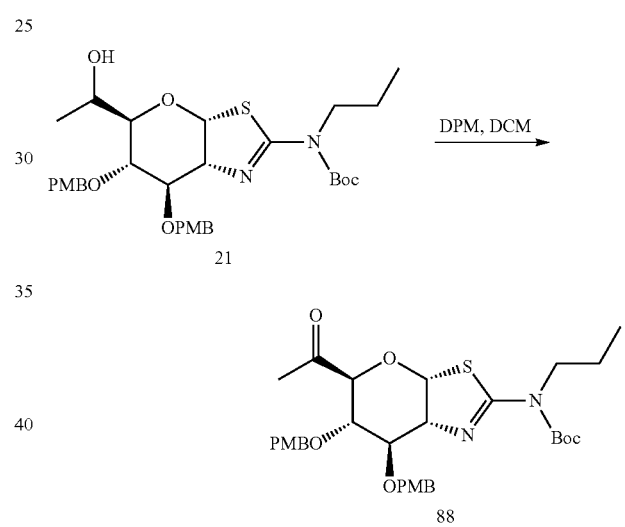

tert-Butyl (3aR,5S,6S,7R,7aR)-5-acetyl-6,7-bis(4-methoxybenzyloxy)-5,6,7,7a-tetrahydro-3aH-pyrano[3,2-d]thiazol-2-yl(propyl)carbamate (88)

A solution of 21 (450 mg, 0.72 mmol) in dichloromethane (10 mL) was treated with Dess-martin reagent (780 mg, 1.83 mmol) for 1 hour at room temperature, then quenched by saturated aqueous Na₂S₂O₃ (20 mL) and saturated aqueous NaHCO₃ aqueous (20 mL), extracted with dichloromethane (2×20 mL). The combined organic layers were dried over anhydrous sodium sulfate and concentrated under reduced pressure to provide a residue, which was purified by 30% ethyl acetate in petroleum ether to give compound 88 as light yellow oil (210 mg, 47%). (ES, m/z): [M+H]⁺ 615.0. ¹H NMR (300 MHz, CDCl₃) δ 7.21-7.31 (m, 4H), 6.84-6.92 (m, 4H), 6.05-6.07 (d, J=6.9 Hz, 1H), 4.26-4.64 (m, 6H), 3.87-3.92 (m, 2H), 3.80 (s, 6H), 3.70-3.79 (m, 2H), 2.21 (s, 3H), 1.60-1.70 (m, 2H), 1.25-1.30 (t, J=7.5 Hz, 3H).

Step 2

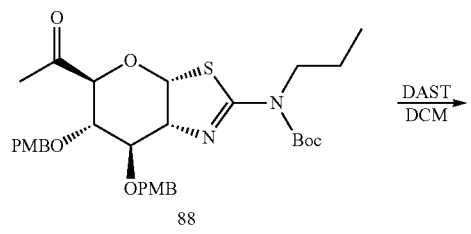
88

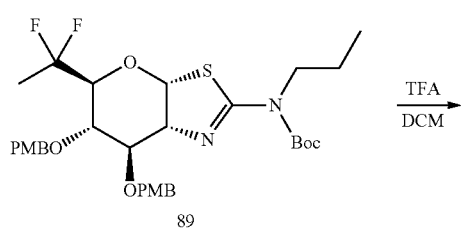
89

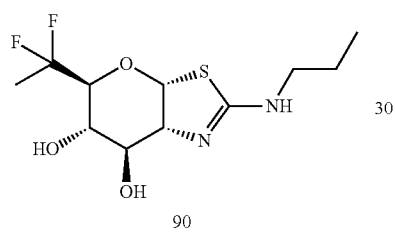
90

(3aR,5S,6S,7R,7aR)-5-(1,1-Difluoroethyl)-2-(propylamino)-5,6,7,7a-tetrahydro-3aH-pyrano[3,2-d]thiazole-6,7-diol (90)

A solution of 88 (200 mg, 0.33 mmol) in dichloromethane (10 mL) was treated with DAST (262 mg, 1.63 mmol) overnight at room temperature, then quenched by saturated aqueous Na$_2$CO$_3$ (10 mL), extracted with dichloromethane (3×10 mL). The combined organic layers were concentrated under vacuum to give crude compound 89 as a yellow foam (100 mg), which was dissolved into dichloromethane (5 mL) and treated with TPA (0.5 mL) for 3 hours at room temperature. Removal of volatiles gave a residue, which was purified by Prep-HPLC with the following conditions [(Agilent 1200 prep HPLC): Column, SunFire Prep C18,19*50 mm 5 um; mobile phase, H$_2$O with 0.03% NH$_4$OH and CH$_3$CN (10% CH$_3$CN up to 45% in 10 min); Detector, UV 220 nm] to give the title compound 90 (Example 147) as a yellow solid (21.8 mg, 21.8%). (ES, m/z) [M+H]$^+$ 297.0; $^1$H NMR (300 MHz, D$_2$O) δ 6.20-6.22 (d, J=6.6 Hz, 1H), 4.33-4.36 (1, J=4.2 Hz, 1H), 4.15-4.18 (t, J=3.0 Hz, 1H), 3.93-3.97 (m, 1H), 3.56-3.66 (m, 1H), 3.10-3.14 (t, f=6.9 Hz, 2H), 1.43-1.68 (m, 5H), 0.81-0.86 (1, J=7.5 Hz, 3H).

The following compound was prepared in a manner analogous to Example 147.

Example 148

(3aR,5S,6S,7R,7aR)-5-(1,1-difluoroethyl)-2-(methylamino)-5,6,7,7a-tetrahydro-3aH-pyrano[3,2-d]thiazole-6,7-diol

| Example | structure | Name | MH+ |
|---|---|---|---|
| 148 | ![structure] | (3aR,5S,6S,7R,7aR)-5-(1,1-difluoroethyl)-2-(methylamino)-5,6,7,7a-tetrahydro-3aH-pyrano[3,2-d]thiazole-6,7-diol | 269.0 |

Examples 149 & 150

(3aR,5S,6S,7R,7aR)-5-((S)-2,2-difluoro-1-hydroxyethyl)-2-(dimethylamino)-5,6,7,7a-tetrahydro-3aH-pyrano[3,2-d]thiazole-6,7-diol (Example 149) &
(3aR,5S,6S,7R,7aR)-5-((R)-2,2-difluoro-1-hydroxyethyl)-2-(dimethylamino)-5,6,7,7a-tetrahydro-3aH-pyrano[3,2-d]thiazole-6,7-diol (Example 150)

Example 149

Example 150

SCHEME XIX

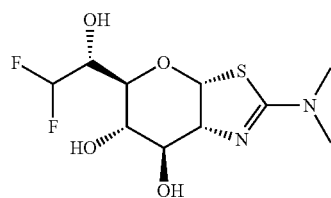

7 from Scheme II

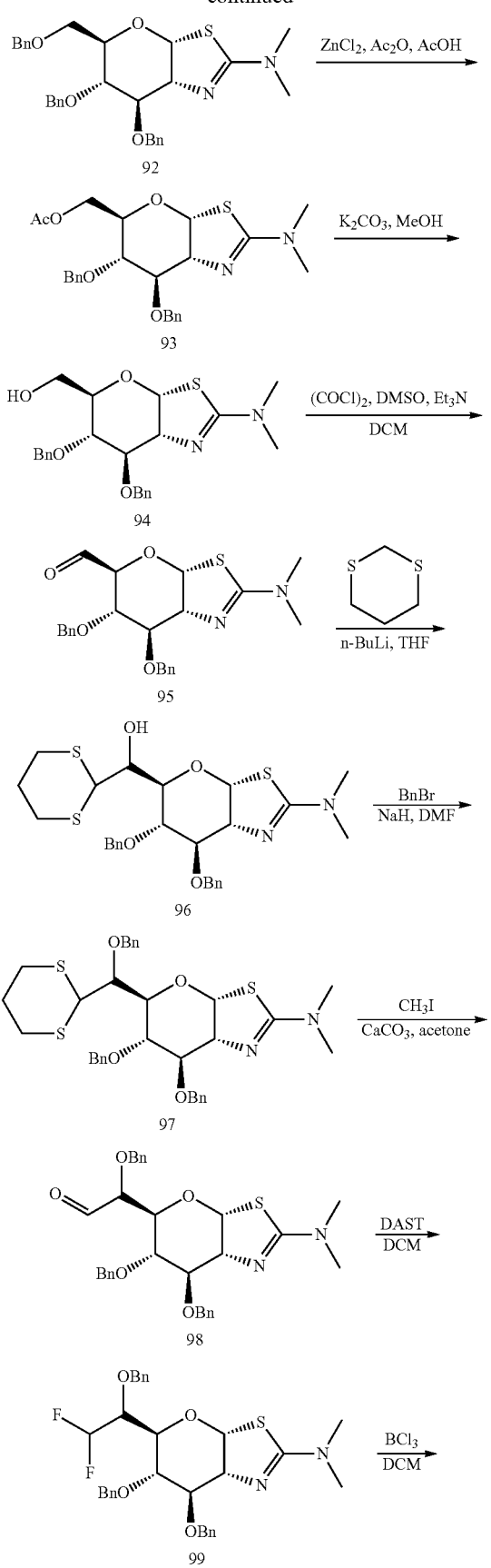

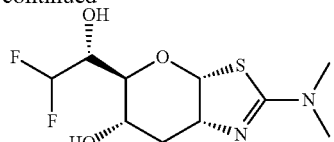

Example 149

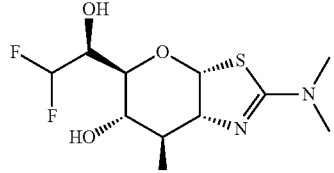

Example 150

Step 1

(3aR,5R,6S,7R,7aR)-6,7-bis(benzyloxy)-5-(benzyloxymethyl)-N,N-dimethyl-5,6,7,7a-tetrahydro-3aH-pyrano[3,2-d]thiazol-2-amine (92)

A solution of 7 (100 g, 0.4 mol) in DMF (600 mL) was treated with NaH (110 g, 3.2 mol, 70% dispersed by mineral oil) at 0° C. for 30 min, followed by the addition of BnBr (410 g, 2.4 mol) dropwise. After kept additional 2 hours at room temperature, the mixture was poured into ice-water (1.5 kg) slowly and extracted with ethyl acetate (3×500 mL). The organic layers were combined, washed with brine (3×300 mL), dried over anhydrous sodium sulfate and concentrated under reduced pressure to give a residue, which was purified by a silica gel column, eluted with 10%-30% ethyl acetate in petroleum ether to afford 92 (166 g, 80%) as a yellow oil; (ES, m/z) [M+H]$^+$ 519.0; $^1$H NMR (300 MHz, CDCl$_3$) δ 7.26-7.48 (m, 15H), 6.40 (d, J=6.6 Hz, 1H), 4.54-4.86 (m, 6H), 4.41 (d, J=4.8 Hz, 1H), 4.17-4.18 (m, 1H), 3.60-3.79 (m, 4H), 3.12 (s, 6H).

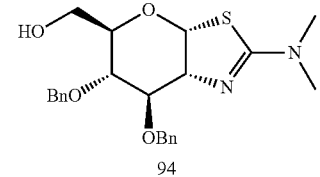

Step 2

((3aR,5R,6S,7R,7aR)-6,7-bis(benzyloxy)-2-(dimethylamino)-5,6,7,7a-tetrahydro-3aH-pyrano[3,2-d]thiazol-5-yl)methanol (94)

To a solution of 92 (166 g, 0.3 mol) in Ac$_2$O (1 L) and AcOH (100 mL) was added anhydrous ZnCl$_2$ (353 g, 2.6 mol) at 0° C. After kept additional 2 hours at room temperature, the reaction was poured into ice-cold H$_2$O (1.5 kg) slowly and extracted with dichloromethane (3×500 mL). The organic layers combined, washed with brine (3×200 mL) and dried over anhydrous sodium sulfate. After filtration, volatiles were distilled out by high vacuum to give crude 93 (160 g, (ES, m/z) [M+H]$^+$ 471.0) as a brown oil. A solution of the above crude 93 in methanol (1 L) was treated with K$_2$CO$_3$ (18 g, 0.13 mol) at 30° C. for 8 hours, after filtration, the solvent was distilled out under vacuum to give a residue, which was purified by a silica gel column with 20%-30% ethyl acetate in petroleum ether to afford the title compound (94) (108 g, 79% 2 steps) as a yellow syrup; (ES, m/z) [M+H]$^+$ 429.0; $^1$H NMR (300 MHz, CDCl$_3$) δ 7.26-7.43 (m, 10H), 6.29 (d, J=6.6 Hz, 1H), 4.54-4.81 (m, 4H), 4.41 (d, J=4.8 Hz, 1H), 4.17-4.18 (m, 1H), 3.57-3.79 (m, 4H), 3.02 (s, 6H).

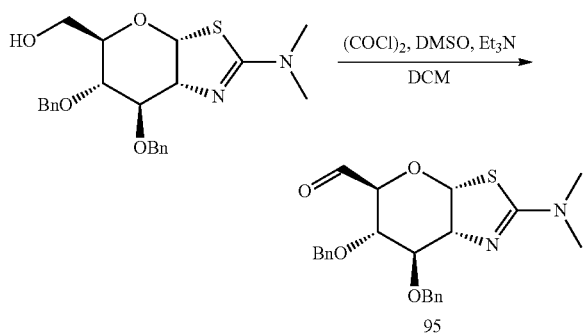

Step 3

(3aR,5S,6S,7R,7aR)-6,7-Bis(benzyloxy)-2-(dimethylamino)-5,6,7,7a-tetrahydro-3aH-pyrano[3,2-d]thiazole-5-carbaldehyde (95)

A solution of DMSO (14.6 g, 187 mmol) in dichloromethane (300 mL) was treated with oxalyl dichloride (17.7 g, 140 mmol) at −78° C. for 1 hour, then a solution of ((3aR,5R,6S,7R,7aR)-6,7-bis(benzyloxy)-2-(dimethylamino)-5,6,7,7a-tetrahydro-3aH-pyrano[3,2-d]thiazol-5-yl)methanol (10 g, 23 mmol) in dichloromethane (30 mL) was added slowly. The resulted solution was kept for 4 hours at −20° C., followed by the addition of triethylamine (28.3 g, 280 mmol) at −78° C. After additional 1 hour at −50° C., the reaction was quenched by water (300 mL) and extracted with dichloromethane (2×200 mL). The organic layers combined, washed with brine (3×100 mL) and dried over anhydrous sodium sulfate. After filtration, the filtrates were concentrated under vacuum to give a residue, which was purified by a silica gel column, eluted with 20% ethyl acetate in dichloromethane to give compound 95 as a yellow syrup (8.1 g, 80%). (ES, m/z): [M+H]$^+$ 426.7; $^1$H NMR (300 MHz, CDCl$_3$) δ 9.62 (s, 1H), 7.28-7.39 (m, 10H), 6.27-6.34 (m, 1H), 4.41-4.84 (m, 6H), 4.10-4.17 (m, 1H), 3.86-3.94 (m, 1H), 3.02 (s, 6H).

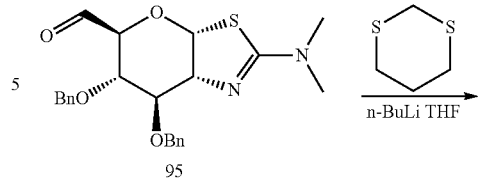

Step 4

(R)-((3aR,5R,6S,7R,7aR)-6,7-bis(benzyloxy)-2-(dimethylamino)-5,6,7,7a-tetrahydro-3aH-pyrano[3,2-d]thiazol-5-yl)(1,3-dithian-2-yl)methanol (96)

A solution of 1,3-dithiane (14.1 g, 117 mmol) in THF (100 mL) was treated with n-BuLi (44.9 mL, 112 mmol, 2.5M in hexane) at 0° C. for 1 hour, followed by the addition of a solution of the above aldehyde 95 in THF (20 mL) at −50° C. After kept additional 1 hour at 0° C., the reaction was quenched by saturated aqueous NH$_4$Cl (150 mL) and extracted with ethyl acetate (3×80 mL). The combined organic layer was dried over anhydrous sodium sulfate, filtered and concentrated under reduced pressure to give a residue, which was purified by a silica gel column, eluted with 20%-50% ethyl acetate in petroleum to afford the title compound as a yellow syrup (6.4 g, 62%, two epimers' ratio is 1:1 by $^1$H NMR); (ES, m/z) [M+H]$^+$ 547.0; $^1$H NMR (300 MHz, CDCl$_3$) δ 7.28-7.44 (m, 10H), 6.33 (d, J=6.6 Hz, 1H), 4.63-4.84 (m, 4H), 4.52-4.58 (m, 1H), 4.12-4.15 (m, 1H), 3.98-4.05 (m, 3H), 3.82-3.85 (m, 1H), 2.99 (s, 6H), 2.80-2.87 (m, 1H), 2.61-2.68 (m, 3H), 1.65-1.69 (m, 2H).

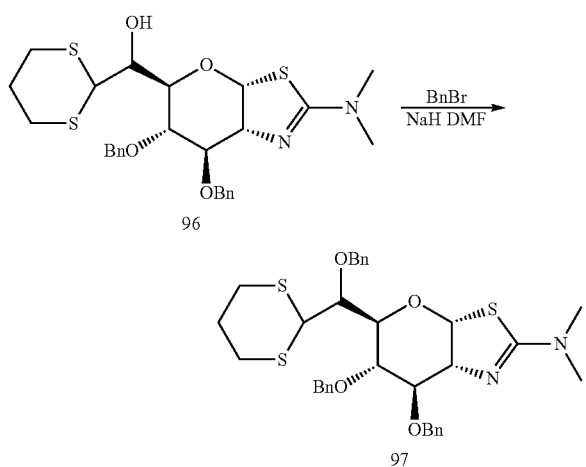

Step 5

(3aR,5S,6S,7R,7aR)-6,7-bis(benzyloxy)-5-((R)-benzyloxy(1,3-dithian-2-yl)methyl)-N,N-dimethyl-5,6,7,7a-tetrahydro-3aH-pyrano[3,2-d]thiazol-2-amine (97)

A solution of 96 (3.3 g, 6 mmol) in DMF (40 mL) was treated with sodium hydride (830 mg, 24 mmol, 70% mineral oil dispersed) for 30 min at room temperature, followed by the addition of (bromomethyl)benzene (2.1 g, 12 mmol). After additional 1 hour at room temperature, the reaction was quenched by water (100 mL) and extracted with ethyl acetate (3×40 mL). The combined organic layer was washed with brine (5×30 mL), dried over anhydrous sodium sulfate, filtered and concentrated under reduced pressure to give a residue, which was purified by a silica gel column, eluted with 10%-30% ethyl acetate in petroleum ether to afford 97 as a brown syrup (2.8 g, 73%); (ES, m/z) [M+H]$^+$ 637.1; $^1$H NMR (300 MHz, CDCl$_3$) δ 7.24-7.41 (m, 15H), 6.32-6.34 (d, J=6.3 Hz, 1H), 4.65-4.82 (m, 5H), 4.37-4.39 (m, 3H), 4.05-4.25 (m, 3H), 3.76-3.89 (m, 1H), 3.02 (s, 6H), 2.77-2.92 (m, 4H), 1.64-1.68 (m, 2H).

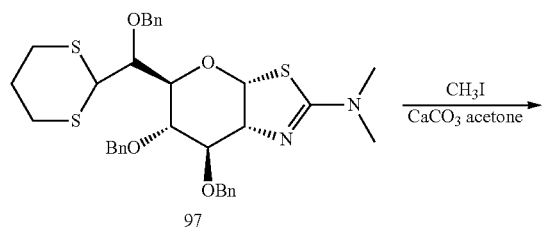

Step 6

(R)-2-(benzyloxy)-2-((3aR,5S,6S,7R,7aR)-6,7-bis(benzyloxy)-2-(dimethylamino)-5,6,7,7a-tetrahydro-3aH-pyrano[3,2-d]thiazol-5-yl)acetaldehyde (98)

To a solution of 97 (3 g, 4.7 mmol) in acetone (16 mL) and water (4 mL) was added CaCO$_3$ (4.7 g, 47 mmol) and CH$_3$I (13.2 g, 94 mmol). After kept 20 hours at 50° C., the resulting solution was diluted with dichloromethane (30 mL), filtered and extracted with dichloromethane (2×30 mL). The combined organic layer was dried over anhydrous sodium sulfate and concentrated under reduced pressure to afford crude 98, which was used in next step directly; (ES, m/z) [M+H]$^+$ 547.0.

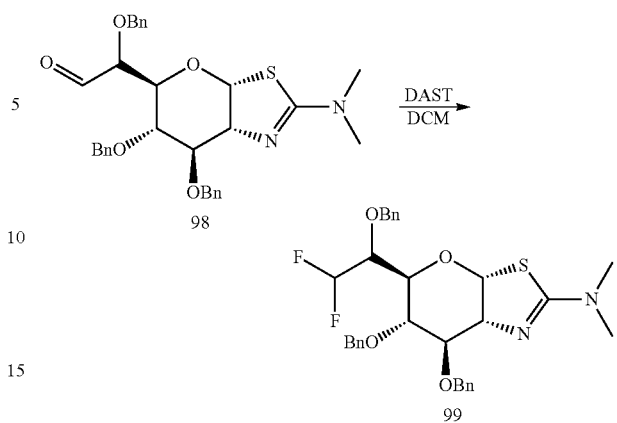

Step 7

(3aR,5S,6S,7R,7aR)-6,7-bis(benzyloxy)-5-((R)-1-(benzyloxy)-2,2-difluoroethyl)-N,N-dimethyl-5,6,7,7a-tetrahydro-3aH-pyrano[3,2-d]thiazol-2-amine (99)

To a solution of the above crude 98 in dichloromethane (20 mL) was added DAST (2.9 g, 18 mmol) at −78° C. under nitrogen atmosphere. After additional 2 hours at 0° C., the reaction was quenched with water (10 mL) and neutralized by saturated aqueous sodium carbonate. The resulting solution was extracted with dichloromethane (3×20 mL) and the combined organic layer was washed with brine (20 mL), dried over anhydrous sodium sulfate. After filtration, the filtrates were concentrated under reduced pressure to give a residue, which was purified by a silica gel column, eluted with 10%-50% ethyl acetate in petroleum ether to afford 99 as a yellow syrup (1.1 g, 41%); (ES, m/z) [M+H]$^+$ 568.9; $^1$H NMR (300 MHz, CDCl$_3$) δ 7.31-7.46 (m, 15H), 6.34 (d, J=6.6 Hz, 1H), 5.61-5.95 (m, 1H), 4.64-4.79 (m, 5H), 4.64-4.79 (m, 1H), 4.09-4.23 (m, 4H), 3.74-3.82 (m, 1H), 3.02 (s, 6H).

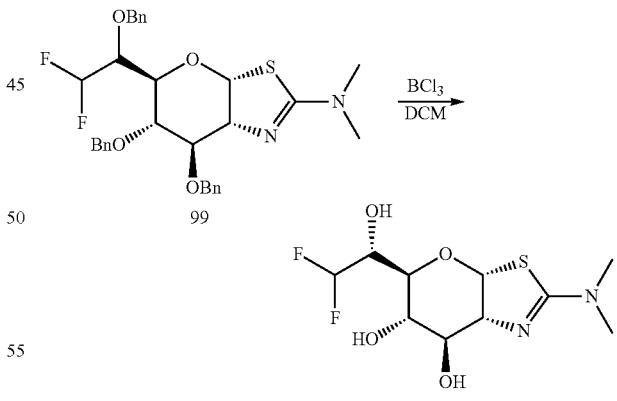

Example 149

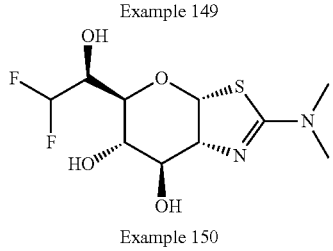

Example 150

Step 8

(3aR,5S,6S,7R,7aR)-5-((S)-2,2-difluoro-1-hydroxy-ethyl)-2-(dimethylamino)-5,6,7,7a-tetrahydro-3aH-pyrano[3,2-d]thiazole-6,7-diol (Example 149) & (3aR,5S,6S,7R,7aR)-5-((R)-2,2-difluoro-1-hydroxy-ethyl)-2-(dimethylamino)-5,6,7,7a-tetrahydro-3aH-pyrano[3,2-d]thiazole-6,7-diol (Example 150)

A solution of 99 (600 mg, 1 mmol) in dichloromethane (20 mL) was treated with BCl₃ (10 mL, 10 mmol, 1 M in dichloromethane) for 1 hour at −78° C., then quenched with methanol (20 mL). Volatiles were distilled out to give a residue, which was dissolved into methanol (5 mL) and neutralized with Con. NH₄OH (2 ml, 26% aqueous solution). After concentration, the crude product was purified by a silica gel column, eluted with 10% methanol in dichloromethane to give a mixture of the two epimers; the two epimers were separated by Prep-HPLC with the following conditions: (Agilent Prep 1200 Detecl): Column, SunFire Prep C18; mobile phase, Water with 0.05% ammonia and CH₃CN, 5% CH₃CN up to 40% in 8 min; Detector, 220 nm) to afford (3aR,5S,6S,7R,7aR)-5-((S)-2,2-difluoro-1-hydroxyethyl)-2-(dimethylamino)-5,6,7,7a-tetrahydro-3aH-pyrano[3,2-d]thiazole-6,7-diol as a light yellow solid (14.4 mg, 5%), faster eluting isomer; (ES, m/z) [M+H]⁺ 299.0, ¹H NMR (300 MHz, D₂O) δ 6.19 (d, J=6.6 Hz, 1H), 5.71-6.09 (m, 1H), 4.15 (t, J=6.0 Hz, 1H), 3.89-3.99 (m, 2H), 3.78-3.82 (m, 1H), 3.37 (t, J=8.7 Hz, 1H), 2.89 (s, 6H); and (3aR,5S,6S,7R,7aR)-5-((R)-2,2-difluoro-1-hydroxyethyl)-2-(dimethylamino)-5,6,7,7a-tetrahydro-3aH-pyrano[3,2-d]thiazole-6,7-diol as a light yellow solid (53.9 mg, 17.4%), slower eluting isomer; (ES, m/z) [M+H]⁺ 299.0, ¹H NMR (300 MHz, D₂O) δ 6.20 (d, J=6.3 Hz, 1H), 5.62-6.00 (m, 1H), 4.07 (t, J=6.0 Hz, 1H), 3.87-3.96 (m, 2H), 3.72-3.77 (m, 1H), 3.62-3.65 (m, 1H), 2.88 (s, 6H).

Examples 151 & 152

(3aR,5R,6S,7R,7aR)-5-((S)-1,2-dihydroxyethyl)-2-(dimethylamino)-5,6,7,7a-tetrahydro-3aH-pyrano[3,2-d]thiazole-6,7-diol (Example 151) & (3aR,5R,6S,7R,7aR)-5-((R)-1,2-dihydroxyethyl)-2-(dimethylamino)-5,6,7,7a-tetrahydro-3aH-pyrano[3,2-d]thiazole-6,7-diol (Example 152)

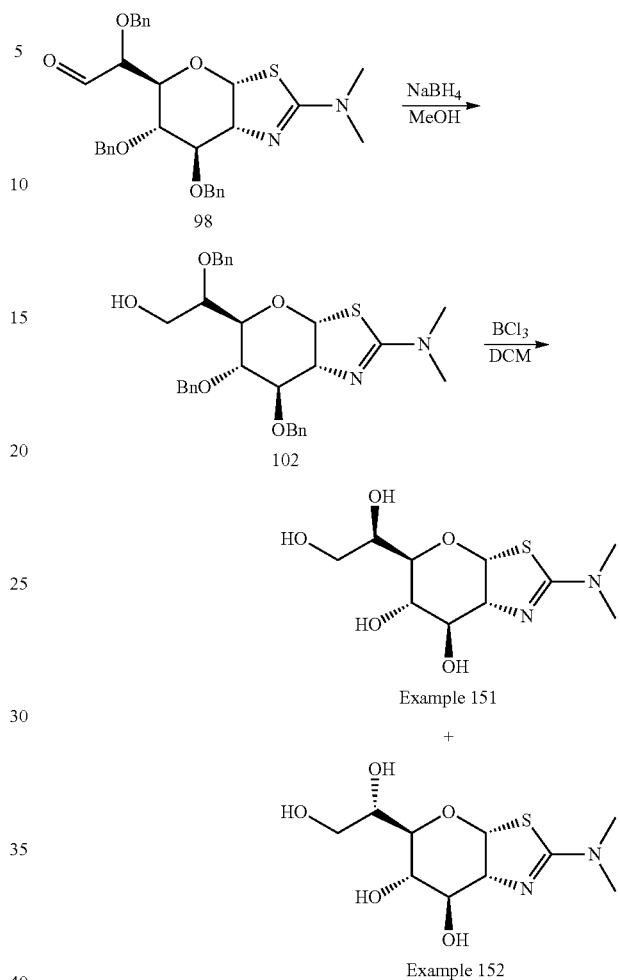

Scheme XX

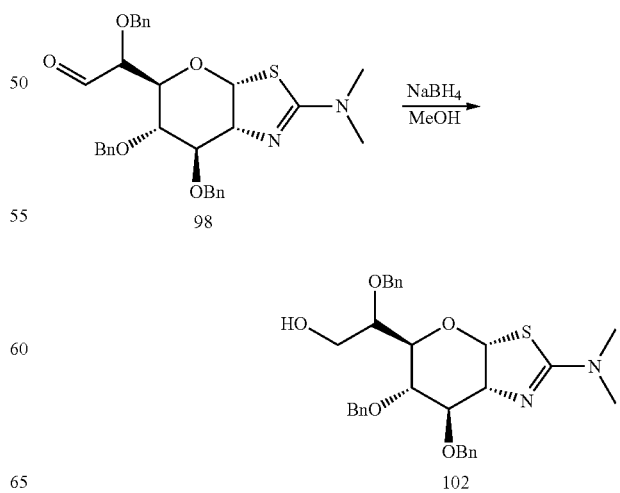

Step 1

(S)-2-(benzyloxy)-2-((3aR,5R,6S,7R,7aR)-6,7-bis(benzyloxy)-2-(dimethylamino)-5,6,7,7a-tetrahydro-3aH-pyrano[3,2-d]thiazol-5-yl)ethanal (102)

A solution of 98 (1.5 g, 2.7 mmol) (Prepared according to the synthesis of Example 149 and 150), step 6) was treated with NaBH$_4$ (504 mg, 13 mmol) for 1 hour at 0° C. The resulting solution was diluted with H$_2$O (60 mL) and extracted with ethyl acetate (3×30 mL). The combined organic layer was dried over anhydrous sodium sulfate, filtered and concentrated to give a residue, which was purified by silica gel column, eluted with 20%-50% ethyl acetate in petroleum ether to give 102 as brown syrup (1.2 g, 80%); (ES, m/z): [M+H]$^+$ 549.1; $^1$H NMR (300 MHz, CDCl$_3$) δ 7.22-7.45 (m, 15H), 6.35 (d, J=6.9 Hz, 1H), 4.61-4.80 (m, 4H), 4.47-4.53 (m, 2H), 4.25-4.36 (m, 1H), 4.08-4.12 (m, 1H), 3.89-3.92 (m, 1H), 3.46-3.78 (m, 4H), 3.01 (s, 6H).

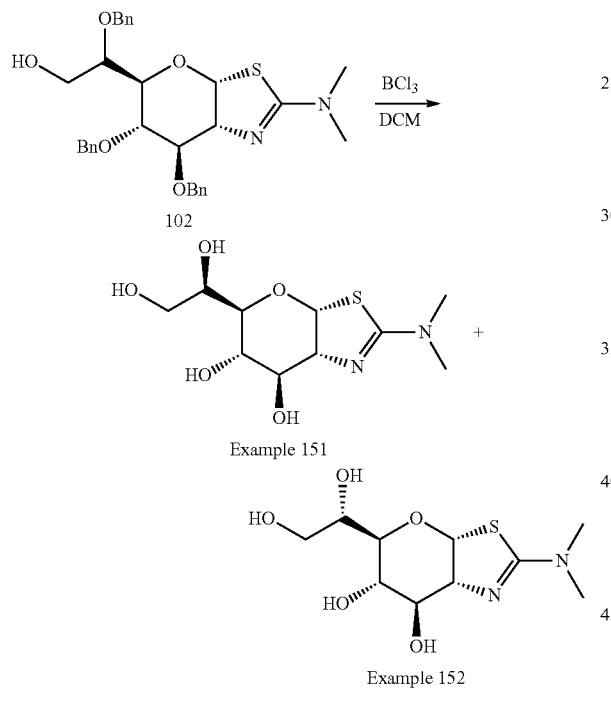

Example 151

Example 152

(3aR,5R,6S,7R,7aR)-5-((S)-1,2-dihydroxyethyl)-2-(dimethylamino)-5,6,7,7a-tetrahydro-3aH-pyrano[3,2-d]thiazole-6,7-diol (Example 152) & (3aR,5R,6S,7R,7aR)-5-((R)-1,2-dihydroxyethyl)-2-(dimethylamino)-5,6,7,7a-tetrahydro-3aH-pyrano[3,2-d]thiazole-6,7-diol (Example 151)

A solution of 102 (500 mg, 0.9 mmol) in dichloromethane (20 mL) was treated with BCl$_3$ (9 ml, 9 mmol, 1 M in dichloromethane) at −60° C. under nitrogen for 30 min. The reaction was then quenched with methanol (20 mL). Volatiles were distilled out to give a residue, which was dissolved into methanol (5 mL) and neutralized with Con. NH$_4$OH (2 ml, 26% aqueous solution). After concentration, the crude product was purified by a silica gel column, eluted with 10° A)

methanol in dichloromethane to give a mixture of the two epimers; the two epimers were separated by Prep-HPLC with the following conditions: Agilent Prep 1200 Detecl): Column, SunFire Prep C18; mobile phase, Water with 0.05% ammonia and CH$_3$CN; 5% CH$_3$CN up to 60% in 8 min; Detector, 220 nm) to afford (3aR,5R,6S,7R,7aR)-5-((R)-1,2-dihydroxyethyl)-2-(dimethylamino)-5,6,7,7a-tetrahydro-3aH-pyrano[3,2-d]thiazole-6,7-diol as a white solid (23.1 mg, 9%), Faster eluting isomer; (ES, m/z): [M+H]$^+$ 279.0; $^1$H NMR (300 MHz, D$_2$O) δ 6.17 (d, J=6.3 Hz, 1H), 4.13 (t, J=6.0 Hz, 1H), 3.95 (t, J=4.5 Hz, 1H), 3.78-3.83 (m, 1H), 3.61-3.71 (m, 2H), 3.50-3.54 (m, 2H), 2.88 (s, 6H); and (3aR,5R,6S,7R,7aR)-5-((S)-1,2-dihydroxyethyl)-2-(dimethylamino)-5,6,7,7a-tetrahydro-3aH-pyrano[3,2-d]thiazole-6,7-diol as a white solid (37.5 mg, 13%), Slower eluting isomer; (ES, m/z): [M+H]$^+$ 279.0; $^1$H NMR (300 MHz, D$_2$O) δ 6.18 (d, J=6.3 Hz, 1H), 4.05 (t, J=6.0 Hz, 1H), 3.90 (t, J=5.1 Hz, 1H), 3.75-3.81 (m, 1H), 3.65-3.69 (m, 1H), 3.44-3.53 (m, 3H), 2.87 (s, 6H).

Examples 153 & 154

(3aR,5S,6S,7R,7aR)-2-(dimethylamino)-5-((S)-2-fluoro-1-hydroxyethyl)-5,6,7,7a-tetrahydro-3aH-pyrano[3,2-d]thiazole-6,7-diol (Example 153) & (3aR,5S,6S,7R,7aR)-2-(dimethylamino)-5-((R)-2-fluoro-1-hydroxyethyl)-5,6,7,7a-tetrahydro-3aH-pyrano[3,2-d]thiazole-6,7-diol (Example 154)

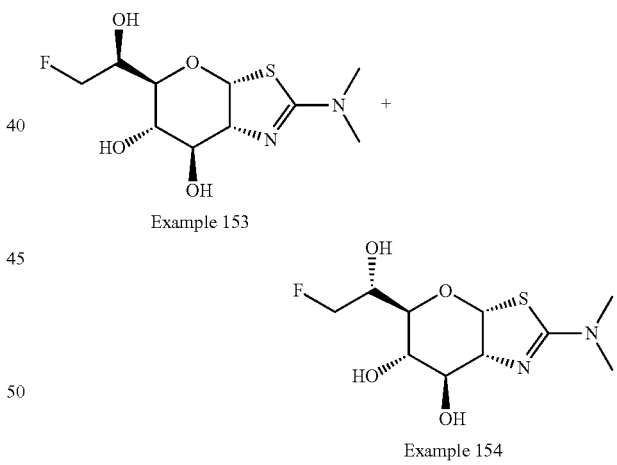

Example 153

Example 154

Scheme XXI

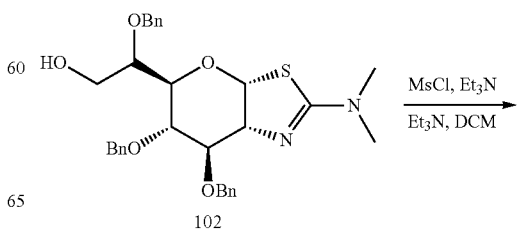

-continued

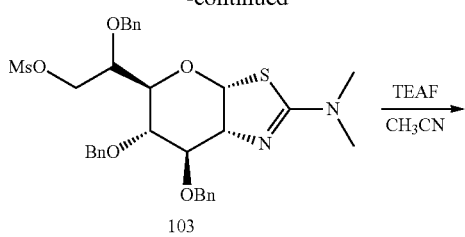

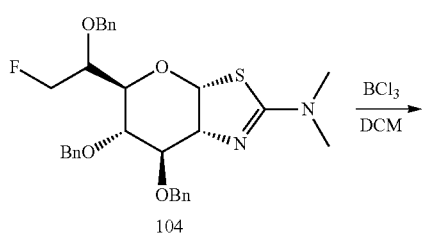

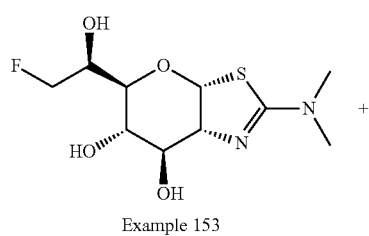

Example 153

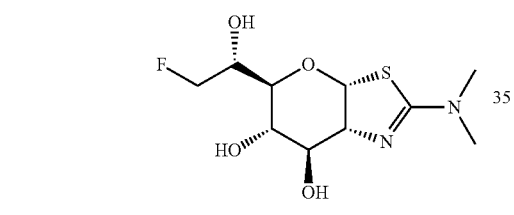

Example 154

Step 1

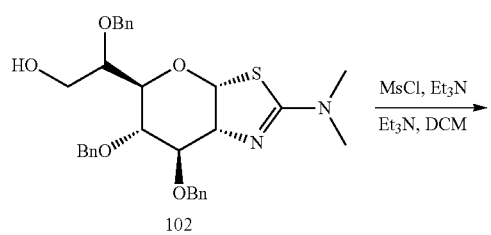

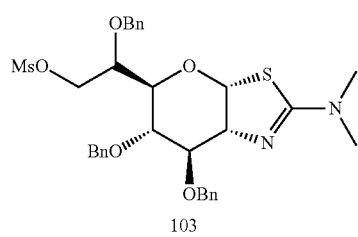

(S)-2-(benzyloxy)-2-((3aR,5R,6S,7R,7aR)-6,7-bis (benzyloxy)-2-(dimethylamino)-5,6,7,7a-tetrahydro-3aH-pyrano[3,2-d]thiazol-5-yl)ethyl methanesulfonate (103)

To a solution of 102 (1.2 g, 2.2 mmol) (Prepared according to the synthesis of Examples 151 and 152, step 1) in dichloromethane (30 mL) was added TEA (664 mg, 6.6 mmol) and MsCl (499 mg, 4.4 mmol) at 0° C. After kept 2 hours at room temperature, the reaction was quenched by water (100 mL) and extracted with dichloromethane (3×30 mL). The combined organic layer was washed with brine (20 mL) and dried over anhydrous sodium sulfate. After filtration, the filtrates were concentrated to give a residue, which was purified by silica gel column with 10%-30% ethyl acetate in petroleum ether to give the title compound (1.1 g, 80%) as brown syrup; (ES, m/z): [M+H]$^+$ 627.0; $^1$H NMR (300 MHz, CDCl$_3$) δ 7.22-7.45 (m, 15H), 6.35 (d, J=6.3 Hz, 1H), 5.03-5.15 (m, 2H), 4.61-4.80 (m, 4H), 4.47-4.53 (m, 2H), 4.25-4.36 (m, 1H), 4.08-4.12 (m, 1H), 3.89-3.92 (m, 1H), 3.46-3.78 (m, 2H), 3.06 (s, 6H), 3.01 (s, 3H).

Step 2

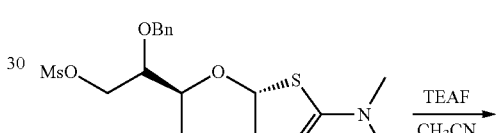

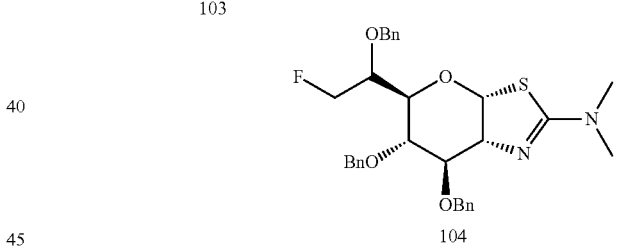

(3aR,5S,6S,7R,7aR)-6,7-bis(benzyloxy)-5-((R)-1-(benzyloxy)-2-fluoroethyl)-N,N-dimethyl-5,6,7,7a-tetrahydro-3aH-pyrano[3,2-d]thiazol-2-amine (104)

A solution of 103 (1 g, 1.6 mmol) in CH$_3$CN (20 mL) was treated with TEAF (2.38 g, 16 mmol) for 20 hours at reflux, then cooled to room temperature and poured into water (100 mL), extracted with dichloromethane (3×50 mL). The combined organic layer was washed with brine (2×50 mL), dried over anhydrous sodium sulfate and concentrated under reduced pressure to give a residue, which was purified by silica gel column with 20%-50% ethyl acetate in petroleum ether to afford the title compound (400 mg. 46%) as light yellow syrup; (ES, m/z): [M+H]$^+$ 551.1; $^1$H NMR (300 MHz, CDCl$_3$) δ 7.28-7.44 (m, 15H), 6.38 (d, J=6.3 Hz, 1H), 4.61-4.80 (m, 4H), 4.47-4.53 (m, 2H), 4.27-4.37 (m, 1H), 4.08-4.12 (m, 1H), 3.91-3.95 (m, 1H), 3.52-3.78 (m, 4H), 3.12 (s, 6H).

Step 3

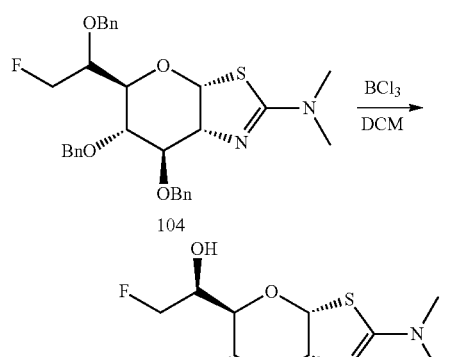

Example 153

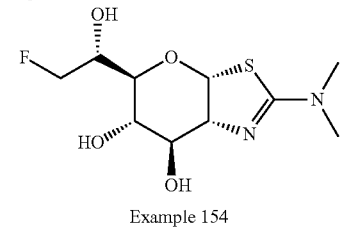

Example 154

(3aR,5S,6S,7R,7aR)-2-(dimethylamino)-5-((S)-2-fluoro-1-hydroxyethyl)-5,6,7,7a-tetrahydro-3aH-pyrano[3,2-d]thiazole-6,7-diol (Example 153) & (3aR,5S,6S,7R,7aR)-2-(dimethylamino)-5-((R)-2-fluoro-1-hydroxyethyl)-5,6,7,7a-tetrahydro-3aH-pyrano[3,2-d]thiazole-6,7-diol (Example 154)

A solution of 104 (400 mg, 0.7 mmol) in dichloromethane (15 mL) was treated with BCl$_3$ (7 mL, 7 mmol, 1M in dichloromethane) for 30 min at −60° C., then quenched with methanol (20 mL). Volatiles were distilled out to give a residue, which was dissolved into methanol (5 mL) and neutralized with Con. NH$_4$OH (2 ml, 26% aqueous solution). After concentration, the crude product was purified by a silica gel column, eluted with 10% methanol in dichloromethane to give a mixture of the two epimers; the two epimers were separated by Prep-HPLC with the following conditions: (Agilent Prep 1200 Detecl): Column, SunFire Prep C18; mobile phase, Water with 0.05% ammonia and CH$_3$CN; 5% CH$_3$CN up to 100% in 8 min Detector, 220 nm to afford (3aR,5S,6S,7R,7aR)-2-(dimethylamino)-5-((S)-2-fluoro-1-hydroxyethyl)-5,6,7,7a-tetrahydro-3aH-pyrano[3,2-d]thiazole-6,7-diol as a white solid (46.3 mg, 23%), faster eluting isomer; (ES, m/z): [M+H]$^+$ 281.0; III NMR (300 MHz, D$_2$O) δ 6.17 (d, J=6.6 Hz, 1H), 4.29-4.69 (m, 2H), 3.95-4.15 (m, 3H), 3.68-3.72 (m, 1H), 3.54-3.58 (m, 1H), 2.88 (s, 3H), 2.87 (s, 3H); and (3aR,5S,6S,7R,7aR)-2-(dimethylamino)-5-((R)-2-fluoro-1-hydroxyethyl)-5,6,7,7a-tetrahydro-3aH-pyrano[3,2-d]thiazole-6,7-diol as a white solid (64 mg, 31%), slower eluting isomer; (ES, m/z): [M+H]$^+$ 281.0; $^1$H NMR (300 MHz, D$_2$O) δ 6.17 (d, 6.3 Hz, 1H), 4.44-4.57 (m, 1H), 4.28-4.39 (m, 1H), 3.92-4.12 (m, 3H), 3.67-3.72 (m, 1H), 3.27-3.49 (m, 1H), 2.89 (s, 3H), 2.87 (s, 3H).

Example 155

(3aR,5R,6S,7R,7aR)-2-(dimethylamino)-5-(2-fluoroethyl)-5,6,7,7a-tetrahydro-3aH-pyrano[3,2-d]thiazole-6,7-diol

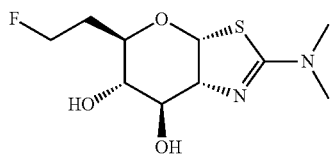

Example 155

Scheme XXII

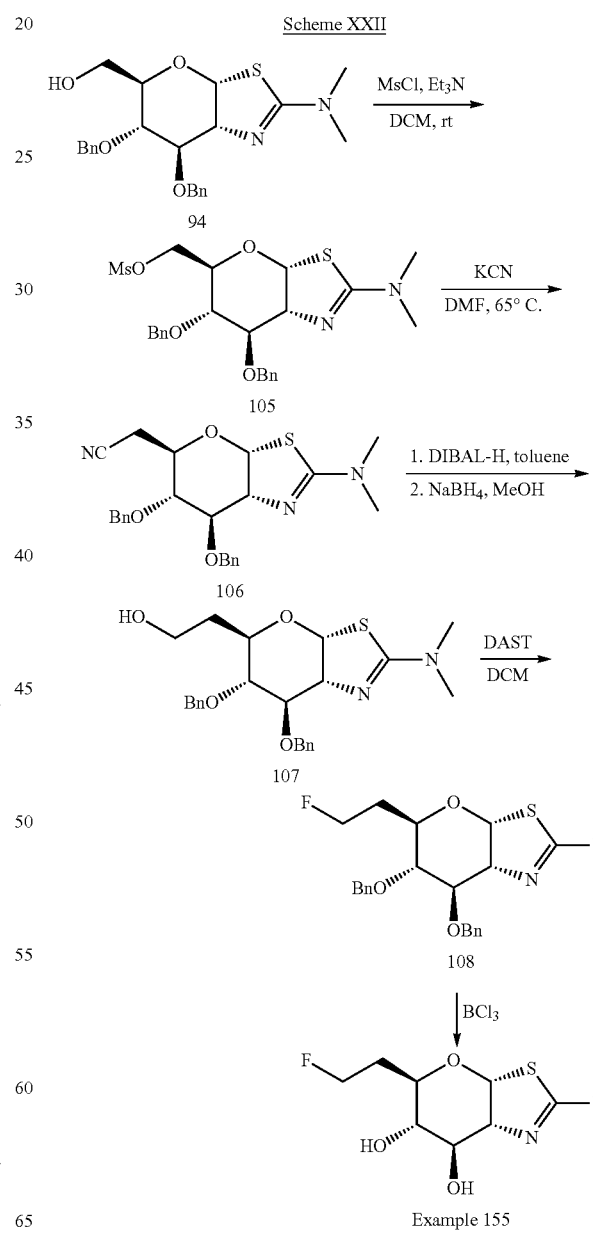

Example 155

Step 1

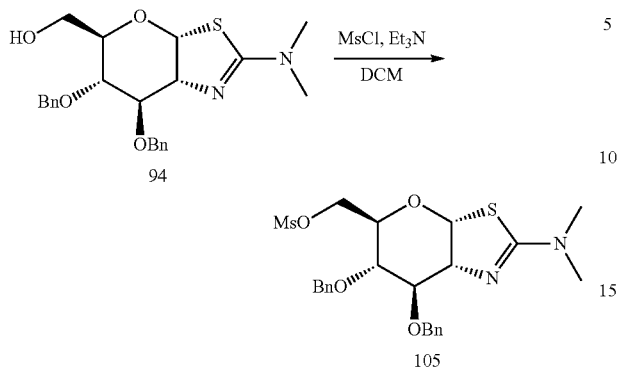

((3aR,5R,6S,7R,7aR)-6,7-bis(benzyloxy)-2-(dimethylamino)-5,6,7,7a-tetrahydro-3aH-pyrano[3,2-d]thiazol-5-yl)methyl methanesulfonate (105)

To a solution of ((3aR,5R,6S,7R,7aR)-6,7-bis(benzyloxy)-2-(dimethylamino)-5,6,7,7a-tetrahydro-3aH-pyrano[3,2-d]thiazol-5-yl)methanol (94) (8 g, 18 mmol) (Prepared according to the synthesis of Example 149, step 2) in dichloromethane (50 mL) was added methanesulfonyl chloride (4.3 g, 37 mmol) and triethylamine (3.8 g, 37 mmol) at 0° C. After kept 2 hours at 25° C., the reaction was quenched by water (50 mL) and extracted with dichloromethane (3×50 mL). The combined organic layer was washed with brine (2×30 mL), dried over anhydrous sodium sulfate, filtered and concentrated under reduced pressure to give a residue, which was purified by a silica gel column, eluted with 20%-30% ethyl acetate in petroleum ether to afford the title compound as a brown syrup (8.5 g, 90%); (ES, m/z) [M+H]$^+$ 507.0; $^1$HNMR (300 MHz, CDCl$_3$) δ 7.28-7.48 (m, 10H), 6.38 (d, J=6.6 Hz, 1H), 5.04-5.08 (m, 1H), 4.72-4.86 (m, 4H), 4.19-4.24 (m, 3H), 3.70-3.83 (m, 1H), 3.56-3.58 (m, 1H), 3.19 (s, 3H), 2.94 (s, 6H).

Step 2

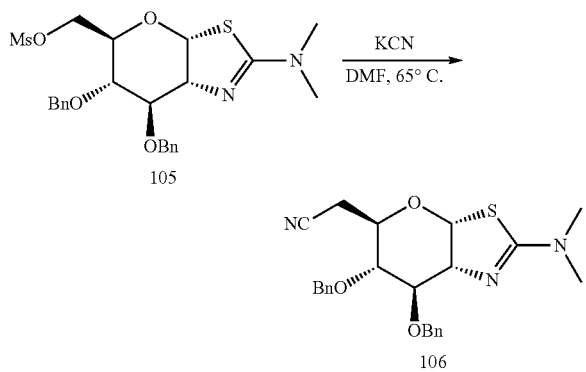

2-03aR,5R,6R,7R,7aR)-6,7-bis(benzyloxy)-2-(dimethylamino)-5,6,7,7a-tetrahydro-3aH-pyrano[3,2-d]thiazol-5-yl)acetonitrile (106)

A mixture of 105 (8.5 g, 17 mmol), KCN (2.7 g, 42 mmol) and TO (282 mg, 1.7 mmol) in DMF (80 mL) was heated to 65° C. for 2 hours, then quenched by water (200 mL) and extracted with ethyl acetate (5×40 mL). The combined organic layer was washed with brine (4×30 mL), dried over anhydrous sodium sulfate and concentrated under reduced pressure to give a residue, which was purified by a silica gel column, eluted with 10%-30% ethyl acetate in petroleum ether to afford the title compound as a yellow syrup (4.3 g, 55%); (ES, m/z) [M+H]$^+$ 438.0; $^1$HNMR (300 MHz, CDCl$_3$) δ 7.25-7.44 (m, 10H), 6.26 (d, J=6.6 Hz, 1H), 4.57-4.84 (m, 3H), 4.54-4.56 (m, 1H), 4.35-4.39 (m, 1H), 4.23-4.26 (m, 1H), 3.70-3.82 (m, 1H), 3.54-3.55 (m, 1H), 3.01 (s, 6H), 2.49-2.66 (m, 2H).

Step 3

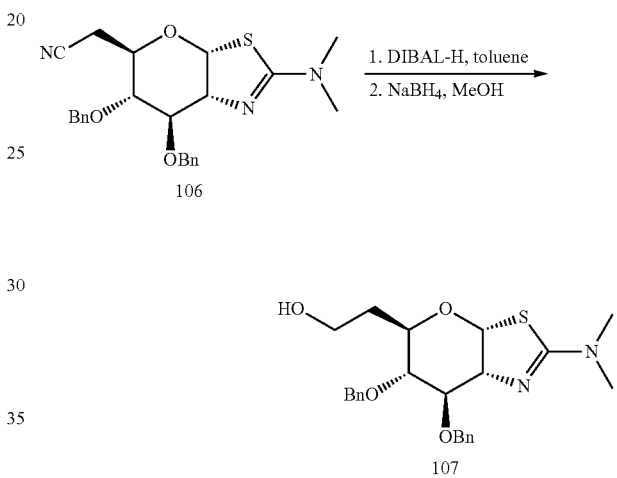

2-03aR,5R,6R,7R,7aR)-6,7-bis(benzyloxy)-2-(dimethylamino)-5,6,7,7a-tetrahydro-3aH-pyrano[3,2-d]thiazol-5-yl)ethanol (107)

A solution of 106 (400 mg, 0.9 mmol) in toluene (20 mL) was treated with DIBAL-H (2.3 mL, 2.3 mmol, 1M in toluene) for 1 hour at −25° C. Then the reaction was quenched with ice water (50 mL), extracted with ethyl acetate (3×40 mL). The combined organic layer was washed with brine (2×30 mL), dried over anhydrous sodium sulfate and concentrated under reduced pressure to afford crude aldehyde, which was dissolved into methanol (20 mL) and treated with NaBH$_4$ (105 mg, 2.7 mmol) for 1 hour at 25° C. Then the reaction was quenched by water (50 mL) and extracted with ethyl acetate (3×30 mL). The combined organic layer was dried over anhydrous sodium sulfate and concentrated under reduced pressure to give a residue, which was purified by a silica gel column, eluted with 20%-40% ethyl acetate in petroleum ether to afford 107 as a yellow syrup (270 mg, 67%); (ES, m/z) [M+H]$^+$ 443.0; $^1$HNMR (300 MHz, CDCl$_3$) δ 7.28-7.45 (m, 10H), 6.27 (d, J=6.3 Hz, 1H), 4.65-4.81 (m, 4H), 4.29-4.37 (m, 2H), 3.66-3.75 (m, 3H), 3.51-3.55 (m, 1H), 3.01 (s, 6H), 1.93-1.99 (m, 2H).

Step 4

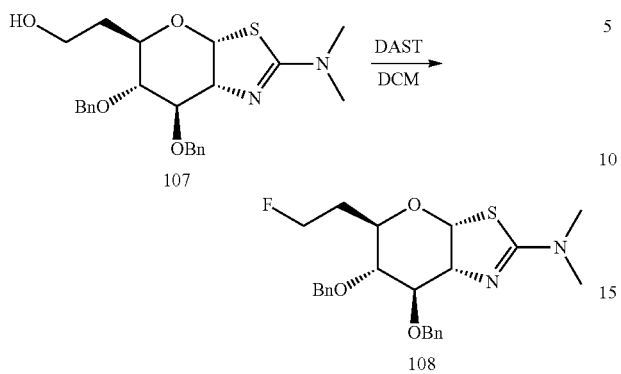

(3aR,5R,6R,7R,7aR)-6,7-bis(benzyloxy)-5-(2-fluoroethyl)-N,N-dimethyl-5,6,7,7a-tetrahydro-3aH-pyrano[3,2-d]thiazol-2-amine (108)

A solution of 107 (250 mg, 0.6 mmol) in dichloromethane (20 mL) was treated with DAST (550 mg, 3.4 mmol) for 2 hours at 0° C. Then the reaction was quenched by saturated aqueous NaHCO$_3$ (30 mL) and the aqueous layer was extracted with dichloromethane (2×20 mL). The combined organic layer was washed by brine (20 mL), dried over anhydrous sodium sulfate and concentrated under reduced pressure to give a residue, which was purified by a silica gel column, eluted with 3%-5% methanol in dichloromethane to afford 108 as a white solid (135 mg, 45%); (ES, m/z) [M+H]$^+$ 445.0; $^1$HNMR (300 MHz, CDCl$_3$) δ 7.32-7.45 (m, 10H), 6.26 (d, J=6.9 Hz, 1H), 4.57-4.82 (m, 5H), 4.40-4.56 (m, 3H), 3.64-3.71 (m, 1H), 3.47-3.49 (m, 1H), 3.01 (s, 6H), 2.06-2.25 (m, 1H), 1.70-1.82 (m, 1H).

Step 5

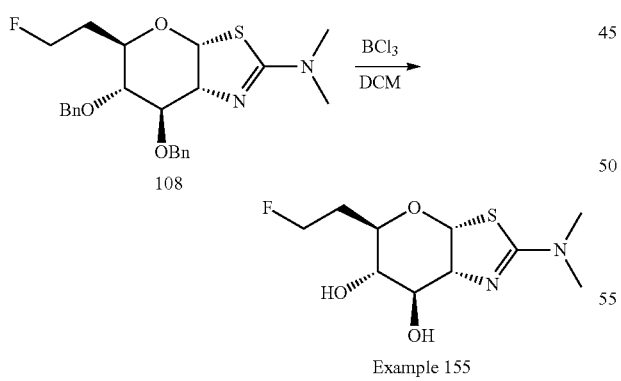

Example 155

(3aR,5R,6S,7R,7aR)-2-(dimethylamino)-5-(2-fluoroethyl)-5,6,7,7a-tetrahydro-3aH-pyrano[3,2-d]thiazole-6,7-diol A solution of 108 (300 mg, 0.7 mmol) in dichloromethane (20 mL) was treated with BCl$_3$ (7 mL, 7 mmol, 1 M in dichloromethane) for 2 hours at −60° C., then quenched by the addition of methanol (10 mL). Volatiles were distilled out under vacuum to give a residue, which was dissolved into methanol (5 mL) and neutralized by Con. NH$_4$OH (2 ml, 26% aqueous solution). After concentration, the crude product was purified by a silica gel column, eluted with 10% methanol in dichloromethane to give the title compound as a white solid (35 mg, 20%); (ES, m/z) [M+H]$^+$ 265.0; $^1$HNMR (300 MHz, D$_2$O) δ 6.16 (d, J=6.3 Hz, 1H), 4.60 (t, J=4.8 Hz, 1H), 4.45 (t, J=4.8 Hz, 1H), 4.10 (t, J=6.0 Hz, 1H), 3.92 (t, J=4.8 Hz, 1H), 3.62-3.66 (m, 1H), 3.42-3.60 (m, 1H), 2.90 (s, 6H), 2.06-2.20 (m, 1H), 1.67-1.88 (m, 1H).

Example 156

(3aR,5R,6S,7R,7aR)-5-(2,2-difluoroethyl)-2-(dimethylamino)-5,6,7,7a-tetrahydro-3aH-pyrano[3,2-d]thiazole-6,7-diol

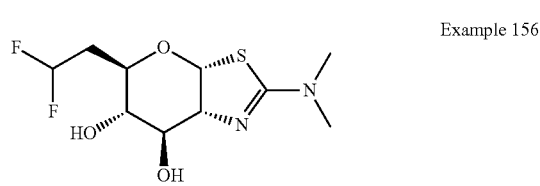 [SMILES: CN(C)C1=N[C@@H]2[C@@H](O)[C@H](O)[C@@H](CC(F)F)O[C@@H]2S1]

Example 156

Scheme XXIII

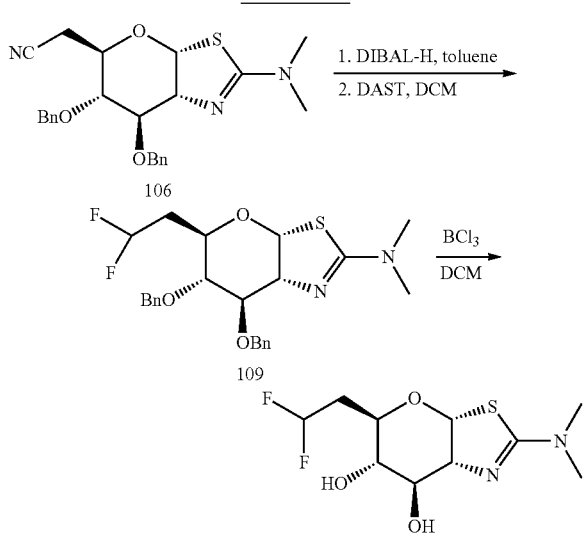

Example 156

Step 1

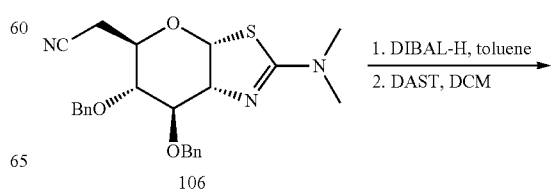

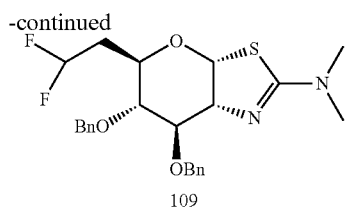

109

(3aR,5R,6R,7R,7aR)-6,7-bis(benzyloxy)-5-(2,2-difluoroethyl)-N,N-dimethyl-5,6,7,7a-tetrahydro-3aH-pyrano[3,2-d]thiazol-2-amine (109)

A solution of 106 (400 mg, 0.9 mmol) (Prepared according to the synthesis of Example 155, step 2) in toluene (20 mL) was treated with DIBAL-H (2.3 mL, 2.3 mmol, 1M in toluene) for 1 hour at −25° C. Then the reaction was quenched with ice water (50 mL), extracted with ethyl acetate (3×40 mL). The combined organic layers were washed with brine (2×30 mL), dried over anhydrous sodium sulfate and concentrated under reduced pressure to afford crude aldehyde, which was dissolved into dichloromethane (20 mL) and treated with DAST (370 mg, 2.3 mmol) at −78° C. under nitrogen for 30 min. After additional 2 hours at 0° C., the reaction was quenched with saturated aqueous sodium carbonate (10 mL) and the aqueous layer was extracted with dichloromethane (3×20 mL). The combined organic layer was washed with brine (20 mL) and dried over anhydrous sodium sulfate. After filtration, the filtrates were concentrated under reduced pressure to give a residue, which was purified by a silica gel column, eluted with 10%-40% ethyl acetate in petroleum ether to afford the title compound as a yellow syrup (110 mg, 48%); (ES, m/z) [M+H]+ 4610; $^1$HNMR (300 MHz, CDCl$_3$) δ 7.28-7.43 (m, 10H), 6.25 (d, J=6.6 Hz, 1H), 5.71-6.09 (m, 1H), 4.59-4.81 (m, 4H), 4.25-4.37 (m, 2H), 3.67-3.74 (m, 1H), 3.44-3.47 (m, 1H), 3.03 (s, 6H), 2.16-2.24 (m, 1H), 1.88-2.08 (m, 1H).

Step 2

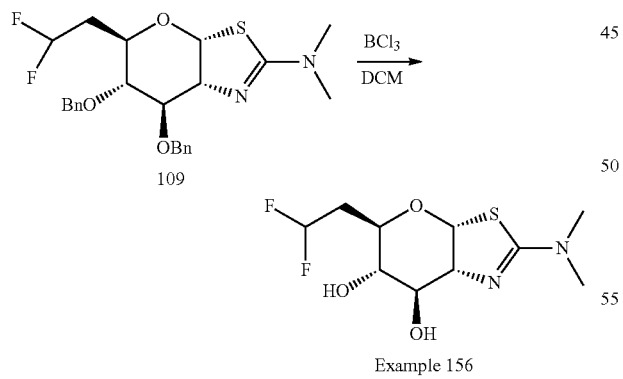

(3aR,5R,6S,7R,7aR)-5-(2,2-difluoroethyl)-2-(dimethylamino)-5,6,7,7a-tetrahydro-3aH-pyrano[3,2-d]thiazole-6,7-diol A solution of 109 (270 mg, 0.6 mmol) in dichloromethane (20 mL) was treated with BCl$_3$ (6 mL, 6 mmol, 1M in dichloromethane) for 2 hours at −60° C., then the reaction was quenched with methanol (20 mL). Volatiles were distilled out under vacuum to give a residue, which was dissolved into methanol (5 mL) and neutralized by Con. NH$_4$OH (2 ml, 26% aqueous solution). After concentration, the crude product was purified by a silica gel column, eluted with 10% methanol in dichloromethane to give the title compound as a white solid (41 mg, 25%); (ES, m/z) [M+H]+ 283.0; $^1$HNMR (300 MHz, D$_2$O) δ 6.17 (d, J=6.3 Hz, 1H), 5.77-6.14 (m, 1H), 4.12 (t, J=6.0 Hz, 1H), 3.93 (t, J=5.1 Hz, 1H), 3.68-3.73 (m, 1H), 3.43-3.48 (m, 1H), 2.91 (s, 6H), 1.99-2.35 (m, 2H).

Example 157

(3aR,5R,6S,7R,7aR)-2-(dimethylamino)-5-(2,2,2-trifluoroethyl)-5,6,7,7a-tetrahydro-3aH-pyrano[3,2-d]thiazole-6,7-diol

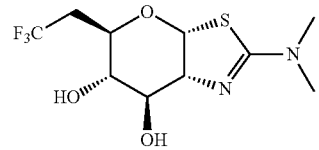

Example 157

Scheme XXIV

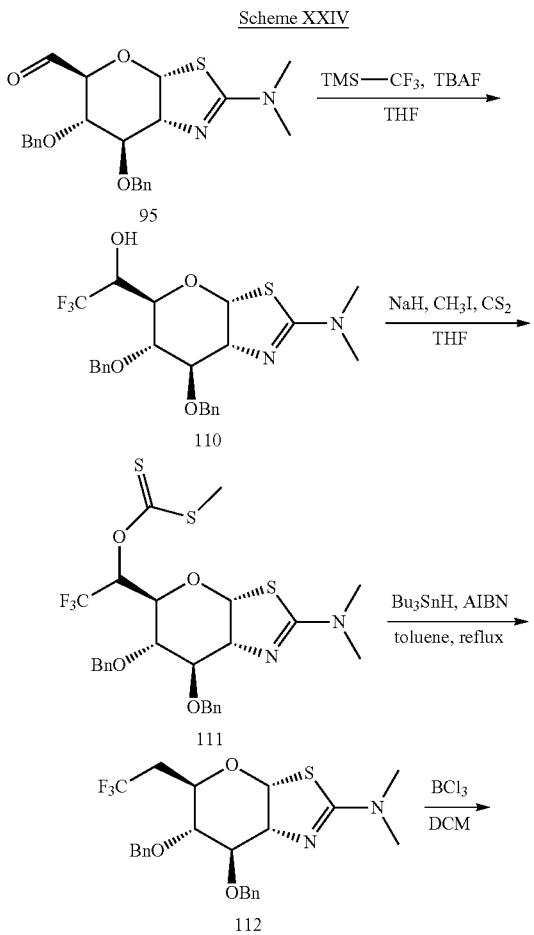

-continued

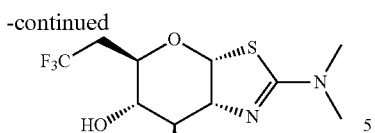

Example 157

Step 1

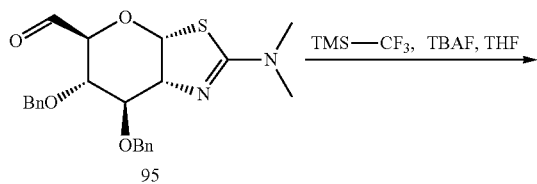

(R)-1-((3aR,5R,6S,7R,7aR)-6,7-bis(benzyloxy)-2-(dimethylamino)-5,6,7,7a-tetrahydro-3aH-pyrano[3,2-d]thiazol-5-yl)-2,2,2-trifluoroethanol (110)

A mixture of the aldehyde (95) (3.0 g, 7 mmol) (Prepared according to the synthesis of Example 149 step 3) TBAF (1.06 g, 3 mmol) and 4 Å molecular sieves (2.0 g) in THF (60 mL) was stirred for 30 min followed by the addition of $CF_3SiMe_3$ (5.8 g, 40 mmol) at −30° C. The mixture was kept overnight at room temperature, additional TBAF (20 g, 63 mmol) was added. After stirred additional 1 hour, the reaction was quenched by brine (40 mL) and extracted with ethyl acetate (3×50 mL). The organic layers combined, washed with brine (3×50 mL), dried over anhydrous sodium sulfate and concentrated under reduced pressure to give a residue, which was purified by a silica gel column, eluted with 5%-25% ethyl acetate in petroleum ether to afford 110 as a light yellow syrup (1.7 g, 49%). (ES, m/z): [M+H]$^+$ 497.7; $^1$H NMR (300 MHz, CDCl$_3$) δ 7.31-7.40 (m, 10H), 6.29 (d, J=6.6 Hz, 1H), 4.57-4.78 (m, 4H), 4.30-4.43 (m, 2H), 3.80-4.17 (m, 4H), 3.01 (s, 6H).

Step 2

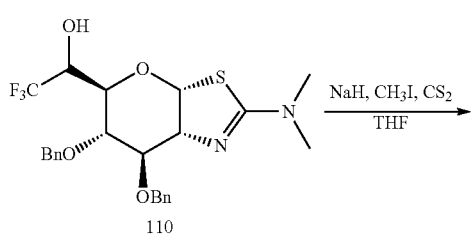

-continued

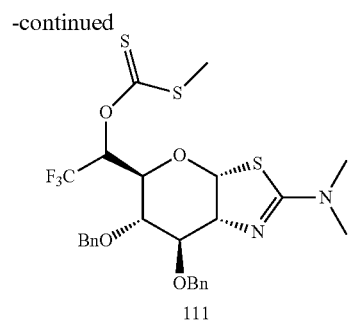

O—(R)-1-((3aR,5S,6S,7R,7aR)-6,7-bis(benzyloxy)-2-(dimethylamino)-5,6,7,7a-tetrahydro-3aH-pyrano[3,2-d]thiazol-5-yl)-2,2,2-trifluoroethyl S-methyl carbonodithioate (111)

A solution of compound 110 (1.5 g, 3 mmol), CS$_2$ (8 mL) and CH$_3$I (8 mL) in tetrahydrofuran (50 mL) was treated with sodium hydride (242 mg, 6 mmol, 60% mineral oil dispersed) at 0-5° C. for 1.5 hours, then the reaction was quenched by the addition of water (50 mL) and extracted with dichloromethane (3×40 mL). The organic layers were combined, washed with brine (2×30 mL) and dried over magnesium sulfate. After filtration, the filtrates were concentrated under vacuum to give a residue, which was purified by a silica gel column, eluted with 15%-30% ethyl acetate in petroleum ether to give compound III as a yellow syrup (1.4 g, 79%). (ES, m/z): [M+H]$^+$ 586.7; $^1$H NMR (CD$_3$Cl, 300 MHz) δ 7.29-7.39 (m, 10H), 6.62-6.65 (m, 0.5H), 6.29-6.48 (m, 0.5H), 4.51-4.78 (m, 4H), 4.25-4.32 (m, 2H), 4.03-4.15 (m, 2H), 3.01 (s, 6H), 2.56 (s, 3H).

Step 3

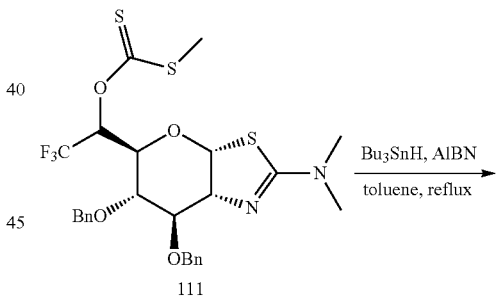

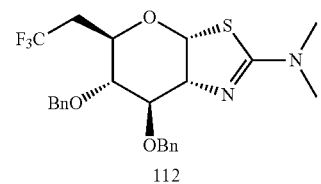

(3aR,5R,6R,7R,7aR)-6,7-bis(benzyloxy)-N,N-dimethyl-5-(2,2,2-trifluoroethyl)-5,6,7,7a-tetrahydro-3aH-pyrano[3,2-d]thiazol-2-amine (112)

To a solution of compound 111 (1.4 g, 2 mmol) in toluene (40 mL) was added tributylstannane (3.5 g, 12 mmol) and AIBN (20 mg, 0.1 mmol) at room temperature. The resulting solution was kept at 100° C. for 1 hour, then cooled to room temperature and quenched by water (50 mL). The organic layer was separated and the aqueous layer was extracted with ethyl acetate (2×30 mL). The combined organic layers were dried over magnesium sulfate. After filtration, the filtrates were concentrated under vacuum to give a residue, which was purified by a silica gel column, eluted with 10%-20% ethyl acetate in petroleum ether to give compound 112 as a light yellow syrup (1.0 g, 87%). (ES, m/z): [M+H]+ 480.7; 1H NMR (CD3Cl, 300 MHz) δ 7.29-7.43 (m, 10H), 6.23 (d, J=6.6 Hz, 1H), 4.55-4.83 (m, 4H), 4.25-4.36 (m, 2H), 3.80-3.84 (m, 1H), 3.39-3.42 (m, 1H), 3.02 (s, 6H), 2.35-2.40 (m, 1H), 2.13-2.21 (m, 1H).

Step 4

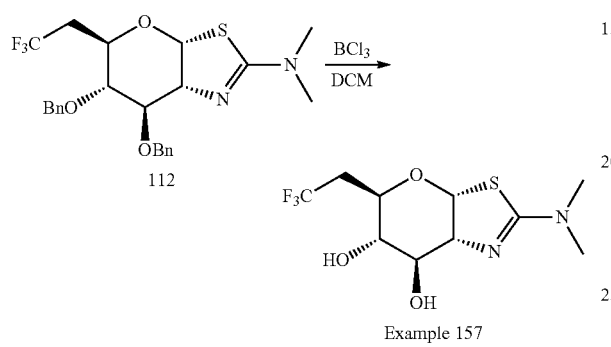

112

Example 157

(3aR,5R,6S,7R,7aR)-2-(dimethylamino)-5-(2,2,2-trifluorethyl)-5,6,7,7a-tetrahydro-3aH-pyrano[3,2-d]thiazole-6,7-diol A solution of compound 112 (300 mg, 0.6 mmol) in dichloromethane (10 mL) was added BCl3 (3 mL, 3 mmol, 1M in dichloromethane) at −78° C. The resulting solution was kept at −20° C. for 1 hour, then quenched by the addition of methanol (10 mL). Volatiles were distilled out under vacuum to give a residue, which was dissolved into methanol (5 mL) and neutralized by Con. NH4OH (2 ml, 26% aqueous solution). After concentration, the crude product was purified by a silica gel column, eluted with 10% methanol in dichloromethane to give the title compound as a white solid (94.2 mg, 49%). (ES, m/z): [M+H]+ 300.9; 1H NMR (D2O, 300 MHz) δ 6.16 (d, J=6.3 Hz, 1H), 4.11-4.15 (m, 1H), 3.93-3.97 (m, 1H), 3.77-3.83 (m, 1H), 3.44-3.48 (m, 1H), 2.91 (s, 6H), 2.52-2.68 (m, 1H), 2.37-2.49 (m, 1H).

Example 158 & 159

(3aR,5S,6S,7R,7aR)-2-(methylamino)-5-((S)-1,1,1-trifluoro-2-hydroxypropan-2-yl)-5,6,7,7a-tetrahydro-3aH-pyrano[3,2-d]thiazole-6,7-diol & (3aR,5S,6S,7R,7aR)-2-(methylamino)-5-(1,1,1-trifluoro-2-hydroxypropan-2-yl)-5,6,7,7a-tetrahydro-3aH-pyrano[3,2-d]thiazole-6,7-diol

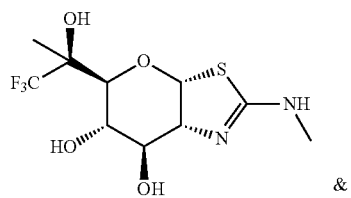

Example 158

Example 159

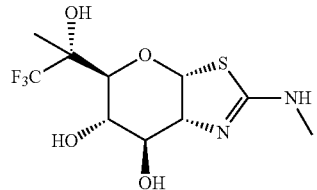

Scheme XXV

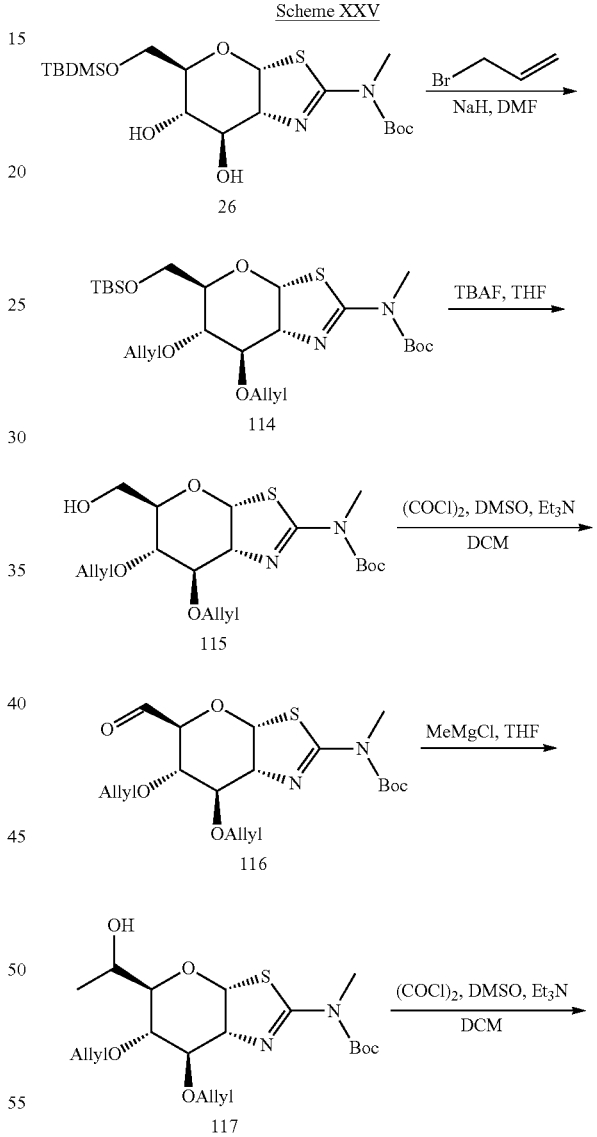

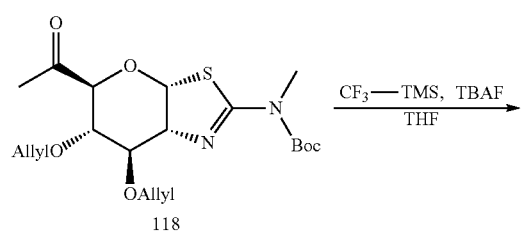

-continued

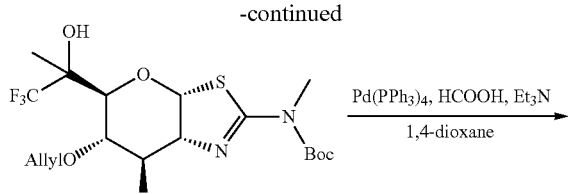
119

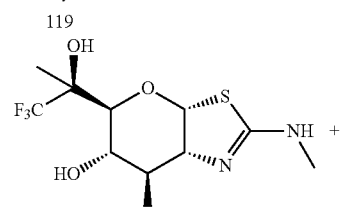
Example 158

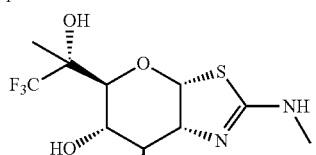
Example 159

Step 1

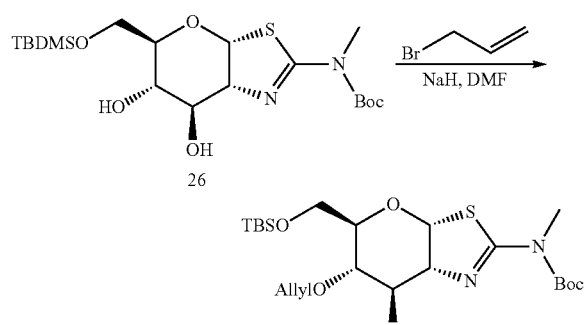

tert-butyl (3aR,5R,6S,7R,7aR)-6,7-bis(allyloxy)-5-((tert-butyldimethylsilyloxy)methyl)-5,6,7,7a-tetrahydro-3aH-pyrano[3,2-d]thiazol-2-yl(methyl)carbamate (114)

A solution of 26 (35 g, 78 mmol) (Prepared according to the synthesis of Example 3, step 4) in DMF (250 mL) was treated with NaH (70%, 8 g, 233 mmol) at 5° C. for 30 min, then Allyl-Br (28 g, 233 mmol) was added slowly. After stirring for 1.5 hours at 15° C., the reaction was quenched by H$_2$O (300 mL), extracted with ethyl acetate (3×200 mL). The organic layers were collected, washed with brine (5×100 mL), dried over anhydrous sodium sulfate and concentrated under reduced pressure to give a residue, which was purified by a silica gel column, eluted with 5%~10% ethyl acetate in petroleum ether to afford the title compound (32 g, 78%) as a yellow oil; (ES, m/z) [M+H]$^+$ 529.1; $^1$H NMR (300 MHz, CDCl$_3$) δ 6.07 (d, J=6.3 Hz, 1H), 5.85-6.05 (m, 2H), 5.15-5.38 (m, 4H), 4.22-4.30 (m, 4H), 4.02-4.07 (m, 2H), 3.76-3.78 (m, 2H), 3.60-3.62 (m, 1H), 3.48-3.52 (m, 1H), 3.31 (s, 3H), 1.55 (s, 9H), 0.93 (s, 9H), 0.08 (s, 6H).

Step 2

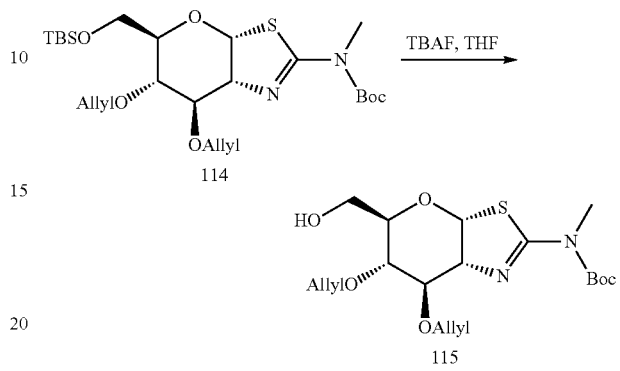

tert-butyl (3aR,5R,6S,7R,7aR)-6,7-bis(allyloxy)-5-(hydroxymethyl)-5,6,7,7a-tetrahydro-3aH-pyrano[3,2-(1]thiazol-2-yl(methyl)carbamate (115)

A solution of 114 (104 g, 197 mmol) in THF (700 mL) was treated with TBAF (77 g, 296 mmol) at 20° C. for 6 hours, then the reaction was quenched by water (500 mL), extracted with ethyl acetate (5×300 mL). The organic layers combined, washed with brine (2×150 mL), dried over anhydrous sodium sulfate and concentrated under reduced pressure to give a residue, which was purified by a silica gel column, eluted with 5% 30% ethyl acetate in petroleum ether to afford the title compound (72 g, 88%) as a yellow oil; (ES, m/z) [M+H]$^+$ 415.0; NMR (300 MHz, CDCl$_3$) δ 6.07 (d, J=6.9 Hz, 1H), 5.94-6.01 (m, 2H), 5.17-5.38 (m, 4H), 4.02-4.45 (m, 6H), 3.74-3.85 (m, 1H), 3.51-3.71 (m, 2H), 3.55-3.68 (m, 1H), 3.33 (s, 3H), 1.55 (s, 9H).

Step 3

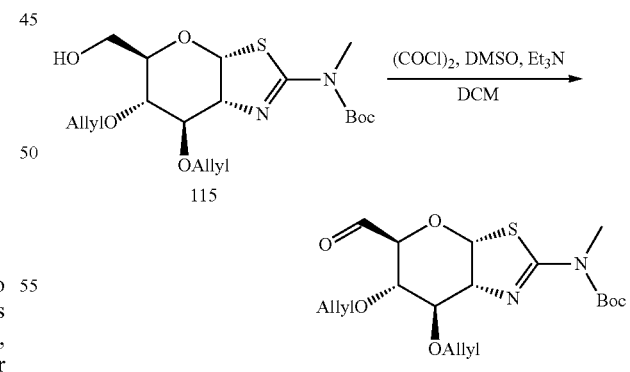

tert-butyl (3aR,5S,6S,7R,7aR)-6,7-bis(allyloxy)-5-formyl-5,6,7,7a-tetrahydro-3aH-pyrano[3,2-d]thiazol-2-yl(methyl)carbamate (116)

A solution of DMSO (45 g, 580 mmol) in dichloromethane (450 mL) was treated with oxalyl dichloride (55 g, 435 mmol)

at −78° C. for 1 hour, then a solution of 115 (30 g, 72 mmol) in dichloromethane (100 mL) was added slowly. The resulted solution was stirred for 4 hours at −20° C. followed by the addition of triethylamine (73 g, 725 mmol) at −78° C. After stirring for additional 1 hour at −20° C., the reaction was quenched by water (600 mL), extracted with dichloromethane (2×300 mL). The organic layers combined, washed with brine (2×150 mL), dried over anhydrous sodium sulfate and concentrated under reduced pressure to afford crude 116 as a yellow syrup, used for next step without further purification; (ES, m/z) [M+H]+ 413.0.

Step 4

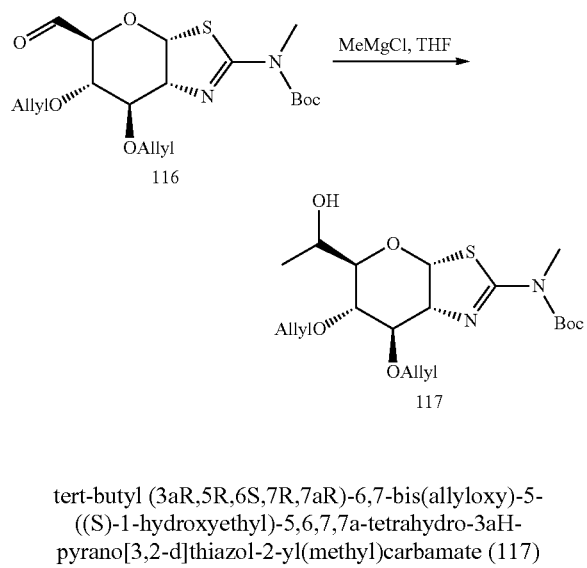

tert-butyl (3aR,5R,6S,7R,7aR)-6,7-bis(allyloxy)-5-((S)-1-hydroxyethyl)-5,6,7,7a-tetrahydro-3aH-pyrano[3,2-d]thiazol-2-yl(methyl)carbamate (117)

A solution of crude 116 in anhydrous THF (300 mL) was treated with methylmagnesium chlorine (48 mL, 3M in THF, 145 mmol) at 10° C. overnight, then quenched with saturated aqueous NH4Cl (300 mL), extracted with ethyl acetate (3×200 mL). The organic layers combined, washed with brine (2×100 mL), dried over anhydrous magnesium sulfate and concentrated under reduced pressure to give a residue, which was purified by silica gel column, eluted with 3% 25% ethyl acetate in petroleum ether to afford 117 (18 g, 58% 2 steps) as a yellow syrup; [M+H]+ 429.1; $^1$H NMR (300 MHz, CDCl$_3$) δ 5.97-6.11 (m, 1H), 5.87-5.95 (m, 2H), 5.21-5.36 (m, 4H), 4.21-4.45 (m, 4H), 3.68-4.05 (m, 3H), 3.65-3.68 (m, 1H), 3.32 (d, J=4.2 Hz, 3H), 3.21-3.22 (m, 1H), 1.54-1.56 (s, 9H), 1.27 (s, 3H).

Step 5

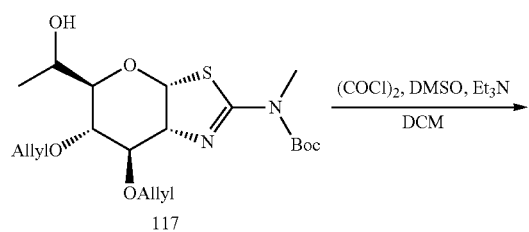

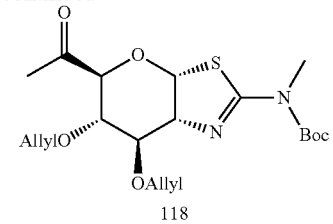

tert-butyl (3aR,5S,6S,7R,7aR)-5-acetyl-6,7-bis(allyloxy)-5,6,7,7a-tetrahydro-3aH-pyrano[3,2-d]thiazol-2-yl(methyl)carbamate (118)

A solution of DMSO (52 g, 672 mmol) in dichloromethane (500 mL) was treated with oxalyl dichloride (64 g, 505 mmol) at −78° C. for 1 hour, then a solution of 117 (36 g, 84 mmol) in dichloromethane (150 mL) was added. The resulted solution was stirred for 4 hours at −20° C. followed by the addition of triethylamine (85 g, 841 mmol) at −78° C. After stirring at −20° C. for additional 1 hour, the reaction was quenched with water (600 mL), extracted with dichloromethane (2×300 mL). The organic layers combined, washed with brine (2×200 mL), dried over anhydrous sodium sulfate and concentrated under reduced pressure to give a residue, which was purified by silica gel column, eluted with 3% 20% ethyl acetate in petroleum ether to afford 118 (26 g, 73%) as a yellow syrup; [M+H]+ 427.0; $^1$H NMR (300 MHz, CDCl$_3$) δ 6.02 (d, J=6.3 Hz, 1H), 5.82-5.99 (m, 2H), 5.17-5.35 (m, 4H), 4.20-4.29 (m, 1H), 4.03-4.29 (m, 5H), 3.71-3.77 (m, 2H), 3.25 (s, 3H), 2.14 (s, 3H), 1.52 (s, 9H).

Step 6

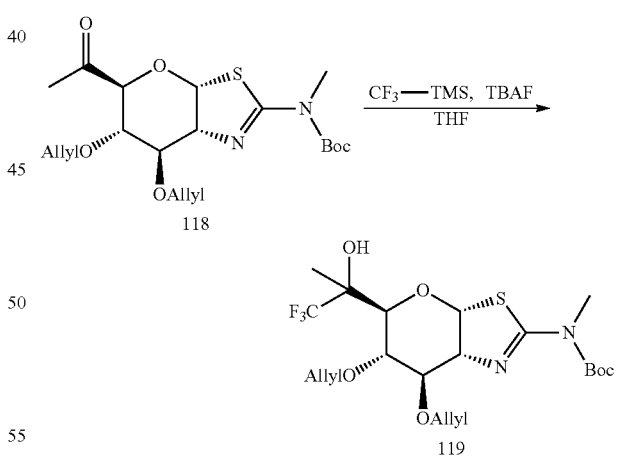

tert-butyl (3aR,5S,6S,7R,7aR)-6,7-bis(allyloxy)-5-((S)-1,1,1-trifluoro-2-hydroxypropan-2-yl)-5,6,7,7a-tetrahydro-3aH-pyrano[3,2-d]thiazol-2-yl(methyl)carbamate (119)

A mixture of TBAF (3.7 g, 14 mmol) and 4 Å molecule sieves in THF (200 mL) was stirred for 30 min at 0° C. followed by the addition of a solution of 118 (15 g, 35 mmol) and TMS-CF$_3$ (20 g, 141 mmol) in THF (80 mL). After stirring for additional 12 hours at 25° C., additional TBAF (14 g, 54 mmol) was added, and the mixture was stirred for 1 hour. The reaction was quenched by brine (200 mL), extracted with ethyl acetate (3×150 mL), the organic layers combined, washed with brine (3×100 mL), dried over anhydrous sodium sulfate and concentrated under reduced pressure to give a residue, which was purified by a silica gel column, eluted with 5%-25% ethyl acetate in petroleum ether to afford 119 (12 g, 69%) as a yellow oil; (ES, m/z) [M+H]⁺ 497.1. ¹H NMR (300 MHz, CDCl₃) δ 6.12-6.18 (m, 1H), 5.86-6.00 (m, 2H), 5.19-5.37 (m, 4H), 4.02-4.45 (m, 6H), 3.92-3.96 (m, 1H), 3.62-3.64 (m, 1H), 3.25 (d, J=3.6 Hz, 3H), 1.54-1.56 (m, 9H), 1.27-1.38 (m, 3H).

Step 7

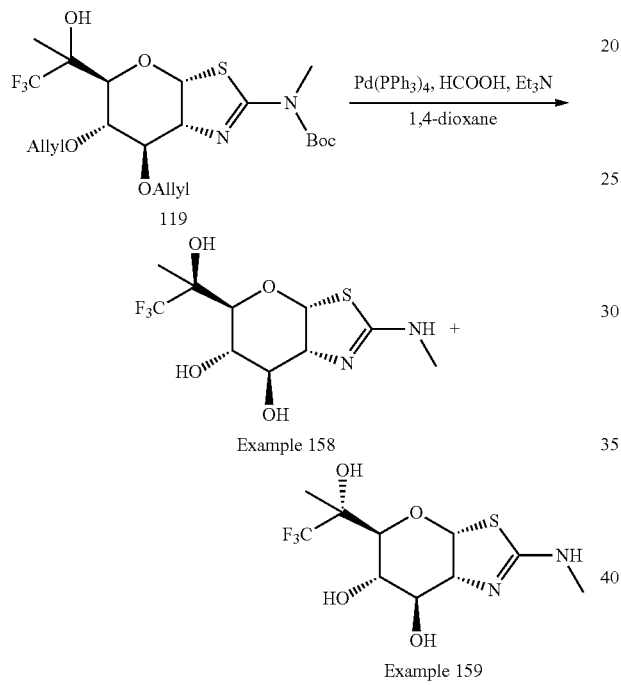

(3aR,5S,6S,7R,7aR)-2-(methylamino)-5-((S)-1,1,1-trifluoro-2-hydroxypropan-2-yl)-5,6,7,7a-tetrahydro-3aH-pyrano[3,2-d]thiazole-6,7-diol & (3aR,5S,6S,7R,7aR)-2-(methylamino)-5-(1,1,1-trifluoro-2-hydroxypropan-2-yl)-5,6,7,7a-tetrahydro-3aH-pyrano[3,2-d]thiazole-6,7-diol To a solution of 119 (4.5 g, 9 mmol) in 1,4-dioxane (50 mL) was added Pd(PPh₃)₄ (2.1 g, 1.8 mmol), Et₃N (23 g, 22.7 mmol) and HCOOH (0.8 g, 18 mmol) at 25° C. under N₂ atmosphere. After 20 min at 60° C., additional HCOOH (6.3 g, 136 mmol) was added and the mixture was stirred for additional 12 hours at 60° C., then quenched by H₂O (60 mL), extracted with dichloromethane (2×40 mL) to remove the organic impurities. The pH value of aqueous phase was adjusted to 7-8 by saturated aqueous NaHCO₃, then concentrated under reduced pressure to give a residue, which was purified by a silica gel column, eluted with 2%-10% methanol in dichloromethane to give the mixture of the two epimer. Further separation by Prep HPLC [(Agilent 1200 prep HPLC): Column, Sun Fire Prep C18*50 mm 5 um; mobile phase, WATER with CH₃CN (5% CH₃CN up to 40% in 10 min); Detector, UV, 220 nm] to afford (3aR,5S,6S,7R,7aR)-2-(methylamino)-5-((S)-1,1,1-trifluoro-2-hydroxypropan-2-yl)-5,6,7,7a-tetrahydro-3aH-pyrano[3,2-d]thiazole-6,7-diol as white solid (730 mg, 25.4%), Faster eluting isomer. (ES, m/z): 317.0; ¹HNMR (300 MHz, D₂O) δ 6.27 (d, J=6.9 Hz, 1H), 4.38-4.41 (m, 1H), 4.22-4.23 (m, 1H), 3.94-3.97 (d, J=8.4 Hz, 1H), 3.56-3.60 (d, J=8.4 Hz, 1H), 2.77 (s, 3H), 1.34 (s, 31-1); and (3aR,5S,6S,7R,7aR)-2-(methylamino)-5-(1,1,1-trifluoro-2-hydroxypropan-2-yl)-5,6,7,7a-tetrahydro-3aH-pyrano[3,2-d]thiazole-6,7-diol as white solid (810 mg, 28.2%), Slower eluting isomer. (ES, m/z): 317.0; ¹HNMR (300 MHz, D₂O) δ 6.26 (d, J=6.9 Hz, 1H), 4.37-4.39 (m, 1H), 4.18-4.20 (m, 1H), 3.96-3.99 (m, 1H), 3.60-3.62 (d, J=8.4 Hz, 1H), 2.77 (s, 3H), 1.33 (s, 3H).

Example 160 and 161

(3aR,5S,6S,7R,7aR)-2-(ethylamino)-5-((S)-2,2,2-trifluoro-1-hydroxyethyl)-5,6,7,7a-tetrahydro-3aH-pyrano[3,2-d]thiazole-6,7-diol and (3aR,5S,6S,7R,7aR)-2-(ethylamino)-5-((R)-2,2,2-trifluoro-1-hydroxyethyl)-5,6,7,7a-tetrahydro-3aH-pyrano[3,2-d]thiazole-6,7-diol

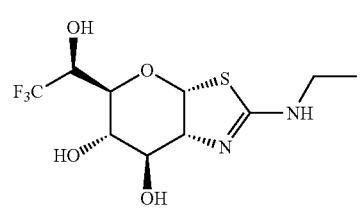

Example 160

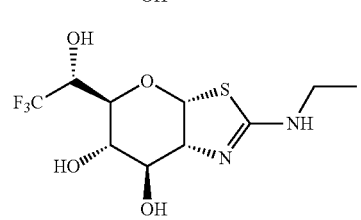

Example 161

Scheme XXVI

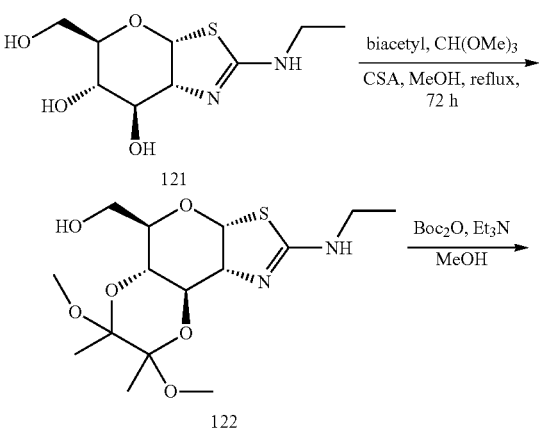

-continued

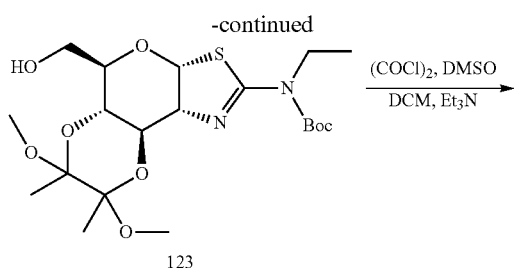
123

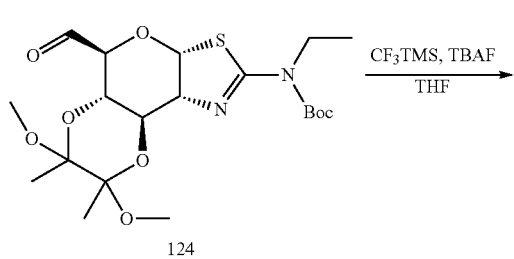
124

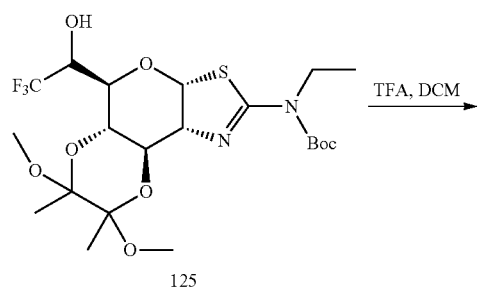
125

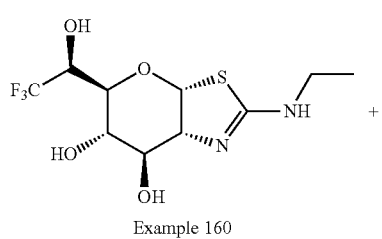
Example 160

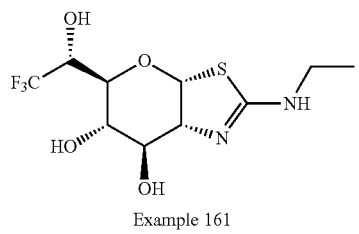
Example 161

Step 1-2

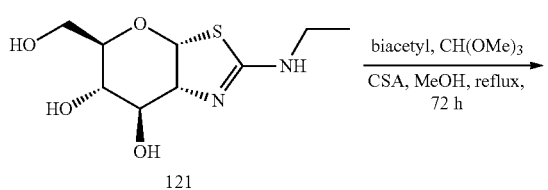
121

-continued

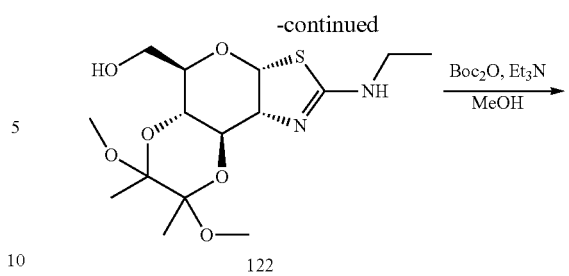
122

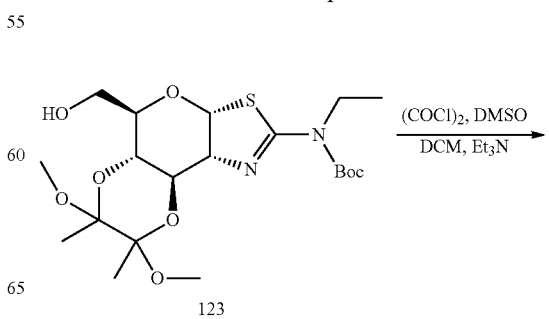
123 tert-butyl N-ethyl-N-[(1R,2R,6R,8R,9S)-8-(hydroxymethyl)-11,12-dimethoxy-11,12-dimethyl-7,10,13-trioxa-5-thia-3-azatricyclo[7.4.0.0[2,6]]-tridec-3-en-4-yl]carbamate (123)

D-(+)-10-Camphorsulfonic acid (112 g, 0.48 mol) was added to a solution of (3aR,5R,6S,7R,7aR)-2-(ethylamino)-5-(hydroxymethyl)-5,6,7,7a-tetrahydro-3aH-pyrano[3,2-d]thiazole-6,7-diol (121) (ref. Yuzwa, et al, *Nature Chemical Biology*, 2008, 4, 483 and WO 2008/025170, published Mar. 6, 2008) (100 g, 0.4 mol), biacetyl (173 g, 2 mol) and trimethyl orthoformate (427 g, 4 mol) in anhydrous methanol (2 L). The mixture was heated at reflux for 72 hours, and followed by addition of triethylamine (53 g, 0.53 mol) at room temperature. The mixture containing crude 122 was treated with Boc anhydride (170 g, 0.78 mol) and stirred overnight at room temperature. Removal of volatiles gave a residue, which was dissolved into dichloromethane (1 L), washed with brine (5×100 mL), dried over anhydrous sodium sulphate and concentrated. The crude material was purified by a silica gel column, eluted with 10%-20% ethyl acetate in petroleum ether to give 123 as a brown syrup (92 g, 49%) as a 1:1 mixture of two isomers based on $^1$H NMR. (ES, m/z) [M+H]$^+$463.0; $^1$H NMR (300 MHz, CDCl$_3$) δ 6.11 (m, 2H), 4.26-4.29 (m, 1H), 3.74-4.09 (m, 15H), 3.39 (s, 3H), 3.31 (s, 3H), 3.27 (s, 3H), 3.24 (s, 3H), 1.52 (s, 9H), 1.45 (s, 3H), 1.42 (s, 3H), 1.39 (s, 3H), 1.36 (s, 3H), 1.13-1.19 (m, 6H).

Step 3

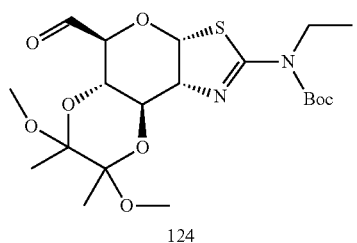

tert-butyl N-ethyl-N-[(1R,2R,6R,8S,9S)-8-formyl-11,12-dimethoxy-11,12-dimethyl-7,10,13-trioxa-5-thia-3-azatricyclo[7.4.0.0[2,6]]tridec-3-en-4-yl]carbamate (124)

A solution of DMSO (40 g, 0.52 mol) in anhydrous dichloromethane (1.5 L) was treated with oxallyl dichloride (49 g, 0.39 mol) at −78° C. for 1 hour, followed by addition of 123 (30 g, 65 mmol). The resulting solution was stirred for 4 hours at −30° C. and then cooled down to −78° C. again at which time triethylamine (86 g, 0.85 mol) was added. After 1 hour at −50° C., the reaction mixture was quenched by $H_2O$ (500 mL), washed with brine (3×100 mL), dried over anhydrous sodium sulfate and concentrated under vacuum to give a residue, which was purified by a short silica gel column, eluted with 30% ethyl acetate in petroleum ether to give 124 as a brown syrup (18 g, 60%). (ES, m/z) [M+H]+ 461.0; $^1$H NMR (300 MHz, $CDCl_3$) δ 8.93 (s, 1H), 8.90 (s, 1H), 6.15-6.18 (m, 2H), 4.41-4.45 (m, 1H), 4.28-4.30 (m, 1H), 3.76-4.09 (m, 13H), 3.38 (s, 3H), 3.32 (s, 3H), 3.28 (s, 3H), 3.26 (s, 3H), 1.58 (s, 9H), 1.47 (s, 3H), 1.43 (s, 3H), 1.39 (s, 3H), 1.37 (s, 3H), 1.14-1.21 (m, 6H).

Step 4-5

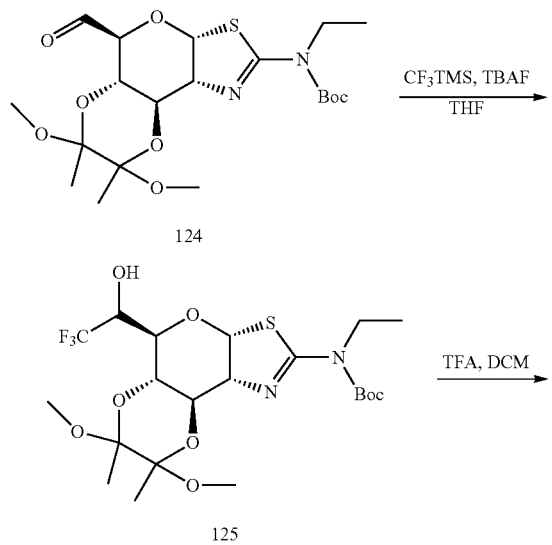

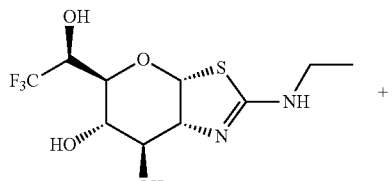

Example 160

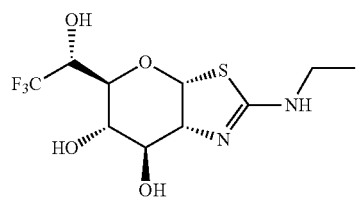

Example 161

(3aR,5S,6S,7R,7aR)-2-(ethylamino)-5-((R)-2,2,2-trifluoro-1-hydroxyethyl)-5,6,7,7a-tetrahydro-3aH-pyrano[3,2-d]thiazole-6,7-diol A solution of 124 (21 g, 45 mmol) and $CF_3TMS$ (41 g, 290 mmol) in THF (100 mL) was added to a mixture of TBAF (6.6 g, 25 mmol) and 4 Å molecular sieves in THF (400 mL) at 0° C. The mixture was stirred at room temperature overnight before addition of additional TBAF (26.4 g, 100 mmol). After an additional 1 hour, a filtration was performed and the filtrates were concentrated to give a residue, which was dissolved into dichloromethane (500 mL), washed with brine (3×100 mL), dried over anhydrous $Na_2SO_4$ and concentrated to give crude 125 as a brown syrup (four isomers based on TLC and LCMS), which was treated with TFA (100 ml, 90% in dichloromethane, v/v) overnight at room temperature. Removal of volatiles gave a residue, which was dissolved into methanol (50 mL) and neutralized with concentrated $NH_4OH$ (10 mL). After concentration under reduced pressure, the crude product was purified by a silica gel column, eluted with 1%-10% methanol in dichloromethane to give Example 160 (3aR,5S,6S,7R,7aR)-2-(ethylamino)-5-((S)-2,2,2-trifluoro-1-hydroxyethyl)-5,6,7,7a-tetrahydro-3aH-pyrano[3,2-d]thiazole-6,7-diol as a white solid (2.41 g, 16%, faster eluting isomer by HPLC). (ES, m/z): [M+H]+ 317.0; $^1$H NMR (300 MHz, $D_2O$) 6.18 (d, J=6.6 Hz, 1H), 4.21-4.30 (m, 2H), 4.08 (t, J=3.6 Hz, 1H), 3.88-3.93 (m, 1H), 3.69-3.74 (m, 1H), 3.13-3.21 (m, 2H), 1.07 (d, J=7.2 Hz, 3H); and Example 161 (3aR,5S,6S,7R,7aR)-2-(ethylamino)-5-((R)-2,2,2-trifluoro-1-hydroxyethyl)-5,6,7,7a-tetrahydro-3aH-pyrano[3,2-d]thiazole-6,7-diol (2.48 g, 17%, slower eluting isomer by HPLC). (ES, m/z) [M+H]+ 317.0; $^1$H NMR (300 MHz, $D_2O$) 6.21 (d, J=6.3 Hz, 1H), 4.23-4.31 (m, 1H), 4.09 (t, 3.0 Hz, 1H), 3.97-4.00 (m, 1H), 3.72-3.77 (m, 2H), 3.16 (q, J=7.2 Hz, 2H), 1.05 (d, J=7.2 Hz, 3H).

Examples 162 and 163
(3aR,5R,6S,7R,7aR)-5-((R)-1-hydroxyethyl)-2-(2-hydroxyethylamino)-5,6,7,7a-tetrahydro-3aH-pyrano[3,2-d]thiazole-6,7-diol & (3aR,5R,6S,7R,7aR)-5-((S)-1-hydroxyethyl)-2-(2-hydroxyethylamino)-5,6,7,7a-tetrahydro-3aH-pyrano[3,2-d]thiazole-6,7-diol
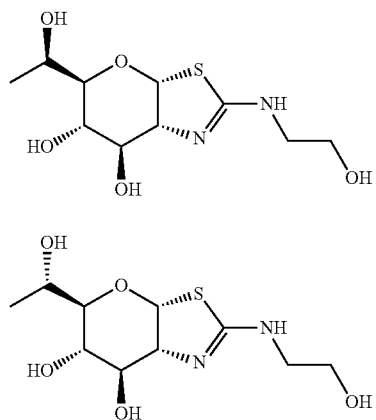
Example 162
Example 163
Scheme XXVII
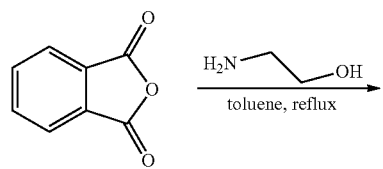
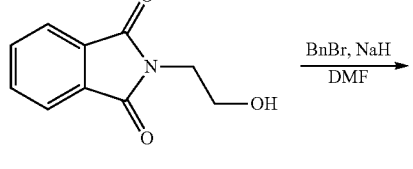
126
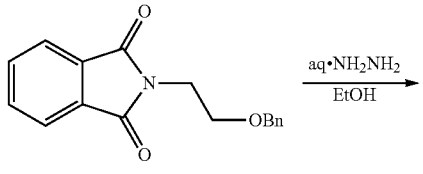
127
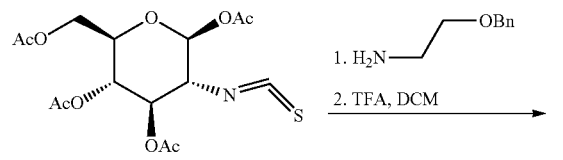
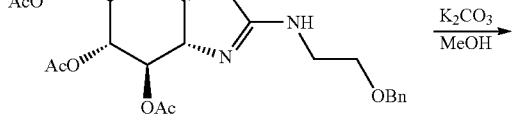
129
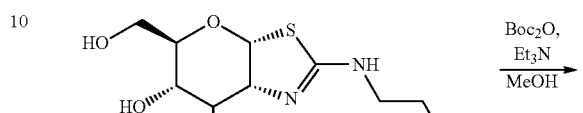
130
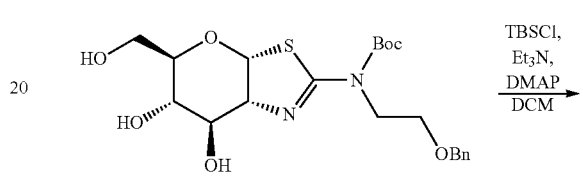
131
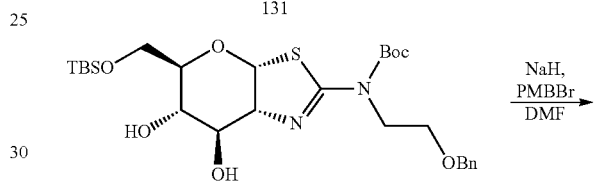
132
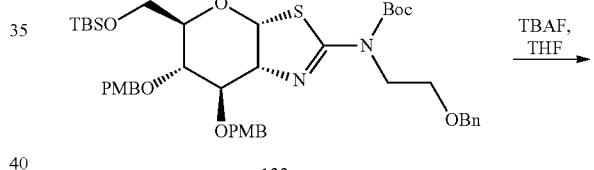
133
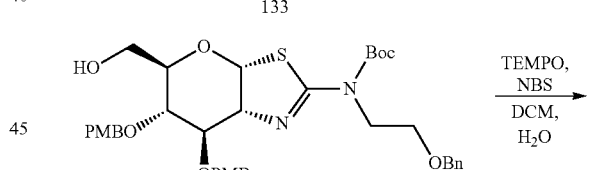
134
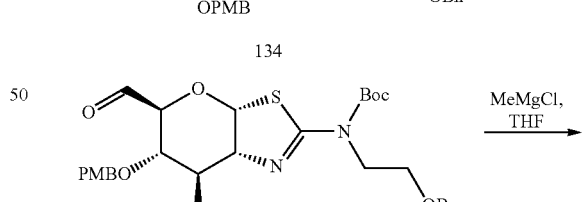
135
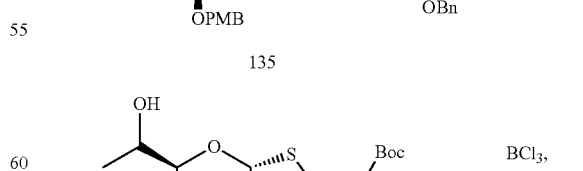
136
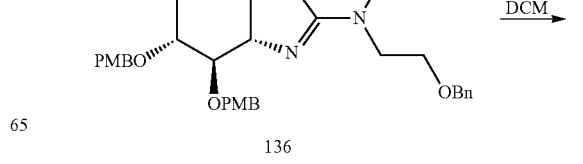

-continued

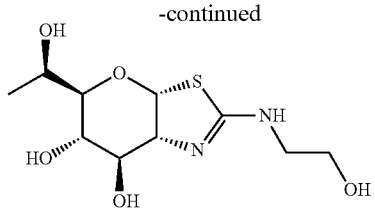

Example 162

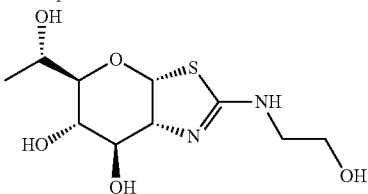

Example 163

Step 1

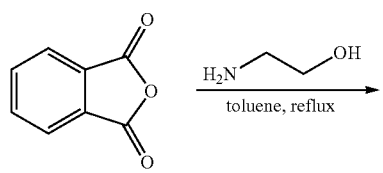

2-(2-hydroxyethyl)isoindoline-1,3-dione (126)

A solution of 2-aminoethanol (41 g, 0.67 mol) and isobenzofuran-1,3-dione (100 g, 0.52 mol) in toluene (300 mL) was refluxed for 12 hours. Volatiles were distilled out to give a residue, which was purified by re-crystallization from chloroform/hexane (v/v, 1:6) to afford 126 as a white solid (110 g, 85%). (ES, m/z) [M+H]$^+$ 192.0; $^1$H NMR (300 MHz, CDCl$_3$) δ 7.84-7.90 (m, 2H), 7.71-7.77 (m, 2H), 3.87-3.93 (m, 4H), 2.10 (br, 1H).

Step 2

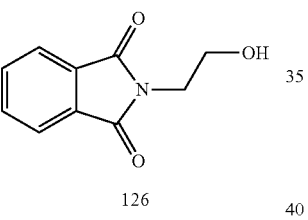

-continued

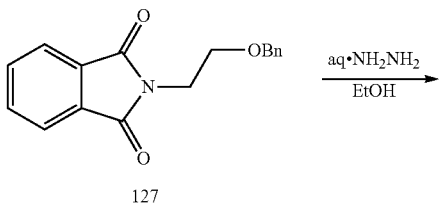

2-(2-(benzyloxy)ethyl)isoindoline-1,3-dione (127)

A solution of 126 (5 g, 26 mmol) in DMF (50 mL) was treated with sodium hydride (1.1 g, 32 mmol, 70% dispersed in mineral oil) for 30 minutes at room temperature, followed by addition of BnBr (6.7 g, 39 mmol). After additional 1 hour, the reaction was quenched by water (200 mL) and extracted with ethyl acetate (4×50 mL). The combined organic layer was washed with brine (3×50 mL), dried over anhydrous sodium sulfate and concentrated under vacuum to give a residue, which was purified by a silica gel column, eluted with 10%-20% ethyl acetate in petroleum ether to afford 127 as a white solid (4.8 g, 65%). (ES, m/z) [M+H]$^+$ 282.0; $^1$H NMR (300 MHz, CDCl$_3$) δ 7.85-7.88 (m, 2H), 7.71-7.74 (m, 2H), 7.25-7.31 (m, 5H), 4.55 (s, 2H), 3.95 (t, J=6.0 Hz, 2H), 3.74 (t, J=6.0 Hz, 2H).

Step 3

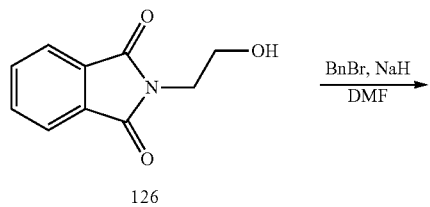

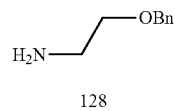

2-(benzyloxy)ethanamine (128)

A solution of 127 (10 g, 35 mmol) in ethanol (200 mL) was treated with hydrazine (84 g, 71 mmol, 80% in water) at reflux for 12 hours. After a filtration, the filtrate was concentrated under vacuum to give a residue, which was purified by a silica gel column, eluted with 5% methanol in dichloromethane to afford 128 as light yellow oil (4 g, 74%). (ES, m/z) [M+H]$^+$ 152.0; $^1$H NMR (300 MHz, CDCl$_3$) δ 7.28-7.40 (m, 5H), 4.56 (s, 2H), 3.54 (t, J=5.4 Hz, 2H), 2.94 (t, J=5.1 Hz, 2H).

Step 4

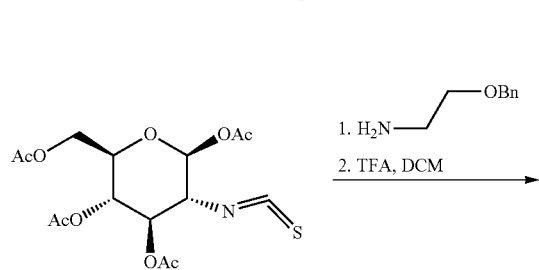

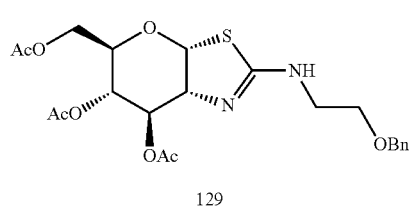

(3aR,5R,6S,7R,7aR)-5-(acetoxymethyl)-2-(2-(benzyloxy)ethylamino)-5,6,7,7a-tetrahydro-3aH-pyrano[3,2-d]thiazole-6,7-diyl diacetate (129)

To a solution of (2S,3R,4R,5S,6R)-6-(acetoxymethyl)-3-isothiocyanato-tetrahydro-2H-pyran-2,4,5-triyl triacetate (9.8 g, 25 mmol) in dichloromethane (100 mL) was added 128 (4 g, 26 mmol) at 0° C. After stirred for 2 hours, trifluoroacetic acid (15.4 g, 159 mmol) was added. The resulting solution was stirred for 12 hours at room temperature, then quenched with ice-water (200 mL) and neutralized by the addition of NaHCO$_3$ (26 g, 318 mmol). The organic layer was separated and the aqueous layer was extracted with dichloromethane (3×100 mL). The combined organic layer was washed with brine (2×100 mL), dried over anhydrous sodium sulfate, and concentrated under vacuum to give a residue, which was purified by silica gel column, eluted with 10%-50% ethyl acetate in petroleum ether to afford 129 as a white syrup (9.8 g, 77%). (ES, m/z) [M+H]$^+$ 481.0; $^1$H NMR (300 MHz, CDCl$_3$) δ 7.31-7.38 (m, 5H), 6.24 (d, J=6.3 Hz, 1H), 5.41-5.43 (m, 1H), 4.94-4.98 (m, 1H), 4.55 (s, 2H), 4.34-4.37 (m, 1H), 4.14-4.16 (m, 3H), 3.83-3.87 (m, 1H), 3.64 (t, J=5.4 Hz, 2H), 3.53 (t, J=5.1 Hz, 2H), 2.12 (s, 3H), 2.10 (s, 3H), 2.09 (s, 3H).

Step 5

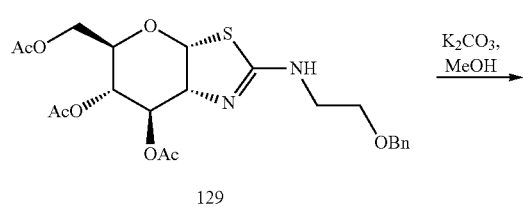

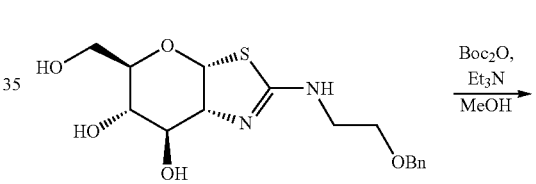

(3aR,5R,6S,7R,7aR)-2-(2-(benzyloxy)ethylamino)-5-(hydroxymethyl)-5,6,7,7a-tetrahydro-3aH-pyrano[3,2-d]thiazole-6,7-diol (130)

A solution of 129 (4.5 g, 9.4 mmol) in methanol (40 mL) was treated with potassium carbonate (260 mg, 2 mmol) for 3 hours at room temperature, then neutralized by the addition of acetic acid (0.5 mL). Volatiles were distilled out to give a residue, which was solidified from ethyl acetate. The solids were washed with ethyl acetate (3×20 mL) to give 130 as a light yellow solid (2.58 g, 80%). (ES, m/z) [M+H]$^+$ 355.0; $^1$H NMR (300 MHz, D$_2$O) δ 7.27-7.37 (m, 5H), 6.17 (d, J=6.3 Hz, 1H), 4.48 (s, 2H), 4.34-4.37 (m, 1H), 4.03-4.07 (m, 1H), 3.88-3.91 (m, 1H), 3.58-3.67 (m, 2H), 3.31-3.55 (m, 5H).

Step 6

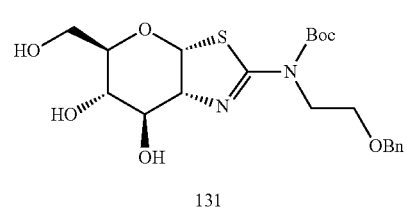

tert-butyl 2-(benzyloxy)ethyl((3aR,5R,6S,7R,7aR)-6,7-dihydroxy-5-(hydroxymethyl)-5,6,7,7a-tetrahydro-3aH-pyrano[3,2-d]thiazol-2-yl)carbamate (131)

To a solution of 130 in methanol (30 mL) was added Boc$_2$O (3.1 g, 14 mmol) and triethylamine (1.9 g, 19 mmol). After stirred for 5 hours at room temperature, the resulting mixture was concentrated under vacuum to give a residue, which was purified by a silica gel column, eluted with 1%-5% methanol in dichloromethane to afford 131 as a white solid (3.1 g, 73%). (ES, m/z) [M+H]$^{30}$ 455.0; $^1$14 NMR (300 MHz, CDCl$_3$) δ 7.28-7.39 (m, 5H), 6.18 (d, J=6.3 Hz, 1H), 4.49 (s, 2H), 4.34-4.37 (m, 1H), 4.03-4.07 (m, 1H), 3.89-3.93 (m, 1H), 3.59-3.67 (m, 2H), 3.32-3.57 (m, 5H), 1.58 (s, 9H).

Step 7

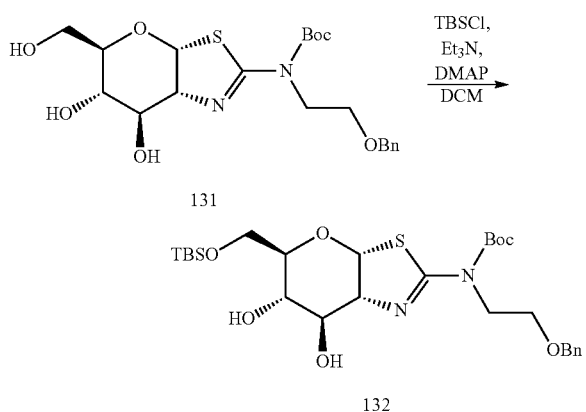

tert-butyl 2-(benzyloxy)ethyl((3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl)carbamate (132)

A mixture of 131 (2.8 g, 6.2 mmol), DMAP (150 mg, 1.2 mmol), triethylamine (930 g, 9.2 mol) and tert-butylchlorodimethylsilane (1.1 g, 7.5 mmol) in dichloromethane (40 mL) was stirred for 12 hours at room temperature, then quenched with saturated aqueous NaHCO₃ solution (30 mL). The aqueous layer was extracted with dichloromethane (2×40 mL), and the combined organic layer was dried over anhydrous sodium sulfate and concentrated under vacuum. The crude product was purified by a silica gel column, eluted with 1%-3% methanol in dichloromethane to afford 132 as a white solid (2.6 g, 75%). (ES, m/z) [M+H]⁺ 569.0; ¹H NMR (300 MHz, CDCl₃) δ 7.28-7.38 (m, 5H), 6.13 (d, J=6.3 Hz, 1H), 4.49 (s, 2H), 4.34-4.36 (m, 1H), 4.06-4.08 (m, 1H), 3.83-390 (m, 1H), 3.59-3.67 (m, 2H), 3.30-3.55 (m, 5H), 1.58 (s, 9H), 0.98 (s, 9H), 0.15 (s, 3H), 0.08 (s, 3H).

Step 8

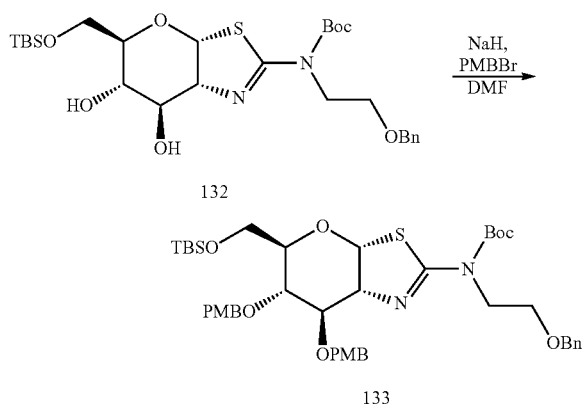

tert-butyl 2-(benzyloxy)ethyl((3aR,5R,6S,7R,7aR)-5-((tert-butyldimethylsilyloxy)methyl)-6,7-bis(4-methoxybenzyloxy)-5,6,7,7a-tetrahydro-3aH-pyrano[3,2-d]thiazol-2-yl)carbamate (133)

A solution of 132 (12 g, 21 mmol) in DMF (60 mL) was treated with sodium hydride (2.9 g, 84 mmol, 70% dispersed by mineral oil) for 30 minutes at 0° C., followed by addition of PMBBr (25 g, 126 mmol). After additional 1.5 hours at 15° C., the reaction was quenched with water (200 mL), and extracted with dichloromethane (3×100 mL). The combined organic layer was washed with brine (3×50 mL), dried over anhydrous sodium sulfate and concentrated under vacuum to give a residue, which was purified by a silica gel column, eluted with 5%-20% ethyl acetate in petroleum ether to afford 133 as light yellow oil (8.5 g, 50%). (ES, m/z) [M+H]⁺ 809.0; ¹H NMR (300 MHz, CDCl₃) δ 7.21-7.34 (m, 9H), 6.82-6.89 (m, 4H), 6.08 (d, J=6.3 Hz, 1H), 4.52-4.57 (m, 4H), 4.50 (s, 2H), 4.33-4.35 (m, 1H), 4.05-4.06 (m, 1H), 3.84-3.91 (m, 1H), 3.81 (s, 3H), 3.80 (s, 3H), 3.58-3.66 (m, 2H), 3.31-3.54 (m, 5H), 1.56 (s, 9H), 0.96 (s, 9H), 0.14 (s, 3H), 0.07 (s, 3H).

Step 9

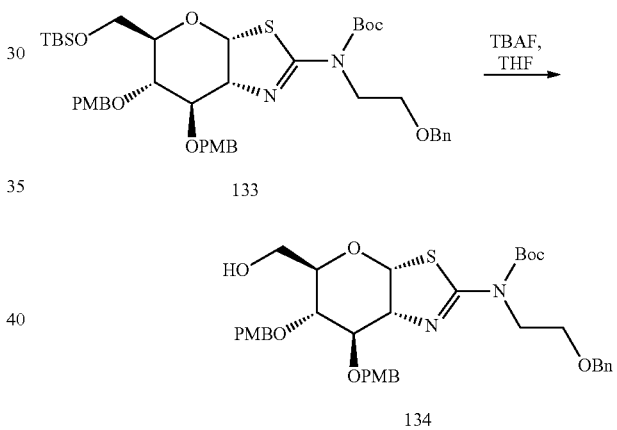

tert-butyl-2-(benzyloxy)ethyl((3aR,5R,6S,7R,7aR)-5-(hydroxymethyl)-6,7-bis(4-methoxybenzyloxy)-5,6,7,7a-tetrahydro-3aH-pyrano[3,2-d]thiazol-2-yl)carbamate (134)

A solution of 133 (7.5 g, 9.3 mmol) in THF (30 mL) was treated with TBAF (4.9 g, 18.6 mmol) for 3 hours at room temperature. The reaction was quenched with water (100 mL) and extracted with ethyl acetate (3×50 mL). The combined organic layer was washed with brine (2×30 mL), dried over anhydrous sodium sulfate and concentrated under vacuum to give a residue, which was purified by a silica gel column, eluted with 3%-10% ethyl acetate in petroleum ether to afford 134 as a light yellow syrup (5.8 g, 90%). (ES, m/z) [M+H]⁺ 695.0; ¹H NMR (300 MHz, CDCl₃) δ 7.21-7.36 (m, 9H), 6.80-6.85 (m, 4H), 6.09 (d, J=6.3 Hz, 1H), 4.50-4.55 (m, 4H), 4.49 (s, 2H), 4.31-4.33 (m, 1H), 4.05-4.06 (m, 1H), 3.84-3.91 (m, 1H), 3.82 (s, 3H), 3.83 (s, 3H), 3.56-3.67 (m, 2H), 3.30-3.53 (m, 5H), 1.56 (s, 9H).

Step 10

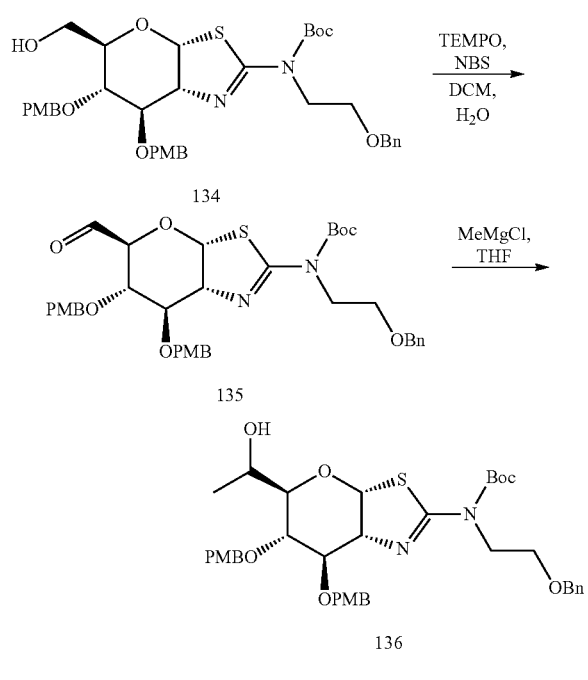

tert-butyl 2-(benzyloxy)ethyl((3aR,5R,6S,7R,7aR)-
5-((S)-1-hydroxyethyl)-6,7-bis(4-methoxybenzy-
loxy)-5,6,7,7a-tetrahydro-3aH-pyrano[3,2-d]thiazol-
2-yl)carbamate (136)

To a solution of 134 (1.5 g, 2.2 mmol), KHCO₃ (970 mg, 9.7 mmol), TBAB (70 mg, 0.2 mmol), TEMPO (31 mg, 0.2 mmol) in dichloromethane (50 mL) and H₂O (10 mL) was added NBS (423 mg, 2.4 mmol) at 0° C. After stirred for 30 minutes at room temperature, the reaction was diluted with water (50 mL) and the aqueous layer was extracted with dichloromethane (2×30 mL). The combined organic layers was dried over anhydrous sodium sulfate, and concentrated under vacuum to give crude 135, which was dissolved into THF (20 mL). To the solution of 135 in THF was added MeMgBr (3 mL, 6 mmol, 2M in THF) at room temperature. After 1 hr, the reaction mixture was quenched with saturated aqueous NH₄Cl solution (10 mL) and extracted with ethyl acetate (4×20 mL). The combined organic layer was washed with brine (2×20 mL), dried over anhydrous sodium sulfate and concentrated under vacuum. The crude residue was purified by a silica gel column, eluted with 10%-20% ethyl acetate in petroleum ether to afford 136 (0.95 g, 63%, two epimers, the ratio was 1:4 determined by ¹H NMR) as a light yellow syrup. (ES, m/z) [M+H]⁺ 709.0; ¹H NMR (300 MHz, CDCl₃) δ 7.15-7.38 (m, 9H), 6.79-6.92 (m, 4H), 6.11 (m, 1H), 4.50-4.55 (m, 4H), 4.49 (s, 2H), 4.31-4.33 (m, 1H), 4.05-4.06 (m, 1H), 3.83-3.90 (m, 1H), 3.82 (s, 3H), 3.81 (s, 3H), 3.54-3.66 (m, 2H), 3.31-3.52 (m, 3H), 3.11-3.15 (m, 1H) 1.54 (s, 9H), 1.12 (d, J=1.8 Hz, 3H).

Step 11

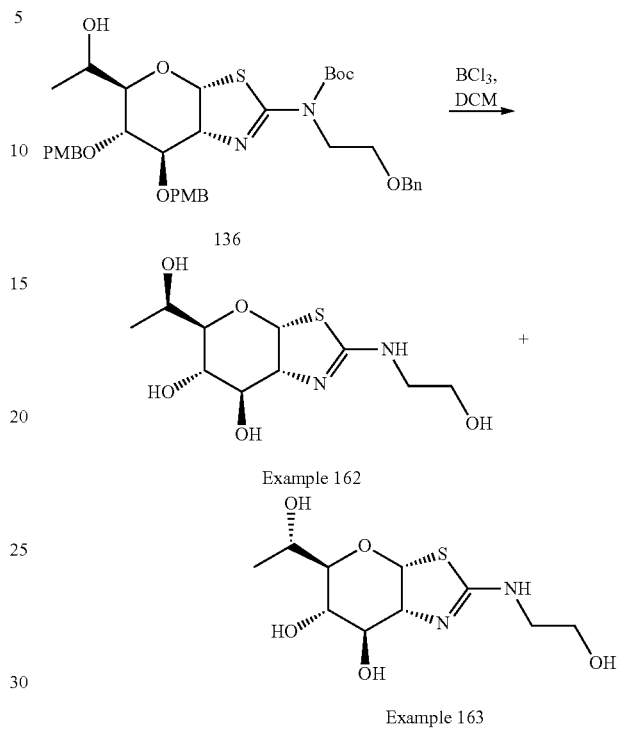

Example 162

Example 163

(3aR,5R,6S,7R,7aR)-5-((R)-1-hydroxyethyl)-2-(2-
hydroxyethylamino)-5,6,7,7a-tetrahydro-3aH-pyrano
[3,2-d]thiazole-6,7-diol and (3aR,5R,6S,7R,7aR)-5-
((S)-1-hydroxyethyl)-2-(2-hydroxyethylamino)-5,6,
7,7a-tetrahydro-3aH-pyrano[3,2-d]thiazole-6,7-diol A solution of 136 (1 g, 1.5 mmol) in dichloromethane (15 mL) was treated with BCl₃ (15 mL, 15 mmol, 1M in dichloromethane) at −78° C. for 3 hours, and then quenched by addition of methanol (10 mL). Volatiles were distilled out to give a residue, which was dissolved into methanol (5 mL) and neutralized with concentrated NH₄OH (2 mL). After concentrated under reduced pressure, the crude product was purified by a silica gel column, eluted with 5%-20% methanol in dichloromethane to give a mixture of the above two compounds. Separation by Prep-HPLC with the following conditions (Column, Sun fire prep. C18; mobile phase, water with 0.03% NH₄OH and CH₃CN (10% up to 45% in time 10); Detector, UV 220 nm) gave Example 162 as a white solid (35 mg, 8.3%, faster eluting isomer). (ES, m/z): [M+H]⁺ 279.0; ¹H NMR (300 MHz, D₂O) δ 6.25 (d, J=7.2 Hz, 1H), 4.16-4.17 (m, 1H), 3.97-3.99 (m, 2H), 3.55-3.59 (m, 3H), 3.51-3.52 (m, 1H), 3.28-3.29 (m, 2H), 1.08 (d, J=6.6 Hz, 1H); and Example 163 (200 mg, 47.7%, slower eluting isomer). (ES, m/z): [M+H]⁺ 279.0; ¹H NMR (300 MHz, D₂O) δ 6.24 (d, J=6.3 Hz, 1H), 4.15 (t, J=5.7 Hz, 1H), 3.97 (t, J=5.7 Hz, 1H), 3.84-3.87 (m, 1H), 3.57-3.63 (m, 3H), 3.21-3.30 (m, 3H), 1.11 (d, J=6.6 Hz, 1H).

Examples 164 and 165
(3aR,5S,6S,7R,7aR)-2-amino-5-[(1S)-2,2,2-trifluoro-1-hydroxyethyl]-3aH,5H,6H,7H,7aH-pyrano[3,2-d][1,3]thiazole-6,7-diol and (3aR,5S,6S,7R,7aR)-2-amino-5-[(1R)-2,2,2-trifluoro-1-hydroxyethyl]-3aH,5H,6H,7H,7aH-pyrano[3,2-d][1,3]thiazole-6,7-diol
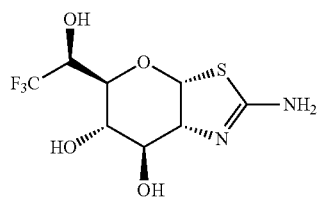
Example 164
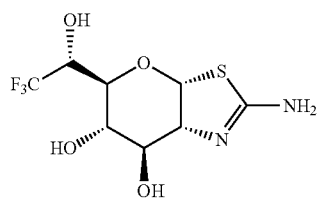
Example 165
Scheme XXVIII
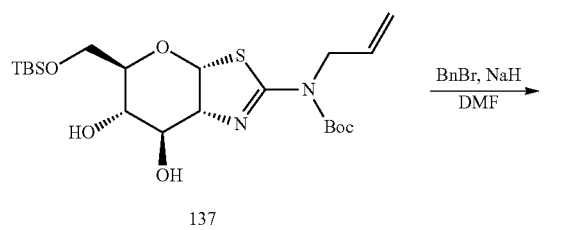
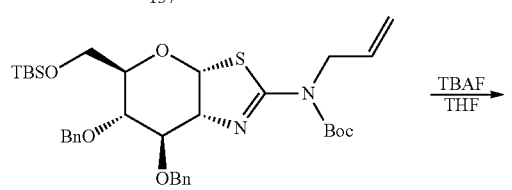
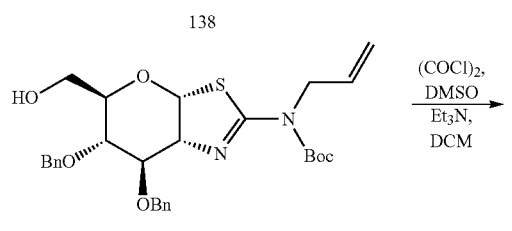
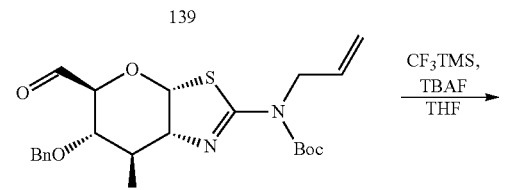
-continued
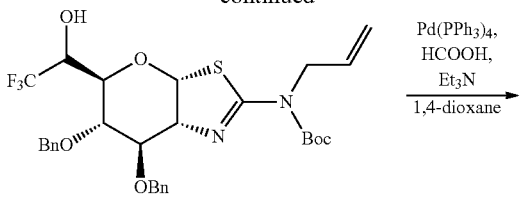
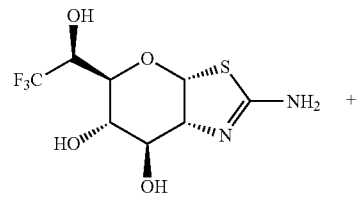
Example 164
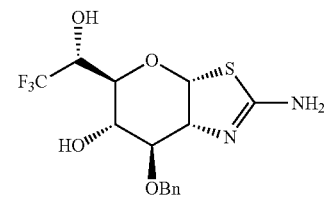
Example 165
Step 1
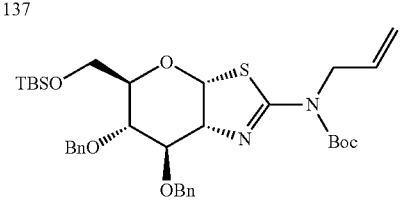

tert-butyl N-[(3aR,5R,6S,7R,7aR)-6,7-bis(benzyloxy)-5-[[(tert-butyldimethylsilyl)oxy]methyl]-3aH,5H,6H,7H,7aH-pyrano[3,2-d][1,3]thiazol-2-yl]-N-(prop-2-en-1-yl)carbamate (138)

To a solution of tert-butyl N-[(3aR,5R,6S,7R,7aR)-5-[[(tert-butyldimethylsilyl)oxy]methyl]-6,7-dihydroxy-3aH,5H,6H,7H,7aH-pyrano[3,2-d][1,3]thiazol-2-yl]-N-(prop-2-en-1-yl)carbamate 137 (prepared in a manner analogous to compound 17, Example 2 Steps 1-4, except substituting allyl amine for propyl ylamine in step 1) (9 g, 19 mmol)) in DMF (80 mL) was added sodium hydride (3.1 g, 92 mmol, 70% dispersed by mineral oil) at 0° C. After additional 30 min, benzyl bromide (5.2 mL, 48 mmol) was added. The resulting solution was stirred for 1 hour at 15° C., then quenched by addition of saturated aqueous NH₄Cl solution (200 mL) and extracted with dichloromethane (3×50 mL). The combined organic layer was washed with brine (3×50 mL), dried over anhydrous magnesium sulfate, and concentrated under vacuum. The residue was purified by flash column chromatography with 1%-5% ethyl acetate in petroleum ether to afford 138 as a light yellow oil (9.5 g, 77%). (ES, m/z): [M+H]⁺ 655.0; ¹H NMR (300 MHz, CDCl₃) δ 7.38-7.26 (m, 10H), 6.09 (d, J=6.6 Hz, 1H), 5.89-5.75 (m, 1H), 5.14-5.00 (m, 2H), 4.80-4.56 (m, 3H), 4.45-4.32 (m, 3H), 4.16 (t, J=4.1 Hz, 1H), 4.05-3.45 (m, 5H), 1.50 (s, 9H), 0.88 (s, 9H), 0.04 (s, 6H).

Step 2

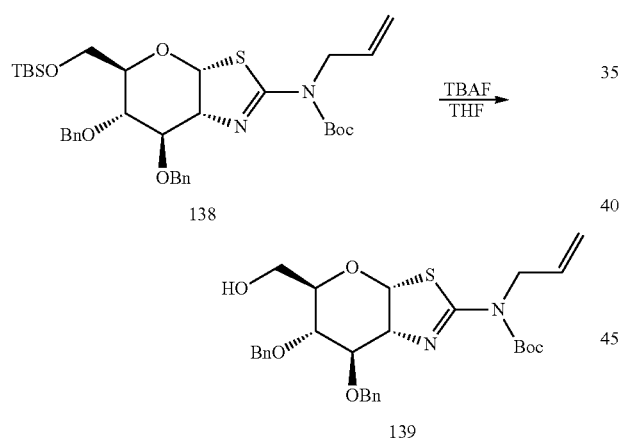

tert-butyl N-[(3aR,5R,6S,7R,7aR)-6,7-bis(benzyloxy)-5-(hydroxymethyl)-3aH-5H,6H,7H,7aH-pyrano[3,2-d][1,3]thiazol-2-yl]-N-(prop-2-en-1-yl)carbamate (139)

A solution of 138 (10 g, 15 mmol) in THF (50 mL) was treated with TBAF (8.5 g, 32 mmol) for 1.5 hours at room temperature. The reaction was then quenched by addition of water (100 mL) and extracted with ethyl acetate (3×50 mL). The combined organic layer was washed with brine (2×30 mL), dried over sodium sulfate, and concentrated under vacuum. The residue was purified by flash column chromatography with 5%-10% ethyl acetate in petroleum ether to afford 139 as a light yellow syrup (6 g, 73%). (ES, m/z): [M+H]⁺ 541.0; ¹H NMR (300 MHz, CDCl₃) δ 7.39-7.24 (m, 10H), 6.08 (d, J=6.9 Hz, 1H), 5.92-5.75 (m, 1H), 5.13-4.99 (m, 2H), 4.76-4.64 (m, 2H), 4.55 (d, J=11.4 Hz, 1H), 4.43-4.34 (m, 3H), 4.28-4.26 (m, 1H), 3.71-3.46 (m, 5H), 1.82 (t, J=6.5 Hz, 1H), 1.51 (s, 9H).

Step 3

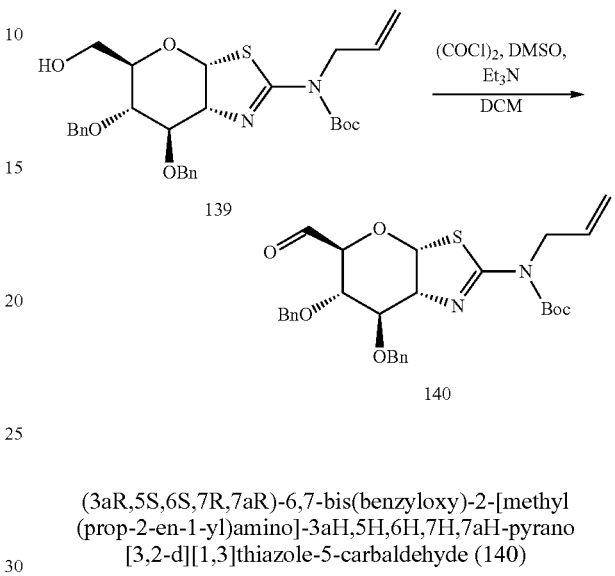

(3aR,5S,6S,7R,7aR)-6,7-bis(benzyloxy)-2-[methyl(prop-2-en-1-yl)amino]-3aH,5H,6H,7H,7aH-pyrano[3,2-d][1,3]thiazole-5-carbaldehyde (140)

A solution of DMSO (4.1 g, 52 mmol) in dry dichloromethane (70 mL) was treated with (COCl)₂ (4.9 g, 40 mmol) at −78° C. for 30 minutes, followed by addition of 139 (3 g, 6.6 mmol) in dichloromethane (10 mL) slowly. The resulting solution was stirred for 3 hours at −30° C., then cooled down to −78° C. again and triethylamine (10 g, 90 mmol) was added. After additional 30 minutes at −50° C., the resulting mixture was quenched by water (50 mL), and the aqueous layer was extracted with dichloromethane (3×30 mL). The combined organic layer was dried over sodium sulfate, and concentrated to afford crude the title compound as light yellow syrup, which was used in the next step without further purification.

Step 4

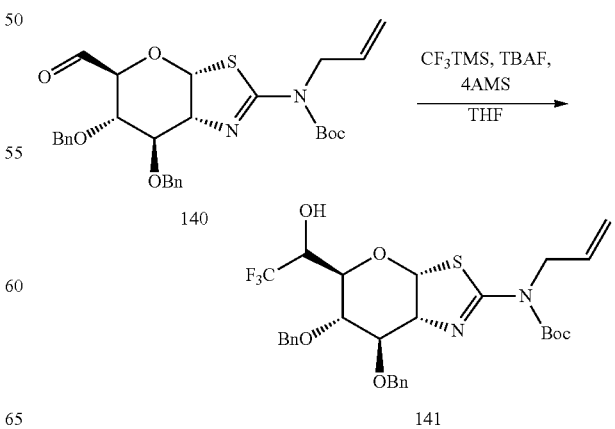

tert-butyl N-[(3aR,5R,6S,7R,7aR)-6,7-bis(benzyloxy)-5-(2,2,2-trifluoro-1-hydroxyethyl)-3aH,5H,6H,7H,7aH-pyrano[3,2-d][1,3]thiazol-2-yl]-N-(prop-2-en-1-yl)carbamate (141)

A mixture of TBAF (500 mg, 2 mmol) and 4 Å molecular sieves (3 g) in THF (30 mL) was stirred for 30 minutes at 0° C., followed by addition of a mixture of crude 140 and CF$_3$TMS (3.7 g, 26 mmol) in THF (30 mL). The mixture was stirred for 2.5 hours at room temperature, followed by addition of additional TBAF (3 g, 11 mmol). After 1 hour, the reaction was then quenched by addition of water (20 mL). A filtration was performed and the filtrate was extracted with ethyl acetate (3×20 mL). The combined organic layer was washed with brine (2×20 mL), dried over magnesium sulfate, and concentrated. The residue was purified by flash column chromatography with 10%-20% ethyl acetate in petroleum ether to afford the title compound as a light yellow oil (1.8 g, 53%, two isomers, ratio is 1:1 determined by $^1$H NMR). (ES, m/z): [M+H]$^+$ 609.0; $^1$H NMR (300 MHz, CDCl$_3$) δ 7.38-7.22 (m, 10H), 6.11-6.08 (m, 1H), 5.80-5.75 (m, 1H), 5.13-5.00 (m, 2H), 4.76-4.56 (m, 4H), 4.56-4.28 (m, 5H), 3.82-3.64 (m, 2H), 1.51 (s, 9H).

Step 5

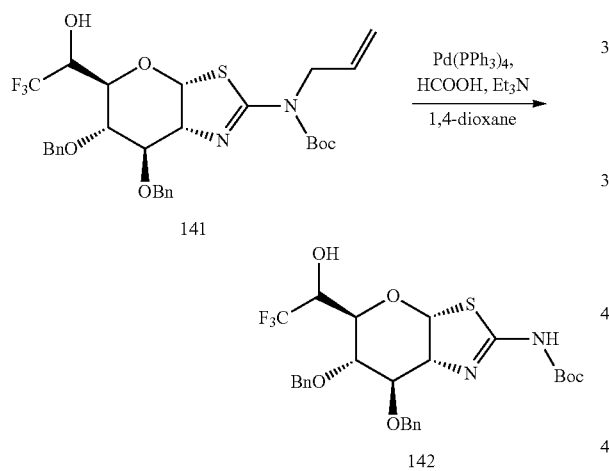

tert-butyl N-[(3aR,5R,6S,7R,7aR)-6,7-bis(benzyloxy)-5-(2,2,2-trifluoro-1-hydroxyethyl)-3aH,5H,6H,7H,7aH-pyrano[3,2-d][1,3]thiazol-2-yl]carbamate (142)

To a solution of 141 (1.6 g, 2.6 mmol) in 1,4-dioxane (20 mL) was added Pd(PPh$_3$)$_4$ (760 mg, 0.6 mmol), triethylamine (664 mg, 6.5 mmol) and formic acid (242 mg, 5.2 mmol) at room temperature under nitrogen atmosphere. The resulting mixture was heated to 60° C. for 20 minutes, and followed by addition of additional formic acid (605 mg, 26 mmol). After stirred overnight at 60° C., removal of volatiles gave a residue, which was dissolved into dichloromethane (50 mL) and neutralized with saturated aqueous NaHCO$_3$ solution (30 mL). The aqueous layer was extracted with dichloromethane (3×30 mL). The combined organic layer was dried over anhydrous sodium sulfate, and concentrated. The residue was purified by flash column chromatography with 20%-30% ethyl acetate in petroleum ether to afford 142 as colorless oil (1.1 g, 77%). (ES, m/z): [M+H]$^+$ 569.0; $^1$H NMR (300 MHz, CDCl$_3$) δ 7.34-7.23 (m, 10H), 6.17-6.13 (m, 1H), 4.62-4.46 (m, 2H), 4.43-4.00 (m, 4H), 3.91-3.73 (m, 3H), 1.52 (s, 9H).

Step 6

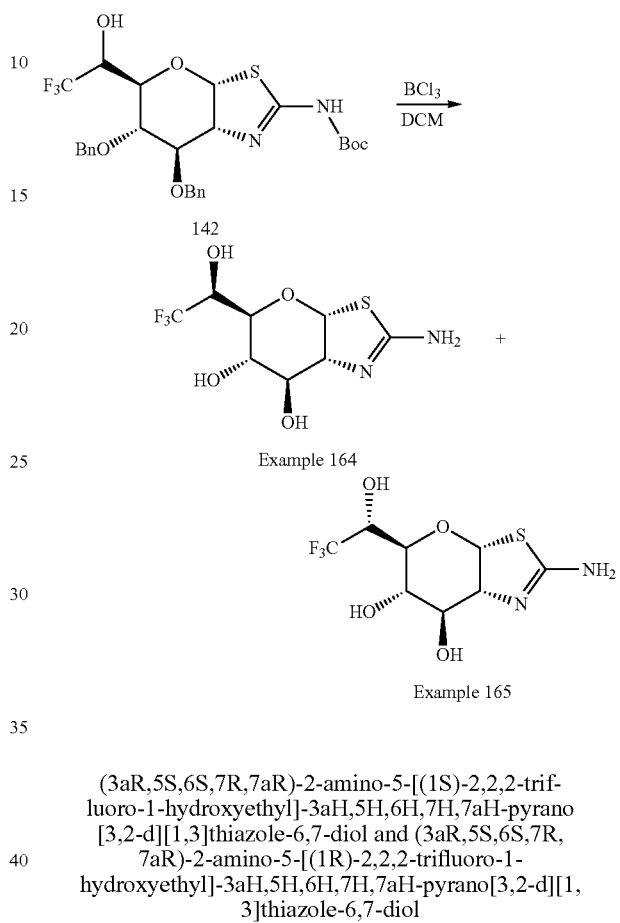

(3aR,5S,6S,7R,7aR)-2-amino-5-[(1S)-2,2,2-trifluoro-1-hydroxyethyl]-3aH,5H,6H,7H,7aH-pyrano[3,2-d][1,3]thiazole-6,7-diol and (3aR,5S,6S,7R,7aR)-2-amino-5-[(1R)-2,2,2-trifluoro-1-hydroxyethyl]-3aH,5H,6H,7H,7aH-pyrano[3,2-d][1,3]thiazole-6,7-diol A solution of 142 (1 g, 1.7 mmol) in dichloromethane (30 mL) was treated with BCl$_3$ (17 mL, 17 mmol, 1M dichloromethane) at −78° C. for 4 hours. The reaction was quenched by addition of methanol (10 mL). Removal of volatiles gave a residue, which was dissolved into methanol (5 mL) and neutralized with concentrated NH$_4$OH (2 mL). After concentrated under reduced pressure, the crude product was purified by a silica gel column, eluted with 5%-20% methanol in dichloromethane to give a mixture of the above two compounds. Separation by Prep-HPLC with the following conditions (Column, Sun fire prep. C18; mobile phase, water with 0.03% NH$_4$OH and CH$_3$CN (10% up to 45% in 10 min); Detector, UV 220 nm) gave (3aR,5S,6S,7R,7aR)-2-amino-5-[(1S)-2,2,2-trifluoro-1-hydroxyethyl]-3aH,5H,6H,7H,7aH-pyrano[3,2-d][1,3]thiazole-6,7-diol Example 164 as a light yellow solid (49 mg, 20%, faster eluting isomer); (ES, m/z): [M+H]$^+$ 289.0; $^1$H NMR (400 MHz, D$_2$O) δ 6.25 (d, J=6.8 Hz, 1H), 4.29-4.26 (m, 2H), 4.07 (t, J=4.0 Hz, 1H), 3.93 (dd, J=8.4, 3.2 Hz, 1H), 3.73 (dd, J=8.4, 4.8 Hz, 1H); and (3aR,5S,6S,7R,7aR)-2-amino-5-[(1R)-2,2,2-trifluoro-1-hydroxyethyl]-3aH,5H,6H,7H,7aH-pyrano[3,2-d][1,3]thiazole-6,7-diol as a light yellow solid (74 mg, 30%, slower eluting isomer); (ES, m/z): [M+H]$^+$ 289.0; $^1$HNMR (400 MHz, D$_2$O) δ 6.32 (d, J=6.4 Hz, 1H), 4.31 (q, J=7.6 Hz, 1H), 4.15 (t, J=6.0 Hz, 1H), 4.00 (t, J=5.0 Hz, 1H), 3.83-3.76 (m, 2H).

The following compounds listed in Table were prepared by methods substantially as described above for the previous examples.

TABLE

| Example | Structure | Name | MH+ |
|---|---|---|---|
| 166 | 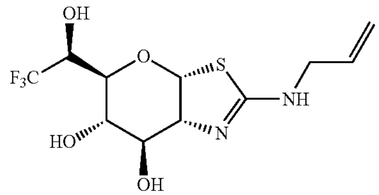 [SMILES: C=CCNC1=N[C@@H]2[C@@H](O)[C@H](O)[C@@H]([C@H](O)C(F)(F)F)O[C@@H]2S1] | (3aR,5S,6S,7R,7aR)-2-(allylamino)-5-((S)-2,2,2-trifluoro-1-hydroxyethyl)-5,6,7,7a-tetrahydro-3aH-pyrano[3,2-d]thiazole-6,7-diol (Faster eluting isomer by HPLC) | 328.9 |
| 167 | 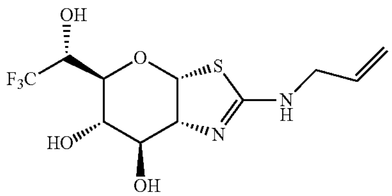 [SMILES: C=CCNC1=N[C@@H]2[C@@H](O)[C@H](O)[C@@H]([C@@H](O)C(F)(F)F)O[C@@H]2S1] | (3aR,5S,6S,7R,7aR)-2-(allylamino)-5-((R)-2,2,2-trifluoro-1-hydroxyethyl)-5,6,7,7a-tetrahydro-3aH-pyrano[3,2-d]thiazole-6,7-diol (Slower eluting isomer by HPLC) | 328.9 |
| 168 | 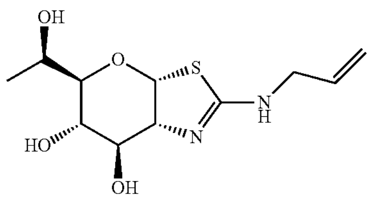 [SMILES: C=CCNC1=N[C@@H]2[C@@H](O)[C@H](O)[C@@H]([C@@H](C)O)O[C@@H]2S1] | (3aR,5R,6S,7R,7aR)-2-(allylamino)-5-((R)-1-hydroxyethyl)-5,6,7,7a-tetrahydro-3aH-pyrano[3,2-d]thiazole-6,7-diol (Faster eluting isomer by HPLC) | 275.0 |
| 169 | 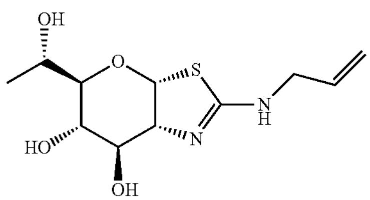 [SMILES: C=CCNC1=N[C@@H]2[C@@H](O)[C@H](O)[C@@H]([C@H](C)O)O[C@@H]2S1] | (3aR,5R,6S,7R,7aR)-2-(allylamino)-5-((S)-1-hydroxyethyl)-5,6,7,7a-tetrahydro-3aH-pyrano[3,2-d]thiazole-6,7-diol (Slower eluting isomer by HPLC) | 275.0 |
| 170 | 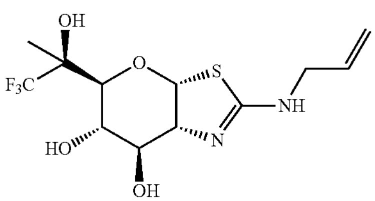 [SMILES: C=CCNC1=N[C@@H]2[C@@H](O)[C@H](O)[C@@H]([C@](C)(O)C(F)(F)F)O[C@@H]2S1] | (3aR,5S,6S,7R,7aR)-2-(allylamino)-5-((S)-1,1,1-trifluoro-2-hydroxypropan-2-yl)-5,6,7,7a-tetrahydro-3aH-pyrano[3,2-d]thiazole-6,7-diol (Faster eluting isomer by HPLC) | 343.0 |
| 171 | 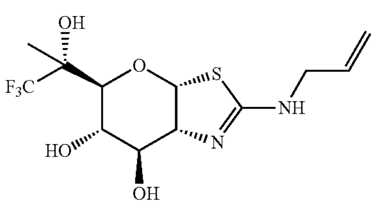 [SMILES: C=CCNC1=N[C@@H]2[C@@H](O)[C@H](O)[C@@H]([C@@](C)(O)C(F)(F)F)O[C@@H]2S1] | (3aR,5S,6S,7R,7aR)-2-(allylamino)-5-(1,1,1-trifluoro-2-hydroxypropan-2-yl)-5,6,7,7a-tetrahydro-3aH-pyrano[3,2-d]thiazole-6,7-diol (Slower eluting isomer by HPLC) | 343.0 |
| 172 | 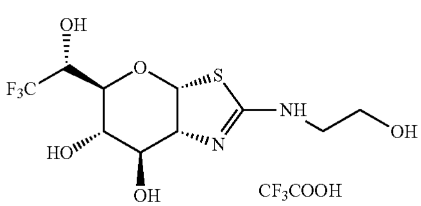 | (3aR,5S,6S,7R,7aR)-2-(2-hydroxyethylamino)-5-((R)-2,2,2-trifluoro-1-hydroxyethyl)-5,6,7,7a-tetrahydro-3aH-pyrano[3,2-d]thiazole-6,7-diol (Slower eluting isomer by HPLC)2,2,2-trifluoroacetate (Slower eluting isomer by HPLC) | 333.0 |

TABLE-continued

| Example | Structure | Name | MH+ |
|---|---|---|---|
| 173 | 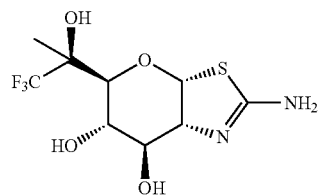 | (3aR,5R,6S,7R,7aR)-2-(allylamino)-5-(2-hydroxyethyl)-5,6,7,7a-tetrahydro-3aH-pyrano[3,2-d]thiazole-6,7-diol | 275.0 |
| 174 | 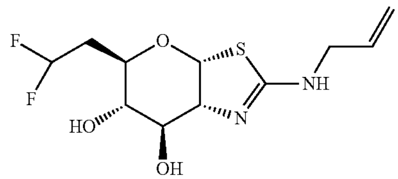 [SMILES: C=CCNC1=N[C@@H]2[C@@H](O)[C@H](O)[C@@H](CC(F)F)O[C@@H]2S1] | (3aR,5R,6S,7R,7aR)-2-(allylamino)-5-(2,2-difluoroethyl)-5,6,7,7a-tetrahydro-3aH-pyrano[3,2-d]thiazole-6,7-diol | 295.0 |

Example 175 and 176

(3aR,5S,6S,7R,7aR)-2-amino-5-[(2S)-1,1,1-trifluoro-2-hydroxypropan-2-yl]-3aH,5H,6H,7H,7aH-pyrano[3,2-d][1,3]thiazole-6,7-diol and (3aR,5S,6S,7R,7aR)-2-amino-5-[(2R)-1,1,1-trifluoro-2-hydroxypropan-2-yl]-3aH,5H,6H,7H,7aH-pyrano[3,2-d][1,3]thiazole-6,7-diol Example 175

Example 176

Scheme XXIV

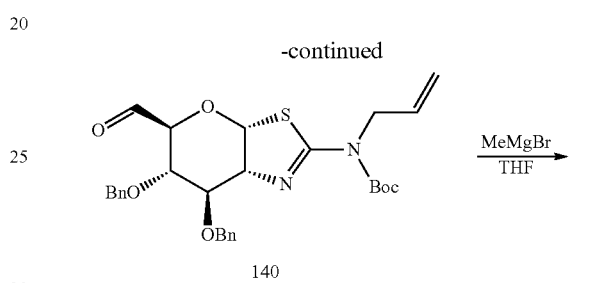

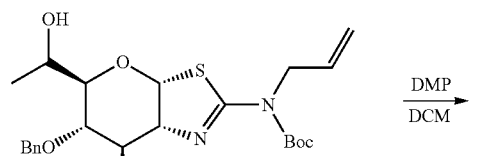

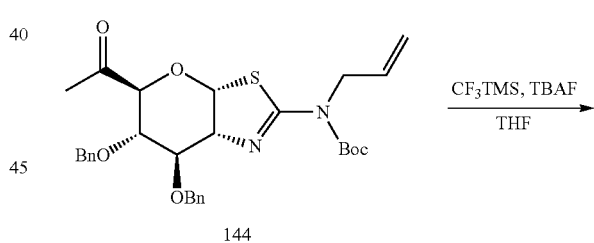

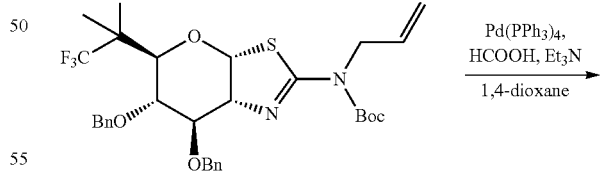

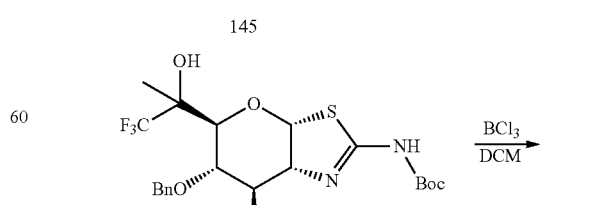

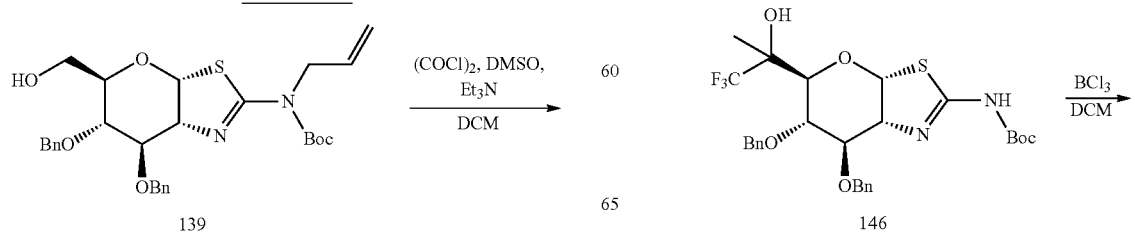

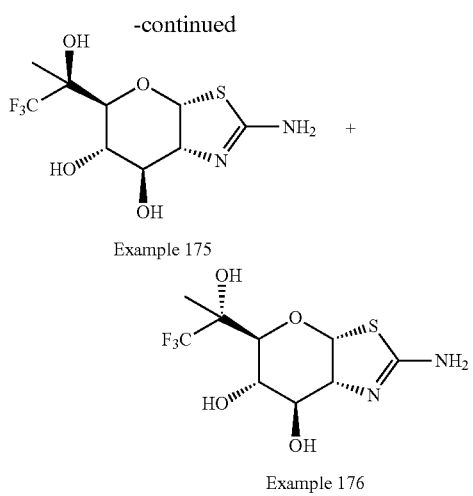

Example 175

Example 176

Step 1

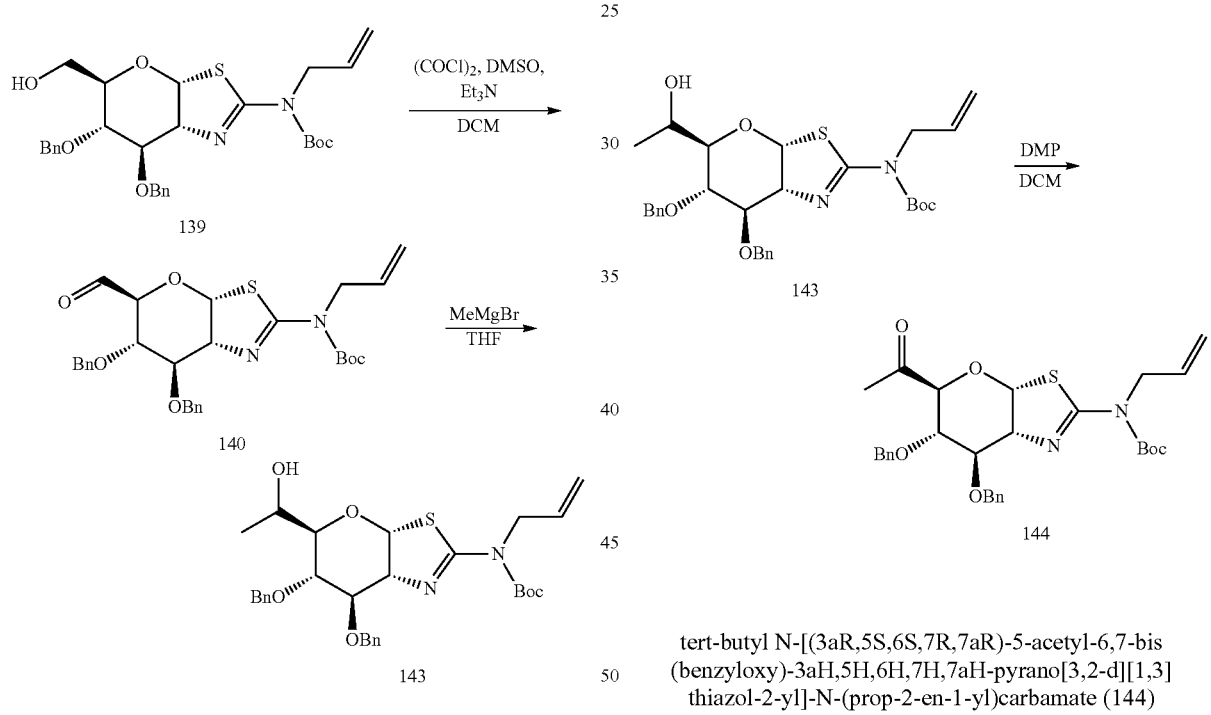

tert-butyl N-[(3aR,5R,6S,7R,7aR)-6,7-bis(benzyloxy)-5-(1-hydroxyethyl)-3aH,5H,6H,7H,7aH-pyrano[3,2-d][1,3]thiazol-2-yl]-N-(prop-2-en-1-yl)carbamate (143)

A solution of DMSO (9.2 g, 118 mmol) in dry dichloromethane (70 mL) was treated with (COCl)₂ (11.6 g, 92 mmol) at −78° C. for 30 minutes, followed by addition of tert-butyl N-[(3aR,5R,6S,7R,7aR)-6,7-bis(benzyloxy)-5-(hydroxymethyl)-3aH,5H,6H,7H,7aH-pyrano[3,2-d][1,3]thiazol-2-yl]-N-(prop-2-en-1-yl)carbamate (8 g, 15 mmol) in dichloromethane (15 mL) slowly. The resulting solution was stirred for 3 hours at −30° C., then cooled down to −78° C. again before addition of triethylamine (20 g, 180 mmol).

After additional 30 minutes at −50° C., the resulting mixture was quenched by water (50 mL), and the aqueous layer was extracted with dichloromethane (3×50 mL). The combined organic layer was dried over sodium sulfate, and concentrated to afford crude 140 as a light yellow syrup, which was dissolved into anhydrous THF (100 mL). The solution was treated with bromo(methyl)magnesium (20 ml, 40 mmol, 2M in THF) at 0° C. overnight. The reaction was then quenched with saturated aqueous NH₄Cl solution (100 mL), and extracted with ethyl acetate (3×100 mL). The combined organic layer was washed with brine (2×50 mL), dried over anhydrous magnesium sulfate and concentrated under vacuum. The residue was purified by flash column chromatography with 10%-20% ethyl acetate in petroleum ether to afford 143 as a yellow syrup (7 g, 87%, two isomers, the ratio is 1:3.8 determined by ¹HNMR). (ES, m/z): [M+H]⁺ 555.0; ¹H NMR (300 MHz, CDCl₃): 7.38-7.25 (m, 10H), 6.13-6.11 (m, 1H), 5.82-5.70 (m, 1H), 5.99-4.96 (m, 2H), 4.76-4.56 (m, 2H), 4.54-4.27 (m, 6H), 4.13-3.73 (m, 3H), 1.50 (s, 9H), 1.28-1.20 (m, 3H).

Step 2

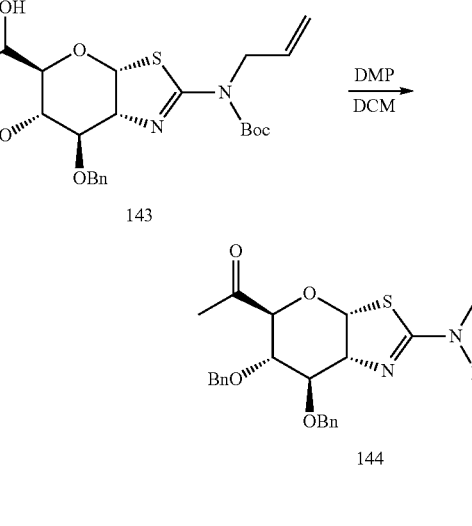

tert-butyl N-[(3aR,5S,6S,7R,7aR)-5-acetyl-6,7-bis(benzyloxy)-3aH,5H,6H,7H,7aH-pyrano[3,2-d][1,3]thiazol-2-yl]-N-(prop-2-en-1-yl)carbamate (144)

To a solution of 143 (6 g, 11 mmol) in dichloromethane (120 mL) was added DMP (6.9 g, 16 mmol). The resulting solution was stirred for 1.5 hours at room temperature, then quenched by saturated aqueous sodium bicarbonate solution (80 mL), and extracted with dichloromethane (3×100 mL). The combined organic layer was washed with brine (2×50 mL), dried over anhydrous magnesium sulfate and concentrated under vacuum. The residue was purified by flash column chromatography with 5%-10% ethyl acetate in petroleum ether to afford 144 as a yellow syrup (4 g, 67%). (ES, m/z): [M+H]⁺ 553.0; ¹H NMR (300 MHz, CDCl₃): 7.34-7.19 (m, 10H), 6.10 (d, J=6.9 Hz, 1H), 5.85-5.76 (m, 1H), 5.10-4.94 (m, 2H), 4.69-4.25 (m, 7H), 4.15-4.10 (m, 1H), 3.97-3.83 (m, 2H), 2.19 (s, 3H), 1.50 (s, 9H).

Step 3

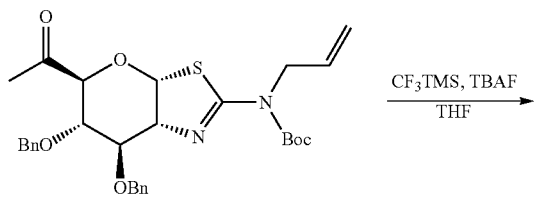

144

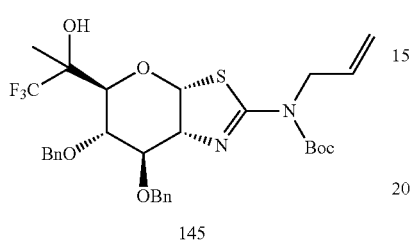

145 tert-butyl N-[(3aR,5S,6S,7R,7aR)-6,7-bis(benzyloxy)-5-(1,1,1-trifluoro-2-hydroxypropan-2-yl)-3aH,5H,6H,7H,7aH-pyrano[3,2-d][1,3]thiazol-2-yl]-N-(prop-2-en-1-yl)carbamate (145)

A mixture of TBAF (1.1, 4.2 mmol) and 4 Å molecular sieves (4 g) in THF (40 mL) was stirred for 30 minutes at 0° C., followed by addition of a mixture of 144 (4.6 g, 8.3 mmol) and CF₃TMS (5.9 g, 42 mmol) in THF (40 mL). The mixture was stirred for 3 hours at room temperature, followed by addition of additional TBAF (6 g, 22 mmol). After 1 hour, the reaction was then quenched by addition of water (80 mL). A filtration was performed and the filtrate was extracted with ethyl acetate (3×50 mL). The combined organic layer was washed with brine (2×30 mL), dried over magnesium sulfate, and concentrated. The residue was purified by flash column chromatography with 6%-12% ethyl acetate in petroleum ether to afford the title compound as a brown syrup (3.5 g, 68%, two isomers, ratio is 1:1 determined by ¹H NMR). (ES, m/z): [M+H]⁺ 623.0; ¹H NMR (300 MHz, CDCl₃): 7.37-7.23 (m, 10H), 6.13-6.07 (m, 1H), 5.76-5.74 (m, 1H), 5.05-4.92 (m, 2H), 4.74-4.67 (m, 2H), 4.47-4.25 (m, 7H), 3.93-3.88 (m, 1H), 1.50 (s, 9H), 1.28-1.23 (m, 3H).

Step 4

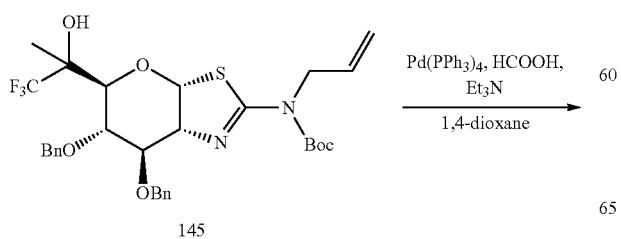

145

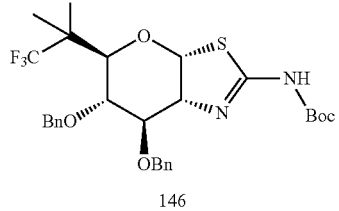

146 tert-butyl (3aR,5S,6S,7R,7aR)-6,7-bis(benzyloxy)-5-((S)-1,1,1-trifluoro-2-hydroxypropan-2-0)-5,6,7,7a-tetrahydro-3aH-pyrano[3,2-d]thiazol-2-ylcarbamate (146)

To a solution of 145 (1.7 g, 2.7 mmol) in 1,4-dioxane (50 mL) was added Pd(PPh₃)₄ (643 mg, 0.5 mmol), formic acid (260 mg, 5.6 mmol) and triethylamine (702 mg, 7.0 mmol) at room temperature under nitrogen atmosphere. The resulting mixture was heated to 60° C. for 20 minutes, and followed by addition of additional formic acid (1.3 g, 28 mmol). After stirred overnight at 60° C., removal of volatiles gave a residue, which was dissolved into dichloromethane (50 mL) and neutralized with saturated aqueous NaHCO₃ solution (30 L). The aqueous layer was extracted with dichloromethane (3×30 mL). The combined organic layer was dried over anhydrous sodium sulfate, and concentrated. The residue was purified by flash column chromatography with 15%-30% ethyl acetate in petroleum ether to afford the title compound as a orange syrup (1.4 g, 86%). (ES, m/z): [M+H]⁺: 583.0; ¹H NMR (300 MHz, CDCl₃): 7.71-7.23 (m, 10H), 6.20-6.14 (m, 1H), 4.71-4.66 (m, 2H), 4.63-4.38 (m, 3H), 4.21-4.10 (m, 1H), 3.93-3.92 (m, 1H), 3.79-3.66 (m, 1H), 1.50 (s, 9H), 1.38-1.08 (m, 3H).

Step 5

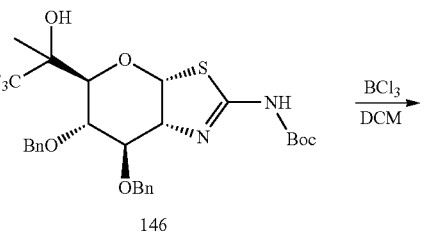

146

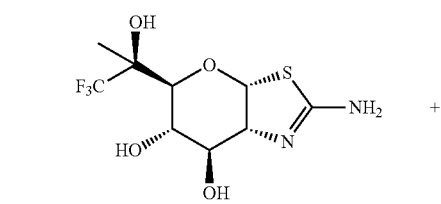

Example 175

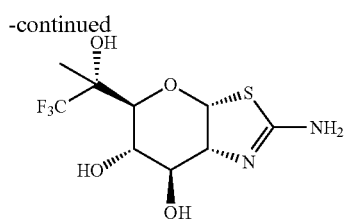

Example 176

(3aR,5S,6S,7R,7aR)-2-amino-5-[(2S)-1,1,1-trifluoro-2-hydroxypropan-2-yl]-3aH,5H,6H,7H,7aH-pyrano[3,2-d][1,3]thiazole-6,7-diol and (3aR,5S,6S,7R,7aR)-2-amino-5-[(2R)-1,1,1-trifluoro-2-hydroxypropan-2-yl]-3aH,5H,6H,7H,7aH-pyrano[3,2-d][1,3]thiazole-6,7-diol A solution of 146 (0.9 g, 1.5 mmol) in dichloromethane (20 mL) was treated with BCl$_3$ (15 mL, 15 mmol, 1M dichloromethane) at −78° C. for 4 hours. The reaction was quenched by addition of methanol (10 mL). Removal of volatiles gave a residue, which was dissolved into methanol (5 mL) and neutralized with concentrated NH$_4$OH (2 mL). After concentrated under reduced pressure, the crude product was purified by a silica gel column, eluted with 5%-20% methanol in dichloromethane to give a mixture of the above two compounds. Separation by Prep-HPLC with the following conditions (Column, Sun fire prep. C18; mobile phase, water with 0.03% NH$_4$OH and CH$_3$CN (15% up to 30% in 20 min); Detector, UV 220 nm) gave (3aR,5S,6S,7R,7aR)-2-amino-5-[(2S)-1,1,1-trifluoro-2-hydroxypropan-2-yl]-3aH,5H,6H,7H,7aH-pyrano[3,2-d][1,3]thiazole-6,7-diol as a white solid (35.2 mg, 8%, faster eluting isomer). (ES, m/z): [M+H]$^+$: 303.0; $^1$H NMR (300 MHz, D$_2$O): 6.27 (d, J=6.9 Hz, 1H), 4.37-4.34 (m, 1H), 4.15-4.13 (m, 1H), 3.92 (d, J=8.4 Hz, 1H), 3.56 (d, J=8.4 Hz, 1H), 1.31 (s, 3H); and (3aR,5S,6S,7R,7aR)-2-amino-5-[(2R)-1,1,1-trifluoro-2-hydroxypropan-2-yl]-3aH,5H,6H,7H,7aH-pyrano[3,2-d][1,3]thiazole-6,7-diol as a white solid (35.1 mg, 8%, slower eluting isomer). (ES, m/z): [M+H]$^+$: 303.0; $^1$H NMR (300 MHz, D$_2$O): 6.27 (d, J=6.9 Hz, 1H), 4.38-4.35 (m, 1H), 4.16-4.14 (m, 1H), 3.96 (d, J=8.1 Hz, 1H), 3.58 (d, J=8.4 Hz, 1H), 1.32 (s, 3H).

Examples 177 and 178

(3aR,5R,6S,7R,7aR)-2-amino-5-vinyl-5,6,7,7a-tetrahydro-3aH-pyrano[3,2-d]thiazole-6,7-diol & (3aR,5R,6S,7R,7aR)-2-amino-5-ethyl-5,6,7,7a-tetrahydro-3aH-pyrano[3,2-d]thiazole-6,7-diol

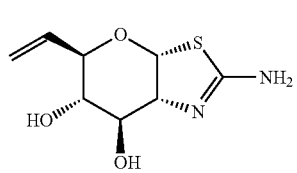

Example 177

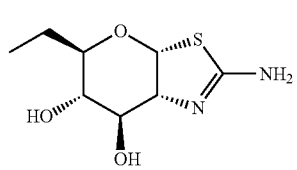

Example 178

Scheme XXX

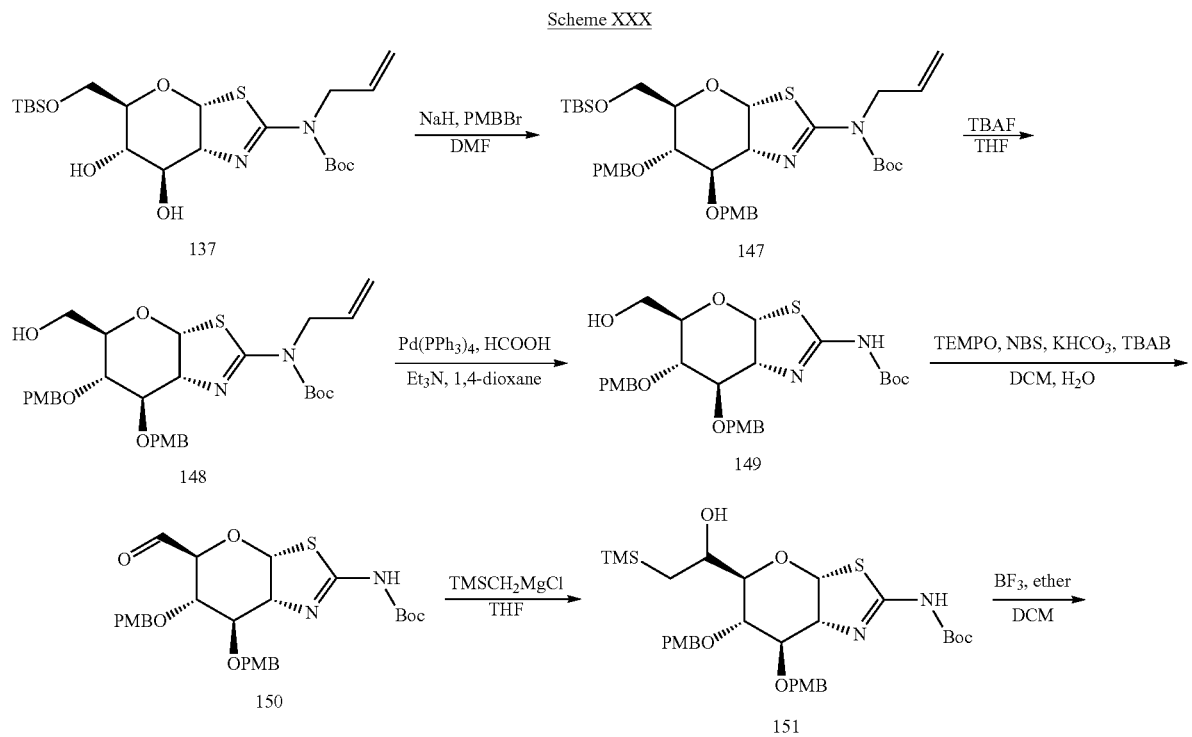

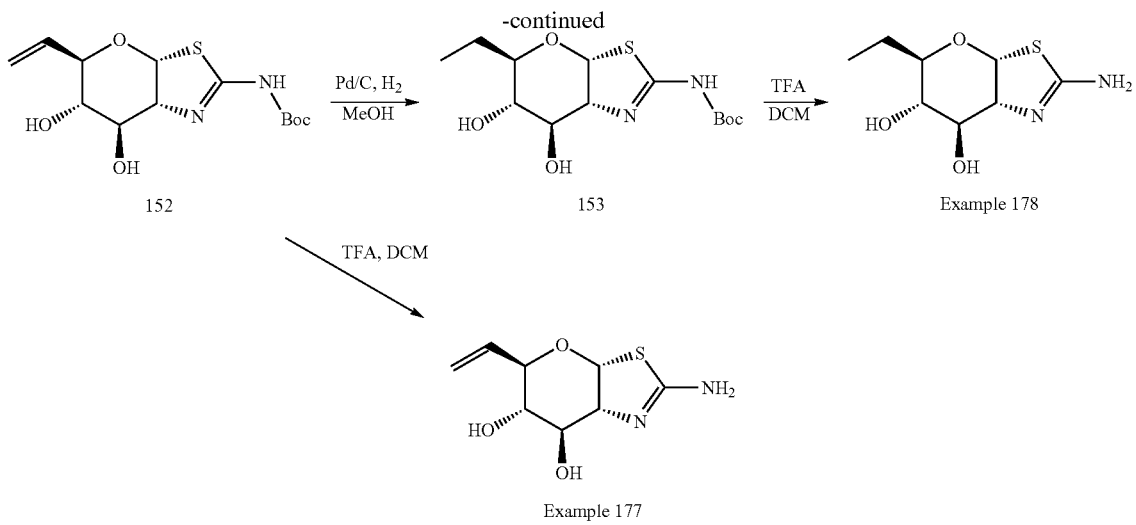

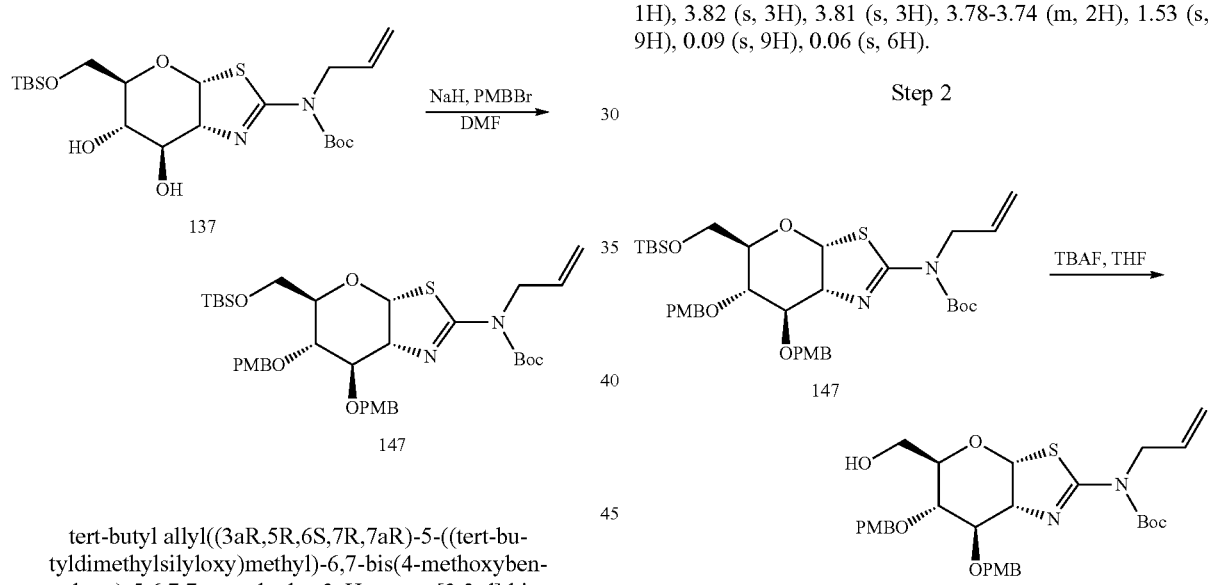

Step 1 tert-butyl allyl((3aR,5R,6S,7R,7aR)-5-((tert-butyldimethylsilyloxy)methyl)-6,7-bis(4-methoxybenzyloxy)-5,6,7,7a-tetrahydro-3aH-pyrano[3,2-d]thiazol-2-yl)carbamate (147)

A solution of tert-butyl allyl((3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl)carbamate 137 (prepared in a manner analogous to compound 17, Example 2 Steps 1-4, except substituting allyl amine for propyl ylamine in step 1) (20 g, 42 mmol) in DMF (300 mL) was treated with sodium hydride (5.8 g, 168 mmol, 70% dispersed by mineral oil) for 30 minutes at 0° C., followed by addition of PMBBr (34 g, 168 mmol). After additional 1.5 hours at 15° C., the reaction was quenched with water (300 mL), and extracted with ethyl acetate (3×200 mL). The combined organic layer was washed with brine (3×150 mL), dried over anhydrous sodium sulfate and concentrated under vacuum. The residue was purified by flash column chromatography with 5%-20% ethyl acetate in petroleum ether to afford the title compound as a light yellow oil (16 g, 53%). (ES, m/z): [M+H]$^+$ 715.0; $^1$H NMR (300 MHz, CDCl$_3$) δ 7.36-7.33 (m, 2H), 7.24-7.21 (m, 2H), 6.92-6.85 (m, 4H), 6.10 (d, J=6.6 Hz, 1H), 6.80-5.95 (m, 1H), 5.21-5.03 (m, 2H), 4.71-4.66 (m, 3H), 4.53-4.44 (m, 2H), 4.43-4.34 (m, 3H), 4.15 (t, J=5.4 Hz, 1H), 3.91-3.84 (m, 1H), 3.82 (s, 3H), 3.81 (s, 3H), 3.78-3.74 (m, 2H), 1.53 (s, 9H), 0.09 (s, 9H), 0.06 (s, 6H).

Step 2 tert-butyl allyl-((3aR,5R,6S,7R,7aR)-5-(hydroxymethyl)-6,7-bis(4-methoxybenzyloxy)-5,6,7,7a-tetrahydro-3aH-pyrano[3,2-d]thiazol-2-yl)carbamate (148)

A solution of 147 (15 g, 21 mmol) in THF (100 mL) was treated with TBAF (8.4 g, 32 mmol) for 3 hours at room temperature. The reaction was quenched with water (150 mL) and extracted with ethyl acetate (3×100 mL). The combined organic layer was washed with brine (2×50 mL), dried over anhydrous sodium sulfate and concentrated under vacuum. The residue was purified by flash column chromatography with 10%-30% ethyl acetate in petroleum ether to afford 148 as a light yellow syrup (11.3 g, 90%). (ES, m/z): [M+H]$^+$ 601.0; $^1$H NMR (300 MHz, CDCl$_3$) δ 7.36-7.33 (m, 2H), 7.21-7.19 (m, 2H), 6.91-6.82 (m, 4H), 6.09 (d, J=6.6 Hz, 1H), 5.92-5.80 (m, 1H), 5.19-5.00 (m, 2H), 4.70-4.58 (m, 2H), 4.55-4.36 (m, 4H), 4.32-4.24 (m, 2H), 3.82 (s, 3H), 3.83 (s, 3H), 3.75-3.68 (m, 2H), 3.64-3.52 (m, 2H), 1.56 (s, 9H).

Step 3

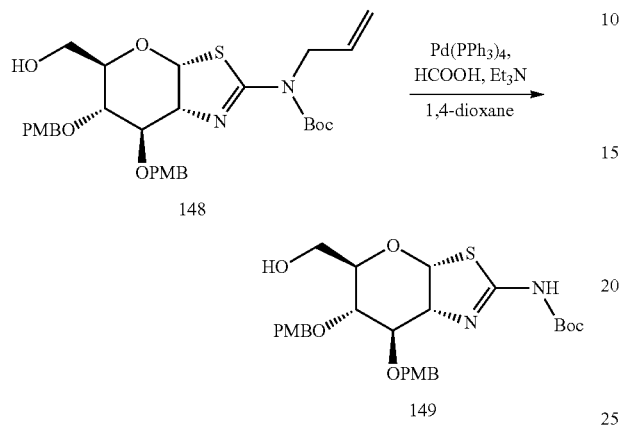

tert-butyl (3aR,5R,6S,7R,7aR)-5-(hydroxymethyl)-6,7-bis(4-methoxybenzyloxy)-5,6,7,7a-tetrahydro-3aH-pyrano[3,2-d]thiazol-2-ylcarbamate (149)

To a solution of 148 (10.5 g, 18 mmol) in 1,4-dioxane (100 mL) was added Pd(PPh$_3$)$_4$ (4.2 g, 3.6 mmol), Et$_3$N (4.6 g, 45 mmol) and formic acid (4.9 g, 107 mmol) at room temperature under N$_2$ atmosphere. After 20 minutes at 60° C., additional formic acid (24.5 g, 535 mmol) was added. The reaction was stirred at 60° C. for additional 3 hours. Removal of volatiles gave a residue, which was dissolved into dichloromethane (100 mL) and neutralized with saturated aqueous NaHCO$_3$ solution (30 mL). The aqueous layer was extracted with dichloromethane (3×50 mL). The combined organic layer was dried over anhydrous sodium sulfate, and concentrated under vacuum. The residue was purified by flash column chromatography with 10%-50% ethyl acetate in petroleum ether to afford the title compound as a white syrup (6.4 g, 65%). (ES, m/z): [M+H]$^+$ 561.0; $^1$H NMR (300 MHz, CDCl$_3$) δ 7.30-7.23 (m, 4H), 6.92-6.87 (m, 4H), 6.14 (d, J=6.9 Hz, 1H), 4.56-4.52 (m, 3H), 4.36-4.32 (m, 1H), 4.25-4.19 (m, 1H), 4.13-4.07 (m, 1H), 3.82-3.80 (m, 1H), 3.79 (s, 3H), 3.78 (s, 3H), 3.76-3.51 (m, 3H), 1.54 (s, 9H).

Step 4

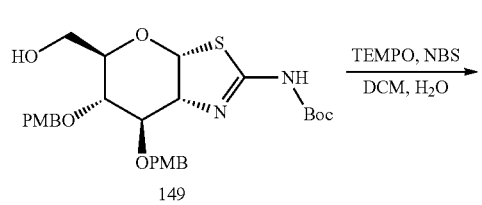

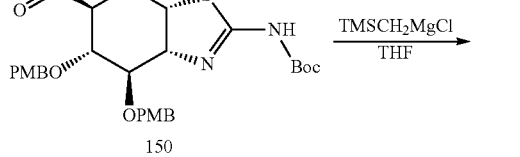

tert-butyl (3aR,5R,6S,7R,7aR)-5-((R)-1-hydroxy-2-(trimethylsilyl)ethyl)-6,7-bis(4-methoxybenzyloxy)-5,6,7,7a-tetrahydro-3aH-pyrano[3,2-d]thiazol-2-ylcarbamate (51)

To a mixture of 3 (2 g, 3.6 mmol), KHCO$_3$ (1.6 g, 16 mmol), TBAB (105 mg, 0.4 mmol), TEMPO (62 mg, 0.4 mmol) in dichloromethane (50 mL) and H$_2$O (10 mL) was added NBS (695 mg, 3.9 mmol) at 0° C. After stirred for 30 minutes at room temperature, the reaction was diluted with water (50 mL) and the aqueous layer was extracted with dichloromethane (2×40 mL). The combined organic layer was dried over anhydrous sodium sulfate, and concentrated under vacuum to give crude aldehyde 150, which was dissolved into THF (20 mL). The solution was treated with ((trimethylsilyl)methyl)magnesium chloride (7.2 mL, 7.2 mmol, 1M in ether). After 2 hours at 10° C., the reaction was quenched with saturated aqueous NH$_4$Cl solution (40 mL) and extracted with ethyl acetate (4×20 mL). The combined organic layer was washed with brine (2×30 mL), dried over anhydrous sodium sulfate and concentrated under vacuum. The residue was purified by flash column chromatography with 5%-30% ethyl acetate in petroleum ether to afford 151 as a light yellow syrup (1.1 g, 48%, two epimers, the ratio is 1:3 determined by $^1$HNMR). (ES, m/z): [M+H]$^+$ 647.0; $^1$H NMR (300 MHz, CDCl$_3$) δ 7.31-7.19 (m, 4H), 6.93-6.85 (m, 4H), 6.23-6.19 (m, 1H), 4.62-4.50 (m, 4H), 4.47-4.43 (m, 3H), 3.85-3.83 (m, 1H), 3.81 (s, 3H), 3.80 (s, 3H), 3.25-3.21 (m, 1H), 1.54 (s, 9H), 0.89-0.87 (m, 1H), 0.74-0.72 (m, 1H), 0.05 (s, 3H), 0.04 (s, 3H), 0.03 (s, 3H).

Step 5

-continued

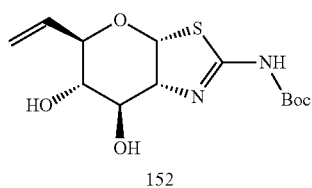

152 tert-butyl (3aR,5R,6S,7R,7aR)-6,7-dihydroxy-5-vinyl-5,6,7,7a-tetrahydro-3aH-pyrano[3,2-d]thiazol-2-ylcarbamate (6)

A solution of 151 (900 mg, 1.4 mmol) in dichloromethane (20 mL) was treated with $BF_3$ (0.1 mL, 0.1 mmol, 1M in ether) for 20 minutes at 10° C. Removal of volatiles gave a residue, which was dissolved into dichloromethane (20 mL) and neutralized with saturated aqueous $NaHCO_3$ solution (10 mL). The aqueous layer was extracted with dichloromethane (5×20 mL). The combined organic layer was dried over anhydrous sodium sulfate, and concentrated under vacuum. The residue was purified by flash column chromatography with 1%-10% methanol in dichloromethane to afford 152 as a light yellow syrup (240 mg, 55%). (ES, m/z): $[M+H]^+$ 317.0; $^1H$ NMR (300 MHz, $CDCl_3$) δ 6.11 (d, J=6.6 Hz, 1H), 5.77-5.63 (m, 1H), 5.24-5.16 (m, 2H), 4.08-4.02 (m, 1H), 3.76-3.61 (m, 2H), 3.55-3.46 (m, 1H), 1.53 (s, 9H).

Step 6

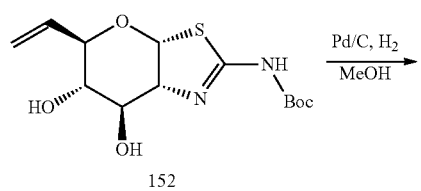

tert-butyl (3aR,5R,6S,7R,7aR)-5-ethyl-6,7-dihydroxy-5,6,7,7a-tetrahydro-3aH-pyrano[3,2-d]thiazol-2-ylcarbamate (7)

A mixture of 152 (160 mg, 0.5 mmol) and Pd/C (16 mg, 10% w/w) in methanol (20 mL) was stirred for 3 hours at room temperature under $H_2$ atmosphere (1 atm). After filtration, removal of solvents provided a residue, which was purified by flash column chromatography with 2%-10% methanol in dichloromethane to afford 153 as a white syrup (130 mg, 81%). (ES, m/z): $[M+H]^+$ 319.0; $^1H$ NMR (300 MHz, $CDCl_3$) δ 6.07 (d, J=6.3 Hz, 1H), 4.40 (t, J=5.9 Hz, 1H), 4.17 (t, J=6.6 Hz, 1H), 3.65-3.59 (m, 2H), 1.84-1.72 (m, 1H), 1.62-1.45 (m, 1H), 1.53 (s, 9H), 0.84 (t, J=7.5 Hz, 3H).

Step 7

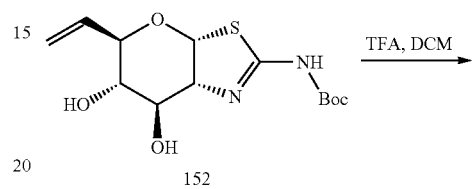

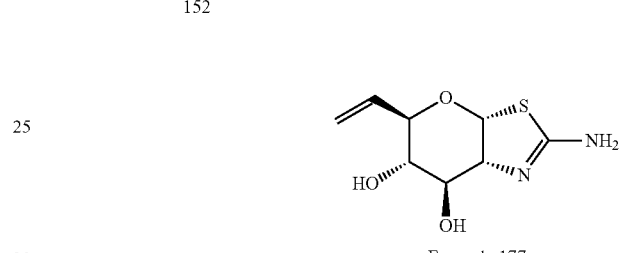

Example 177

(3aR,5R,6S,7R,7aR)-2-amino-5-vinyl-5,6,7,7a-tetrahydro-3aH-pyrano[3,2-d]thiazole-6,7-diol To solution of 152 (65 mg, 0.2 mmol) in dichloromethane (10 mL) was added TFA (1 mL). After 2 hours at room temperature, Removal of volatiles gave a residue, which was dissolved into methanol (3 mL) and neutralized with concentrated $NH_4OH$ (1 mL). After concentrated under reduced pressure, the crude product was purified by flash column chromatography with 5%-30% methanol in dichloromethane to give (3aR,5R,6S,7R,7aR)-2-amino-5-vinyl-5,6,7,7a-tetrahydra-3aH-pyrano[3,2-d]thiazole-6,7-diol as a white solid (30 mg, 68%). (ES, m/z): $[M+H]^+$ 217.0; $^1H$ NMR (300 MHz, $D_2O$) δ 6.24 (d, J=6.3 Hz, 1H), 5.87-5.75 (m, 1H), 5.35-5.26 (m, 2H), 4.07 (t, J=6.3 Hz, 1H), 3.98-3.88 (m, 2H), 3.50-3.24 (m, 1H).

Step 8

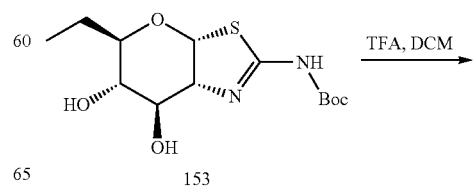

Example 178

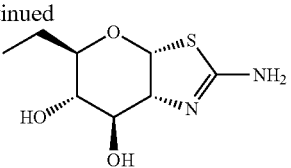

(3aR,5R,6S,7R,7aR)-2-amino-5-ethyl-5,6,7,7a-tetrahydro-3aH-pyrano[3,2-d]thiazole-6,7-diol To a solution of 153 (70 mg, 0.2 mmol) in dichloromethane (10 mL) was added TFA (1 mL). After 2 hours at room temperature, removal of volatiles gave a residue, which was dissolved into methanol (3 mL) and neutralized with concentrated NH$_4$OH (1 mL). After concentrated under reduced pressure, the crude product was purified by flash column chromatography with 5%-30% methanol in dichloromethane to give (3aR,5R,6S,7R,7aR)-2-amino-5-ethyl-5,6,7,7a-tetrahydro-3aH-pyrano[3,2-d]thiazole-6,7-diol as a white solid (33 mg, 69%). (ES, m/z): [M+H]$^+$ 219.0; $^1$H NMR (300 MHz, D$_2$O) δ 6.18 (d, J=6.6 Hz, 1H), 4.08 (t, J=5.7 Hz, 1H), 3.89 (t, J=4.5 Hz, 1H), 3.42-3.34 (m, 2H), 1.71-1.63 (m, 1H), 1.45-1.35 (m, 1H), 0.81 (t, J=7.5 Hz, 3H).

Examples 179 and 180

(3aR,5S,6S,7R,7aR)-2-(dimethylamino)-5-((R)-1-fluoroethyl)-5,6,7,7a-tetrahydro-3aH-pyrano[3,2-d]thiazole-6,7-diol & (3aR,5S,6S,7R,7aR)-2-(dimethylamino)-5-((S)-1-fluoroethyl)-5,6,7,7a-tetrahydro-3aH-pyrano[3,2-d]thiazole-6,7-diol

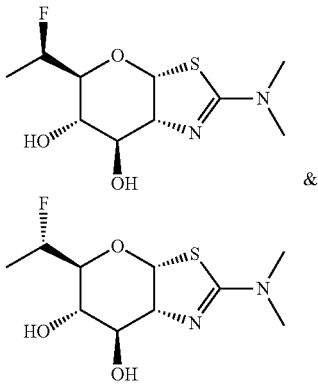

Scheme XXXI

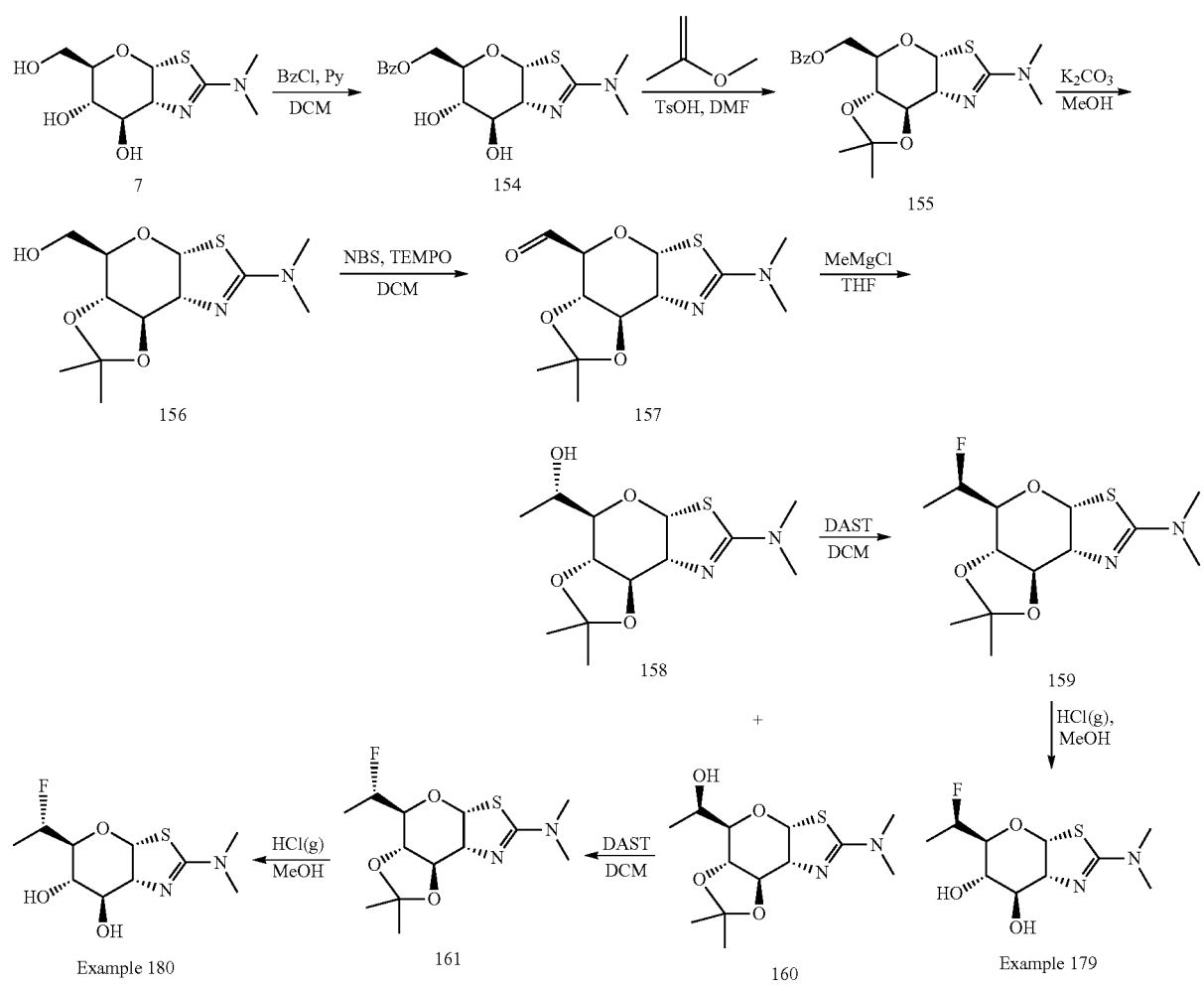

Step 1

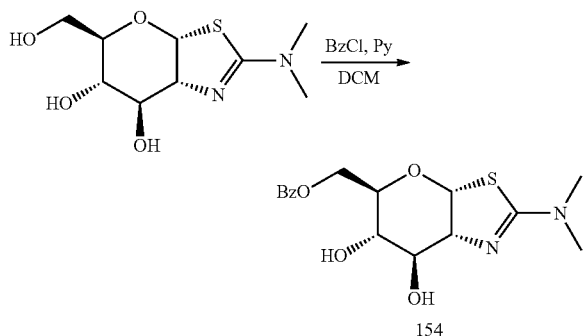

((3aR,5R,6S,7R,7aR)-2-(dimethylamino)-6,7-dihydroxy-5,6,7,7a-tetrahydro-3aH-pyrano[3,2-d]thiazol-5-yl)methyl benzoate (154)

To a solution of (3aR,5R,6S,7R,7aR)-2-(dimethylamino)-5-(hydroxymethyl)-5,6,7,7a-tetrahydro-3aH-pyrano[3,2-d]thiazole-6,7-diol (5 g, 20 mmol) in pyridine (150 mL) was added a solution of benzoyl chloride (3.4 g, 24 mmol) in dichloromethane (10 mL) at 0° C. within 10 minutes, and then stirred for 5 hours at 0° C. in an ice/salt bath. The reaction was quenched by the addition of saturated aqueous NaHCO₃ solution (100 mL), and extracted with dichloromethane (3×100 mL). The combined organic layer was washed with brine (2×20 mL), dried over sodium sulfate, filtered and concentrated under vacuum. The crude residue was purified by flash column chromatography with 2% 5% methanol in dichloromethane to afford the title compound as an off-white solid (4.5 g, 63%). (ES, m/z): [M+H]+ 353.0; ¹H NMR (300 MHz, CD₃OD) δ 8.07-8.01 (m, 2H), 7.99-7.40 (m, 3H), 6.43 (d, J=6.6 Hz, 1H), 4.88-4.85 (m, 1H), 4.63-4.45 (m, 1H), 4.19-4.15 (m, 1H), 3.99-3.93 (m, 2H), 3.36-3.32 (m, 1H), 3.06 (s, 6H).

Step 2

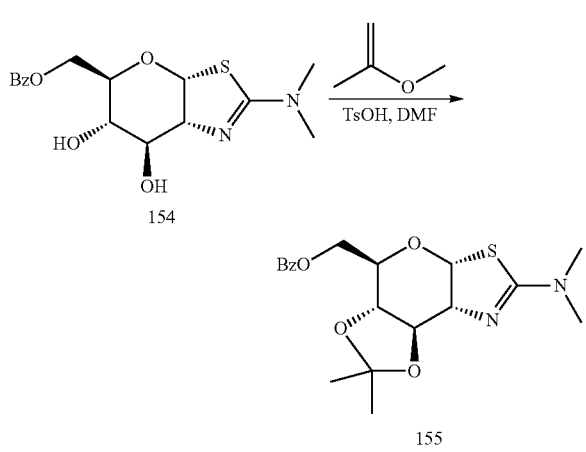

[(1R,2R,6R,8R,9S)-4-(dimethylamino)-11,11-dimethyl-7,10,12-trioxa-5-thia-3-azatricyclo[7.3.0.0{2,6}]dodec-3-en-8-yl]methyl benzoate (155)

To a solution of 154 (3.0 g, 8.5 mmol) in DMF (20 mL) was added 4-methylbenzenesulfonic acid hydrate (3.2 g, 17 mmol) and 2-methoxyprop-1-ene (6.1 g, 85 mmol) sequentially. The resulting solution was stirred for 15 minutes at room temperature, before the reaction was quenched by the addition of saturated aqueous sodium bicarbonate solution (20 mL), which was then extracted with dichloromethane (3×20 mL). The combined organic layer was washed with brine (2×10 mL), dried over sodium sulfate, filtered and concentrated under vacuum. The crude residue was purified by flash column chromatography with 1%-10% ethyl acetate in petroleum ether to afford 155 as an off-white solid (1.6 g, 48%). (ES, m/z): [M+H]+ 393.0; ¹H NMR (300 MHz, CDCl₃) δ 8.08-8.05 (m, 2H), 7.63-7.45 (m, 3H), 6.32-6.30 (m, 1H), 4.60-4.52 (m, 2H), 4.41-4.31 (m, 2H), 3.97-3.91 (m, 1H), 3.70-3.63 (m, 1H), 3.55-3.50 (m, 1H), 3.39-3.30 (m, 1H), 3.10 (s, 6H), 1.50 (s, 6H).

Step 3

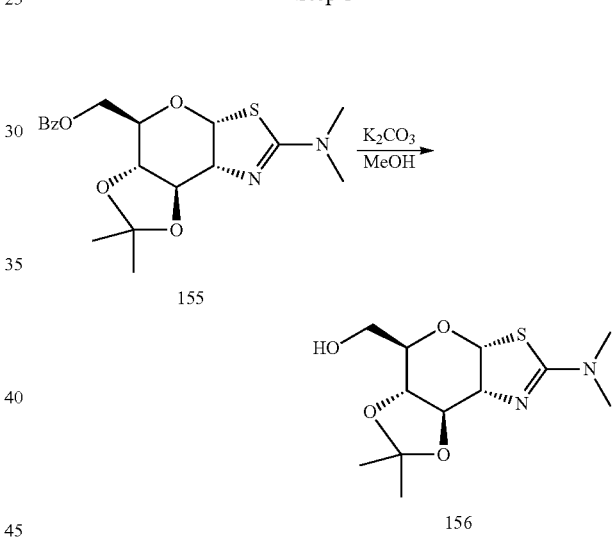

[(1R,2R,6R,8R,9S)-4-(dimethylamino)-11,11-dimethyl-7,10,12-trioxa-5-thia-3-azatricyclo[7.3.0.0{2,6}]dodec-3-en-8-yl]methanol (156)

To a solution of 155 (4.0 g, 10 mmol) in methanol (30 mL) was added potassium carbonate (704 mg, 5.1 mmol). The resulting solution was stirred for 2 hours at room temperature, before the reaction was quenched by the addition of water (20 mL), which was then extracted with dichloromethane (3×20 mL). The combined organic layer was washed with brine (2×10 mL), dried over sodium sulfate, filtered and concentrated under vacuum. The crude residue was purified by flash column chromatography with 1%-5% methanol in dichloromethane to afford the title compound as a white solid (2.6 g, 88%). (ES, m/z): [M+H]+ 289.0; ¹H NMR (300 MHz, CDCl₃) δ 6.34 (d, J=6.0 Hz, 1H), 4.37-4.32 (m, 1H), 4.11-4.05 (m, 1H), 3.94-3.82 (m, 2H), 3.61-3.54 (m, 1H), 3.36-3.23 (m, 1H), 3.08 (s, 6H), 1.46 (s, 6H).

Step 4

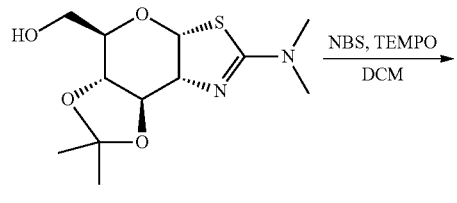

156

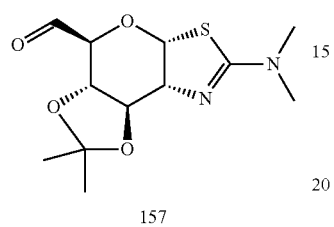

157

(1R,2R,6R,8S,9S)-4-(dimethylamino)-11,11-dimethyl-7,10,12-trioxa-5-thia-3-azatricyclo[7.3.0.0{2,6}]dodec-3-ene-8-carbaldehyde (157)

To a solution of 156 (500 mg, 1.7 mmol) in dichloromethane (20 mL) and water (5 mL) was added 2,2,6,6-tetramethylpiperidinooxy (13 mg, 0.08 mmol), tetrabutylammonium bromide (27 mg, 0.08 mmol), potassium bicarbonate (788 mg, 7.9 mmol) and N-bromosuccinimide (342 mg, 1.9 mmol). The resulting solution was stirred for 30 minutes at room temperature, before the reaction was quenched by the addition of saturated aqueous sodium sulfite solution (10 mL), which was then extracted with dichloromethane (2×10 mL). The combined organic layer was washed with brine (2×10 mL), dried over sodium sulfate, filtered and concentrated under vacuum. The crude residue was purified by flash column chromatography with 10% ethyl acetate in dichloromethane to afford 157 as an off-white solid (300 mg, 54%). (ES, m/z): [M+H]$^+$ 287.0; $^1$H NMR (300 MHz, CDCl$_3$) δ 9.82 (s, 1H), 6.34 (d, J=6.0 Hz, 1H), 4.37-4.32 (m, 1H), 4.11-4.05 (m, 1H), 3.94-3.82 (m, 1H), 3.61-3.54 (m, 1H), 3.36-3.23 (m, 1H), 3.08 (s, 6H), 1.46 (s, 6H).

Step 5

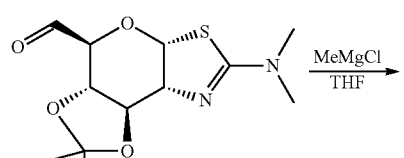

157

-continued

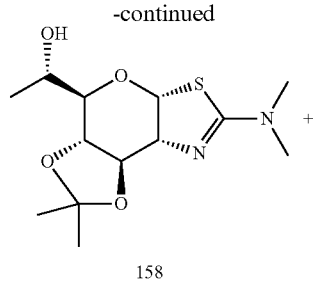

158

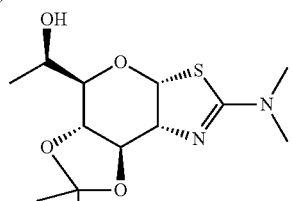

160

(1S)-1-[(1R,2R,6R,8R,9S)-4-(dimethylamino)-11,11-dimethyl-7,10,12-trioxa-5-thia-3-azatricyclo[7.3.0.0{2,6}]dodec-3-en-8-yl]ethan-1-ol (5) & (1R)-1-[(1R,2R,6R,8R,9S)-4-(dimethylamino)-11,11-dimethyl-7,10,12-trioxa-5-thia-3-azatricyclo[7.3.0.0{2,6}]dodec-3-en-8-yl]ethan-1-ol (159)

To a stirred solution of 157 (1.0 g, 3.1 mmol) in THF (30 mL) was added MeMgCl (4.6 mL, 4.6 mmol, 1M solution in THF) at 0° C. The resulting solution was stirred for 2 hours at room temperature, before the reaction was quenched by the addition of 10% aqueous NH$_4$Cl solution (10 mL), which was then extracted with ethyl acetate (3×20 mL). The combined organic layer was washed with brine (2×10 mL), dried over sodium sulfate, filtered and concentrated under vacuum. The crude residue was purified by chiral preparative HPLC with the following condition: (Chiralpak IC(SFC)2*25 cm, 5 umChiral-P(IC)002S09C00CJ-MI001, 220 nm, Mobile Phase: ethanol/hexane=1/1, run 14 minutes) to afford 158 as an off-white solid (230 mg, 23%, slower eluting isomer), (ES, m/z): [M+H]$^+$ 303.0; $^1$H NMR (300 MHz, CDCl$_3$) δ 6.16 (d, J=5.7 Hz, 1H), 4.33-4.28 (m, 1H), 3.97-3.82 (m, 2H), 3.76-3.69 (m, 1H), 3.61-3.55 (m, 1H), 3.02 (s, 6H), 2.38 (s, 1H), 1.47 (s, 6H), 1.28 (d, J=3.6 Hz, 3H); and 160 as an off-white solid (270 mg, 30%, faster eluting isomer). (ES, m/z): [M+H]$^+$ 303.0; $^1$H NMR (300 MHz, CDCl$_3$) δ 6.32 (d, J=6.0 Hz, 1H), 4.30-4.26 (m, 1H), 4.06-4.01 (m, 1H), 3.88-3.73 (m, 2H), 3.71-3.63 (m, 1H), 3.02 (s, 6H), 2.31 (s, 1H), 1.47 (s, 6H), 1.30-1.22 (m, 3H).

Step 6

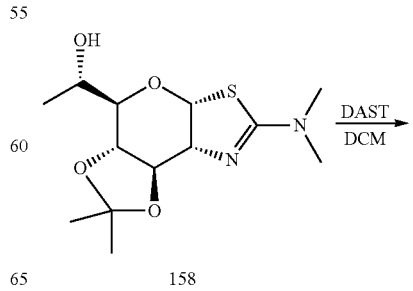

158

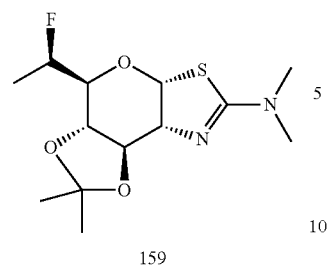

159

(1R,2R,6R,8S,9S)-8-[(1R)-1-fluoroethyl]-N,N,11,11-tetramethyl-7,10,12-trioxa-5-thia-3-azatricyclo[7.3.0.0{2,6}]dodec-3-en-4-amine (159)

To a solution of 158 (230 mg, 1 mmol) in dichloromethane (10 mL) was treated with DAST (0.6 mL, 5.0 mmol) for 1 hour at −20° C. and additional 1 hour at room temperature. The reaction was quenched with saturated aqueous sodium bicarbonate solution (10 mL), which was then extracted with dichloromethane (2×10 mL). The combined organic layer was washed with brine (2×5 mL), dried over sodium sulfate, filtered and concentrated under vacuum. The crude residue was purified by flash column chromatography with 1% 5% methanol in dichloromethane to afford the title compound as a white solid (160 mg, 34%). (ES, m/z): [M+H]$^+$ 305.0; $^1$H NMR (300 MHz, CDCl$_3$) δ 6.16 (d, J=5.7 Hz, 1H), 5.04-4.85 (m, 1H), 4.37-4.33 (m, 1H), 3.93-3.81 (m, 3H), 3.03 (s, 6H), 1.49 (s, 6H), 1.41 (dd, J=6.6 Hz, 24.3 Hz, 3H).

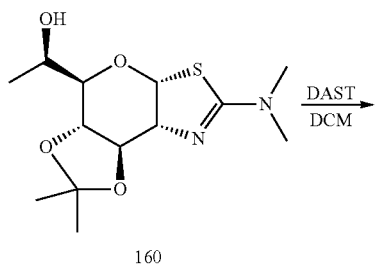

160

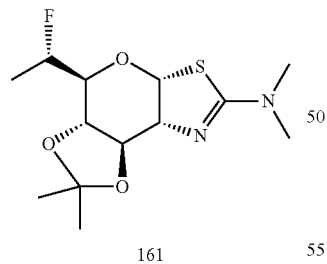

161

(1R,2R,6R,8S,9S)-8-[(1S)-1-fluoroethyl]-N,N,11,11-tetramethyl-7,10,12-trioxa-5-thia-3-azatricyclo 17.3.0.0{2,6}dodec-3-en-4-amine (161)

Using the same procedure as Step 6, 160 was converted to the title compound. Compound. 161 (160 mg, 30%) was obtained as white solid. (ES, m/z): [M+H]$^+$ 305.0; $^1$H NMR (300 MHz, CDCl$_3$) δ 6.42 (d, J=6.6 Hz, 1H), 4.95-4.76 (m, 1H), 4.62-4.56 (m, 1H), 4.11-4.00 (m, 1H), 3.89-3.85 (m, 1H), 3.15 (s, 6H), 1.49 (s, 6H), 1.43-1.41 (m, 3H).

Step 7

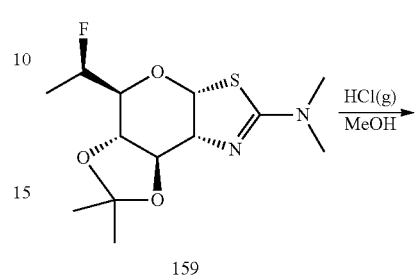

159

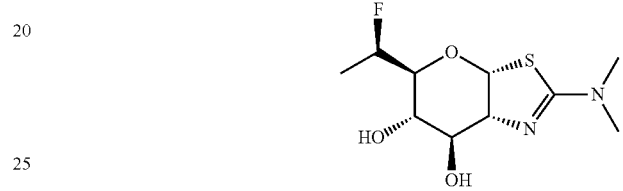

Example 179

(3aR,5S,6S,7R,7aR)-2-(dimethylamino)-5-((R)-1-fluoroethyl)-5,6,7,7a-tetrahydro-3aH-pyrano[3,2-d]thiazole-6,7-diol A solution of 159 (150 mg, 0.16 mmol) in methanol (10 mL) was treated with concentrated aqueous HCl (1 mL) for 1 hour at room temperature, then the resulting solution was concentrated under vacuum to give a residue, which was dissolved into methanol (5 mL) and neutralized with concentrated NH$_4$OH (1 mL). After removal of all the solvent, the residue was purified by flash column chromatography with 10% methanol in dichloromethane to afford the title compound as a white solid (50.1 mg, 38%). (ES, m/z); [M+H]$^+$ 265.0; $^1$H NMR (300 MHz, D$_2$O) δ 6.23 (d, J=6.6 Hz, 1H), 4.97-4.70 (m, 1H), 4.22-4.19 (m, 1H), 4.02-3.99 (m, 1H), 3.67-3.62 (m, 2H), 2.91 (s, 6H), 1.26 (dd, J=6.6 Hz, 26.1 Hz, 3H).

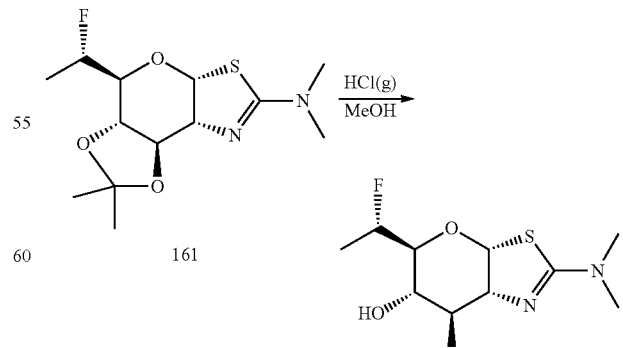

161

Example 180

(3aR,5S,7R,7aR)-2-(dimethylamino)-5-((S)-1-fluoroethyl)-5,6,7,7a-tetrahydro-3aH-pyrano[3,2-d]thiazole-6,7-diol Example 180

Compound 161 was converted to the title compound using the same procedure as described above in Step 7.

The title compound was obtained as a white solid (30 mg, 23%). (ES, m/z): [M+H]$^+$ 265.0; $^1$H NMR (300 MHz, D$_2$O) δ 6.22 (d, J=6.6 Hz, 1H), 4.96-4.73 (m, 1H), 4.15-4.11 (m, 1H), 3.97-3.93 (m, 1H), 3.69-3.65 (m, 1H), 3.46-3.33 (m, 1H), 2.90 (s, 6H), 1.26 (dd, J=6.6 Hz, 26.1 Hz, 3H).

| Example | Structure | Name | MH+ |
|---|---|---|---|
| 181 | 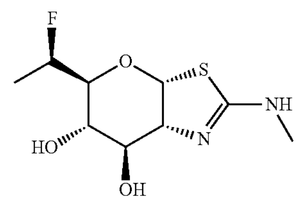 [SMILES: CNC1=N[C@@H]2[C@@H](O)[C@H](O)[C@@H]([C@@H](C)F)O[C@@H]2S1] | (3aR,5S,6S,7R,7aR)-5-((R)-1-fluoroethyl)-2-(methylamino)-5,6,7,7a-tetrahydro-3aH-pyrano[3,2-d]thiazole-6,7-diol (Faster eluting isomer by HPLC) | 251.0 |
| 182 | 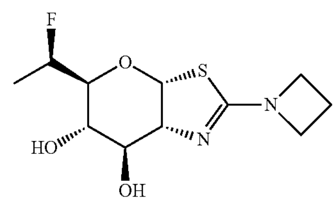 [SMILES: C[C@@H](F)[C@H]1O[C@@H]2SC(N3CCC3)=N[C@@H]2[C@@H](O)[C@@H]1O] | (3aR,5S,6S,7R,7aR)-2-(azetidin-1-yl)-5-((R)-1-fluoroethyl)-5,6,7,7a-tetrahydro-3aH-pyrano[3,2-d]thiazole-6,7-diol (Faster eluting isomer by HPLC) | 276.9 |
| 183 | 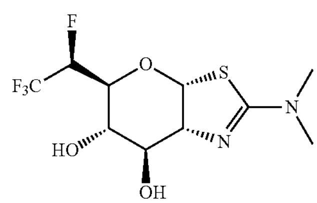 [SMILES: CN(C)C1=N[C@@H]2[C@@H](O)[C@H](O)[C@@H]([C@H](F)C(F)(F)F)O[C@@H]2S1] | (3aR,5S,6S,7R,7aR)-2-(dimethylamino)-5-((S)-1,2,2,2-tetrafluoroethyl)-5,6,7,7a-tetrahydro-3aH-pyrano[3,2-d]thiazole-6,7-diol (Faster eluting isomer by HPLC) | 318.9 |
| 184 | 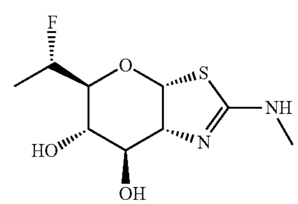 [SMILES: CNC1=N[C@@H]2[C@@H](O)[C@H](O)[C@@H]([C@H](C)F)O[C@@H]2S1] | (3aR,5S,6S,7R,7aR)-5-((S)-1-fluoroethyl)-2-(methylamino)-5,6,7,7a-tetrahydro-3aH-pyrano[3,2-d]thiazole-6,7-diol (Slower eluting isomer by HPLC) | 251.0 |
| 185 | 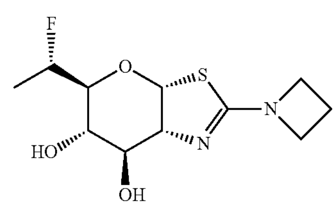 [SMILES: C[C@H](F)[C@H]1O[C@@H]2SC(N3CCC3)=N[C@@H]2[C@@H](O)[C@@H]1O] | (3aR,5S,6S,7R,7aR)-2-(azetidin-1-yl)-5-((S)-1-fluoroethyl)-5,6,7,7a-tetrahydro-3aH-pyrano[3,2-d]thiazole-6,7-diol (Slower eluting isomer by HPLC) | 276.9 |
| 186 | 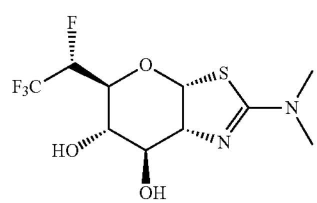 [SMILES: CN(C)C1=N[C@@H]2[C@@H](O)[C@H](O)[C@@H]([C@@H](F)C(F)(F)F)O[C@@H]2S1] | (3aR,5S,6S,7R,7aR)-2-(dimethylamino)-5-((R)-1,2,2,2-tetrafluoroethyl)-5,6,7,7a-tetrahydro-3aH-pyrano[3,2-d]thiazole-6,7-diol (Slower eluting isomer by HPLC) | 318.9 |
| 187 | 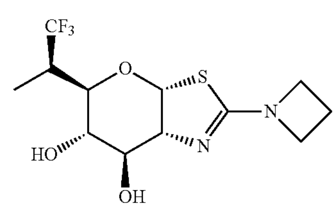 [SMILES: C[C@H]([C@H]1O[C@@H]2SC(N3CCC3)=N[C@@H]2[C@@H](O)[C@@H]1O)C(F)(F)F] | (3aR,5R,6S,7R,7aR)-2-(azetidin-1-yl)-5-((R)-1,1,1-trifluoropropan-2-yl)-5,6,7,7a-tetrahydro-3aH-pyrano[3,2-d]thiazole-6,7-diol (Faster eluting isomer by HPLC) | 327.1 |

-continued

| Example | Name | MH+ |
|---|---|---|
| 188 | (3aR,5R,6S,7R,7aR)-2-(azetidin-1-yl)-5-((S)-1,1,1-trifluoropropan-2-yl)-5,6,7,7a-tetrahydro-3aH-pyrano[3,2-d]thiazole-6,7-diol (Slower eluting isomer by HPLC) | 327.1 |
| 189 | (3aR,5R,6S,7R,7aR)-2-(dimethylamino)-5-((R)-1,1,1-trifluoropropan-2-yl)-5,6,7,7a-tetrahydro-3aH-pyrano[3,2-d]thiazole-6,7-diol (Faster eluting isomer by HPLC) | 314.9 |
| 190 | (3aR,5R,6S,7R,7aR)-2-(dimethylamino)-5-((S)-1,1,1-trifluoropropan-2-yl)-5,6,7,7a-tetrahydro-3aH-pyrano[3,2-d]thiazole-6,7-diol (Slower eluting isomer by HPLC) | 314.9 |
| 191 | (3aR,5S,6S,7R,7aR)-5-((R)-2,2-difluoro-1-hydroxyethyl)-2-(methylamino)-5,6,7,7a-tetrahydro-3aH-pyrano[3,2-d]thiazole-6,7-diol | 285.0 |
| 192 | (3aR,5S,6S,7R,7aR)-5-((S)-2-fluoro-1-hydroxyethyl)-2-(methylamino)-5,6,7,7a-tetrahydro-3aH-pyrano[3,2-d]thiazole-6,7-diol (Faster eluting isomer by HPLC) | 267.0 |
| 193 | (3aR,5S,6S,7R,7aR)-5-((R)-2-fluoro-1-hydroxyethyl)-2-(methylamino)-5,6,7,7a-tetrahydro-3aH-pyrano[3,2-d]thiazole-6,7-diol (Slower eluting isomer by HPLC) | 267.0 |
| 194 | (3aR,5R,6S,7R,7aR)-5-(2-fluoroethyl)-2-(methylamino)-5,6,7,7a-tetrahydro-3aH-pyrano[3,2-d]thiazole-6,7-diol | 251.0 |
| 195 | (3aR,5R,6S,7R,7aR)-5-(2,2-difluoroethyl)-2-(methylamino)-5,6,7,7a-tetrahydro-3aH-pyrano[3,2-d]thiazole-6,7-diol | 269.0 |

-continued

| Example | Structure | Name | MH+ |
|---|---|---|---|
| 196 | 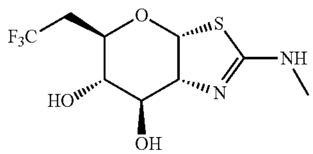 [SMILES: CNC1=N[C@@H]2[C@@H](O)[C@H](O)[C@@H](CC(F)(F)F)O[C@@H]2S1] | (3aR,5R,6S,7R,7aR)-2-(methylamino)-5-(2,2,2-trifluoroethyl)-5,6,7,7a-tetrahydro-3aH-pyrano[3,2-d]thiazole-6,7-diol | 287.0 |
| 197 | 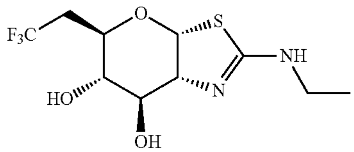 [SMILES: CCNC1=N[C@@H]2[C@@H](O)[C@H](O)[C@@H](CC(F)(F)F)O[C@@H]2S1] | (3aR,5R,6S,7R,7aR)-2-(ethylamino)-5-(2,2,2-trifluoroethyl)-5,6,7,7a-tetrahydro-3aH-pyrano[3,2-d]thiazole-6,7-diol | 301.0 |
| 198 | 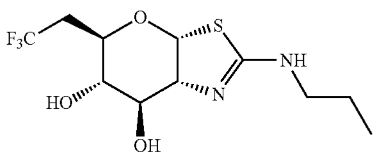 [SMILES: CCCNC1=N[C@@H]2[C@@H](O)[C@H](O)[C@@H](CC(F)(F)F)O[C@@H]2S1] | (3aR,5R,6S,7R,7aR)-2-(propylamino)-5-(2,2,2-trifluoroethyl)-5,6,7,7a-tetrahydro-3aH-pyrano[3,2-d]thiazole-6,7-diol | 315.0 |
| 199 | 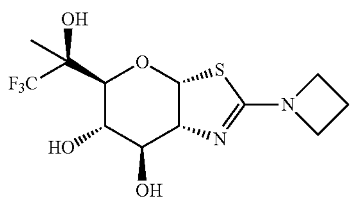 [SMILES: C[C@](O)([C@H]1O[C@@H]2SC(N3CCC3)=N[C@@H]2[C@@H](O)[C@@H]1O)C(F)(F)F] | (3aR,5S,6S,7R,7aR)-2-(azetidin-1-yl)-5-((S)-1,1,1-trifluoro-2-hydroxypropan-2-yl)-5,6,7,7a-tetrahydro-3aH-pyrano[3,2-d]thiazole-6,7-diol (Faster eluting isomer by HPLC) | 343.0 |
| 200 | 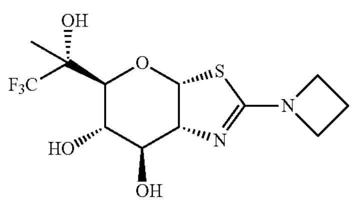 [SMILES: C[C@@](O)([C@H]1O[C@@H]2SC(N3CCC3)=N[C@@H]2[C@@H](O)[C@@H]1O)C(F)(F)F] | (3aR,5S,6S,7R,7aR)-2-(azetidin-1-yl)-5-((R)1,1,1-trifluoro-2-hydroxypropan-2-yl)-5,6,7,7a-tetrahydro-3aH-pyrano[3,2-d]thiazole-6,7-diol (Slower eluting isomer by HPLC) | 343.0 |
| 201 | 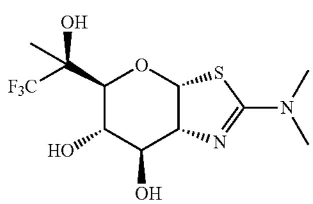 [SMILES: CN(C)C1=N[C@@H]2[C@@H](O)[C@H](O)[C@@H]([C@](C)(O)C(F)(F)F)O[C@@H]2S1] | (3aR,5S,6S,7R,7aR)-2-(dimethylamino)-5-((S)-1,1,1-trifluoro-2-hydroxypropan-2-yl)-5,6,7,7a-tetrahydro-3aH-pyrano[3,2-d]thiazole-6,7-diol (Faster eluting isomer by HPLC) | 330.9 |
| 202 | 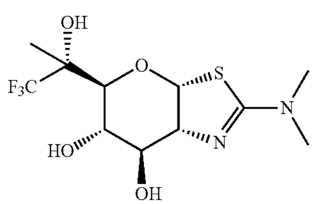 [SMILES: CN(C)C1=N[C@@H]2[C@@H](O)[C@H](O)[C@@H]([C@@](C)(O)C(F)(F)F)O[C@@H]2S1] | (3aR,5S,6S,7R,7aR)-2-(dimethylamino)-5-((R)1,1,1-trifluoro-2-hydroxypropan-2-yl)-5,6,7,7a-tetrahydro-3aH-pyrano[3,2-d]thiazole-6,7-diol (Slower eluting isomer by HPLC) | 331.0 |
| 203 | 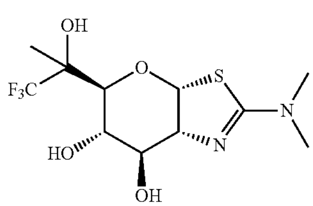 [SMILES: CN(C)C1=N[C@@H]2[C@@H](O)[C@H](O)[C@@H](C(C)(O)C(F)(F)F)O[C@@H]2S1] | (3aR,5S,6S,7R,7aR)-2-(dimethylamino)-5-((S)-1,1,1-trifluoro-2-hydroxypropan-2-yl)-5,6,7,7a-tetrahydro-3aH-pyrano[3,2-d]thiazole-6,7-diol (two epimers ratio 1:1) | 330.9 |

-continued

| Example | Structure | Name | MH+ |
|---|---|---|---|
| 204 | 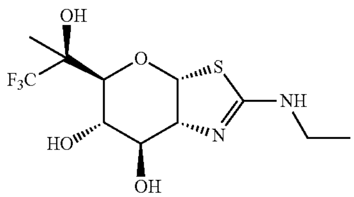 [SMILES: CCNC1=N[C@@H]2[C@@H](O)[C@H](O)[C@@H]([C@](C)(O)C(F)(F)F)O[C@@H]2S1] | (3aR,5S,6S,7R,7aR)-2-(ethylamino)-5-((S)-1,1,1-trifluoro-2-hydroxypropan-2-yl)-5,6,7,7a-tetrahydro-3aH-pyrano[3,2-d]thiazole-6,7-diol (Faster eluting isomer by HPLC) | 331.0 |
| 205 | 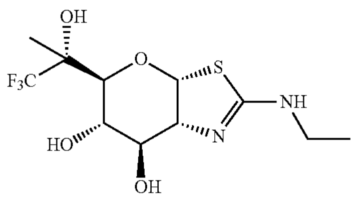 [SMILES: CCNC1=N[C@@H]2[C@@H](O)[C@H](O)[C@@H]([C@@](C)(O)C(F)(F)F)O[C@@H]2S1] | (3aR,5S,6S,7R,7aR)-2-(ethylamino)-5-((R)1,1,1-trifluoro-2-hydroxypropan-2-yl)-5,6,7,7a-tetrahydro-3aH-pyrano[3,2-d]thiazole-6,7-diol (Slower eluting isomer by HPLC) | 331.0 |
| 206 | 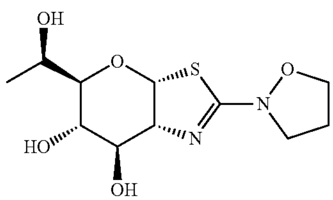 [SMILES: C[C@@H](O)[C@H]1O[C@@H]2SC(N3CCCO3)=N[C@@H]2[C@@H](O)[C@@H]1O] | (3aR,5R,6S,7R,7aR)-5-((R)-1-hydroxyethyl)-2-(isoxazolidin-2-yl)-5,6,7,7a-tetrahydro-3aH-pyrano[3,2-d]thiazole-6,7-diol(Fasler eluting isomer by HPLC) | 291.0 |
| 207 | 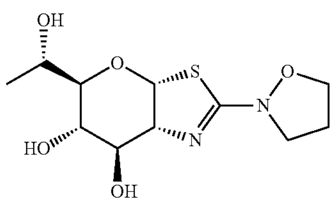 [SMILES: C[C@H](O)[C@H]1O[C@@H]2SC(N3CCCO3)=N[C@@H]2[C@@H](O)[C@@H]1O] | (3aR,5R,6S,7R,7aR)-5-((S)-1-hydroxyethyl)-2-(isoxazolidin-2-yl)-5,6,7,7a-tetrahydro-3aH-pyrano[3,2-d]thiazole-6,7-diol (Slower eluting isomer by HPLC) | 291.0 |
| 208 | 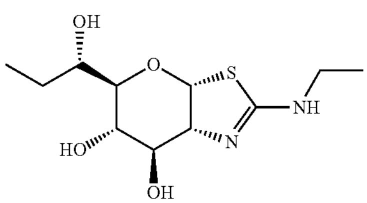 [SMILES: CCNC1=N[C@@H]2[C@@H](O)[C@H](O)[C@@H]([C@@H](O)CC)O[C@@H]2S1] | (3aR,5R,6S,7R,7aR)-2-(ethylamino)-5-((S)-1-hydroxypropyl)-5,6,7,7a-tetrahydro-3aH-pyrano[3,2-d]thiazole-6,7-diol (Slower eluting isomer by HPLC) | 277.1 |
| 209 | 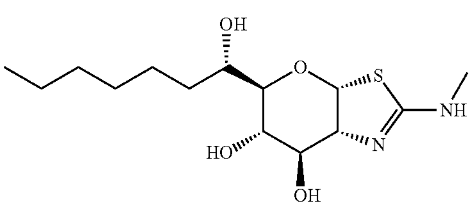 [SMILES: CCCCCC[C@H](O)[C@H]1O[C@@H]2SC(NC)=N[C@@H]2[C@@H](O)[C@@H]1O] | (3aR,5R,6S,7R,7aR)-5-((S)-1-hydroxyheptyl)-2-(methylamino)-5,6,7,7a-tetrahydro-3aH-pyrano[3,2-d]thiazole-6,7-diol (Slower eluting isomer by HPLC) | 319.0 |
| 210 | 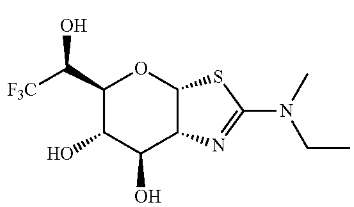 [SMILES: CCN(C)C1=N[C@@H]2[C@@H](O)[C@H](O)[C@@H]([C@H](O)C(F)(F)F)O[C@@H]2S1] | (3aR,5S,6S,7R,7aR)-2-(ethyl(methyl)amino)-5-((S)-2,2,2-trifluoro-1-hydroxyethyl)-5,6,7,7a-tetrahydro-3aH-pyrano[3,2-d]thiazole-6,7-diol (Faster eluting isomer by HPLC) | 331.0 |

-continued

| Example | Structure | Name | MH+ |
|---|---|---|---|
| 211 | 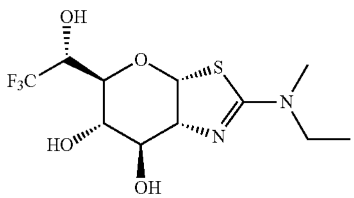 [SMILES: CCN(C)C1=N[C@@H]2[C@@H](O)[C@H](O)[C@@H]([C@@H](O)C(F)(F)F)O[C@@H]2S1] | (3aR,5S,6S,7R,7aR)-2-(ethyl(methyl)amino)-5-((R)-2,2,2-trifluoro-1-hydroxyethyl)-5,6,7,7a-tetrahydro-3aH-pyrano[3,2-d]thiazole-6,7-diol (Slower eluting isomer by HPLC) | 330.9 |
| 212 | 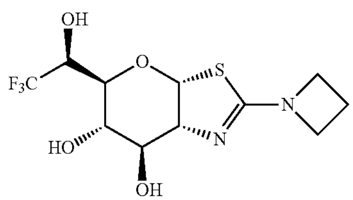 [SMILES: O[C@H]1[C@H](O)[C@@H]([C@H](O)C(F)(F)F)O[C@@H]2SC(N3CCC3)=N[C@H]12] | (3aR,5S,6S,7R,7aR)-2-(azetidin-1-yl)-5-((S)-2,2,2-trifluoro-1-hydroxyethyl)-5,6,7,7a-tetrahydro-3aH-pyrano[3,2-d]thiazole-6,7-diol (Faster eluting isomer by HPLC) | 329.0 |
| 213 | 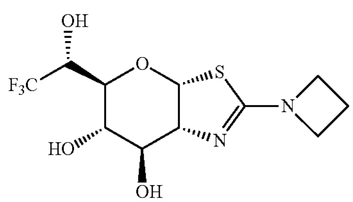 [SMILES: O[C@H]1[C@H](O)[C@@H]([C@@H](O)C(F)(F)F)O[C@@H]2SC(N3CCC3)=N[C@H]12] | (3aR,5S,6S,7R,7aR)-2-(azetidin-1-yl)-5-((R)-2,2,2-trifluoro-1-hydroxyethyl)-5,6,7,7a-tetrahydro-3aH-pyrano[3,2-d]thiazole-6,7-diol (Slower eluting isomer by HPLC) | 329.0 |
| 214 | 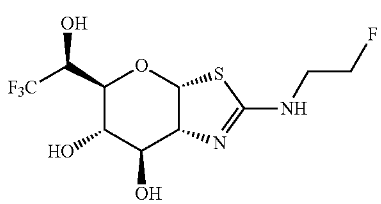 [SMILES: O[C@H]1[C@H](O)[C@@H]([C@H](O)C(F)(F)F)O[C@@H]2SC(NCCF)=N[C@H]12] | (3aR,5S,6S,7R,7aR)-2-(2-fluoroethylamino)-5-((R)-2,2,2-trifluoro-1-hydroxyethyl)-5,6,7,7a-tetrahydro-3aH-pyrano[3,2-d]thiazole-6,7-diol (Faster eluting isomer by HPLC) | 335.0 |
| 215 | 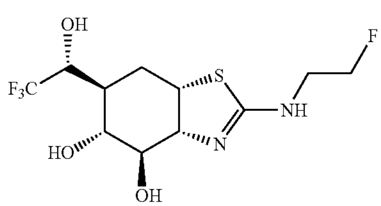 [SMILES: O[C@H]1[C@H](O)[C@H]2N=C(NCCF)S[C@H]2C[C@@H]1[C@@H](O)C(F)(F)F] | (3aR,5S,6S,7R,7aR)-2-(2-fluoroethylamino)-5-((S)-2,2,2-trifluoro-1-hydroxyethyl)-5,6,7,7a-tetrahydro-3aH-pyrano[3,2-d]thiazole-6,7-diol | 335.0 |
| 216 | 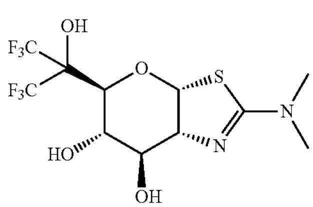 [SMILES: CN(C)C1=N[C@@H]2[C@@H](O)[C@H](O)[C@@H](C(O)(C(F)(F)F)C(F)(F)F)O[C@@H]2S1] | (3aR,5S,6S,7R,7aR)-2-(dimethylamino)-5-(1,1,1,3,3,3-hexafluoro-2-hydroxypropan-2-yl)-5,6,7,7a-tetrahydro-3aH-pyrano[3,2-d]thiazole-6,7-diol | 384.9 |
| 217 | 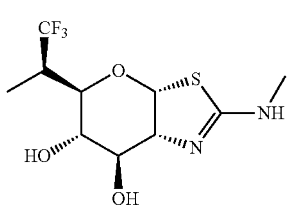 [SMILES: CNC1=N[C@@H]2[C@@H](O)[C@H](O)[C@@H]([C@@H](C)C(F)(F)F)O[C@@H]2S1] | (3aR,5R,6S,7R,7aR)-2-(methylamino)-5-((R)-1,1,1-trifluoropropan-2-yl)-5,6,7,7a-tetrahydro-3aH-pyrano[3,2-d]thiazole-6,7-diol (Faster eluting isomer by HPLC) | 301.2 |

| Example | Structure | Name | MH+ |
|---|---|---|---|
| 218 | (structure with CF$_3$, O, S, NH, N, HO, OH groups) | (3aR,5R,6S,7R,7aR)-2-(methylamino)-5-((S)-1,1,1-trifluoropropan-2-yl)-5,6,7,7a-tetrahydro-3aH-pyrano[3,2-d]thiazole-6,7-diol (Slower eluting isomer by HPLC) | 301.2 |

Biological Activity

Assay for Determination of $K_I$ Values for Inhibition of O-GlcNAcase Activity
Experimental Procedure for Kinetic Analyses Enzymatic reactions are carried out in a reaction containing 50 mM NaH$_2$PO$_4$, 100 mM NaCl and 0.1% BSA (pH 7.0) using 2 mM 4-Methylumbelliferyl N-acetyl-β-D-glucosaminide dihydrate (Sigma M2133) dissolved in ddH$_2$O, as a substrate. The amount of purified human O-GlcNAcase enzyme used in the reaction is 0.7 nM. Test compound of varying concentrations is added to the enzyme prior to initiation of the reaction. The reaction is performed at room temperature in a 96-well plate and is initiated with the addition of substrate. The production of fluorescent product is measured every 60 sec for 45 min with a Tecan Infinite M200 plate-reader with excitation at 355 nM and emission detected at 460 nM, with 4-Methylumbelliferone (Sigma M1381) used to produce a standard curve. The slope of product production is determined for each concentration of compound tested and plotted, using standard curve fitting algorithms for sigmoidal dose response curves. The values for a four parameter logistic curve fit of the data are determined.

Ki values are determined using the Cheng-Prusoff equation; the Km of O-GlcNacase for substrate is 0.2 mM.

Examples 1 to 218 were tested in the above described assay and exhibited $K_I$ values for inhibition of O-GlcNAcase in the range 0.1 nM-10 μM.

Assay for Determination of $K_I$ Values for Inhibition of β-Hexosaminidase Activity
Experimental Procedure for Kinetic Analyses Enzymatic reactions are carried out in a reaction containing 50 mM NaH$_2$PO$_4$, 100 mM NaCl and 0.1% BSA (pH 7.0) using 2 mM 4-Methylumbelliferyl N-acetyl-β-D-glueosaminide dihydrate (Sigma M2133) dissolved in ddH2O, as a substrate. The amount of purified human β hexosaminidase enzyme used in the reaction is 24 nM. Test compound of varying concentrations is added to the enzyme prior to initiation of the reaction. The reaction is performed at room temperature in a 96-well plate and is initiated with the addition of substrate. The production of fluorescent product is measured every 60 sec for 45 min with a Tecan Infinite M200 plate-reader with excitation at 355 nM and emission detected at 460 nM, with 4-Methylumbelliferone (Sigma M1381) used to produce a standard curve. The slope of product production is determined for each concentration of compound tested and plotted, using standard curve fitting algorithms for sigmoidal dose response curves. The values for a four parameter logistic curve fit of the data are determined, Ki values are determined using the Cheng-Prusoff equation.

When tested in this assay, many of the compounds described herein exhibit $K_I$ values for inhibition of β-hexosaminidase in the range 10 nM to greater than 100 μM.

The selectivity ratio for inhibition of O-GlcNAcase over β-hexosaminidase is defined here as:

$$K_I(\beta\text{-hexosamimidase})/K_I(\text{O-GlcNAcase})$$

In general, the compounds described herein exhibit a selectivity ratio in the range of about 10 to 100000. Thus, many compounds of the invention exhibit high selectivity for inhibition of O-GlcNAcase over β-hexosaminidase.

Assay for Determination of Cellular Activity for Compounds that Inhibit O-GlcNAcase Activity Inhibition of O-GlcNAcase, which removes O-GlcNAc from cellular proteins, results in an increase in the level of O-GlcNAcylated protein in cells. An increase in O-GlcNAcylated protein can be measured by an antibody, such as RL-2, that binds to O-GlcNAcylated protein. The amount of O-GlcNAcylated protein:RL2 antibody interaction can be measured by enzyme linked immunosorbant assay (ELISA) procedures.

A variety of tissue culture cell lines, expressing endogenous levels of O-GlcNAcase, can be utilized; examples include rat PC-12, and human U-87, or SK-N-SH cells. Cells are plated in 96-well plates with approximately 10,000 cells/well. Compounds to be tested are dissolved in DMSO, either 2 or 10 mM stock solution, and then diluted with DMSO and water in a two-step process using a Tecan workstation. Cells are treated with diluted compounds for 24 hours (5.4 μL into 200 μL I well volume) to reach a final concentration of inhibitor desired to measure a compound concentration dependent response, typically, ten 3 fold dilution steps, starting at 10 μM are used to determine a concentration response curve. To prepare a cell lysate, the media from compound treated cells is removed, the cells are washed once with phosphate buffered saline (PBS) and then lysed for 5 minutes at room temperature in 50 μL of Phosphosafe reagent (Novagen Inc, Madison, Wis.) with protease inhibitors and PMSF. The cell lysate is collected and transferred to a new plate, which is then either coated to assay plates directly or frozen −80° C. until used in the ELISA procedure. If desired, the total protein concentration of samples is determined using 20 μL of the sample using the BCA method.

The ELISA portion of the assay is performed in a black Maxisorp 96-well plate that is coated overnight at 4° C. with 100 μL/well of the cell lysate (1:10 dilution of the lysate with PBS containing protease inhibitors, phosphatase inhibitors, and PMSF. The following day the wells are washed 3 times with 300 μL/well of Wash buffer (Tris-buffered saline with 0.1% Tween 20). The wells are blocked with 100 μL/well Blocking buffer (Tris buffered saline w/0.05% Tween 20 and 2.5% Bovine serum albumin). Each well is then washed two times with 300 ul/well of wash buffer. The anti O-GlcNAc antibody RL-2 (Abeam, Cambridge, Mass.), diluted 1:1000 in blocking buffer, is added at 100 ul/well. The plate is sealed and incubated at 37° C. for 2 hr with gentle shaking. The wells are then washed 3-times with 300 ul/well wash buffer. To detect the amount of RL-2 bound horse-radish peroxidase (HRP) conjugated goat anti-mouse secondary antibody (diluted 1:3000 in blocking buffer) is added at 100 µL/well. The plate is incubated for 60 min at 37° C. with gentle shaking. Each wells is then washed 3-times with 300 ul/well wash buffer. The detection reagent is added, 100 µL/well of Amplex Ultra RED reagent (prepared by adding 30 µL of 10 mM Amplex Ultra Red stock solution to 10 ml PBS with 18 µL 3% hydrogen peroxide, $H_2O_2$). The detection reaction is incubated for 15 minutes at room temperature and then read with excitation at 530 nm and emission at 590 nm.

The amount of O-GlcNAcylated protein, as detected by the ELISA assay, is plotted for each concentration of test compound using standard using standard curve fitting algorithms for sigmoidal dose response curves. The values for a four parameter logistic curve fit of the data are determined, with the inflection point of the curve being the potency value for the test compound.

Representative data from the binding and cell-based assays described above are shown in the following table. Certain compounds of the invention exhibited superior potency in one or more of these assays as compared to compounds disclosed in WO 2006/092049 and WO 2008/025170,

| Example # | Cell-based ELISA EC50 (nM) | Fluorescence-based hOGA Ki (nM) |
|---|---|---|
| 1 | 2.37 | 0.17 |
| 2 | 1.34 | 0.05 |
| 3 | 16.69 | 0.90 |
| 4 | ND | 3.1 |
| 8 | 15.1 | 0.68 |
| 11 | 0.8 | 0.3 |
| 13 | ND | 0.4 |
| 25 | 9.01 | 0.70 |
| 27 | 3.23 | 0.12 |
| 40 | 139.00 | 7.95 |
| 42 | 8.75 | 1.03 |
| 47 | 187.20 | 6.40 |
| 51 | 22.22 | 5.1 |
| 53 | 9.26 | 0.7 |
| 57 | 5.90 | 0.33 |
| 61 | 25.31 | 2.46 |
| 63 | 2.57 | 0.22 |
| 65 | 2.7 | 0.45 |
| 67 | 17.13 | 1.25 |
| 69 | 134.10 | 9.36 |
| 71 | 48.83 | 9.12 |
| 76 | 3.63 | 0.18 |
| 77 | 195.80 | 16.28 |
| 80 | 5.31 | 0.5 |
| 82 | 97.17 | 5.84 |
| 91 | 11.85 | 0.53 |
| 95 | 1.05 | 0.16 |
| 96 | 4.55 | 0.19 |
| 97 | 2.79 | 0.17 |
| 98 | 15.28 | 1.43 |
| 104 | 17.50 | 3.63 |
| 105 | 14.74 | 3.4 |
| 141 | 62.7 | 0.82 |
| 159 | 27.6 | 1.25 |
| 181 | 11.3 | 0.8 |
| 191 | 20.7 | 0.14 |
| 203 | 38.2 | 3.16 |
| 211 | 19.5 | 0.44 |
| 215 | 67.5 | 1.8 |

REFERENCES

1. C. R. Torres, G. W. Hart, *J Biol Chem* 1984, 259, 3308.
2. R. S. Haltiwanger, G. D. Holt, G. W. Hart, *J Biol Chem* 1990, 265, 2563.
3. L. K. Kreppel, M. A. Blomberg, G. W. Hart, *J Biol Chem* 1997, 272, 9308.
4. W. A. Lubas, D. W. Frank, M. Krause, J. A. Hanover, *J Biol Chem* 1997, 272, 9316.
5. W. A. Lubas, J. A. Hanover, *J Biol Chem* 2000, 275, 10983.
6. D. L. Dong, G. W. Hart, *J Biol Chem* 1994, 269, 19321.
7. Y. Gao, L. Wells, F. I. Comer, Q. J. Parker, G. W. Hart, *J Biol Chem* 2001, 276, 9838.
8. E. P. Roquemore, M. R. Chevrier, R. J. Cotter, G. W. Hart, *Biochemistry* 1996, 35, 3578,
9. S. P. Jackson, R. Tjian, *Cell* 1988, 55, 125.
10. W. G. Kelly, M. E. Dahmus, G. W. Hart, *J Biol Chem* 1993, 268, 10416.
11. M. D. Roos, K. Su, J. R. Baker, J. E. Kudlow, *Mol Cell Biol* 1997, 17, 6472.
12. N. Lamarre-Vincent, L. C. Hsieh-Wilson, *J Am Chem Soc* 2003, 125, 6612.
13. F. Zhang, K. Su, X. Yang, D. B. Bowe, A. J. Paterson, J. E. Kudlow, *Cell* 2003, 115, 715.
14. K. Vosseller, L. Wells, M. D. Lane, G. W. Hart, *Proc Natl Acad Sci USA* 2002, 99, 5313.
15. W. A. Lubas, M. Smith, C. M. Starr, J. A. Hanover, *Biochemistry* 1995, 34, 1686.
16. L. S, Griffith, B. Schmitz, *Biochem Biophys Res Commun* 1995, 213, 424.
17. R. N. Cole, G. W. Hart, *J Neurochem* 1999, 73, 418.
18. I. Braidman, M. Carroll, N. Dance, D. Robinson, *Biochem* 11974, 143, 295.
19. R. Ueno, C. S. Yuan, *Biochim Biophys Acta* 1991, 1074, 79.
20. C. Toleman, A. J. Paterson, T. R. Whisenhunt, J. E. Kudlow, *J Biol Chem* 2004.
21. F. Liu, K. Iqbal, I. Grundke-Iqbal, G. W. Hart, C. X. Gong, *Proc Natl Acad Sci USA* 2004, 101, 10804.
22. T. Y. Chou, G. W. Hart, *Adv Exp Med Biol* 2001, 491, 413.
23. M. Goedert, M. G. Spillantini, N. J. Cairns, R. A. Crowther, *Neuron* 1992, 8, 159.
24. M. Goedert, M. G. Spillantini, R. Japes, D. Rutherford, R. A. Crowther, *Neuron* 1989, 3, 519.
25. E. Kopke, Y. C. Tung, S. Shaikh, A. C. Alonso, K. Iqbal, I. Grundke-Iqbal, *J Biol Chem* 1993, 268, 24374.
26. H. Ksiezak-Reding, W. K. Liu, S. H. Yen, *Brain Res* 1992, 597, 209.
27. B. Henrissat, A. Bairoch, *Biochem J* 1996, 316 (Pt 2), 695.
28. B. Henrissat, A. Bairoch, *Biochem J* 1993, 293 (Pt 3), 781.
29. C. X. Gong, F. Liu, I. Grundke-Iqbal, K. Iqbal, *J Neural Transm* 2005, 112, 813.
30. K. Iqbal, C. Alonso Adel, E. El-Akkad, C. X. Gong, N. Hague, S. Khatoon, I. Tsujio, I. Grundke-Iqbal, *J Neural Transm Suppl* 2002, 309.
31. K. Iqbal, C. Alonso Adel, E. El-Akkad, C. X. Gong, N. Hague, S. Khatoon, J. J. Pei, H. Tanimukai, I. Tsujio, et al., *J Mol Neurosci* 2003, 20, 425.
32. W. Noble, E. Planel, C. Zehr, V. Olm, J. Meyerson, F. Suleman, K. Gaynor, L. Wang, J. LaFrancois, et al., *Proc Natl Acad Sci USA* 2005, 102, 6990.
33. S. Le Corre, H. W. Klafki, N. Plesnila, G. Hubinger, A. Obermeier, H. Sahagun, B. Monse, P. Seneci, J. Lewis, et al., *Proc Natl Acad Sci USA* 2006, 103, 9673.
34. S. J. Liu, J. Y. Zhang, H. L. Li, Z. Y. Fang, Q. Wang, H, M. Deng, C. X. Gong, I. Grundke-Iqbal, K. Iqbal, et al., *J Biol Chem* 2004, 279, 50078.
35. G. Li, H. Yin, J. Kuret, *J Biol Chem* 2004, 279, 15938.
36. T. Y. Chou, G. W. Hart, C. V. Dang, *J Biol Chem* 1995, 270, 18961.
37. X. Cheng, G. W. Hart, *J Biol Chem* 2001, 276, 10570.

38. X. Cheng, R. N. Cole, J. Zaia, G. W. Hart, *Biochemistry* 2000, 39, 11609.
39. L. S. Griffith, B. Schmitz, *Eur J Biochem* 1999, 262, 824.
40. K. Kamemura, G. W. Hart, *Prog Nucleic Acid Res Mol Biol* 2003, 73, 107.
41. L. Wells, L. K. Kreppel, F. I. Comer, B. E. Wadzinski, G. W. Hart, *J Biol Chem* 2004, 279, 38466.
42. L. Bertram, D. Blacker, K. Mullin, D. Keeney, J. Jones, S. Basu, S. Yhu, M. G. McInnis, R. C. Go, et al., *Science* 2000, 290, 2302.
43. S. Hoyer, D. Blum-Degen, H. G. Bernstein, S. Engelsberger, J. Humrich, S. Laufer, D. Muschner, A. Thalheimer, A. Turk, et al., *Journal of Neural Transmission* 1998, 105, 423.
44. C. X. Gong, F. Liu, 1. Grundke-Iqbal, K. Iqbal, *Journal of Alzheimers Disease* 2006, 9, 1.
45. W. J. Jagust, J. P. Seab, R. H. Huesman, P. E. Valk, C. A. Mathis, B. R. Reed, P. G. Coxson, T. F. Budinger, *Journal of Cerebral Blood Flow and Metabolism* 1991, 11, 323.
46. S. Hoyer, *Experimental Gerontology* 2000, 35, 1363.
47. S. Hoyer, in *Frontiers in Clinical Neuroscience: Neurodegeneration and Neuroprotection, Vol.* 541, 2004, pp. 135.
48. R. N. Kalaria, S. I. Harik, *Journal of Neurochemistry* 1989, 53, 1083.
49. I. A. Simpson, K. R. Chundu, T. Davieshill, W. G. Honer, P. Davies, *Annals of Neurology* 1994, 35, 546.
50. S. M. de la Monte, J. R. Wands, *Journal of Alzheimers Disease* 2005, 7, 45.
51. X. W. Zhu, G. Perry, M. A. Smith, *Journal of Alzheimers Disease* 2005, 7, 81.
52. J. C. de la Torre, *Neurological Research* 2004, 26, 517.
53. S. Marshall, W. T. Garvey, R. R. Traxinger, *Faseb J* 1991, 5, 3031.
54. S. P. Iyer, Y. Akimoto, G. W. Hart, *J Biol Chem* 2003, 278, 5399.
55. K. Brickley, M. J. Smith, M. Beck, F. A. Stephenson, *J Biol Chem* 2005, 280, 14723.
56. S. Knapp, C. H. Yang, T. Haimowitz, *Tetrahedron Letters* 2002, 43, 7101.
57. S. P. Iyer, G. W. Hart, *J Biol Chem* 2003, 278, 24608.
58. M. Jinek, J. Rehwinkel, B. D. Lazarus, E. Izaurralde, J. A. Hanover, E. Conti, *Nat Struct Mol Biol* 2004, 11, 1001.
59. K. Kamemura, B. K. Hayes, F. I. Corner, G. W. Hart, *J Biol Chem* 2002, 277, 19229.
60. Y. Deng, B. Li, F. Liu, K. Iqbal, I. Grundke-Iqbal, R. Brandt, C.-X. Gong, *FASEB J* 2007, fj.07.
61. L. F. Lau, J. B. Schachter, P. A. Seymour, M, A. Sanner, *Curr Top Med Chem* 2002, 2, 395.
62. M. P. Mazanetz, P. M. Fischer, *Nature Reviews Drug Discovery* 2007, 6, 464.
63. S. A. Yuzwa, M. S. Macauley, J, E, Heinonen, X. Shan, R. J. Dennis, Y. He, G. E. Whitworth, K. A. Stubbs, E. J. McEachern, et al., *Nat Chem Biol* 2008, 4, 483.
64. P. Bounelis, J. Liu, Y. Pang, J. C. Chatham, R. B. Marchase, *Shock* 2004, 21 170 Suppl. 2, 58.
65. N. Fulop, V. Champattanachal, R. B. Marchase, J. C. Chatham, *Circulation Research* 2005, 97, E28.
66. J. Liu, R. B. Marchase, J. C. Chatham, *Faseb Journal* 2006, 20, A317.
67. R. Marchase, P. Bounelis, J. Chatham, I. Chaudry, Y. Pang, PCT Int. Appl. WO 2006016904 2006.
68. N. Fulop, P. P. Wang, R. B. Marchase, J. C. Chatham, *Journal of Molecular and Cellular Cardiology* 2004, 37, 286.
69. N. Fulop, P. P. Wang, R. B. Marchase, J. C. Chatham, *Faseb Journal* 2005, 19, A689.
70. J. Liu, R. B. Marchase, J. C. Chatham, *Journal of Molecular and Cellular Cardiology* 2007, 42, 177.
71. L. G. Not, C. A. Brocks, N. Fulop, R. B. Marchase, J. C. Chatham, *Faseb Journal* 2006, 20, A1471.
72. S. L. Yang, L. Y. Zou, P. Bounelis, I. Chaudry, J. C. Chatham, R. B. Marchase, *Shock* 2006, 25, 600.
73. L. Y. Zou, S. L. Yang, P. Bounelis, I. H. Chaudry, J. C. Chatham, R. B. Marchase, *Faseb Journal* 2005, 19, A1224.
74. R. B. Marchase, J. Liu, L. Y. Zou, V. Champattanachai, Y. Pang, N. Fulop, P. P. Wang, S. L. Yang, P. Bounelis, et al., *Circulation* 2004, 110, 1099.
75. J. Liu, Y. Pang, T. Chang, P. Bounelis, J. C. Chatham, R. B. Marchase, *Journal of Molecular and Cellular Cardiology* 2006, 40, 303.
76. J. Liu, J. C. Chatham, R. B. Marchase, *Faseb Journal* 2005, 19, A691.
77. T. Nagy, V. Champattanachai, R. B. Marchase, J. C. Chatham, *American Journal of Physiology-Cell Physiology* 2006, 290, C57.
78. N. Fulop, R. B. Marchase, J. C. Chatham, *Cardiovascular Research* 2007, 73, 288.
79. T. Lefebvre, C. Guinez, V. Dehennaut, O. Beseme-Dekeyser, W. Morelle, J. C. Michalski, *Expert Review of Proteomics* 2005, 2, 265.
80. L. Wells, K. Vosseller, G. W. Hart, *Science* 2001, 291, 2376.
81. J. A. Hanover, *FASEB J* 2001, 15, 1865.
82. D. A. McClain, W. A. Lubas, R. C. Cooksey, M. Hazel, 0. J, Parker, D. C. Love, J. A. Hanover, *Proc Natl Acad Sci USA* 2002, 99, 10695.
83. P. J. Yao, P. D. Coleman, *J Neurosci* 1998, 18, 2399.
84. W. H. Yang, J. E. Kim, H. W. Nam, J. W. Ju, H. S. Kim, Y. S. Kim, J. W. Cho, *Nature Cell Biology* 2006, 8, 1074.
85. B. Triggs-Raine, D. J. Mahuran, R. A. Gravel, *Adv Genet* 2001, 44, 199.
86. D. Zhou, J. Mattner, C. Cantu Iii, N. Schrantz, N. Yin, Y. Gao, Y. Sagiv, K. Hudspeth, Y. Wu, et al., *Science* 2004.
87. G. Legler, E. Lullau, E. Kappes, F. Kastenholz, *Biochim Biophys Acta* 1991, 1080, 89.
88. M. Horsch, L. Hoesch, A. Vasella, D. M. Rast, *Eur J Biochem* 1991, 197, 815.
89. J. Liu, A. R. Shikhman, M. K. Lotz, C. H. Wong, *Chem Biol* 2001, 8, 701.
90. S. Knapp, D. J. Vocadlo, Z. N. Gao, B. Kirk, J. P. Lou, S. G. Withers, *J. Am. Chem. Soc.* 1996, 118, 6804.
91. V. H. Lillelund, H. H. Jensen, X. Liang, M. Bols, *Chem Rev* 2002, 102, 515.
92. R. J. Konrad, I. Mikolaenko, J. F. Tolar, K. Liu, 3. E. Kudlow, *Biochem J* 2001, 356, 31.
93. K. Liu, A. J. Paterson, F. Zhang, J. McAndrew, K. Fukuchi, J. M. Wyss, L. Peng, Y. Hu, J. E. Kudlow, *J Neurochem* 2004, 89, 1044.
94. G. Parker, R. Taylor, D. Jones, D. McClain, *J Biol Chem* 2004, 279, 20636.
95. E. B. Arias, J. Kim, G. D. Cartee, *Diabetes* 2004, 53, 921.
96. A. Junod, A. E. Lambert, L. Orci, R. Pictet, A. E. Gonet, A. E. Renold, *Proc Soc Exp Biol Med* 1967, 126, 201,
97. R. A. Bennett, A. E. Pegg, *Cancer Res* 1981, 41, 2786.
98. K. D. Kroncke, K. Fehsel, A. Sommer, M. L. Rodriguez, V. Kolb-Bachofen, *Biol Chem Hoppe Seyler* 1995, 376, 179.
99. H. Yamamoto, Y, Uchigata, H. Okamoto, *Nature* 1981, 294, 284.
100. K. Yamada, K. Nonaka, T. Hanafusa, A. Miyazaki, H. Toyoshima, S. Tarui, *Diabetes* 1982, 31, 749.
101. V. Burkart, Z. Q. Wang, J. Radons, B. Heller, Z. Herceg, L. Stingl, E. F. Wagner, H. Kolb, *Nat Med* 1999, 5, 314.

102. M. D. Roos, W. Xie, K. Su, J. A. Clark, X. Yang, E. Chin, A. J. Paterson, J. E, Kudlow, Proc Assoc Am Physicians 1998, 110, 422.

103. Y. Gao, G. J. Parker, G. W. Hart, Arch Biochem Biophys 2000, 383, 296.

104. R. Okuyama, M. Yachi, *Biochem Biophys Res Commun* 2001, 287, 366.

105. N. E. Zachara, N. O'Donnell, W. D. Cheung, J. J. Mercer, J. D. Marth, G. W. Hart, *J Biol Chem* 2004, 279, 30133.

106. J. A. Hanover, Z. Lai, G. Lee, W. A. Lubas, S. M. Sato, *Arch Biochem Biophys* 1999, 362, 38.

107. K. Liu, A. J. Paterson, R. 3. Konrad, A. F. Parlow, S. Jimi, M. Roh, E. Chin, Jr., J. E. Kudlow, *Mol Cell Endocrinol* 2002, 194, 135.

108. M. S. Macauley, G. E. Whitworth, A. W. Debowski, D. Chin, D. J. Vocadlo, *J Biol Chem* 2005, 280, 25313.

109. B. L. Mark, D. J. Vocadlo, S. Knapp, B. L. Triggs-Raine, S. G. Withers, M. N. James, *J Biol Chem* 2001, 276, 10330.

110. R. S. Haltiwanger, K. Grove, G. A. Philipsberg, *J Biol Chem* 1998, 273, 3611.

111. D. J. Miller, X. Gong, B. D. Shur, *Development* 1993, 118, 1279.

112. L. Y, Zou, S. L. Yang, S. H. Hu, I. H. Chaudry, R. B. Marchase, J. C. Chatham, *Shock* 2007, 27, 402.

113. J. B. Huang, A. J. Clark, H. R. Petty, *Cellular Immunology* 2007, 245, 1.

114. U. J. G. Conference, in *US/Japan Glyco* 2004 *Conference*, Honolulu, Hi., 2004.

115. L. Y. Zou, S. L. Yang, S. H. Hu, I. H. Chaudry, R. B. Marchase, J. C. Chatham, *Faseb Journal* 2006, 20, A1471.

116. V. Champattanachai, R. B. Marchase, J. C. Chatham, *American Journal of Physiology-Cell Physiology* 2007, 292, C178.

117. V. Champattanachai, R. B. Marchase, J. C. Chatham, *American Journal of Physiology-Cell Physiology* 2008, 294, C1509.

118.1. Khlistunova, M. Pickhardt, J. Biernat, Y. P. Wang, E. M. Mandelkow, E. Mandelkow, *Current Alzheimer Research* 2007, 4, 544.

119. P. Friedhoff, A. Schneider, E. M. Mandelkow, E. Mandelkow, *Biochemistry* 1998, 37, 10223.

120. M. Pickhardt, Z. Gazova, M. von Bergen, I. Khlistunova, Y. P. Wang, A. Hascher, E. M. Mandelkow, J. Biernat, E. Mandelkow, *Journal of Biological Chemistry* 2005, 280, 3628.

121. P. H. Liang, W. C. Cheng, Y. L. Lee, H. P. Yu, Y. T. Wu, Y. L. Lin, C. H. Wong, *Chembiochem* 2006, 7, 165.

122. J. J. Liu, M. M. D. Numa, H. T. Liu, S. J. Huang, P. Sears, A. R. Shikhman, C. H. Wong, *Journal of Organic Chemistry* 2004, 69, 6273, 123. Y. Takaoka, T. Kajimoto, C. H. Wong, *Journal of Organic Chemistry* 1993, 58, 4809.

124. T. M. Wrodnigg, A. E. Stutz, S. G. Withers, *Tetrahedron Letters* 1997, 38, 5463.

What is claimed is:

1. A compound of Formula (I) or a pharmaceutically acceptable salt thereof:

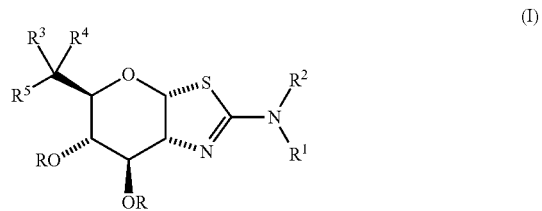

(I)

wherein:
each R is independently H or $C(O)CH_3$;
$R^1$ and $R^2$ are independently selected from the group consisting of: H, $C_{1-6}$alkyl, $C_{2-6}$alkenyl, $C_{1-6}$alkoxy, —$(CH_2)_n$-cyclopropyl and —$(CH_2)_n$-cyclobutyl wherein n is 0, 1, 2, 3 or 4; or $R^1$ and $R^2$ may be joined together with the nitrogen atom to which they are attached to form azetidine, pyrrolidine, piperidine or isoxazolidine, said $C_{1-6}$alkyl, $C_{2-6}$alkenyl, $C_{1-6}$alkoxy, —$(CH_2)_n$-cyclopropyl, —$(CH_2)_n$-cyclobutyl, azetidine, pyrrolidine, piperidine and isoxazolidine optionally substituted from one up to the maximum number of substituents with fluoro, hydroxy and methyl;
$R^3$ is selected from the group consisting of: $C_{1-8}$alkyl, $C_{2-8}$alkenyl, $C_{2-8}$alkynyl, $C_{3-6}$cycloalkyl, aryl and heteroaryl, each optionally substituted from one up to the maximum number of substituents with fluoro and OH;
$R^4$ is selected from the group consisting of: H, F, $C_{1-8}$alkyl, $C_{2-8}$alkenyl and $C_{2-8}$alkynyl, each excluding hydrogen optionally substituted from one up to the maximum number of substituents with fluoro and OH; or $R^3$ and $R^4$ and the carbon atom to which they are attached may join together to form vinyl or a 3 to 7-membered carbocyclic or heterocyclic ring, said 3 to 7-membered carbocyclic or heterocyclic ring optionally containing a double bond and optionally substituted from one up to the maximum number of substituents with fluoro and OH; and
$R^5$ is selected from H, F, OH and $OC(O)CH_3$;
with the proviso that when $R^4$ is F then $R^5$ is other than OH and $OC(O)CH_3$.

2. The compound of claim 1 or a pharmaceutically acceptable salt thereof, wherein $R^1$ and $R^2$ are independently selected from the group consisting of: H, $C_{1-6}$alkyl, $C_{1-6}$alkoxy, —$(CH_2)_n$-cyclopropyl and —$(CH_2)_n$-cyclobutyl wherein n is 0, 1, 2, 3 or 4; or $R^1$ and $R^2$ may be joined together with the nitrogen atom to which they are attached to form azetidine, pyrrolidine or piperidine, said $C_{1-6}$alkyl, $C_{1-6}$alkoxy, —$(CH_2)_n$-cyclopropyl, —$(CH_2)_n$-cyclobutyl, azetidine, pyrrolidine and piperidine optionally substituted from one up to the maximum number of substituents with fluoro and methyl.

3. The compound according to claim 2 of Formula (Ia) or a pharmaceutically acceptable salt thereof:

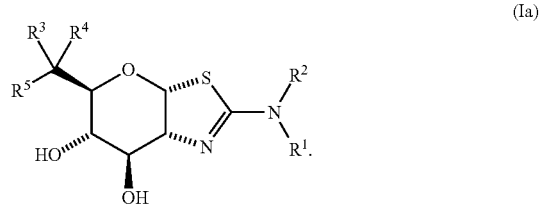

(Ia)

4. The compound according to claim 3 or a pharmaceutically acceptable salt thereof, wherein:

R¹ and R² are independently $C_{1-4}$alkyl;

R³ is $C_{1-6}$alkyl;

R⁴ is selected from the group consisting of: H and $C_{1-6}$alkyl; and

R⁵ is OH.

5. The compound according to claim 4 or a pharmaceutically acceptable salt thereof, wherein:

R¹ and R² are independently methyl or ethyl;

R³ is methyl or ethyl; and

R⁴ is selected from the group consisting of: H, methyl and ethyl.

6. The compound according to claim 3 or a pharmaceutically acceptable salt thereof, wherein R³ and R⁴ and the carbon atom to which they are attached may join together to form a 3 to 7-membered carbocyclic or heterocyclic ring, said 3 to 7-membered carbocyclic or heterocyclic ring optionally containing a double bond and optionally substituted from one up to the maximum number of substituents with fluoro and OH.

7. The compound according to claim 3 or a pharmaceutically acceptable salt thereof, wherein:

R¹ and R² are independently selected from the group consisting of: H, $C_{1-6}$alkyl and cyclopropylmethyl; or R¹ and R² may be joined together with the nitrogen atom to which they are attached to form azetidine or pyrrolidine, said $C_{1-6}$alkyl, cyclopropylmethyl, azetidine or pyrrolidine optionally substituted with 1 to 3 substituents selected from fluoro and methyl;

R³ is selected from the group consisting of: $C_{1-8}$alkyl, $C_{2-8}$alkenyl, $C_{2-8}$alkynyl and $C_{3-6}$cycloalkyl, each optionally substituted with 1 to 3 substituents selected from fluoro and OH; and R⁴ is selected from the group consisting of: H, F, $C_{1-8}$alkyl, $C_{2-8}$alkenyl and $C_{2-8}$alkynyl, each excluding hydrogen optionally substituted with 1 to 3 substituents selected from fluoro and OH; or R³ and R⁴ and the carbon atom to which they are attached may join together to form a 5-membered carbocyclic ring optionally containing a double bond and optionally substituted with 1 to 3 substituents selected from fluoro and OH.

8. The compound according to claim 3 or a pharmaceutically acceptable salt thereof, wherein R³ is $CF_3$ and R⁵ is OH.

9. A compound which is selected from the group consisting of:

(3aR,5R,6S,7R,7aR)-2-(Dimethylamino)-5-((S)-1-hydroxyethyl)-5,6,7,7a-tetrahydro-3aH-pyrano[3,2-d]thiazole-6,7-diol;

(3aR,6S,7R,7aR)-5-((S)-1-hydroxyethyl)-2-(propylamino)-5,6,7,7a-tetrahydro-3aH-pyrano[3,2-d]thiazole-6,7-diol;

(3aR,5S,6S,7R,7aR)-5-(2-Hydroxypropan-2-yl)-2-(methylamino)-5,6,7,7a-tetrahydro-3aH-pyrano[3,2-d]thiazole-6,7-diol;

(3aR,5S,6S,7R,7aR)-2-(dimethylamino)-5-(2-hydroxypropan-2-yl)-5,6,7,7a-tetrahydro-3aH-pyrano[3,2-d]thiazole-6,7-diol;

(3aR,5R,6S,7R,7aR)-2-(Dimethylamino)-5-(2-hydroxyethyl)-5,6,7,7a-tetrahydro-3aH-pyrano[3,2-d]thiazole-6,7-diol;

(3aR,5R,6S,7R,7aR)-2-(Dimethylamino)-5-ethyl-5,6,7,7a-tetrahydro-3aH-pyrano[3,2-d]thiazole-6,7-diol;

(3aR,5R,6S,7R,7aR)-2-(dimethylamino)-5-vinyl-5,6,7,7a-tetrahydro-3aH-pyrano[3,2-d]thiazole-6,7-diol;

(3aR,5R,6S,7R,7aR)-5-Ethyl-2-(methylamino)-5,6,7,7a-tetrahydro-3aH-pyrano[3,2-d]thiazole-6,7-diol;

(3aR,5S,6S,7R,7aR)-2-(Dimethylamino)-5-((S)-1-fluoroethyl)-5,6,7,7a-tetrahydro-3aH-pyrano[3,2-d]thiazole-6,7-diol;

(3aR,5S,6S,7R,7aR)-2-(dimethylamino)-5-((S)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(dimethylamino)-5-((R)-2,2,2-trifluoro-1-hydroxyethyl)-5,6,7,7a-tetrahydro-3aH-pyrano[3,2-d]thiazole-6,7-diol;

(3aR,5S,6S,7R,7aR)-5-(1,1-Difluoroethyl)-2-(dimethylamino)-5,6,7,7a-tetrahydro-3aH-pyrano[3,2-d]thiazole-6,7-diol;

(3aR,5R,6S,7R,7aR)-5-((S)-1-hydroxyethyl)-2-(methylamino)-5,6,7,7a-tetrahydro-3aH-pyrano[3,2-d]thiazole-6,7-diol;

(3aR,5R,6S,7R,7aR)-5-((R)-1-hydroxyethyl)-2-(methylamino)-5,6,7,7a-tetrahydro-3aH-pyrano[3,2-d]thiazole-6,7-diol;

(3aR,5R,6S,7R,7aR)-5-((S)-1-hydroxypropyl)-2-(methylamino)-5,6,7,7a-tetrahydro-3aH-pyrano[3,2-d]thiazole-6,7-diol;

(3aR,5R,6S,7R,7aR)-5-((R)-1-hydroxypropyl)-2-(methylamino)-5,6,7,7a-tetrahydro-3aH-pyrano[3,2-d]thiazole-6,7-diol;

(3aR,5R,6S,7R,7aR)-5-(1-hydroxy-2-methylpropyl)-2-(methylamino)-5,6,7,7a-tetrahydro-3aH-pyrano[3,2-d]thiazole-6,7-diol;

(3aR,5R,6S,7R,7aR)-5-(cyclopropyl(hydroxy)methyl)-2-(methylamino)-5,6,7,7a-tetrahydro-3aH-pyrano[3,2-d]thiazole-6,7-diol;

(3aR,5R,6S,7R,7aR)-5-(hydroxy(pyridin-3-yl)methyl)-2-(methylamino)-5,6,7,7a-tetrahydro-3aH-pyrano[3,2-d]thiazole-6,7-diol;

(3aR,5R,6S,7R,7aR)-5-(hydroxy(phenyl)methyl)-2-(methylamino)-5,6,7,7a-tetrahydro-3aH-pyrano[3,2-d]thiazole-6,7-diol;

(3aR,5R,6S,7R,7aR)-5-((R)-1-hydroxyallyl)-2-(methylamino)-5,6,7,7a-tetrahydro-3aH-pyrano[3,2-d]thiazole-6,7-diol;

(3aR,5R,6S,7R,7aR)-5-((S)-1-hydroxyallyl)-2-(methylamino)-5,6,7,7a-tetrahydro-3aH-pyrano[3,2-d]thiazole-6,7-diol;

(3aR,5R,6S,7R,7aR)-5-((R)-1-hydroxy-2-methylallyl)-2-(methylamino)-5,6,7,7a-tetrahydro-3aH-pyrano[3,2-d]thiazole-6,7-diol;

(3aR,5R,6S,7R,7aR)-5-((R)-1-hydroxybut-3-enyl)-2-(methylamino)-5,6,7,7a-tetrahydro-3aH-pyrano[3,2-d]thiazole-6,7-diol;

(3aR,5R,6S,7R,7aR)-5-((S)-1-hydroxybut-3-enyl)-2-(methylamino)-5,6,7,7a-tetrahydro-3aH-pyrano[3,2-d]thiazole-6,7-diol;

(3aR,5R,6S,7R,7aR)-2-(ethylamino)-5-((R)-1-hydroxyethyl)-5,6,7,7a-tetrahydro-3aH-pyrano[3,2-d]thiazole-6,7-diol;

(3aR,5R,6S,7R,7aR)-2-(ethylamino)-5-((S)-1-hydroxyethyl)-5,6,7,7a-tetrahydro-3aH-pyrano[3,2-d]thiazole-6,7-diol;

(3aR,5R,6S,7R,7aR)-5-((S)-cyclopropyl(hydroxy)methyl)-2-(ethylamino)-5,6,7,7a-tetrahydro-3aH-pyrano[3,2-d]thiazole-6,7-diol;

(3aR,5R,6S,7R,7aR)-2-(ethylamino)-5-(1-hydroxy-2-methylpropyl)-5,6,7,7a-tetrahydro-3aH-pyrano[3,2-d]thiazole-6,7-diol;

(3aR,5R,6S,7R,7aR)-2-(ethylamino)-5-(hydroxy(phenyl)methyl)-5,6,7,7a-tetrahydro-3aH-pyrano[3,2-d]thiazole-6,7-diol;

(3aR,5R,6S,7R,7aR)-2-(ethylamino)-5-((R)-1-hydroxyallyl)-5,6,7,7a-tetrahydro-3aH-pyrano[3,2-d]thiazole-6,7-diol;

- (3aR,5R,6S,7R,7aR)-2-(ethylamino)-5-((S)-1-hydroxyallyl)-5,6,7,7a-tetrahydro-3aH-pyrano[3,2-d]thiazole-6,7-diol;
- (3aR,5R,6S,7R,7aR)-2-(ethylamino)-5-(2-hydroxypropan-2-yl)-5,6,7,7a-tetrahydro-3aH-pyrano[3,2-d]thiazole-6,7-diol;
- (3aR,5R,6S,7R,7aR)-2-(ethylamino)-5-((R)-1-hydroxy-2-methylallyl)-5,6,7,7a-tetrahydro-3aH-pyrano[3,2-d]thiazole-6,7-diol;
- (3aR,5R,6S,7R,7aR)-2-(ethylamino)-5-((R)-1-hydroxybutyl)-5,6,7,7a-tetrahydro-3aH-pyrano[3,2-d]thiazole-6,7-diol;
- (3aR,5R,6S,7R,7aR)-2-(ethylamino)-5-((S)-1-hydroxybutyl)-5,6,7,7a-tetrahydro-3aH-pyrano[3,2-d]thiazole-6,7-diol;
- (3aR,5R,6S,7R,7aR)-2-(ethylamino)-5-((R)-1-hydroxypentyl)-5,6,7,7a-tetrahydro-3aH-pyrano[3,2-d]thiazole-6,7-diol;
- (3aR,5R,6S,7R,7aR)-2-(ethylamino)-5-((S)-1-hydroxypentyl)-5,6,7,7a-tetrahydro-3aH-pyrano[3,2-d]thiazole-6,7-diol;
- (3aR,5R,6S,7R,7aR)-2-(ethylamino)-5-((R)-1-hydroxybut-3-enyl)-5,6,7,7a-tetrahydro-3aH-pyrano[3,2-d]thiazole-6,7-diol;
- (3aR,5R,6S,7R,7aR)-2-(ethylamino)-5-((S)-1-hydroxybut-3-enyl)-5,6,7,7a-tetrahydro-3aH-pyrano[3,2-d]thiazole-6,7-diol;
- (3aR,5S,6S,7R,7aR)-5-(2-hydroxypropan-2-yl)-2-(propylamino)-5,6,7,7a-tetrahydro-3aH-pyrano[3,2-d]thiazole-6,7-diol;
- (3aR,5R,6S,7R,7aR)-5-((S)-1-hydroxyallyl)-2-(propylamino)-5,6,7,7a-tetrahydro-3aH-pyrano[3,2-d]thiazole-6,7-diol;
- (3aR,5R,6S,7R,7aR)-5-((R)-1-hydroxybutyl)-2-(propylamino)-5,6,7,7a-tetrahydro-3aH-pyrano[3,2-d]thiazole-6,7-diol;
- (3aR,5R,6S,7R,7aR)-5-((S)-1-hydroxybutyl)-2-(propylamino)-5,6,7,7a-tetrahydro-3aH-pyrano[3,2-d]thiazole-6,7-diol;
- (3aR,5R,6S,7R,7aR)-5-((R)-1-hydroxypentyl)-2-(propylamino)-5,6,7,7a-tetrahydro-3aH-pyrano[3,2-d]thiazole-6,7-diol;
- (3aR,5R,6S,7R,7aR)-5-((S)-1-hydroxypentyl)-2-(propylamino)-5,6,7,7a-tetrahydro-3aH-pyrano[3,2-d]thiazole-6,7-diol;
- (3aR,5R,6S,7R,7aR)-5-(1-hydroxypropyl)-2-(propylamino)-5,6,7,7a-tetrahydro-3aH-pyrano[3,2-d]thiazole-6,7-diol;
- (3aR,5R,6S,7R,7aR)-5-((R)-1-hydroxybut-3-enyl)-2-(propylamino)-5,6,7,7a-tetrahydro-3aH-pyrano[3,2-d]thiazole-6,7-diol;
- (3aR,5R,6S,7R,7aR)-5-((S)-1-hydroxybut-3-enyl)-2-(propylamino)-5,6,7,7a-tetrahydro-3aH-pyrano[3,2-d]thiazole-6,7-diol;
- (3aR,5R,6S,7R,7aR)-5-((R)-1-hydroxyethyl)-2-(methoxy(methyl)amino)-5,6,7,7a-tetrahydro-3aH-pyrano[3,2-d]thiazole-6,7-diol;
- (3aR,5R,6S,7R,7aR)-5-((S)-1-hydroxyethyl)-2-(methoxy(methyl)amino)-5,6,7,7a-tetrahydro-3aH-pyrano[3,2-d]thiazole-6,7-diol;
- (3aR,5R,6S,7R,7aR)-2-(cyclopropylmethylamino)-5-((R)-1-hydroxyethyl)-5,6,7,7a-tetrahydro-3aH-pyrano[3,2-d]thiazole-6,7-diol;
- (3aR,5R,6S,7R,7aR)-2-(cyclopropylmethylamino)-5-((S)-1-hydroxyethyl)-5,6,7,7a-tetrahydro-3aH-pyrano[3,2-d]thiazole-6,7-diol;
- (3aR,5R,6S,7R,7aR)-2-(ethyl(methyl)amino)-5-((S)-1-hydroxybut-3-enyl)-5,6,7,7a-tetrahydro-3aH-pyrano[3,2-d]thiazole-6,7-diol;
- (3aR,5R,6S,7R,7aR)-2-(ethyl(methyl)amino)-5-((R)-1-hydroxybut-3-enyl)-5,6,7,7a-tetrahydro-3aH-pyrano[3,2-d]thiazole-6,7-diol;
- (3aR,5S,6S,7R,7aR)-2-(ethyl(methyl)amino)-5-(2-hydroxypropan-2-yl)-5,6,7,7a-tetrahydro-3aH-pyrano[3,2-d]thiazole-6,7-diol;
- (3aR,5R,6S,7R,7aR)-2-(ethyl(methyl)amino)-5-(1-hydroxyethyl)-5,6,7,7a-tetrahydro-3aH-pyrano[3,2-d]thiazole-6,7-diol;
- (3aR,5R,6S,7R,7aR)-2-(ethyl(methyl)amino)-5-((R)-1-hydroxypropyl)-5,6,7,7a-tetrahydro-3aH-pyrano[3,2-d]thiazole-6,7-diol;
- (3aR,5R,6S,7R,7aR)-2-(ethyl(methyl)amino)-5-(1-hydroxypropyl)-5,6,7,7a-tetrahydro-3aH-pyrano[3,2-d]thiazole-6,7-diol;
- (3aR,5S,6S,7R,7aR)-2-(ethyl(methyl)amino)-5-((R)-1-hydroxyallyl)-5,6,7,7a-tetrahydro-3aH-pyrano[3,2-d]thiazole-6,7-diol;
- (3aR,5S,6S,7R,7aR)-2-(ethyl(methyl)amino)-5-(1-hydroxyallyl)-5,6,7,7a-tetrahydro-3aH-pyrano[3,2-d]thiazole-6,7-diol;
- (3aR,5R,6S,7R,7aR)-2-(dimethylamino)-5-((S)-1-hydroxypropyl)-5,6,7,7a-tetrahydro-3aH-pyrano[3,2-d]thiazole-6,7-diol;
- (3aR,5R,6S,7R,7aR)-2-(dimethylamino)-5-((S)-1-hydroxyallyl)-5,6,7,7a-tetrahydro-3aH-pyrano[3,2-d]thiazole-6,7-diol;
- (3aR,5R,6S,7R,7aR)-2-(dimethylamino)-5-((R)-1-hydroxy-2-methylallyl)-5,6,7,7a-tetrahydro-3aH-pyrano[3,2-d]thiazole-6,7-diol;
- (3aR,5R,6S,7R,7aR)-2-(dimethylamino)-5-((S)-1-hydroxy-2-methylallyl)-5,6,7,7a-tetrahydro-3aH-pyrano[3,2-d]thiazole-6,7-diol;
- (3aR,5R,6S,7R,7aR)-2-(dimethylamino)-5-((R)-1-hydroxybut-3-enyl)-5,6,7,7a-tetrahydro-3aH-pyrano[3,2-d]thiazole-6,7-diol;
- (3aR,5R,6S,7R,7aR)-2-(dimethylamino)-5-((S)-1-hydroxybut-3-enyl)-5,6,7,7a-tetrahydro-3aH-pyrano[3,2-d]thiazole-6,7-diol;
- (3aR,5R,6S,7R,7aR)-2-(dimethylamino)-5-((R)-1-hydroxybutyl)-5,6,7,7a-tetrahydro-3aH-pyrano[3,2-d]thiazole-6,7-diol;
- (3aR,5R,6S,7R,7aR)-2-(dimethylamino)-5-((S)-1-hydroxybutyl)-5,6,7,7a-tetrahydro-3aH-pyrano[3,2-d]thiazole-6,7-diol;
- (3aR,5R,6S,7R,7aR)-2-(dimethylamino)-5-((R)-1-hydroxypentyl)-5,6,7,7a-tetrahydro-3aH-pyrano[3,2-d]thiazole-6,7-diol;
- (3aR,5R,6S,7R,7aR)-2-(dimethylamino)-5-((S)-1-hydroxypentyl)-5,6,7,7a-tetrahydro-3aH-pyrano[3,2-d]thiazole-6,7-diol;
- (3aR,5R,6S,7R,7aR)-2-(dimethylamino)-5-((S)-1-hydroxyhexyl)-5,6,7,7a-tetrahydro-3aH-pyrano[3,2-d]thiazole-6,7-diol;
- (3aR,5R,6S,7R,7aR)-2-(dimethylamino)-5-((R)-1-hydroxyheptyl)-5,6,7,7a-tetrahydro-3aH-pyrano[3,2-d]thiazole-6,7-diol;
- (3aR,5R,6S,7R,7aR)-2-(dimethylamino)-5-((S)-1-hydroxyheptyl)-5,6,7,7a-tetrahydro-3aH-pyrano[3,2-d]thiazole-6,7-diol;
- (3aR,5R,6S,7R,7aR)-2-(azetidin-1-yl)-5-((R)-1-hydroxyethyl)-5,6,7,7a-tetrahydro-3aH-pyrano[3,2-d]thiazole-6,7-diol;

(3aR,5R,6S,7R,7aR)-2-(azetidin-1-yl)-5-((S)-1-hydroxyethyl)-5,6,7,7a-tetrahydro-3aH-pyrano[3,2-d]thiazole-6,7-diol;

(3aR,5S,6S,7R,7aR)-2-(azetidin-1-yl)-5-(2-hydroxypropan-2-yl)-5,6,7,7a-tetrahydro-3aH-pyrano[3,2-d]thiazole-6,7-diol;

(3aR,5R,6S,7R,7aR)-2-(azetidin-1-yl)-5-((S)-1-hydroxypropyl)-5,6,7,7a-tetrahydro-3aH-pyrano[3,2-d]thiazole-6,7-diol;

(3aR,5R,6S,7R,7aR)-2-(azetidin-1-yl)-5-((R)-1-hydroxyallyl)-5,6,7,7a-tetrahydro-3aH-pyrano[3,2-d]thiazole-6,7-diol;

(3aR,5R,6S,7R,7aR)-2-(azetidin-1-yl)-5-((S)-1-hydroxyallyl)-5,6,7,7a-tetrahydro-3aH-pyrano[3,2-d]thiazole-6,7-diol;

(3aR,5R,6S,7R,7aR)-2-(azetidin-1-yl)-5-((R)-1-hydroxybut-3-enyl)-5,6,7,7a-tetrahydro-3aH-pyrano[3,2-d]thiazole-6,7-diol;

(3aR,5R,6S,7R,7aR)-2-(azetidin-1-yl)-5-((S)-1-hydroxybut-3-enyl)-5,6,7,7a-tetrahydro-3aH-pyrano[3,2-d]thiazole-6,7-diol;

(3aR,5S,6S,7R,7aR)-5-(2-hydroxypropan-2-yl)-2-(methyl(propyl)amino)-5,6,7,7a-tetrahydro-3aH-pyrano[3,2-d]thiazole-6,7-diol;

(3aR,5R,6S,7R,7aR)-5-(1-hydroxypropyl)-2-(methyl(propyl)amino)-5,6,7,7a-tetrahydro-3aH-pyrano[3,2-d]thiazole-6,7-diol;

(3aR,5R,6S,7R,7aR)-5-((S)-1-hydroxyethyl)-2-(methyl(propyl)amino)-5,6,7,7a-tetrahydro-3aH-pyrano[3,2-d]thiazole-6,7-diol;

(3aR,5R,6S,7R,7aR)-5-((R)-1-hydroxyallyl)-2-(methyl(propyl)amino)-5,6,7,7a-tetrahydro-3aH-pyrano[3,2-d]thiazole-6,7-diol;

(3aR,5R,6S,7R,7aR)-5-((S)-1-hydroxyallyl)-2-(methyl(propyl)amino)-5,6,7,7a-tetrahydro-3aH-pyrano[3,2-d]thiazole-6,7-diol;

(3aR,5R,6S,7R,7aR)-5-((R)-1-hydroxybut-3-enyl)-2-(methyl(propyl)amino)-5,6,7,7a-tetrahydro-3aH-pyrano[3,2-d]thiazole-6,7-diol;

(3aR,5R,6S,7R,7aR)-5-((S)-1-hydroxybut-3-enyl)-2-(methyl(propyl)amino)-5,6,7,7a-tetrahydro-3aH-pyrano[3,2-d]thiazole-6,7-diol;

(3aR,5S,6S,7R,7aR)-5-(2-hydroxypropan-2-yl)-2-(pyrrolidin-1-yl)-5,6,7,7a-tetrahydro-3aH-pyrano[3,2-d]thiazole-6,7-diol;

(3aR,5R,6S,7R,7aR)-5-((S)-1-hydroxyethyl)-2-(pyrrolidin-1-yl)-5,6,7,7a-tetrahydro-3aH-pyrano[3,2-d]thiazole-6,7-diol;

(3aR,5R,6S,7R,7aR)-5-((R)-1-hydroxypropyl)-2-(pyrrolidin-1-yl)-5,6,7,7a-tetrahydro-3aH-pyrano[3,2-d]thiazole-6,7-diol;

(3aR,5R,6S,7R,7aR)-5-((S)-1-hydroxypropyl)-2-(pyrrolidin-1-yl)-5,6,7,7a-tetrahydro-3aH-pyrano[3,2-d]thiazole-6,7-diol;

(3aR,5R,6S,7R,7aR)-5-((S)-1-hydroxyallyl)-2-(pyrrolidin-1-yl)-5,6,7,7a-tetrahydro-3aH-pyrano[3,2-d]thiazole-6,7-diol;

(3aR,5S,6S,7R,7aR)-2-(methylamino)-5-((R)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(propylamino)-5-((R)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(methoxy(methyl)amino)-5-((R)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(methylamino)-5-((S)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(propylamino)-5-((S)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(methoxy(methyl)amino)-5-((S)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(ethylamino)-5-((S)-1-fluoroethyl)-5,6,7,7a-tetrahydro-3aH-pyrano[3,2-d]thiazole-6,7-diol;

(3aR,5R,6S,7R,7aR)-2-(dimethylamino)-5-((R)-1-hydroxyethyl)-5,6,7,7a-tetrahydro-3aH-pyrano[3,2-d]thiazole-6,7-diol;

(3aR,5R,6S,7R,7aR)-2-(ethylamino)-5-((S)-1-hydroxypropyl)-5,6,7,7a-tetrahydro-3aH-pyrano[3,2-d]thiazole-6,7-diol;

(3aR,5R,6S,7R,7aR)-2-(ethylamino)-5-((R)-1-hydroxypropyl)-5,6,7,7a-tetrahydro-3aH-pyrano[3,2-d]thiazole-6,7-diol;

(3aR,5S,6S,7R,7aR)-5-((S)-1-fluoroethyl)-2-(pyrrolidin-1-yl)-5,6,7,7a-tetrahydro-3aH-pyrano[3,2-d]thiazole-6,7-diol;

(3aR,5R,6S,7R,7aR)-5-((R)-1-hydroxybutyl)-2-(methylamino)-5,6,7,7a-tetrahydro-3aH-pyrano[3,2-d]thiazole-6,7-diol;

(3aR,5R,6S,7R,7aR)-5-((S)-1-hydroxybutyl)-2-(methylamino)-5,6,7,7a-tetrahydro-3aH-pyrano[3,2-d]thiazole-6,7-diol;

(3aR,5R,6S,7R,7aR)-5-((R)-1-hydroxypentyl)-2-(methylamino)-5,6,7,7a-tetrahydro-3aH-pyrano[3,2-d]thiazole-6,7-diol;

(3aR,5R,6S,7R,7aR)-5-((S)-1-hydroxypentyl)-2-(methylamino)-5,6,7,7a-tetrahydro-3aH-pyrano[3,2-d]thiazole-6,7-diol;

(3aR,5R,6S,7R,7aR)-5-((R)-1-hydroxyhexyl)-2-(methylamino)-5,6,7,7a-tetrahydropyrano[3,2-d]thiazole-6,7-diol;

(3aR,5R,6S,7R,7aR)-5-((S)-1-hydroxyhexyl)-2-(methylamino)-5,6,7,7a-tetrahydro-3aH-pyrano[3,2-d]thiazole-6,7-diol;

(3aR,5R,6S,7R,7aR)-5-((R)-1-hydroxyethyl)-2-(propylamino)-5,6,7,7a-tetrahydro-3aH-pyrano[3,2-d]thiazole-6,7-diol;

(3aR,5R,6S,7R,7aR)-2-(cyclopropylmethylamino)-5-((S)-1-hydroxy-2-methylallyl)-5,6,7,7a-tetrahydro-3aH-pyrano[3,2-d]thiazole-6,7-diol;

(3aR,5R,6S,7R,7aR)-2-(cyclopropylmethylamino)-5-((R)-1-hydroxypropyl)-5,6,7,7a-tetrahydro-3aH-pyrano[3,2-d]thiazole-6,7-diol;

(3aR,5R,6S,7R,7aR)-2-(cyclopropylmethylamino)-5-((S)-1-hydroxypropyl)-5,6,7,7a-tetrahydro-3aH-pyrano[3,2-d]thiazole-6,7-diol;

(3aR,5S,6S,7R,7aR)-2-(cyclopropylmethylamino)-5-((R)-1-hydroxybut-3-enyl)-5,6,7,7a-tetrahydro-3aH-pyrano[3,2-d]thiazole-6,7-diol;

(3aR,5S,6S,7R,7aR)-2-(cyclopropylmethylamino)-5-(1-hydroxybut-3-enyl)-5,6,7,7a-tetrahydro-3aH-pyrano[3,2-d]thiazole-6,7-diol;

(3aR,5R,6S,7R,7aR)-2-(cyclopropylmethylamino)-5-((S)-1-hydroxyallyl)-5,6,7,7a-tetrahydro-3aH-pyrano[3,2-d]thiazole-6,7-diol;

(3aR,5R,6S,7R,7aR)-2-(2-cyclopropylethylamino)-5-((R)-1-hydroxyethyl)-5,6,7,7a-tetrahydro-3aH-pyrano[3,2-d]thiazole-6,7-diol;

(3aR,5R,6S,7R,7aR)-2-(2-cyclopropylethylamino)-5-((S)-1-hydroxyethyl)-5,6,7,7a-tetrahydro-3aH-pyrano (3aR,5S,6S,7R,7aR)-2-(2-cyclopropylethylamino)-5-(2-hydroxypropan-2-yl)-5,6,7,7a-tetrahydro-3aH-pyrano[3,2-d]thiazole-6,7-diol;

(3aR,5R,6S,7R,7aR)-2-(ethyl(methyl)amino)-5-((R)-1-hydroxyethyl)-5,6,7,7a-tetrahydro-3aH-pyrano[3,2-d]thiazole-6,7-diol;

(3aR,5R,6S,7R,7aR)-2-(ethyl(methyl)amino)-5-((S)-1-hydroxybutyl)-5,6,7,7a-tetrahydro-3aH-pyrano[3,2-d]thiazole-6,7-diol;

(3aR,5R,6S,7R,7aR)-2-(ethyl(methyl)amino)-5-((S)-1-hydroxypentyl)-5,6,7,7a-tetrahydro-3aH-pyrano[3,2-d]thiazole-6,7-diol;

(3aR,5R,6S,7R,7aR)-2-(dimethylamino)-5-((R)-1-hydroxyhexyl)-5,6,7,7a-tetrahydro-3aH-pyrano[3,2-d]thiazole-6,7-diol;

(3aR,5R,6S,7R,7aR)-5-((S)-1-hydroxybutyl)-2-(pyrrolidin-1-yl)-5,6,7,7a-tetrahydro-3aH-pyrano[3,2-d]thiazole-6,7-diol;

(3aR,5R,6S,7R,7aR)-5-((S)-1-hydroxypentyl)-2-(pyrrolidin-1-yl)-5,6,7,7a-tetrahydro-3aH-pyrano[3,2-d]thiazole-6,7-diol;

(3aR,5S,6S,7R,7aR)-5-(1,1-difluoroethyl)-2-(methoxy(methyl)amino)-5,6,7,7a-tetrahydro-3aH-pyrano[3,2-d]thiazole-6,7-diol;

(3aR,5R,6S,7R,7aR)-5-ethyl-2-(ethyl(methyl)amino)-5,6,7,7a-tetrahydro-3aH-pyrano[3,2-d]thiazole-6,7-diol;

(3aR,5R,6S,7R,7aR)-2-(azetidin-1-yl)-5-ethyl-5,6,7,7a-tetrahydro-3aH-pyrano[3,2-d]thiazole-6,7-diol;

(3aR,5R,6S,7R,7aR)-2-(azetidin-1-yl)-5-vinyl-5,6,7,7a-tetrahydro-3aH-pyrano[3,2-d]thiazole-6,7-diol;

(3aR,5R,6S,7R,7aR)-5-ethyl-2-(propylamino)-5,6,7,7a-tetrahydro-3aH-pyrano[3,2-d]thiazole-6,7-diol;

(3aR,5R,6S,7R,7aR)-5-ethyl-2-(ethylamino)-5,6,7,7a-tetrahydro-3aH-pyrano[3,2-d]thiazole-6,7-diol;

(3aR,5R,6S,7R,7aR)-2-(ethylamino)-5-vinyl-5,6,7,7a-tetrahydro-3aH-pyrano[3,2-d]thiazole-6,7-diol;

(3aR,5S,6S,7R,7aR)-5-(1-hydroxycyclopentyl)-2-(methylamino)-5,6,7,7a-tetrahydro-3aH-pyrano[3,2-d]thiazole-6,7-diol;

(3aR,5S,6S,7R,7aR)-5-(1-hydroxycyclopent-3-enyl)-2-(methylamino)-5,6,7,7a-tetrahydro-3aH-pyrano[3,2-d]thiazole-6,7-diol;

(3aR,5S,6S,7R,7aR)-5-(2-fluoropropan-2-yl)-2-(methylamino)-5,6,7,7a-tetrahydro-3aH-pyrano[3,2-d]thiazole-6,7-diol;

(3aR,5R,6S,7R,7aR)-2-(methylamino)-5-(prop-1-en-2-yl)-5,6,7,7a-tetrahydro-3aH-pyrano[3,2-d]thiazole-6,7-diol;

(3aR,5R,6S,7R,7aR)-2-(2-Fluoroethylamino)-5-((S)-1-hydroxyethyl)-5,6,7,7a-tetrahydro-3aH-pyrano[3,2-d]thiazole-6,7-diol;

(3aR,5R,6S,7R,7aR)-2-(3-Fluoropropylamino)-5-((S)-1-hydroxyethyl)-5,6,7,7a-tetrahydro-3aH-pyrano[3,2-d]thiazole-6,7-diol;

(3aR,5R,6S,7R,7aR)-5-(3-Hydroxypropyl)-2-(methylamino)-5,6,7,7a-tetrahydro-3aH-pyrano[3,2-d]thiazole-6,7-diol;

(3aR,5R,6S,7R,7aR)-2-(Ethylamino)-5-(2-hydroxyethyl)-5,6,7,7a-tetrahydro-3aH-pyrano[3,2-]thiazole-6,7-diol;

(3aR,5R,6S,7R,7aR)-5-(2-hydroxyethyl)-2-(methylamino)-5,6,7,7a-tetrahydro-3aH-pyrano[3,2-d]thiazole-6,7-diol;

(3aR,5S,6S,7R,7aR)-2-(Dimethylamino)-5-(2-fluoropropan-2-yl)-5,6,7,7a-tetrahydro-3aH-pyrano[3,2-d]thiazole-6,7-diol;

(3aR,5S,6S,7R,7aR)-5-(1,1-Difluoroethyl)-2-(propylamino)-5,6,7,7a-tetrahydro-3aH-pyrano[3,2-d]thiazole-6,7-diol;

(3aR,5S,6S,7R,7aR)-5-(1,1-difluoroethyl)-2-(methylamino)-5,6,7,7a-tetrahydro-3aH-pyrano[3,2-d]thiazole-6,7-diol;

(3aR,5S,6S,7R,7aR)-5-((S)-2,2-difluoro-1-hydroxyethyl)-2-(dimethylamino)-5,6,7,7a-tetrahydro-3aH-pyrano[3,2-d]thiazole-6,7-diol;

(3aR,5S,6S,7R,7aR)-5-((R)-2,2-difluoro-1-hydroxyethyl)-2-(dimethylamino)-5,6,7,7a-tetrahydro-3aH-pyrano[3,2-d]thiazole-6,7-diol;

(3aR,5R,6S,7R,7aR)-5-((S)-1,2-dihydroxyethyl)-2-(dimethylamino)-5,6,7,7a-tetrahydro-3aH-pyrano[3,2-d]thiazole-6,7-diol;

(3aR,5R,6S,7R,7aR)-5-((R)-1,2-dihydroxyethyl)-2-(dimethylamino)-5,6,7,7a-tetrahydro-3aH-pyrano[3,2-d]thiazole-6,7-diol;

(3aR,5S,6S,7R,7aR)-2-(dimethylamino)-5-((S)-2-fluoro-1-hydroxyethyl)-5,6,7,7a-tetrahydro-3aH-pyrano[3,2-d]thiazole-6,7-diol;

(3aR,5S,6S,7R,7aR)-2-(dimethylamino)-5-((R)-2-fluoro-1-hydroxyethyl)-5,6,7,7a-tetrahydro-3aH-pyrano[3,2-d]thiazole-6,7-diol;

(3aR,5R,6S,7R,7aR)-2-(dimethylamino)-5-(2-fluoroethyl)-5,6,7,7a-tetrahydro-3aH-pyrano[3,2-d]thiazole-6,7-diol;

(3aR,5R,6S,7R,7aR)-5-(2,2-difluoroethyl)-2-(dimethylamino)-5,6,7,7a-tetrahydro-3aH-pyrano[3,2-d]thiazole-6,7-diol;

(3aR,5R,6S,7R,7aR)-2-(dimethylamino)-5-(2,2,2-trifluoroethyl)-5,6,7,7a-tetrahydro-3aH-pyrano[3,2-d]thiazole-6,7-diol;

(3aR,5S,6S,7R,7aR)-2-(methylamino)-5-((S)-1,1,1-trifluoro-2-hydroxypropan-2-yl)-5,6,7,7a-tetrahydro-3aH-pyrano[3,2-d]thiazole-6,7-diol;

(3aR,5S,6S,7R,7aR)-2-(methylamino)-5-(1,1,1-trifluoro-2-hydroxypropan-2-yl)-5,6,7,7a-tetrahydro-3aH-pyrano[3,2-d]thiazole-6,7-diol;

(3aR,5S,6S,7R,7aR)-2-(ethylamino)-5-((S)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(ethylamino)-5-((R)-2,2,2-trifluoro-1-hydroxyethyl)-5,6,7,7a-tetrahydro-3aH-pyrano[3,2-d]thiazole-6,7-diol;

(3aR,5R,6S,7R,7aR)-5-((R)-1-hydroxyethyl)-2-(2-hydroxyethylamino)-5,6,7,7a-tetrahydro-3aH-pyrano[3,2-d]thiazole-6,7-diol;

(3aR,5R,6S,7R,7aR)-5-((S)-1-hydroxyethyl)-2-(2-hydroxyethylamino)-5,6,7,7a-tetrahydro-3aH-pyrano[3,2-d]thiazole-6,7-diol;

(3aR,5S,6S,7R,7aR)-2-amino-5-[(1S)-2,2,2-trifluoro-1-hydroxyethyl]-3aH,5H,6H,7H,7aH-pyrano[3,2-d][1,3]thiazole-6,7-diol;

(3aR,5S,6S,7R,7aR)-2-amino-5-[(1R)-2,2,2-trifluoro-1-hydroxyethyl]-3aH,5H,6H,7H,7aH-pyrano[3,2-d][1,3]thiazole-6,7-diol;

(3aR,5S,6S,7R,7aR)-2-(allylamino)-5-((S)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(allylamino)-5-((R)-2,2,2-trifluoro-1-hydroxyethyl)-5,6,7,7a-tetrahydro-3aH-pyrano[3,2-d]thiazole-6,7-diol;

(3aR,5R,6S,7R,7aR)-2-(allylamino)-5-((R)-1-hydroxy-ethyl)-5,6,7,7a-tetrahydro-3aH-pyrano[3,2-d]thiazole-6,7-diol;

(3aR,5R,6S,7R,7aR)-2-(allylamino)-5-((S)-1-hydroxy-ethyl)-5,6,7,7a-tetrahydro-3aH-pyrano[3,2-d]thiazole-6,7-diol;

(3aR,5S,6S,7R,7aR)-2-(allylamino)-5-((S)-1,1,1-trifluoro-2-hydroxypropan-2-yl)-5,6,7,7a-tetrahydro-3aH-pyrano[3,2-d]thiazole-6,7-diol;

(3aR,5S,6S,7R,7aR)-2-(allylamino)-5-(1,1,1-trifluoro-2-hydroxypropan-2-yl)-5,6,7,7a-tetrahydro-3aH-pyrano[3,2-d]thiazole-6,7-diol;

(3aR,5S,6S,7R,7aR)-2-(2-hydroxyethylamino)-5-((R)-2,2,2-trifluoro-1-hydroxyethyl)-5,6,7,7a-tetrahydro-3aH-pyrano[3,2-d]thiazole-6,7-diol;

(3aR,5R,6S,7R,7aR)-2-(allylamino)-5-(2-hydroxyethyl)-5,6,7,7a-tetrahydro-3aH-pyrano[3,2-d]thiazole-6,7-diol;

(3aR,5R,6S,7R,7aR)-2-(allylamino)-5-(2,2-difluoroethyl)-5,6,7,7a-tetrahydro-3aH-pyrano[3,2-d]thiazole-6,7-diol;

(3aR,5S,6S,7R,7aR)-2-amino-5-[(2S)-1,1,1-trifluoro-2-hydroxypropan-2-yl]-3aH,5H,6H,7H,7aH-pyrano[3,2-d][1,3]thiazole-6,7-diol;

(3aR,5S,6S,7R,7aR)-2-amino-5-[(2R)-1,1,1-trifluoro-2-hydroxypropan-2-yl]-3aH,5H,6H,7H,7aH-pyrano[3,2-d][1,3]thiazole-6,7-diol;

(3aR,5R,6S,7R,7aR)-2-amino-5-vinyl-5,6,7,7a-tetrahydro-3aH-pyrano[3,2-d]thiazole-6,7-diol;

(3aR,5R,6S,7R,7aR)-2-amino-5-ethyl-5,6,7,7a-tetrahydro-3aH-pyrano[3,2-d]thiazole-6,7-diol;

(3aR,5S,6S,7R,7aR)-2-(dimethylamino)-5-((R)-1-fluoroethyl)-5,6,7,7a-tetrahydro-3aH-pyrano[3,2-d]thiazole-6,7-diol;

(3aR,5S,6S,7R,7aR)-2-(dimethylamino)-5-((S)-1-fluoroethyl)-5,6,7,7a-tetrahydro-3aH-pyrano[3,2-d]thiazole-6,7-diol;

(3aR,5S,6S,7R,7aR)-5-((R)-1-fluoroethyl)-2-(methylamino)-5,6,7,7a-tetrahydro-3aH-pyrano[3,2-d]thiazole-6,7-diol;

(3aR,5S,6S,7R,7aR)-2-(azetidin-1-yl)-5-((R)-1-fluoroethyl)-5,6,7,7a-tetrahydro-3aH-pyrano[3,2-d]thiazole-6,7-diol;

(3aR,5S,6S,7R,7aR)-2-(dimethylamino)-5-((S)-1,2,2,2-tetrafluoroethyl)-5,6,7,7a-tetrahydro-3aH-pyrano[3,2-d]thiazole-6,7-diol;

(3aR,5S,6S,7R,7aR)-5-((S)-1-fluoroethyl)-2-(methylamino)-5,6,7,7a-tetrahydro-3aH-pyrano[3,2-d]thiazole-6,7-diol;

(3aR,5S,6S,7R,7aR)-2-(azetidin-1-yl)-5-((S)-1-fluoroethyl)-5,6,7,7a-tetrahydro-3aH-pyrano[3,2-d]thiazole-6,7-diol;

(3aR,5S,6S,7R,7aR)-2-(dimethylamino)-5-((R)-1,2,2,2-tetrafluoroethyl)-5,6,7,7a-tetrahydro-3aH-pyrano[3,2-d]thiazole-6,7-diol;

(3aR,5R,6S,7R,7aR)-2-(azetidin-1-yl)-5-((R)-1,1,1-trifluoropropan-2-yl)-5,6,7,7a-tetrahydro-3aH-pyrano[3,2-d]thiazole-6,7-diol;

(3aR,5R,6S,7R,7aR)-2-(azetidin-1-yl)-5-((S)-1,1,1-trifluoropropan-2-yl)-5,6,7,7a-tetrahydro-3aH-pyrano[3,2-d]thiazole-6,7-diol;

(3aR,5R,6S,7R,7aR)-2-(dimethylamino)-5-((R)-1,1,1-trifluoropropan-2-yl)-5,6,7,7a-tetrahydro-3aH-pyrano[3,2-d]thiazole-6,7-diol;

(3aR,5R,6S,7R,7aR)-2-(dimethylamino)-5-((S)-1,1,1-trifluoropropan-2-yl)-5,6,7,7a-tetrahydro-3aH-pyrano[3,2-d]thiazole-6,7-diol;

(3aR,5S,6S,7R,7aR)-5-((R)-2,2-difluoro-1-hydroxyethyl)-2-(methylamino)-5,6,7,7a-tetrahydro-3aH-pyrano[3,2-d]thiazole-6,7-diol;

(3aR,5S,6S,7R,7aR)-5-((S)-2-fluoro-1-hydroxyethyl)-2-(methylamino)-5,6,7,7a-tetrahydro-3aH-pyrano[3,2-d]thiazole-6,7-diol;

(3aR,5S,6S,7R,7aR)-5-((R)-2-fluoro-1-hydroxyethyl)-2-(methylamino)-5,6,7,7a-tetrahydro-3aH-pyrano[3,2-d]thiazole-6,7-diol;

(3aR,5R,6S,7R,7aR)-5-(2-fluoroethyl)-2-(methylamino)-5,6,7,7a-tetrahydro-3aH-pyrano[3,2-d]thiazole-6,7-diol;

(3aR,5R,6S,7R,7aR)-5-(2,2-difluoroethyl)-2-(methylamino)-5,6,7,7a-tetrahydro-3aH-pyrano[3,2-d]thiazole-6,7-diol;

(3aR,5R,6S,7R,7aR)-2-(methylamino)-5-(2,2,2-trifluoroethyl)-5,6,7,7a-tetrahydro-3aH-pyrano[3,2-d]thiazole-6,7-diol;

(3aR,5R,6S,7R,7aR)-2-(ethylamino)-5-(2,2,2-trifluoroethyl)-5,6,7,7a-tetrahydro-3aH-pyrano[3,2-d]thiazole-6,7-diol;

(3aR,5R,6S,7R,7aR)-2-(propylamino)-5-(2,2,2-trifluoroethyl)-5,6,7,7a-tetrahydro-3aH-pyrano[3,2-d]thiazole-6,7-diol;

(3aR,5S,6S,7R,7aR)-2-(azetidin-1-yl)-5-((S)-1,1,1-trifluoro-2-hydroxypropan-2-yl)-5,6,7,7a-tetrahydro-3aH-pyrano[3,2-d]thiazole-6,7-diol;

(3aR,5S,6S,7R,7aR)-2-(azetidin-1-yl)-5-((R)1,1,1-trifluoro-2-hydroxypropan-2-yl)-5,6,7,7a-tetrahydro-3aH-pyrano[3,2-d]thiazole-6,7-diol;

(3aR,5S,6S,7R,7aR)-2-(dimethylamino)-5-((S)-1,1,1-trifluoro-2-hydroxypropan-2-yl)-5,6,7,7a-tetrahydro-3aH-pyrano[3,2-d]thiazole-6,7-diol;

(3aR,5S,6S,7R,7aR)-2-(dimethylamino)-5-((R)1,1,1-trifluoro-2-hydroxypropan-2-yl)-5,6,7,7a-tetrahydro-3aH-pyrano[3,2-d]thiazole-6,7-diol;

(3aR,5S,6S,7R,7aR)-2-(dimethylamino)-5-((S)-1,1,1-trifluoro-2-hydroxypropan-2-yl)-5,6,7,7a-tetrahydro-3aH-pyrano[3,2-d]thiazole-6,7-diol;

(3aR,5S,6S,7R,7aR)-2-(ethylamino)-5-((S)-1,1,1-trifluoro-2-hydroxypropan-2-yl)-5,6,7,7a-tetrahydro-3aH-pyrano[3,2-d]thiazole-6,7-diol;

(3aR,5S,6S,7R,7aR)-2-(ethylamino)-5-((R)1,1,1-trifluoro-2-hydroxypropan-2-yl)-5,6,7,7a-tetrahydro-3aH-pyrano[3,2-d]thiazole-6,7-diol;

(3aR,5R,6S,7R,7aR)-5-((R)-1-hydroxyethyl)-2-(isoxazolidin-2-yl)-5,6,7,7a-tetrahydro-3aH-pyrano[3,2-d]thiazole-6,7-diol;

(3aR,5R,6S,7R,7aR)-5-((S)-1-hydroxyethyl)-2-(isoxazolidin-2-yl)-5,6,7,7a-tetrahydro-3aH-pyrano[3,2-d]thiazole-6,7-diol;

(3aR,5R,6S,7R,7aR)-2-(ethylamino)-5-((S)-1-hydroxypropyl)-5,6,7,7a-tetrahydro-3aH-pyrano[3,2-d]thiazole-6,7-diol;

(3aR,5R,6S,7R,7aR)-5-((S)-1-hydroxyheptyl)-2-(methylamino)-5,6,7,7a-tetrahydro-3aH-pyrano[3,2-d]thiazole-6,7-diol;

(3aR,5S,6S,7R,7aR)-2-(ethyl(methyl)amino)-5-((S)-2,2,2-trifluoro-1-hydroxyethyl)-5,6,7,7a-tetrahydro-3aH-pyrano[1,2-d]thiazole-6,7-diol;

(3aR,5S,6S,7R,7aR)-2-(ethyl(methyl)amino)-5-((R)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(azetidin-1-yl)-5-((S)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(azetidin-1-yl)-5-((R)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(2-fluoroethylamino)-5-((R)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(2-fluoroethylamino)-5-((S)-2,2,2-trifluoro-1-hydroxyethyl)-5,6,7,7a-tetrahydro-3aH-pyrano[3,2-d]thiazole-6,7-diol;

(3aR,5S,6S,7R,7aR)-2-(dimethylamino)-5-(1,1,1,3,3,3-hexafluoro-2-hydroxypropan-2-yl)-5,6,7,7a-tetrahydro-3aH-pyrano[3,2-d]thiazole-6,7-diol;

(3aR,5R,6S,7R,7aR)-2-(methylamino)-5-((R)-1,1,1-trifluoropropan-2-yl)-5,6,7,7a-tetrahydro-3aH-pyrano[3,2-d]thiazole-6,7-diol; and (3aR,5R,6S,7R,7aR)-2-(methylamino)-5-((S)-1,1,1-trifluoropropan-2-yl)-5,6,7,7a-tetrahydro-3aH-pyrano[3,2-d]thiazole-6,7-diol;

or a pharmaceutically acceptable salt of any of the foregoing compounds.

10. The compound according to claim 1 or a pharmaceutically acceptable salt thereof, wherein: each R is H, $R^5$ is OH, $R^3$ is $C_{1-6}$alkyl, optionally substituted from one up to the maximum number of substituents with fluoro and hydroxy, and $R^4$ is H.

11. The compound according to claim 1 or a pharmaceutically acceptable salt thereof, wherein: each R is H, $R^5$ is H, $R^3$ is $C_{1-6}$alkyl, optionally substituted from one up to the maximum number of substituents with fluoro and hydroxy, and $R^4$ is H or $C_{1-6}$alkyl.

12. The compound according to claim 1 or a pharmaceutically acceptable salt thereof, wherein $R^1$ is $C_{1-6}$alkyl, optionally substituted from one up to the maximum number of substituents with hydroxy, and $R^2$ is H.

13. The compound according to claim 1 or a pharmaceutically acceptable salt thereof, wherein $R^1$ is $C_{2-6alkenyl}$ and $R^2$ is H.

14. The compound according to claim 1 or a pharmaceutically acceptable salt thereof, wherein each R is H and $R^5$ is F.

15. A pharmaceutical composition comprising a compound according to claim 1 or a pharmaceutically acceptable salt thereof and a pharmaceutically acceptable carrier.

16. A method for treating a condition which is selected from the group consisting of: an inflammatory disease, an allergy, asthma, allergic rhinitis, hypersensitivity lung diseases, hypersensitivity pneumonitis, eosinophilic pneumonias, delayed-type hypersensitivity, atherosclerosis, interstitial lung disease (ILD), idiopathic pulmonary fibrosis, ILD associated with rheumatoid arthritis, systemic lupus erythematosus, ankylosing spondylitis, systemic sclerosis, Sjogren's syndrome, polymyositis or dermatomyositis, systemic anaphylaxis or hypersensitivity response, drug allergy, insect sting allergy, autoimmune disease, rheumatoid arthritis, psoriatic arthritis, multiple sclerosis, Guillain-Barré syndrome, systemic lupus erythematosus, myastenia gravis, glomerulonephritis, autoimmune thyroiditis, graft rejection, allograft rejection, graft-versus-host disease, inflammatory bowel disease, Crohn's disease, ulcerative colitis, spondyloarthropathy, scleroderma, psoriasis, T-cell mediated psoriasis, inflammatory dermatosis, dermatitis, eczema, atopic dermatitis, allergic contact dermatitis, urticaria, vasculitis, necrotizing, cutaneous, and hypersensitivity vasculitis, eosinphilic myotis, eosiniphilic fasciitis, solid organ transplant rejection, heart transplant rejection, lung transplant rejection, liver transplant rejection, kidney transplant rejection, pancreas transplant rejection, kidney allograft, lung allograft, epilepsy, pain, fibromyalgia, stroke, and neuroprotection in a subject in need thereof, the method comprising administering to the subject an effective amount of a compound according to claim 1, or a pharmaceutically acceptable salt thereof.

17. A method for treating a condition which is selected from the group consisting of a neurodegenerative disease, cancer and stress, in a subject in need thereof, the method comprising administering to the subject an effective amount of a compound according to claim 1, or a pharmaceutically acceptable salt thereof.

18. A method for treating a condition which is selected from the group consisting of: Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, Huntington's disease, Parkinson's disease, Schizophrenia, Mild Cognitive Impairment (MCI), Neuropathy (including peripheral neuropathy, autonomic neuropathy, neuritis, and diabetic neuropathy), and Glaucoma in a subject in need thereof, the method comprising administering to the subject an effective amount of a compound according to claim 1, or a pharmaceutically acceptable salt thereof.

19. A method for treating a condition which is selected from the group consisting of: ischemia; hemorrhage; hypovolemic shock; myocardial infarction; an interventional cardiology procedure; cardiac bypass surgery; fibrinolytic therapy; angioplasty; and stent placement in a subject in need thereof, the method comprising administering to the subject an effective amount of a compound according to claim 1, or a pharmaceutically acceptable salt thereof.

20. The compound of claim 9 which is (3aR,5S,6S,7R,7aR)-2-(dimethylamino)-5-(2-hydroxypropan-2-yl)-5,6,7,7a-tetrahydro-3aH-pyrano[3,2-d]thiazole-6,7-diol, or a pharmaceutically acceptable salt thereof.

21. The compound of claim 9 which is (3aR,5S,6S,7R,7aR)-2-(dimethylamino)-5-(2-hydroxypropan-2-yl)-5,6,7,7a-tetrahydro-3aH-pyrano[3,2-d]thiazole-6,7-diol.

22. The compound of claim 9 which is (3aR,5S,6S,7R,7aR)-2-(dimethylamino)-5-(2-hydroxypropan-2-yl)-5,6,7,7a-tetrahydro-3aH-pyrano[3,2-d]thiazole-6,7-diol in the form of a pharmaceutically acceptable salt thereof.

23. The compound of claim 9 which is (3aR,5S,6S,7R,7aR)-2-(dimethylamino)-5-((R)-2,2,2-trifluoro-1-hydroxyethyl)-5,6,7,7a-tetrahydro-3aH-pyrano[3,2-d]thiazole-6,7-diol, or a pharmaceutically acceptable salt thereof.

24. The compound of claim 9 which is (3aR,5S,6S,7R,7aR)-2-(dimethylamino)-5-((R)-2,2,2-trifluoro-1-hydroxyethyl)-5,6,7,7a-tetrahydro-3aH-pyrano[3,2-d]thiazole-6,7-diol.

25. The compound of claim 9 which is (3aR,5S,6S,7R,7aR)-2-(dimethylamino)-5-((R)-2,2,2-trifluoro-1-hydroxyethyl)-5,6,7,7a-tetrahydro-3aH-pyrano[3,2-d]thiazole-6,7-diol in the form of a pharmaceutically acceptable salt thereof.

26. The compound of claim 9 which is (3aR,5S,6S,7R,7aR)-2-(methylamino)-5-((R)-2,2,2-trifluoro-1-hydroxyethyl)-5,6,7,7a-tetrahydro-3aH-pyrano[3,2-d]thiazole-6,7-diol, or a pharmaceutically acceptable salt thereof.

27. The compound of claim 9 which is (3aR,5S,6S,7R,7aR)-2-(methylamino)-5-((R)-2,2,2-trifluoro-1-hydroxyethyl)-5,6,7,7a-tetrahydro-3aH-pyrano[3,2-d]thiazole-6,7-diol.

28. The compound of claim 9 which is (3aR,5S,6S,7R,7aR)-2-(methylamino)-5-((R)-2,2,2-trifluoro-1-hydroxyethyl)-5,6,7,7a-tetrahydro-3aH-pyrano[3,2-d]thiazole-6,7-diol in the form of a pharmaceutically acceptable salt thereof.

29. The compound of claim 9 which is (3aR,5S,6S,7R,7aR)-2-(methylamino)-5-((S)-1,1,1-trifluoro-2-hydroxypropan-2-yl)-5,6,7,7a-tetrahydro-3aH-pyrano[3,2-d]thiazole-6,7-diol, or a pharmaceutically acceptable salt thereof.

30. The compound of claim 9 which is (3aR,5S,6S,7R,7aR)-2-(methylamino)-5-((S)-1,1,1-trifluoro-2-hydroxypropan-2-yl)-5,6,7,7a-tetrahydro-3aH-pyrano[3,2-d]thiazole-6,7-diol.

31. The compound of claim 9 which is (3aR,5S,6S,7R,7aR)-2-(methylamino)-5-((S)-1,1,1-trifluoro-2-hydroxypropan-2-yl)-5,6,7,7a-tetrahydro-3aH-pyrano[3,2-d]thiazole-6,7-diol in the form of a pharmaceutically acceptable salt thereof.

32. The compound of claim 9 which is (3aR,5S,6S,7R,7aR)-2-(methylamino)-5-((R)-1,1,1-trifluoro-2-hydroxypropan-2-yl)-5,6,7,7a-tetrahydro-3aH-pyrano[3,2-d]thiazole-6,7-diol, or a pharmaceutically acceptable salt thereof.

33. The compound of claim 9 which is (3aR,5S,6S,7R,7aR)-2-(methylamino)-5-((R)-1,1,1-trifluoro-2-hydroxypropan-2-yl)-5,6,7,7a-tetrahydro-3aH-pyrano[3,2-d]thiazole-6,7-diol.

34. The compound of claim 9 which is (3aR,5S,6S,7R,7aR)-2-(methylamino)-5-((R)-1,1,1-trifluoro-2-hydroxypropan-2-yl)-5,6,7,7a-tetrahydro-3aH-pyrano[3,2-d]thiazole-6,7-diol in the form of a pharmaceutically acceptable salt thereof.

35. The compound of claim 9 which is (3aR,5S,6S,7R,7aR)-2-(ethylamino)-5-((R)-2,2,2-trifluoro-1-hydroxyethyl)-5,6,7,7a-tetrahydro-3aH-pyrano[3,2-d]thiazole-6,7-diol, or a pharmaceutically acceptable salt thereof.

36. The compound of claim 9 which is (3aR,5S,6S,7R,7aR)-2-(ethylamino)-5-((R)-2,2,2-trifluoro-1-hydroxyethyl)-5,6,7,7a-tetrahydro-3aH-pyrano[3,2-d]thiazole-6,7-diol.

37. The compound of claim 9 which is (3aR,5S,6S,7R,7aR)-2-(ethylamino)-5-((R)-2,2,2-trifluoro-1-hydroxyethyl)-5,6,7,7a-tetrahydro-3aH-pyrano[3,2-d]thiazole-6,7-diol in the form of a pharmaceutically acceptable salt thereof.

38. A pharmaceutical composition comprising the compound of claim 20 or a pharmaceutically acceptable salt thereof and a pharmaceutically acceptable carrier.

39. A pharmaceutical composition comprising the compound of claim 23 or a pharmaceutically acceptable salt thereof and a pharmaceutically acceptable carrier.

40. A pharmaceutical composition comprising the compound of claim 26 or a pharmaceutically acceptable salt thereof and a pharmaceutically acceptable carrier.

41. A pharmaceutical composition comprising the compound of claim 29 or a pharmaceutically acceptable salt thereof and a pharmaceutically acceptable carrier.

42. A pharmaceutical composition comprising the compound of claim 32 or a pharmaceutically acceptable salt thereof and a pharmaceutically acceptable carrier.

43. A pharmaceutical composition comprising the compound of claim 35 or a pharmaceutically acceptable salt thereof and a pharmaceutically acceptable carrier.

* * * * *